United States Patent [19]

Numata et al.

[11] Patent Number: 5,763,413
[45] Date of Patent: Jun. 9, 1998

[54] LEWIS-ASSOCIATED COMPOUND, PROCESS FOR PRODUCING THE SAME, AND ANTI-INFLAMMATORY

[75] Inventors: Masaaki Numata, Kawagoe; Shigeki Nunomura, Iruma; Shuji Fujita, Musashimurayama; Masami Iida; Akira Endo, both of Tokorozawa; Takayuki Ishii, Tokyo; Tomoya Ogawa, Musashino; Mamoru Sugimoto, Tokyo; Ryoichi Osawa, Iruma; Masamichi Fujita, Kunitachi, all of Japan

[73] Assignee: MECT Corporation, Tokyo, Japan

[21] Appl. No.: 505,352

[22] PCT Filed: Mar. 4, 1994

[86] PCT No.: PCT/JP94/00352

§ 371 Date: Aug. 30, 1995

§ 102(e) Date: Aug. 30, 1995

[87] PCT Pub. No.: WO94/20514

PCT Pub. Date: Sep. 15, 1994

[30] Foreign Application Priority Data

Mar. 4, 1993 [JP] Japan ................... 5-044111

[51] Int. Cl.[6] .............. A61K 31/70; C07H 15/00; C07H 17/00
[52] U.S. Cl. ............ 514/25; 514/54; 514/61; 514/62; 536/4.1; 536/17.2; 536/18.5; 536/18.6; 536/18.7; 536/55; 536/55.1; 536/55.2; 536/55.3; 536/123.1; 536/124
[58] Field of Search ................ 536/4.1, 17.2, 536/18.5, 18.6, 18.7, 55, 55.1, 55.2, 55.3, 123.1, 124; 514/25, 54, 61, 62

[56] References Cited

U.S. PATENT DOCUMENTS 5,211,937  5/1993  Brandley et al. .............. 424/1.73
5,296,594  3/1994  Ratcliffe et al. ............... 536/53

FOREIGN PATENT DOCUMENTS

91/16449   10/1991   WIPO.
91/19502   12/1991   WIPO.
93/24505   12/1993   WIPO.
WO 95/08553  3/1995  WIPO.
WO 95/21180  8/1995  WIPO.

OTHER PUBLICATIONS

Hasegawa et al., "Steroecontrolled synthesis of sialyl Lewis X ceramide consisting of a pentasaccharide recognized by the selectin family", *Carbohydrate Research*, 230 (1992) pp. C1–C5.

Nicolaou et al., "Total Synthesis of Sulfated Le[x] and Le[a]-Type Oligosaccharide Selectin Ligands", *J. Am. Chem. Soc.*, vol. 115, No. 19, 1993, pp. 8843–8844.

Nakano et al., "Synthesis of sulfated glucuronyl glycosphingolipids; carbohydrate epitopes of neural cell-adhesion molecules", *Carbohydrate Research*, vol. 243, No. 1, 1993, pp. 43–69.

Lubineau et al., "First Synthesis of the 3'-Sulfated Lewis[a] Trisaccharide, Putative Ligand for the Leucocyte Homing Receptor", *J. Chem. Soc., Chem. Commun.*, 1993, pp. 1419–1420.

Kitagawa et al. *J. Biol. Chem.* Mar. 1990, 265(9), 4859–4862.

Yuen et al. *J. Biol. Chem.* Jan. 21, 1994, 269(3), 1595–1598.

"Synthesis and Structural Analysis Using 2-D NMR of Sialyl Lewis X (SLe[x]) and Lewis X (Le[x]) Oligosaccharides: Ligands Related to E–Selectin [ELAM–1] Binding", *Journal of American Chemical Society* (Jun. 1992) vol. 114, No. 13, pp. 5449–5451.

"Total Synthesis of the Tumor–Associated Le[x]Family of Glycosphingolipids", *Journal of American Chemical Society* (Apr. 1990) vol. 112, No. 9, pp. 3693–3695.

"Synthesis of a Dimeric Lewis X Hexasaccharide Derivative Corresponding to a Tumor–Associated Glycolipid", *Carbohydrate Research* (1988) vol. 183, No. 1, pp. 71–82.

"Chemical–Enzymatic Synthesis and Conformational Analysis of Sialyl Lewis x and Derivatives", *Journal of American Chemical Society* (1992) vol. 114, pp. 9283–9298.

"Novel Sulfated Ligands for the Cell Adhesion Molecule E–Selection Revealed by the Neoglycolipid Technology among O–Linked Oligosaccharides on an Ovarian Cystadenoma Glycoprotein", *Journal of American Chemical Society* (1992) vol. 31, pp. 9126–9131.

"CD62 and endothelial cell–leukocyte adhesion molecule 1 (ELAM–1) recognize the same carbohydrate ligand, sialyl–Lewis X", *Proc. Natl. Acad. Sci, USA* (Jul. 1991) vol. 88, pp. 6224–6228.

"Total Synthesis of Sialyl Dimeric Le", *Journal of American Chemical Society* (1992) vol. 114, pp. 3126–3128.

(List continued on next page.)

Primary Examiner—Kathleen K. Fonda
Attorney, Agent, or Firm—Oliff & Berridge, P.L.C.

[57] ABSTRACT

A Lewis-associated compound, represented by general formula (I), a process for producing the same, and an anti-inflammatory, wherein $R^1$ and $R^3$ represent each hydrogen, $SO_3H$ or $CH_2COOH$; $R^2$ represents hydrogen, $SO_3H$, $CH_2COOH$ or N-acetyl-neutraminic acid residue; $R^4$ represents hydrogen; $R^5$ represents O-lower alkyl, O-lower alkenyl, O-ceramide residue, O-mannose residue, O-galactose residue or O-lactose residue; $R^6$ represents acetylamine; and $R^7$ and $R^8$ represent each hydrogen.

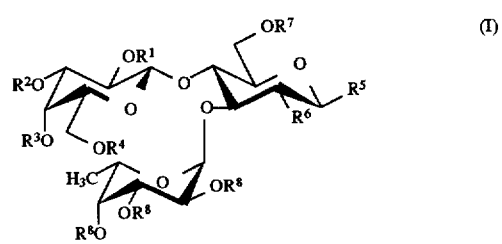

6 Claims, No Drawings

OTHER PUBLICATIONS

"High Affinity Binding of the Leucocyte Adhesion Molecule L–Selectin to 3'–Sulphated' $Le^a$ and $Le^x$ Oligosaccharides and the Predominance of Sulphate in this Interaction Demonstrated by Binding Studies with a Series of Lipid–Linked Oligosaccharides", *Biochemical and Biophysical Research Communications* (Oct. 1992) vol. 188, No. 1, pp. 244–251.

"Preliminary Communication", *Carbohydrate Research* (1991) vol. 209, pp. c1–c4.

"Enzymatic Synthesis of Sialyl $Le^x$ and Derivatives Based on a Recombinant Fucosyltransferase", *Bioorganic & Medicinal Chemistry Letters* (1991) vol. 1, No. 8, pp. 425–428.

LEWIS-ASSOCIATED COMPOUND, PROCESS FOR PRODUCING THE SAME, AND ANTI-INFLAMMATORY

This application is filed under 35 U.S.C. §371 from International Patent Application No. PCT/JP94/00352, filed Mar. 4, 1994.

FIELD OF THE INVENTION

The present invention relates to the method for preparing Lewis-related compounds, especially Lewis x ($Le^x$) and Lewis a ($Le^a$) as well as the anti-inflammatory agents containing said Lewis-related compounds as the active ingredients.

BACKGROUND OF THE INVENTION

Lewis x ($Le^x$) and Lewis a ($Le^a$) belong to a family of oligosaccharide in which fucose is linked to Type II and Type I lactosamine in a $\alpha(1\rightarrow3)$ or $\alpha(1\rightarrow4)$ linkage. Furthermore, the saccharide chain extended by linking sialic acid as the constituent sugar to the non-reducing end of $Le^x$ and $Le^a$ are called sialyl $Le^x$ and sialyl $Le^a$, respectively. Glycolipids and glycoproteins comprising $Le^x$, $Le^a$, sialyl $Le^x$ and sialyl $Le^a$ in their structure have been reported to widely occur as the embryonal antigen or carcinoembryonic antigen (tumor antigen) on the cellular membrane of the animal and play an important role in the intercellular information transport and cell recognition.

Recently, the carbohydrate chain containing such structure as described above, especially sialyl $Le^x$ has been reported to be closely involved in the adhesion of leukocytes to endothelial cells and platelets. In addition, sialyl dimeric $Le^x$, a structural dimer thereof, has been reported to appear as the tumor cell surface antigen and be involved in the metastasis mechanism. Also sulfated $Le^x$ and $Le^a$ wherein the position to which sialic acid residue is linked is substituted with sulfate residue have been found in a cancer tissue.

References cited below disclose the background related arts of the present invention:

1. J. Am. Chem. Soc. 114: 9283–9298 (1992).
2. Biochemistry 31: 9126–9131 (1992),
3. Proc. Natl. Acad. Sci. USA 88: 6224–6228 (1991),
4. J. Am. Chem. Soc. 114: 3126–3128 (1992),
5. Biochem. Biophys. Res. Commun. 188: 244–251 (1992),
6. Carbohydrate Research 209: c1–c4 (1991),
7. Bioorganic & Medicinal Chemistry Letters Vol. 1 (No. 8): 425–428 (1991), and
8. JP-A-2-174696.

Noticing $Le^x$ and $Le^a$ with such a variety of biological functions, the present inventors have achieved the present invention by synthesizing sugar chain derivatives related thereto and further discovering the useful biological activity of said synthesized compounds.

SUMMARY OF THE INVENTION

The present invention aims to provide the method for preparing the Lewis-related compounds, especially $Le^x$, $Le^a$ and related compounds thereof and also the anti-inflammatory agents containing said compounds as the active ingredients.

The present invention is to provide the Lewis-related compounds represented by the following general structural formulas (I), (II), (III), (IV), (V) or (VI):

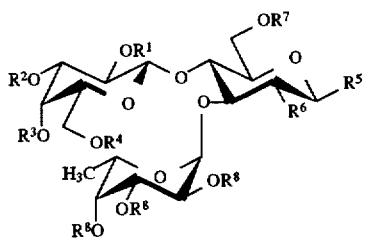

(I)

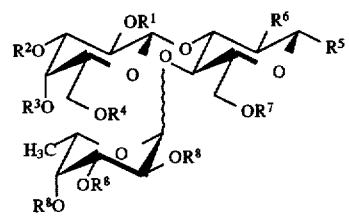

(II)

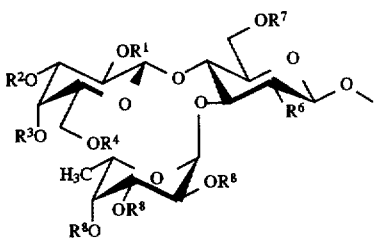

(III)

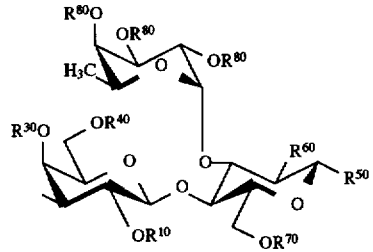

(IV)

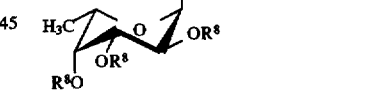

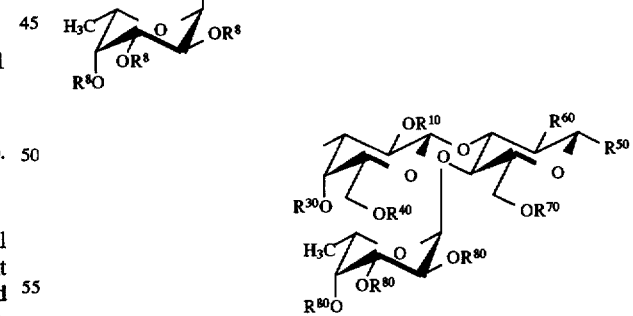

(V)

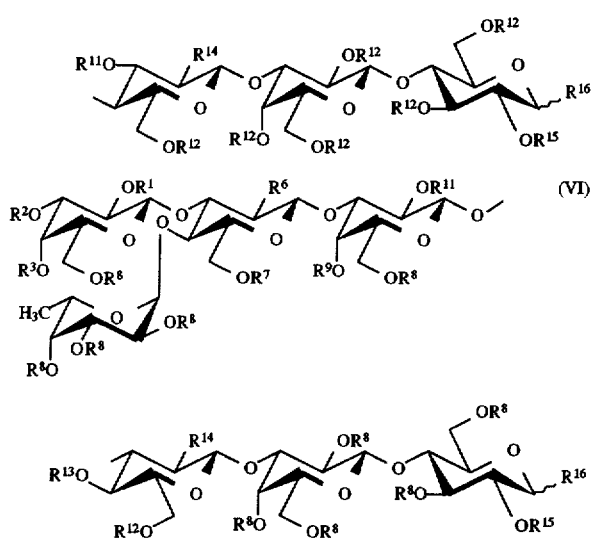

Wherein $R^1$ represents hydrogen atom, $SO_3M$, $CH_2COOM$ (M represents hydrogen atom, alkali metal (sodium, potassium, lithium, and so on) or lower alkyl group (methyl group, ethyl group, propyl group, and so on).), acetyl group, pivaloyl group or levulinoyl group;

$R^2$ represents hydrogen atom, $SO_3M$, $CH_2COOM$ (M represents hydrogen atom, alkali metal (sodium, potassium, lithium, and so on) or lower alkyl group (methyl group, ethyl group, propyl group, and so on).), acethyl group, levulinoyl group or sialic acid residue;

$R^3$ represents hydrogen atom, $SO_3M$, $CH_2COOM$ (M represents hydrogen atom, alkali metal (sodium, potassium, lithium, and so on) or lower alkyl group (methyl group, ethyl group, propyl group, and so on).), acetyl group or levulinoyl group;

$R^2$ and $R^3$ may corporate to form benzylidene group;

$R^4$ represents hydrogen atom, acetyl group, benzyl group or pivaloyl group;

$R^5$ represents O-lower alkyl group, O-lower alkenyl group, O-1-imino-2,2,2-trichloroethyl group, fluorine atom, O-aryl group (e.g., p-methoxyphenyl group), O-ceramide residue, O-mannose residue, O-galactose residue or O-lactose residue;

$R^6$ represents acetylamino group, phthaloylamino group, hydroxyl group or O-pivaloyl group;

$R^7$ represents hydrogen atom, acetyl group, benzyl group or pivaloyl group;

$R^8$ represents hydrogen atom, acetyl group or benzyl group;

$R^{10}$ represents hydrogen atom, acetyl group or benzyl group;

$R^{30}$ represents hydrogen atom, acetyl group or benzyl group;

$R^{40}$ represents hydrogen atom, acetyl group or benzyl group;

$R^{60}$ represents acetylamino group or phthaloylamino group;

$R^{70}$ represents hydrogen atom, acetyl group or benzyl group; and $R^{80}$ represents hydrogen atom, acetyl group or benzyl group.

$R^{11}$ represents hydrogen atom, acetyl group or benzyl group;

$R^{12}$ represents hydrogen atom, acetyl group or benzyl group;

$R^{13}$ represents hydrogen atom, acetyl group or benzyl group;

$R^{12}$ and $R^{13}$ may corporate to form benzylidene group;

$R^{14}$ represents acetylamino group or phthaloylamino group;

$R^{15}$ represents hydrogen atom or pivaloyl group;

$R^{16}$ represents hydoroxyl group, acetyloxy group, benzyloxy group or O-ceramide residue;

except the above compounds in which $R^1$, $R^3$, $R^4$, $R^7$ and $R^8$ are all hydrogen atom, $R^2$ is α-N-acetylneuraminic acid residue, and $R_5$ is galactose residue which does not have protecting group.

The invention offers to a Lewis-associated compound represented by general formula (VII), (VIII), (IX) or (X).

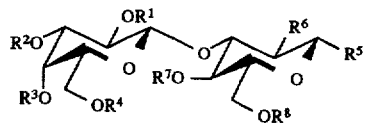

(VII)

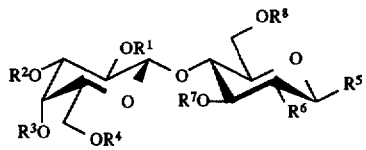

(VIII)

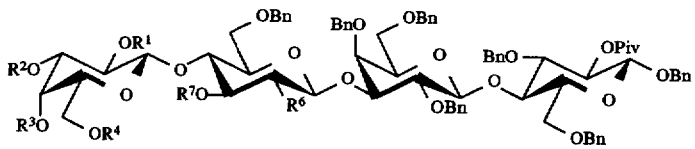

(IX)

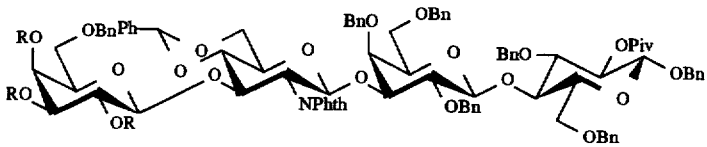

(X)

wherein $R^1$ represents hydrogen atom, acetyl group or benzyl group;

$R^2$ represents acetyl group or N-acetylneuraminic acid residue;

$R^3$ represents hydrogen atom, acetyl group or benzyl group;

$R^4$ represents benzyl group;

$R^5$ represents hydoroxyl group, acetyloxy group, alkylthio group, fluorine atom, O-mannose residue or O-galactose residue;

$R^6$ represents acetylamino group or phthaloylamino group;

$R^7$ represents hydrogen atom, acetyl group or benzyl group;

$R^8$ represents hydrogen atom, acetyl group or benzyl group;

$R^7$ and $R^8$ may corporate to form benzylidene group.

The invention offers to an anti-inflammatory agent in the described above a Lewis-associated compound represented by general formula (I), (II), (III), (IV), (V) or in the formula (VI) that $R^1$–$R^{80}$ is as follows or the pharmacologically acceptable salt thereof as an efficient component.

$R^1$ represents hydrogen atom, $SO_3H$ or $CH_2COOH$;

$R^2$ represents hydrogen atom, $SO_3H$, $CH_2COOH$ or N-acetylneuraminic acid residue;

$R^3$ represents hydrogen atom, SO3H or $CH_2COOH$;

$R^4$ represents hydrogen atom;

$R^5$ represents O-lower alkyl group, O-ceramide residue, O-mannose residue, O-galactose residue or O-lactose residue;

$R^6$ represents acetylamino group;

$R^7$ represents hydrogen atom;

$R^8$ represents hydrogen atom;

$R^{10}$ represents hydrogen atom;

$R^{30}$ represents hydrogen atom;

$R^{40}$ represents hydrogen atom;

$R^{60}$ represents acetylamino group;

$R^{70}$ represents hydrogen atom;

$R^{80}$ represents hydrogen atom;

$R^{11}$ represents hydrogen atom;

$R^{12}$ represents hydrogen atom;

$R^{13}$ represents hydrogen atom;

$R^{14}$ represents acetylamino group;

$R^{15}$ represents hydrogen atom; and $R^{16}$ represents hydroxyl group or O-ceramide residue;

include the above compounds in which $R^1$ and $R^3$ are each hydrogen atom, $R^2$ is α-N-acetylneuraminic acid residue, and $R^5$ is a galactose residue which does not have protecting groups. In the invention the salt such as sodium salt, potassium salt, lithium salt, ammonium salt, are pharmacologically acceptable. The following is the examples of compounds comprising an anti-inflammatory agency in the described above.

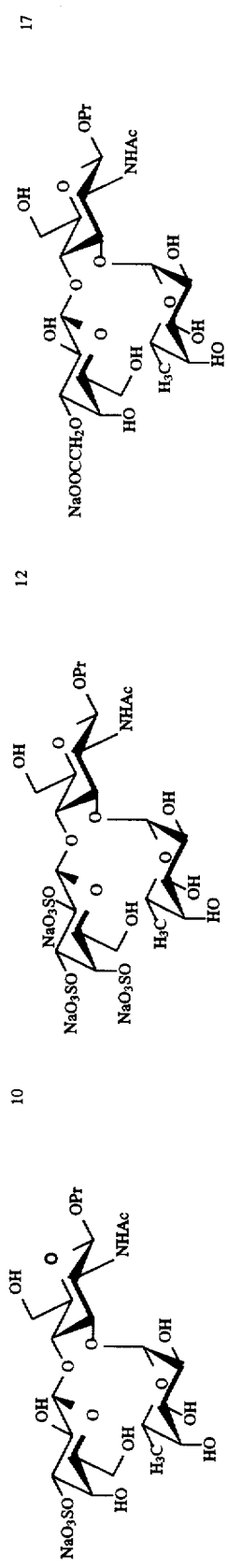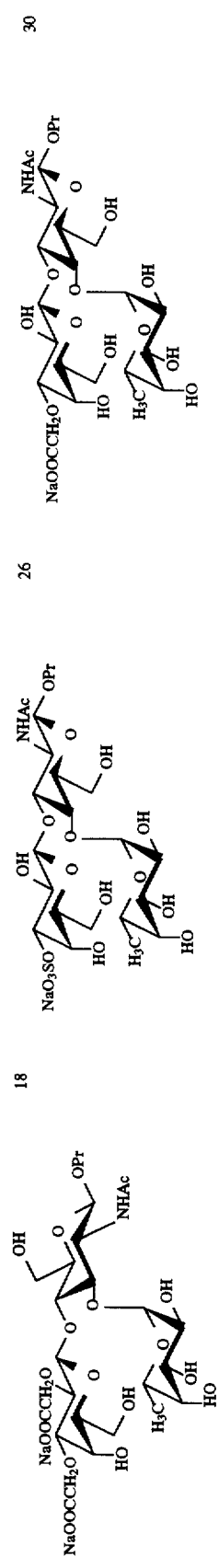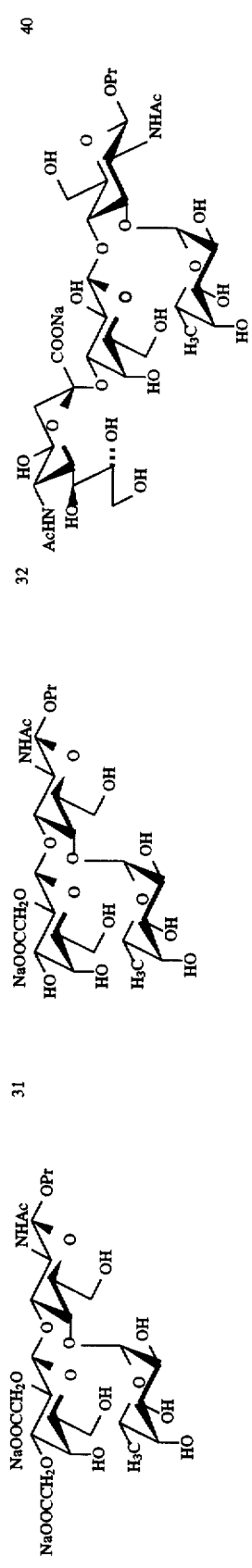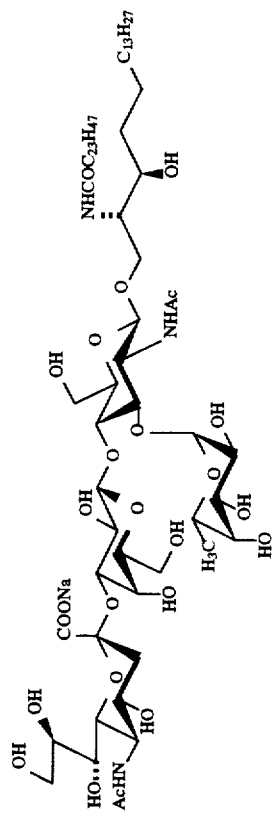

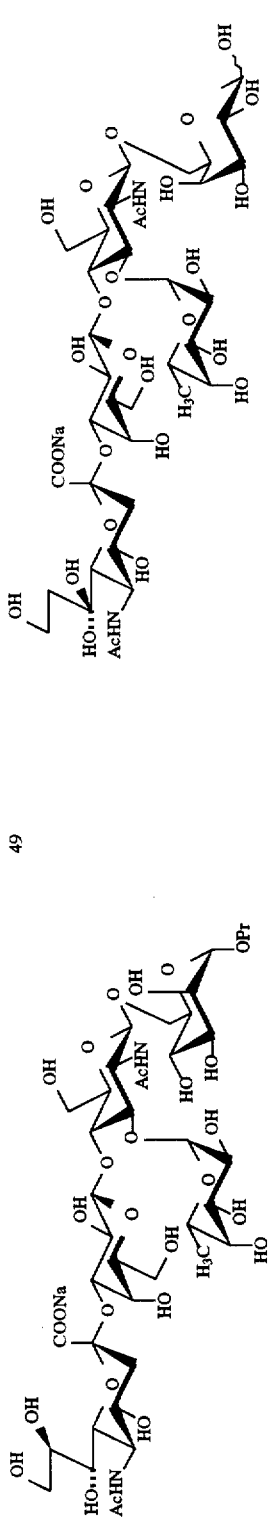
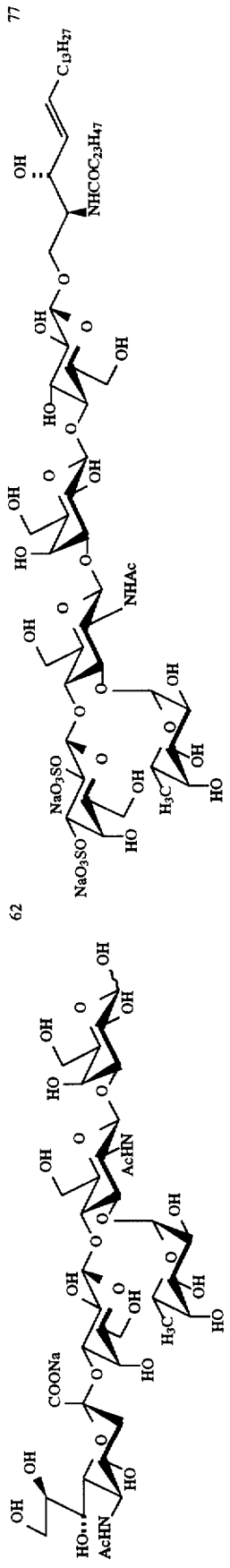
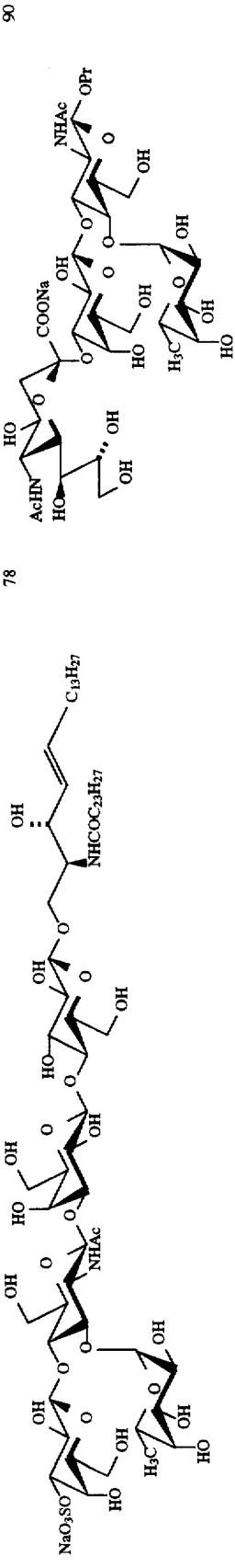

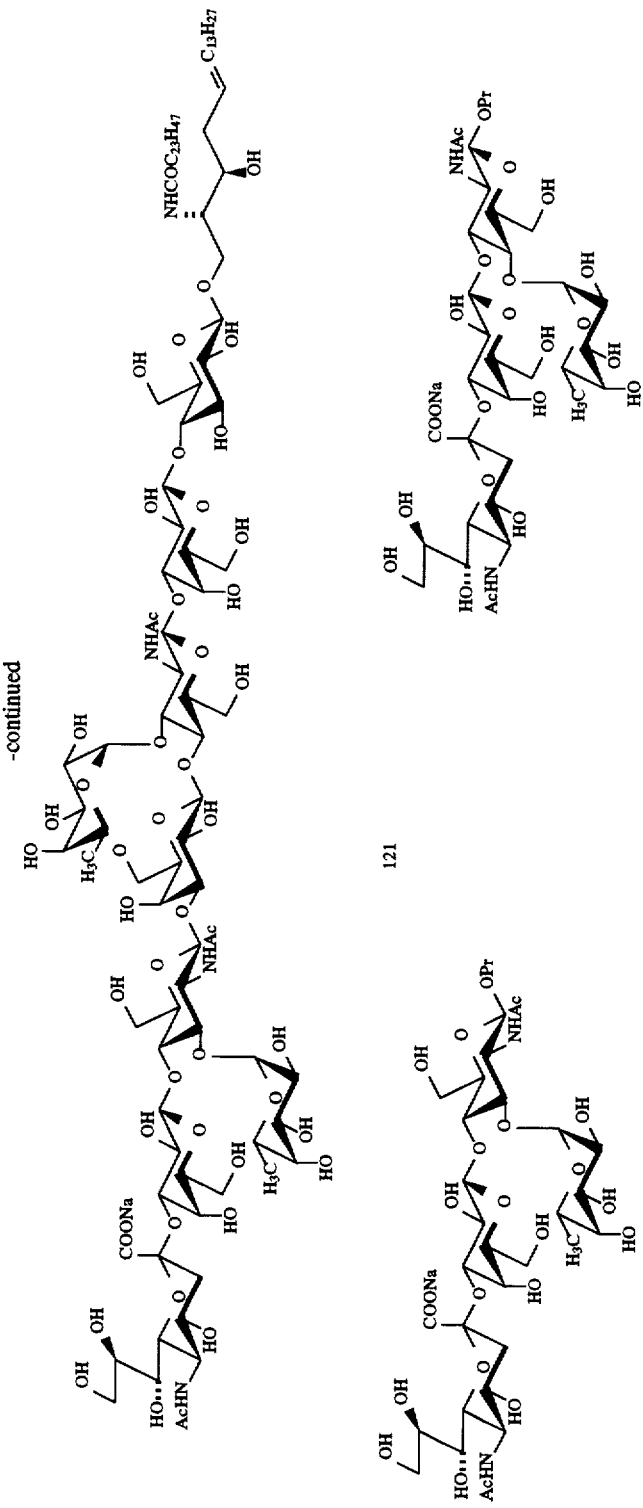

The table as follows shows the example of the compounds sented by general formula (I), (II), (III), (IV), (V) or of the invention.

TABLE 1

Compounds (Le$^x$) represented by general formula (I)

| Compound | R$^1$ | R$^2$ | R$^3$ | R$^4$ | R$^5$ | R$^6$ | R$^7$ | R$^8$ |
|---|---|---|---|---|---|---|---|---|
| 2 | Ac | Ac | Ac | Bn | OAll | NPhth | Bn | Bn |
| 3 | H | H | H | Bn | OAll | NPhth | Bn | Bn |
| 4 | Ac | Ac | Ac | Bn | OAll | NHAc | Bn | Bn |
| 5 | H | H | H | Bn | OAll | NHAc | Bn | Bn |
| 6 | H | H | H | Bn | OPr | NHAc | Bn | Bn |
| 7a | H | Lev | H | Bn | OPr | NHAc | Bn | Bn |
| 7b | Lev | H | H | Bn | OPr | NHAc | Bn | Bn |
| 7c | Lev | Lev | H | Bn | OPr | NHAc | Bn | Bn |
| 8 | Ac | Lev | Ac | Bn | OPr | NHAc | Bn | Bn |
| 9 | Ac | SO$_3$Na | Ac | Bn | OPr | NHAc | Bn | Bn |
| 10 | H | SO$_3$Na | H | H | OPr | NHAc | H | H |
| 11 | SO$_3$Na | SO$_3$Na | SO$_3$Na | Bn | OAll | NHAc | Bn | Bn |
| 12 | SO$_3$Na | SO$_3$Na | SO$_3$Na | H | OPr | NHAc | H | H |
| 13a | H | CH$_2$CO$_2$Me | H | Bn | OAll | NHAc | Bn | Bn |
| 13b | CH$_2$CO$_2$Me | H | H | Bn | OAll | NHAc | Bn | Bn |
| 14 | CH$_2$CO$_2$Me | CH$_2$CO$_2$Me | H | Bn | OAll | NHAc | Bn | Bn |
| 15 | Ac | CH$_2$CO$_2$Me | Ac | Bn | OAll | NHAc | Bn | Bn |
| 16 | CH$_2$CO$_2$Me | CH$_2$CO$_2$Me | Ac | Bn | OAll | NHAc | Bn | Bn |
| 17 | H | CH$_2$CO$_2$Na | H | H | OPr | NHAc | H | H |
| 18 | CH$_2$CO$_2$Na | CH$_2$CO$_2$Na | H | H | OPr | NHAc | H | H |

TABLE 2

Compounds (Le$^x$) represented by general formula (I)

| Compound | R$^1$ | R$^2$ | R$^3$ | R$^4$ | R$^5$ | R$^6$ | R$^7$ | R$^8$ |
|---|---|---|---|---|---|---|---|---|
| 33 | H | AcNeuAcβ(Me) | H | Bn | OAll | NPhth | Bn | Bn |
| 34 | H | AcNeuAcβ(Me) | H | Bn | OAll | NHAc | Bn | Bn |
| 35 | H | AcNeuAcα(Me) | H | Bn | OAll | NHAc | Bn | Bn |
| 36 | H | AcNeuAcα(Me) | H | Bn | OAll | NPhth | Bn | Bn |
| 37 | Ac | AcNeuAcα(Me) | Ac | Bn | OAll | NPhth | Bn | Bn |
| 38 | Ac | AcNeuAcβ(Me) | Ac | Bn | OAll | NHAc | Bn | Bn |
| 39 | H | NeuAcβ(Na) | H | Bn | OAll | NHAc | Bn | Bn |
| 40 | H | NeuAcβ(Na) | H | H | OPr | NHAc | H | H |
| 41 | Ac | AcNeuAcα(Me) | Ac | Bn | OH | NPhth | Bn | Bn |
| 42 | Ac | AcNeuAcα(Me) | Ac | Bn | OC(NH)CCl$_3$ | NPhth | Bn | Bn |
| 43 | Ac | AcNeuAcα(Me) | Ac | Bn | OBzCer(β) | NPhth | Bn | Bn |
| 44 | Ac | AcNeuAcα(Li) | Ac | Bn | OBzCer(β) | NPhth | Bn | Bn |
| 45 | H | NeuAcα(Na) | H | Bn | OCer(β) | NHAc | Bn | Bn |
| 46 | H | NeuAcα(Na) | H | H | OCer(H)(β) | NHAc | H | H |

TABLE 3

Compounds (Le$^x$) represented by general formula (I)

| Compound | R$^1$ | R$^2$ | R$^3$ | R$^4$ | R$^5$ | R$^6$ | R$^7$ | R$^8$ |
|---|---|---|---|---|---|---|---|---|
| 47a | Ac | AcNeuAcα(Me) | Ac | Bn | O(Bn)ManAll | NPhth | Bn | Bn |
| 47b | Ac | AcNeuAcα(Li) | Ac | Bn | O(Bn)ManAll | NPhth | Bn | Bn |
| 48 | H | NeuAcα(Na) | H | Bn | O(Bn)ManAll | NHAc | Bn | Bn |
| 49 | H | NeuAcα(Na) | H | H | OManPr | NHAc | H | H |
| 50 | Ac | AcNeuAcα(Me) | Ac | Bn | O(Bn)6Gal | NPhth | Bn | Bn |
| 51 | Ac | AcNeuAcα(Li) | Ac | Bn | O(Bn)6Gal | NPhth | Bn | Bn |
| 52 | H | NeuAcα(Na) | H | Bn | O(Bn)6Gal | NHAc | Bn | Bn |
| 53 | H | NeuAcα(Na) | H | H | O6Gal | NHAc | H | H(Known) |
| 54a | Ac | Ac | Ac | Bn | OPr | NPhth | Bn | Bn |
| 54b | Ac | Ac | Ac | Bn | OH | NPhth | Bn | Bn |
| 55 | Ac | Ac | Ac | Bn | F | NPhth | Bn | Bn |
| 56 | Ac | Ac | Ac | Bn | OC(NH)CCl$_3$ | NPhth | Bn | Bn |
| 57 | Ac | Ac | Ac | Bn | O(Bn)3Gal* | NPhth | Bn | Bn |
| 58 | H | H | H | Bn | O(Bn)3Gal* | NHAc | Bn | Bn |
| 59 | H | AcNeuAcα(Me) | H | Bn | O(Bn)3Gal* | NHAc | Bn | Bn |
| 60 | H | AcNeuAcα(Me) | H | Bn | O(Bn)3Gal | NHAc | Bn | Bn |
| 61 | H | NeuAcα(Na) | H | Bn | O(Bn)3Gal | NHAc | Bn | Bn |
| 62 | H | NeuAcα(Na) | H | H | O3Gal | NHAc | H | H(Known) |

(Gal* = 6-OTBDPS galactose residue)

TABLE 4

Compounds (Le*) represented by general formula (I)

| Compound | R¹ | R² | R³ | R⁴ | R⁵ | R⁶ | R⁷ | R⁸ |
|---|---|---|---|---|---|---|---|---|
| 63 | Ac | Ac | Ac | Bn | O(Bn)3Lac* OBn | NPhth | Bn | Bn |
| 64 | Ac | Ac | Ac | Bn | O(Bn)3Lac* OBn | NHAc | Bn | Bn |
| 65 | H | H | H | Bn | O(Bn)3Lac* DBn | NHAc | Bn | Bn |
| 66 | Lev | Lev | H | Bn | O(Bn)3Lac* OBn | NHAc | Bn | Bn |
| 67 | Lev | Lev | Ac | Bn | O(Bn)3Lac* OBn | NHAc | Bn | Bn |
| 68 | Lev | Lev | Ac | Ac | O(Ac)3Lac* OAc | NHAc | Ac | Ac |
| 69 | Lev | Lev | Ac | Ac | D(Ac)3Lac* OH | NHAc | Ac | Ac |
| 70 | Lev | Lev | Ac | Ac | O(Ac)3Lac* OC(NH)CCl₃ | NHAc | Ac | Ac |
| 71 | Lev | Lev | Ac | Ac | O(Ac)3Lac* OBzCer | NHAc | Ac | Ac |
| 72 | H | H | Ac | Ac | O(Ac)3Lac* OBzCer | NHAc | Ac | Ac |
| 73 | Lev | H | Ac | Ac | O(Ac)3Lac* OBzCer | NHAc | Ac | Ac |
| 74 | H | Lev | Ac | Ac | O(Ac)3Lac* OBzCer | NHAc | Ac | Ac |
| 75 | SO₃Na | SO₃Na | Ac | Ac | O(Ac)3Lac* OBzCer | NHAc | Ac | Ac |
| 76 | H | SO₃Na | Ac | Ac | O(Ac)3Lac* OBzCer | NHAc | Ac | Ac |
| 77 | SO₃Na | SO₃Na | H | H | O3LacCer | NHAc | H | H |
| 78 | H | SO₃Na | H | H | O3LacCer | NHAc | H | H |

(Lac* = 2-OPiv lactose residue)

TABLE 5

Compounds (Le*) represented by general formula (I)

| Compound | R¹ | R² | R³ | R⁴ | R⁵ | R⁶ | R⁷ | R⁸ |
|---|---|---|---|---|---|---|---|---|
| 120 | Ac | AcNeuAcα(Me) | Ac | Bn | OAll | NHAc | Bn | Bn |
| 121 | H | NeuAcα(Na) | H | H | OPr | NHAc | H | H(Known) |

TABLE 6

Compounds (Le*) represented by general formula (I)

| Compound | R¹ | R² | R³ | R⁴ | R⁵ | R⁶ | R⁷ | R⁸ |
|---|---|---|---|---|---|---|---|---|
| 133 | Piv | —C(CH₃)₂— | | Piv | OMP | OPiv | Piv | Bn |
| 134 | Piv | H | H | Piv | OMP | OPiv | Piv | Bn |
| 135 | Piv | Lev | H | Piv | OMP | OPiv | Piv | Bn |
| 136 | Piv | Lev | Ac | Piv | OMP | OPiv | Piv | Bn |
| 137 | Piv | Lev | Ac | Piv | OMP | OPiv | Piv | Ac |
| 138 | Piv | H | SO₃Na | Piv | CMP | OPiv | Piv | Bn |
| 139 | Piv | SO₃Na | SO₃Na | Piv | OMP | OPiv | Piv | Bn |
| 140 | Piv | H | Ac | Piv | CMP | OPiv | Piv | Bn |
| 141 | Piv | SO₃Na | Ac | Piv | OMP | OPiv | Piv | Bn |
| 142 | Piv | SO₃Na | H | H | OMP | OPiv | H | H |
| 143 | H | SO₃Na | H | H | OMP | OH | H | H |
| 144 | H | H | SO₃Na | H | OMP | OH | H | H |
| 145 | Piv | SO₃Na | SO₃Na | Piv | OMP | OPiv | Piv | H |

TABLE 7

Compounds (Le*) represented by general formula (II) (αFuc)

| Compound | R¹ | R² | R³ | R⁴ | R⁵ | R⁶ | R⁷ | R⁸ |
|---|---|---|---|---|---|---|---|---|
| 22α | Ac | Ac | Ac | Bn | OAll | NPhth | Bn | Bn |
| 23 | H | H | H | Bn | OAll | NPhth | Bn | Bn |
| 24 | H | H | H | Bn | OAll | NHAc | Bn | Bn |
| 25a | H | SO₃Na | H | Bn | OAll | NHAc | Bn | Bn |
| 25b | SO₃Na | H | H | Bn | OAll | NHAc | Bn | Bn |
| 25c | SO₃Na | SO₃Na | SO₃Na | Bn | OAll | NHAc | Bn | Bn |
| 26 | H | SO₃Na | H | H | OPr | NHAc | H | H |
| 27 | H | CH₂CO₂Na | H | Bn | OAll | NHAc | Bn | Bn |
| 28 | CH₂CO₂Na | CH₂CO₂Na | H | Bn | OAll | NHAc | Bn | Bn |
| 29 | CH₂CO₂Na | H | H | Bn | OAll | NHAc | Bn | Bn |
| 30 | H | CH₂CO₂Na | H | H | OPr | NHAc | H | H |
| 31 | CH₂CO₂Na | CH₂CO₂Na | H | H | OPr | NHAc | H | H |
| 32 | CH₂CO₂Na | H | H | H | OPr | NHAc | H | H |

TABLE 8

Compounds (Le$^x$) represented by general formula (II) (αFuc)

| Compound | R$^1$ | R$^2$ | R$^3$ | R$^4$ | R$^5$ | R$^6$ | R$^7$ | R$^8$ |
|---|---|---|---|---|---|---|---|---|
| 87α | H | AcNeuAcα(Me) | H | Bn | OAll | NPhth | Bn | Bn |
| 87β | H | AcNeuAcβ(Me) | H | Bn | OAll | NPhth | Bn | Bn |
| 88 | H | AcNeuAcβ(Li) | H | Bn | OAll | NHAc | Bn | Bn |
| 89 | H | AcNeuAcβ(Na) | H | Bn | OAll | NHAc | Bn | Bn |
| 90 | H | NeuAcβ(Na) | H | H | OPr | NHAc | H | H |
| 100 | Ac | AcNeuAcα(Me) | Ac | Bn | O(Bn)Man* All | NPhth | Bn | Bn |
| 101 | Ac | AcNeuAcα(Li) | Ac | Bn | O(Bn)ManAll | NPhth | Bn | Bn |
| 102 | H | NeuAcα(Na) | H | H | OManPr | NHAc | H | H |
| 105 | Ac | AcNeuAcα(Me) | Ac | Bn | O(Bn)Gal* All | NPhth | Bn | Bn |
| 106 | Ac | AcNeuAcα(Li) | Ac | Bn | O(Bn)Gal* All | NPhth | Bn | Bn |
| 107 | H | NeuAcα(Na) | H | H | OGal | NHAc | H | H |
| 122 | H | NeuAcα(Na) | H | Bn | OAll | NHAc | Bn | Bn |
| 123 | H | NeuAcα(Na) | H | H | OPr | NHAc | H | H(Known) |

TABLE 9

Compounds (Le$^x$) represented by general formula (II) (αFuc)

| Compound | R$^1$ | R$^2$ | R$^3$ | R$^4$ | R$^5$ | R$^6$ | R$^7$ | R$^8$ |
|---|---|---|---|---|---|---|---|---|
| 147 | Ac | AcNeuAcα(Me) | Ac | Bn | F | NPhth | Bn | Bn |
| 148 | Ac | Ac | Ac | Bn | OH | NPhth | Bn | Bn |
| 149 | Ac | Ac | Ac | Bn | F | NPhth | Bn | Bn |
| 150 | H | H | H | Bn | F | NPhth | Bn | Bn |
| 151 | H | AcNeuAcα(Me) | H | Bn | F | NPhth | Bn | Bn |
| 152 | Ac | AcNeuAcα(Me) | Ac | Bn | F | NPhth | Bn | Bn |
| 153 | Ac | AcNeuAcα(Me) | Ac | Bn | O(Bn)3Lac* OBn | NPhth | Bn | Bn |
| 154 | Ac | AcNeuAcα(Me) | Ac | Ac | O(Ac)3Lac* OAc | NPhth | Ac | Ac |
| 155 | Ac | AcNeuAcα(Me) | Ac | Ac | O(Ac)3Lac* OH | NPhth | Ac | Ac |
| 156 | Ac | AcNeuAcα(Me) | Ac | Ac | O(Ac)3Lac* OC(NH)CCl$_3$ | NPhth | Ac | Ac |
| 157 | Ac | AcNeuAcα(Me) | Ac | Ac | O(Ac)3Lac* OR* | NPhth | Ac | Ac |
| 158 | Ac | AcNeuAcα(Me) | Ac | Ac | O(Ac)3Lac* OR** | NPhth | Ac | Ac |
| 159 | Ac | AcNeuAcα(Li) | Ac | Ac | O(Ac)3Lac* OR** | NPhth | Ac | Ac |
| 160 | Ac | NeuAcα(Na) | H | H | O-3LacOCer | NHAc | H | H |
| 161 | Ac | AcNeuAcα(Me) | Ac | Bn | OAll | NPhth | Bn | Bn |
| 162 | Ac | AcNeuAcα(Me) | Ac | Bn | OH | NPhth | Bn | Bn |
| 163 | Ac | AcNeuAcα(Me) | Ac | Bn | OC(NH)CCl$_3$ | NPhth | Bn | Bn |
| 164 | Ac | AcNeuAcα(Me) | Ac | Bn | SCH$_3$ | NPhth | Bn | Bn |
| 165 | Ac | Ac | Ac | Bn | O(Bn)3Lac* OBn | NPhth | Bn | Bn |
| 166 | H | H | H | Bn | O(Bn)3Lac* OBn | NHAc | Bn | Bn |
| 198 | H | Lev | H | Bn | O(Bn)3Lac* OBn | NHAc | Bn | Bn |
| 199 | Lev | Lev | H | Bn | O(Bn)3Lac* OBn | NHAc | Bn | Bn |
| 200 | Ac | Lev | Ac | Bn | O(Bn)3Lac* OBn | NHAc | Bn | Bn |
| 201 | Ac | Lev | Ac | Ac | O(Ac)3Lac* OAc | NHAc | Ac | Ac |
| 202 | Ac | Lev | Ac | Ac | O(Ac)3Lac* OH | NHAc | Ac | Ac |
| 203 | Ac | Lev | Ac | Ac | O(Ac)3Lac* OC(NH)CCl$_3$ | NHAc | Ac | Ac |
| 204 | Ac | Lev | Ac | Ac | O(Ac)3Lac* OR*** | NHAc | Ac | Ac |
| 205 | Ac | H | Ac | Ac | O(Ac)3Lac* OR*** | NHAc | Ac | Ac |
| 206 | Ac | SO$_3$Na | Ac | Ac | O(Ac)3Lac* OR*** | NHAc | Ac | Ac |
| 207 | H | SO$_3$Na | H | H | O-3LacOR**** | NHAc | H | H |

(Gal* = 6-OLev galactose residue)
(Man* = 2-OAc mannose residue)
(R* = CH$_2$(N$_3$)CH(OSitBuPh$_2$)CH=CHC$_{13}$H$_{27}$)
(R** = CH$_2$(NHCOC$_{23}$H$_{47}$)CH(OSitBuPh$_2$)CH=CHC$_{13}$H$_{27}$)
(R*** = CH$_2$(NHCOC$_{23}$H$_{47}$)CH(OBz)CH=CHC$_{13}$H$_{27}$)
(R**** = CH$_2$(NHCOC$_{23}$H$_{47}$)CH(OH)CH=CHC$_{13}$H$_{27}$)

TABLE 10

Compounds (Le$^x$) represented by general formula (II) (αFuc)

| Compound | R$^1$ | R$^2$ | R$^3$ | R$^4$ | R$^5$ | R$^6$ | R$^7$ | R$^8$ |
|---|---|---|---|---|---|---|---|---|
| 175 | SO$_3$Na | H | H | H | OPr | NHAc | H | H |
| 176 | SO$_3$Na | SO$_3$Na | SO$_3$Na | H | OPr | NHAc | H | H |
| 177 | Ac | Ac | Ac | Bn | OC$_8$H$_{17}$ | NPhth | Bn | Bn |
| 178 | H | H | H | Bn | OC$_8$H$_{17}$ | NHAc | Bn | Bn |
| 179 | H | H | H | H | OC$_8$H$_{17}$ | NHAc | H | H |

TABLE 11

Compounds (Le$^x$) represented by general formula (II) (βFuc)

| Compound | R$^1$ | R$^2$ | R$^3$ | R$^4$ | R$^5$ | R$^6$ | R$^7$ | R$^8$ |
|---|---|---|---|---|---|---|---|---|
| 22β | Ac | Ac | Ac | Bn | OAll | NPhth | Bn | Bn |
| 180 | Ac | Ac | Ac | Bn | OAll | NHAc | Bn | Bn |
| 181 | H | H | H | Bn | OAll | NHAc | Bn | Bn |
| 182 | H | H | H | H | OPr | NHAc | H | H |
| 183 | SO$_3$Na | H | H | Bn | OAll | NHAc | Bn | Bn |
| 184 | H | SO$_3$Na | H | Bn | OAll | NHAc | Bn | Bn |
| 185 | H | H | SO$_3$Na | Bn | OAll | NHAc | Bn | Bn |
| 186 | SO$_3$Na | H | SO$_3$Na | Bn | OAll | NHAc | Bn | Bn |
| 187 | H | SO$_3$Na | SO$_3$Na | Bn | OAll | NHAc | Bn | Bn |
| 188 | SO$_3$Na | H | H | H | OPr | NHAc | H | H |
| 189 | H | SO$_3$Na | H | H | OPr | NHAc | H | H |
| 190 | H | H | SO$_3$Na | H | OPr | NHAc | H | H |
| 191 | SO$_3$Na | H | SO$_3$Na | H | OPr | NHAc | H | H |
| 192 | H | SO$_3$Na | SO$_3$Na | H | OPr | NHAc | H | H |
| 193 | Ac | Ac | Ac | Bn | OH | NPhth | Bn | Bn |
| 194 | Ac | Ac | Ac | Bn | OC(NH)CCl$_3$ | NPhth | Bn | Bn |
| 195 | Ac | Ac | Ac | Bn | OC$_8$H$_{17}$ | NPhth | Bn | Bn |
| 196 | H | H | H | Bn | OC$_8$H$_{17}$ | NHAc | Bn | Bn |
| 197 | H | H | H | H | OC$_8$H$_{17}$ | NHAc | H | H |

TABLE 12

Compounds (Le$^x$—Le$^x$) represented by general formula (III)

| Compound | R$^1$ R$^{10}$ | R$^2$ | R$^3$ R$^{30}$ | R$^4$ R$^{40}$ | R$^{50}$ | R$^6$ R$^{60}$ | R$^7$ R$^{70}$ | R$^8$ R$^{80}$ |
|---|---|---|---|---|---|---|---|---|
| 79 | Ac | AcNeuAcα(Me) | Ac | Bn | O(Bn)3Lac* OBn | NPhth | Bn | Bn |
|  | H |  | H | Bn |  | NHAc | Bn | Bn |
| 80 | Ac | AcNeuAcα(Me) | Ac | Bn | O(Bn)3Lac* OBn | NPhth | Bn | Bn |
|  | Ac |  | Ac | Bn |  | NHAc | Bn | Bn |
| 80a | Ac | AcNeuAcα(Me) | Ac | H | O3Lac* OH | NPhth | H | H |
|  | Ac |  | Ac | H |  | NHAc | H | H |
| 81 | Ac | AcNeuAcα(Me) | Ac | Ac | O(Ac)3Lac* OAc | NPhth | Ac | Ac |
|  | Ac |  | Ac | Ac |  | NHAc | Ac | Ac |
| 82 | Ac | AcNeuAcα(Me) | Ac | Ac | O(Ac)3Lac* OH | NPhth | Ac | Ac |
|  | Ac |  | Ac | Ac |  | NHAc | Ac | Ac |
| 83 | Ac | AcNeuAcα(Me) | Ac | Ac | O(Ac)3Lac* OC(NH)CCl$_3$ | NPhth | Ac | Ac |
|  | Ac |  | Ac | Ac |  | NHAc | Ac | Ac |
| 84 | Ac | AcNeuAcα(Me) | Ac | Ac | O(Ac)3Lac* OBzCer | NPhth | Ac | Ac |
|  | Ac |  | Ac | Ac |  | NHAc | Ac | Ac |
| 85 | Ac | AcNeuAcα(Li) | Ac | Ac | O(Ac)3Lac* OBzCer | NPhth | Ac | Ac |
|  | Ac |  | Ac | Ac |  | NHAc | Ac | Ac |
| 86 (Known) | H | NeuAcα(Na) | H | H | O3LacCer | NHAc | H | H |
|  | H |  | H | H |  | NHAc | H | H |

(Lac* = 2-OPiv lactose residue)

TABLE 13

Compounds (Le$^x$—Le$^x$) represented by general formula (IV)

| Compound | R$^1$ R$^{10}$ | R$^2$ | R$^3$ R$^{30}$ | R$^4$ R$^{40}$ | R$^{50}$ | R$^6$ R$^{60}$ | R$^7$ R$^{70}$ | R$^8$ R$^{80}$ |
|---|---|---|---|---|---|---|---|---|
| 167 | Ac | AcNeuAcα(Me) | Ac | Bn | O(Bn)3Lac* OBn | NPhth | Bn | Bn |
|  | H |  | H | Bn |  | NHAc | Bn | Bn |
| 168 | Ac | AcNeuAcα(Me) | Ac | Ac | O(Bn)3Lac* OAc | NPhth | Ac | Ac |
|  | Ac |  | Ac | Ac |  | NHAc | Ac | Ac |
| 169 | Ac | AcNeuAcα(Me) | Ac | Ac | O(Ac)3Lac* OH | NPhth | Ac | Ac |
|  | Ac |  | Ac | Ac |  | NHAc | Ac | Ac |
| 170 | Ac | AcNeuAcα(Me) | Ac | Ac | O(Ac)3Lac* OC(NH)CCl$_3$ | NPhth | Ac | Ac |
|  | Ac |  | Ac | Ac |  | NHAc | Ac | Ac |
| 171 | Ac | AcNeuAcα(Me) | Ac | Ac | O(Ac)3Lac* OR* | NPhth | Ac | Ac |
|  | Ac |  | Ac | Ac |  | NHAc | Ac | Ac |
| 172 | Ac | AcNeuAcα(Me) | Ac | Ac | O(Ac)3Lac* OR** | NPhth | Ac | Ac |
|  | Ac |  | Ac | Ac |  | NHAc | Ac | Ac |
| 173 | Ac | AcNeuAcα(Li) | Ac | Ac | O(Ac)3Lac* OR** | NPhth | Ac | Ac |

TABLE 13-continued

Compounds (Le<sup>a</sup>—Le<sup>a</sup>) represented by general formula (IV)

| Compound | $R^1$ $R^{10}$ | $R^2$ | $R^3$ $R^{30}$ | $R^4$ $R^{40}$ | $R^{50}$ | $R^6$ $R^{60}$ | $R^7$ $R^{70}$ | $R^8$ $R^{80}$ |
|---|---|---|---|---|---|---|---|---|
| 174 | Ac Ac Ac | AcNeuAcα(Na) | Ac H H | Ac H H | O3Lac* Cer | NHAc NHAc NHAc | Ac H H | Ac H H |

(Lac* = 2-OPiv lactose residue)
(R* = CH$_2$(N$_3$)CH(OSitBuPh$_2$)CH=CHC$_{13}$H$_{27}$)
(R** = CH$_2$(NHCOC$_{23}$H$_{47}$)CH(OSitBuPh$_2$)CH=CHC$_{13}$H$_{27}$)

TABLE 14

Compounds (Le$^x$ + tetrasaccharide) represented by general formula (V)

| Compound | $R^1$ | $R^2$ | $R^3$ | $R^4$ | $R^6$ | $R^7$ | $R^8$ | $R^{11}$ | $R^{12}$ | $R^{14}$ | $R^{15}$ | $R^{16}$ |
|---|---|---|---|---|---|---|---|---|---|---|---|---|
| 213 | Ac | AcNeuAcα(Me) | Ac | Bn | NPhth | Bn | Bn | H | Bn | NHAc | Piv | OBn |
| 214 | Ac | AcNeuAcα(Me) | Ac | Bn | NPhth | Bn | Bn | Ac | Bn | NHAc | Piv | OBn |
| 215 | Ac | AcNeuAcα(Me) | Ac | H | NPhth | H | H | Ac | H | NHAc | Piv | OH |
| 216 | Ac | AcNeuAcα(Me) | Ac | Ac | NPhth | Ac | Ac | Ac | Ac | NHAc | Piv | OAc |
| 217 | Ac | AcNeuAcα(Me) | Ac | Ac | NPhth | Ac | Ac | Ac | Ac | NHAc | Piv | OH |
| 218 | Ac | AcNeuAcα(Me) | Ac | Ac | NPhth | Ac | Ac | Ac | Ac | NHAc | Piv | OC(NH)CCl$_3$ |
| 219 | Ac | AcNeuAcα(Me) | Ac | Ac | NPhth | Ac | Ac | Ac | Ac | NHAc | Piv | OBzCer |
| 220 | Ac | AcNeuAcα(Li) | Ac | Ac | NPhth | Ac | Ac | Ac | Ac | NHAc | Piv | OBzCer |
| 221 | H | NeuAcα(Na) | H | H | NHAc | H | H | H | H | NHAc | H | OCer |

TABLE 15

Compounds (Le$^a$+ tetrasaccharide) represented by general formula (VI)

| Compound | $R^1$ | $R^2$ | $R^3$ | $R^4$ | $R^6$ | $R^7$ | $R^8$ | $R^9$ | $R^{11}$ | $R^{12}$ | $R^{13}$ | $R^{14}$ | $R^{15}$ | $R^{16}$ |
|---|---|---|---|---|---|---|---|---|---|---|---|---|---|---|
| 224 | Ac | AcNeuAcα(Me) | Ac | Bn | NPhth | Bn | Bn | H | H | CHPh | | NPhth | Piv | OBn |
| 225 | Ac | AcNeuAcα(Me) | Ac | Bn | NPhth | Bn | Bn | Ac | H | CHPh | | NPhth | Piv | OBn |
| 226 | Ac | AcNeuAcα(Me) | Ac | Ac | NPhth | Ac | Ac | Ac | Ac | Ac | Ac | NPhth | Piv | OAc |
| 227 | Ac | AcNeuAcα(Me) | Ac | Ac | NPhth | Ac | Ac | Ac | Ac | Ac | Ac | NPhth | Piv | OH |
| 228 | Ac | AcNeuAcα(Me) | Ac | Ac | NPhth | Ac | Ac | Ac | Ac | Ac | Ac | NPhth | Piv | OC(NH)CCl$_3$ |
| 229 | Ac | AcNeuAcα(Me) | Ac | Ac | NPhth | Ac | Ac | Ac | Ac | Ac | Ac | NPhth | Piv | OBzCer |
| 230 | H | NeuAcα(Na) | H | H | NHAc | H | H | H | H | H | H | NHAc | H | OCer |

The following is the example of intermediate compounds represented by general formula (VII), (VIII), (IX) or (X).

TABLE 16

Compounds represented by general formula (VII)

| Compound | $R^1$ | $R^2$ | $R^3$ | $R^4$ | $R^5$ | $R^6$ | $R^7$ | $R^8$ |
|---|---|---|---|---|---|---|---|---|
| 94 | H | AcNeuAcα(Me) | H | Bn | F | NPhth | CHPh | |
| 95 | H | AcNeuAcα(Me) | H | Bn | F | NPhth | CHPh | |
| 96 | Ac | AcNeuAcα(Me) | Ac | Bn | F | NPhth | CHPh | |
| 97 | Ac | AcNeuAcα(Me) | Ac | Bn | O(Bn)Man* All | NPhth | CHPh | |
| 98 | Ac | AcNeuAcα(Me) | Ac | Bn | O(BnAc)ManAll | NPhth | CHPh | |
| 99 | Ac | AcNeuAcα(Me) | Ac | Bn | O(BnAc)ManAll | NPhth | H | Bn |
| 103 | Ac | AcNeuAcα(Me) | Ac | Bn | O(Bn)Gal* All | NPhth | CHPh | |
| 104 | Ac | AcNeuAcα(Me) | Ac | Bn | O(Bn)Gal* All | NPhth | H | Bn |
| 146 | Ac | AcNeuAcα(Me) | Ac | Bn | F | NPhth | H | Bn |

[Compound 17]
Compounds represented by general formula (VIII)

| Compound | $R^1$ | $R^2$ | $R^3$ | $R^4$ | $R^5$ | $R^6$ | $R^7$ | $R^8$ |
|---|---|---|---|---|---|---|---|---|
| 208 | Ac | Ac | Ac | Bn | OH | NPhth | H | Bn |
| 209 | Ac | Ac | Ac | Bn | OAc | NPhth | Ac | Bn |
| 210 | Ac | Ac | Ac | Bn | $SCH_3$ | NPhth | Ac | Bn |

Table 18

Compounds represented by general formula (IX)

| Compound | $R^1$ | $R^2$ | $R^3$ | $R^4$ | $R^6$ | $R^7$ |
|---|---|---|---|---|---|---|
| 211 | Ac | Ac | Ac | Bn | NPhth | Ac |
| 212 | H | H | H | Bn | NHAC | H |

Table 19

Compounds represented by general formula (X)

| Compound | R |
|---|---|
| 222 | Ac |
| 223 | H |

The formulas of the starting materials used herein and of the compounds of this invention are described below. Wherein, the compounds having R and compound 53, 62, 86, 121 and 123 are known.

Abbreviation described below may be used in this specification.

| | |
|---|---|
| All | allyl group |
| Ac | acetyl group |
| Bn | benzyl group |
| Bz | benzoyl group |
| Cer | ceramide group ($OCH_2CH$ ($NHCOC_{23}H_{47}$)$CH(OH)CH=CHC_{13}H_{27}$) |
| Cer(H) | dihydroceramide group ($OCH_2CH(NHCOC_{23}H_{47})CH(OH)C_{15}H_{31}$) |
| CHPh | benzylidene group |
| Et | ethyl group |
| Fuc | fucose residue |
| Gal | galactose residue |
| Lac | lactose residue |
| Lev | levulinoyl group |
| Man | mannose residue |
| Me | methyl group |
| MP | p-methoxyphenyl group |
| NeuAc | N-acetylneuraminic acid residue |
| Piv | pivaloyl group |
| Pr | propyl group |
| phth | phthaloyl group |
| MS | molecular sieves |
| TBDPS | t-butyldiphenylsilyl group |

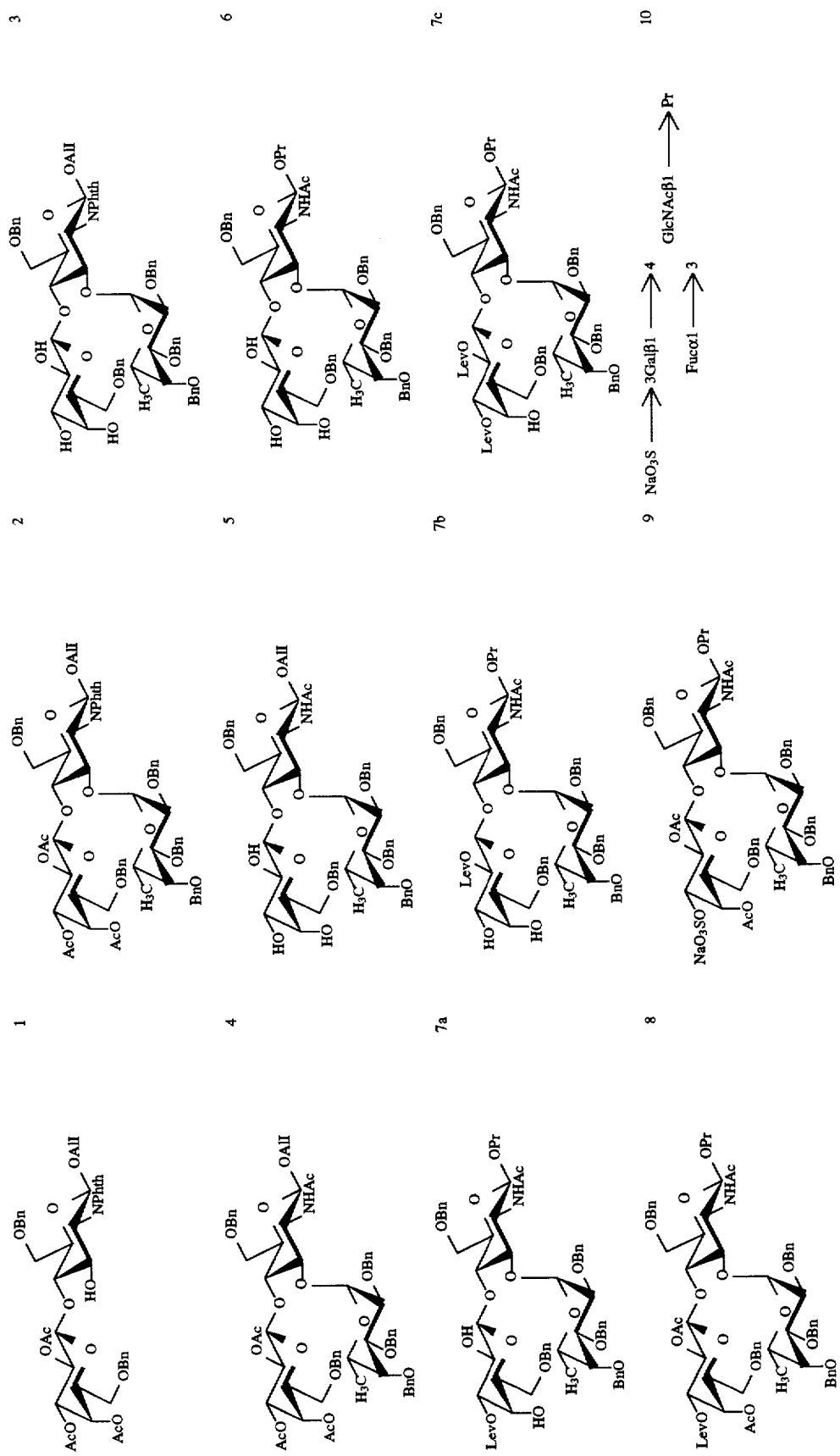

-continued

-continued

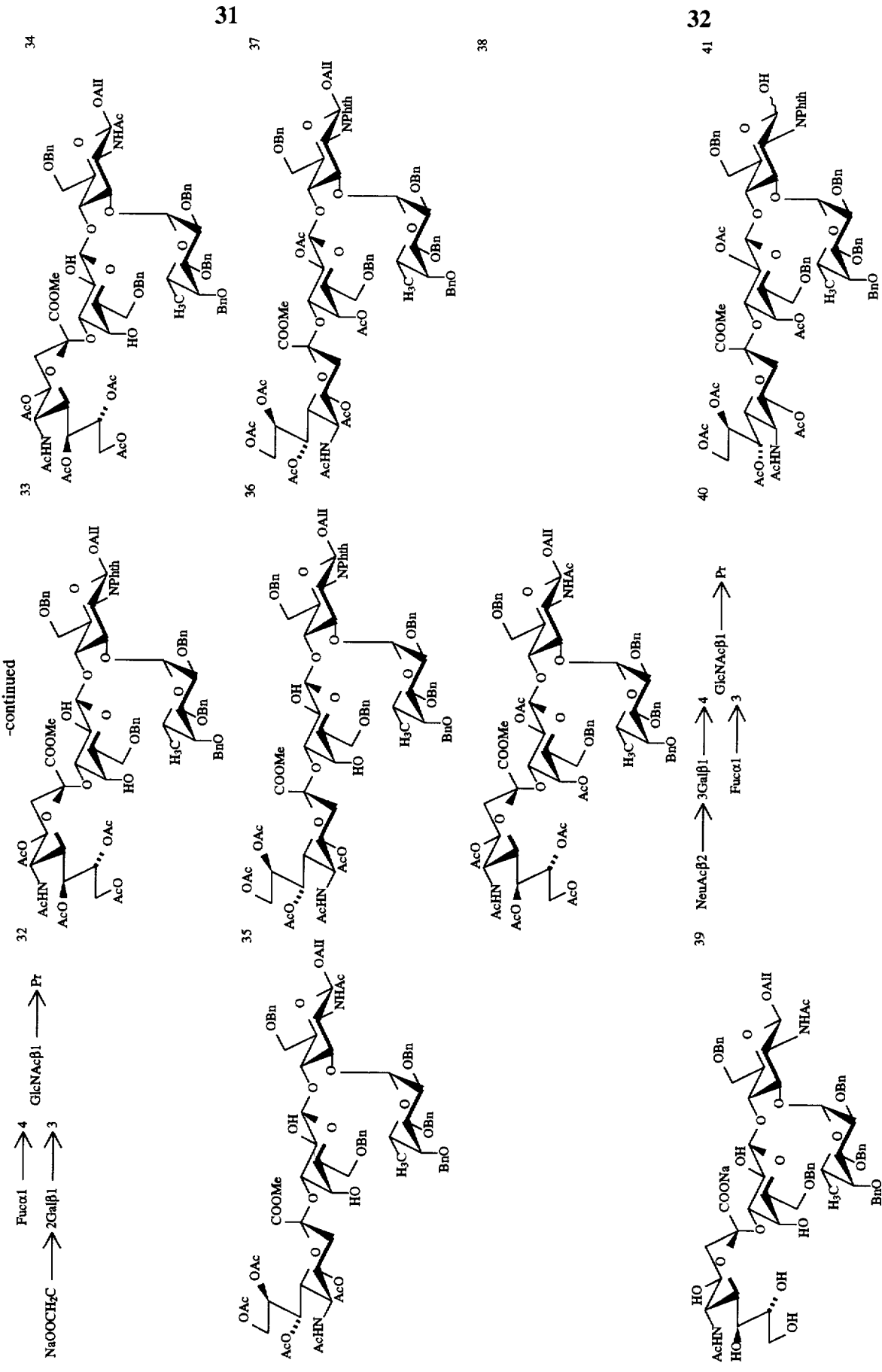

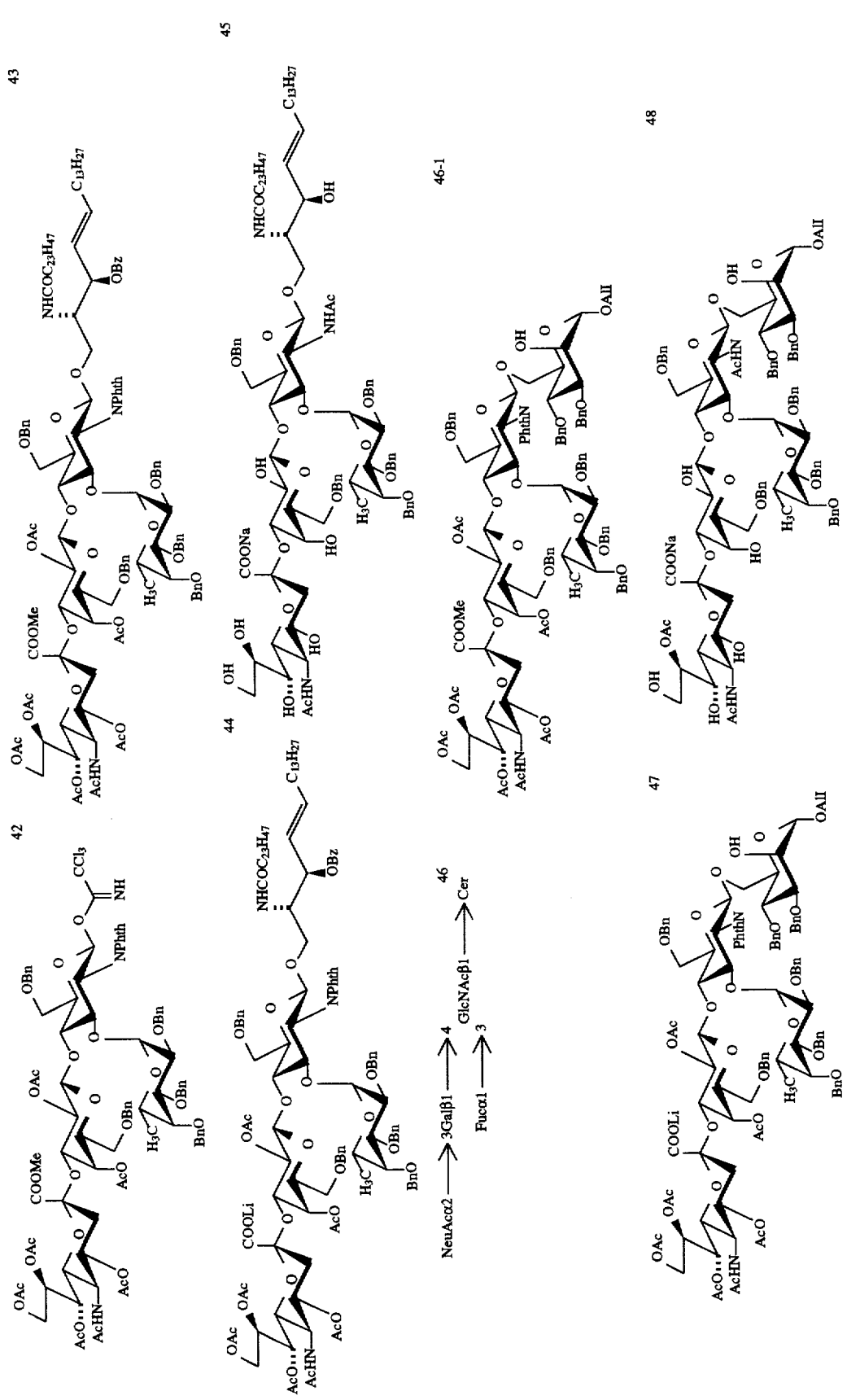

-continued
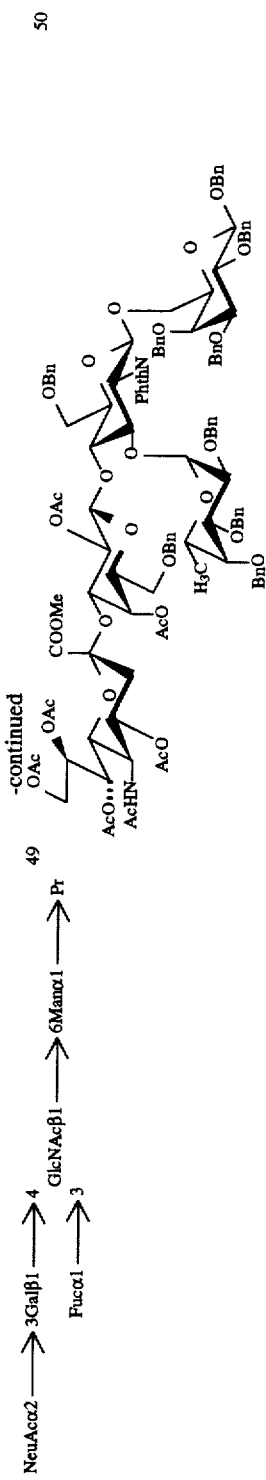
NeuAcα2⟶3Galβ1⟶4GlcNAcβ1⟶6Manα1⟶Pr
            Fucα1⟶3
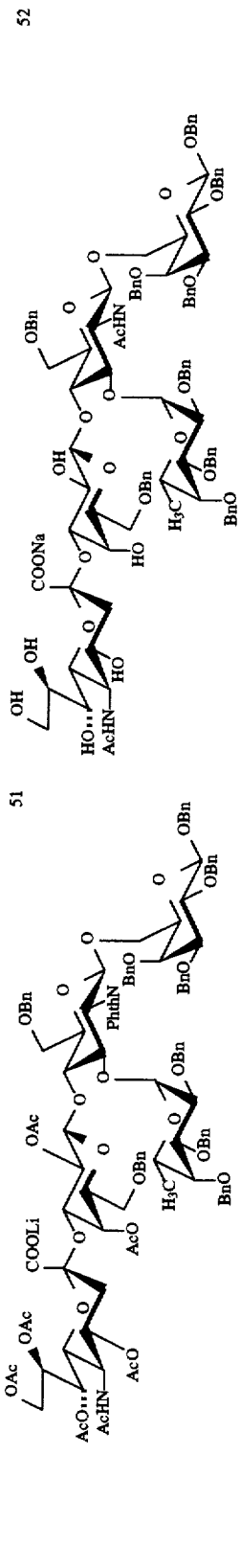
NeuAcα2⟶3Galβ1⟶4GlcNAcβ1⟶6Gal
            Fucα1⟶3
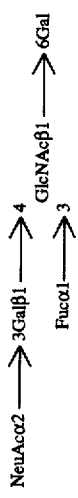
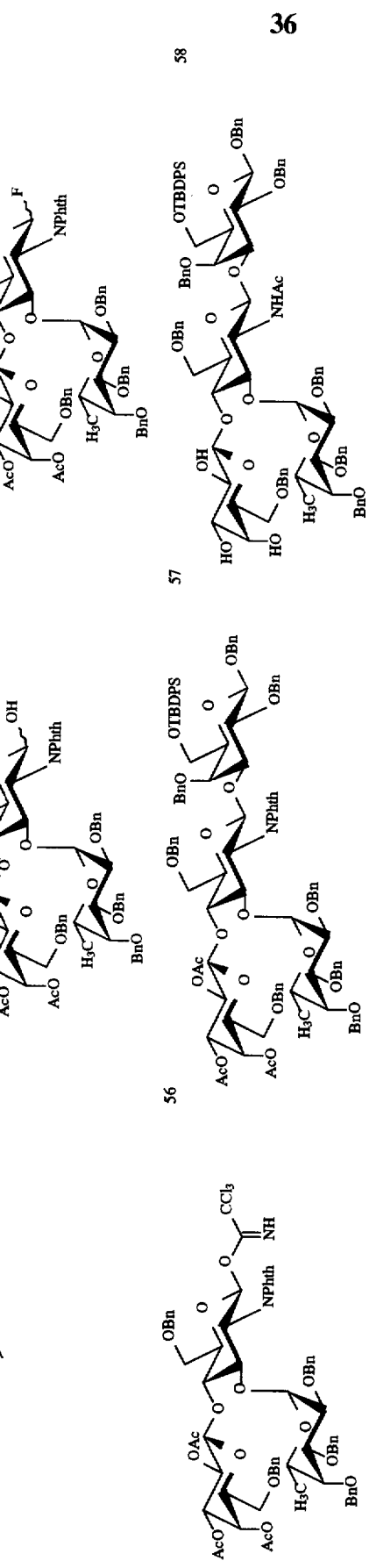

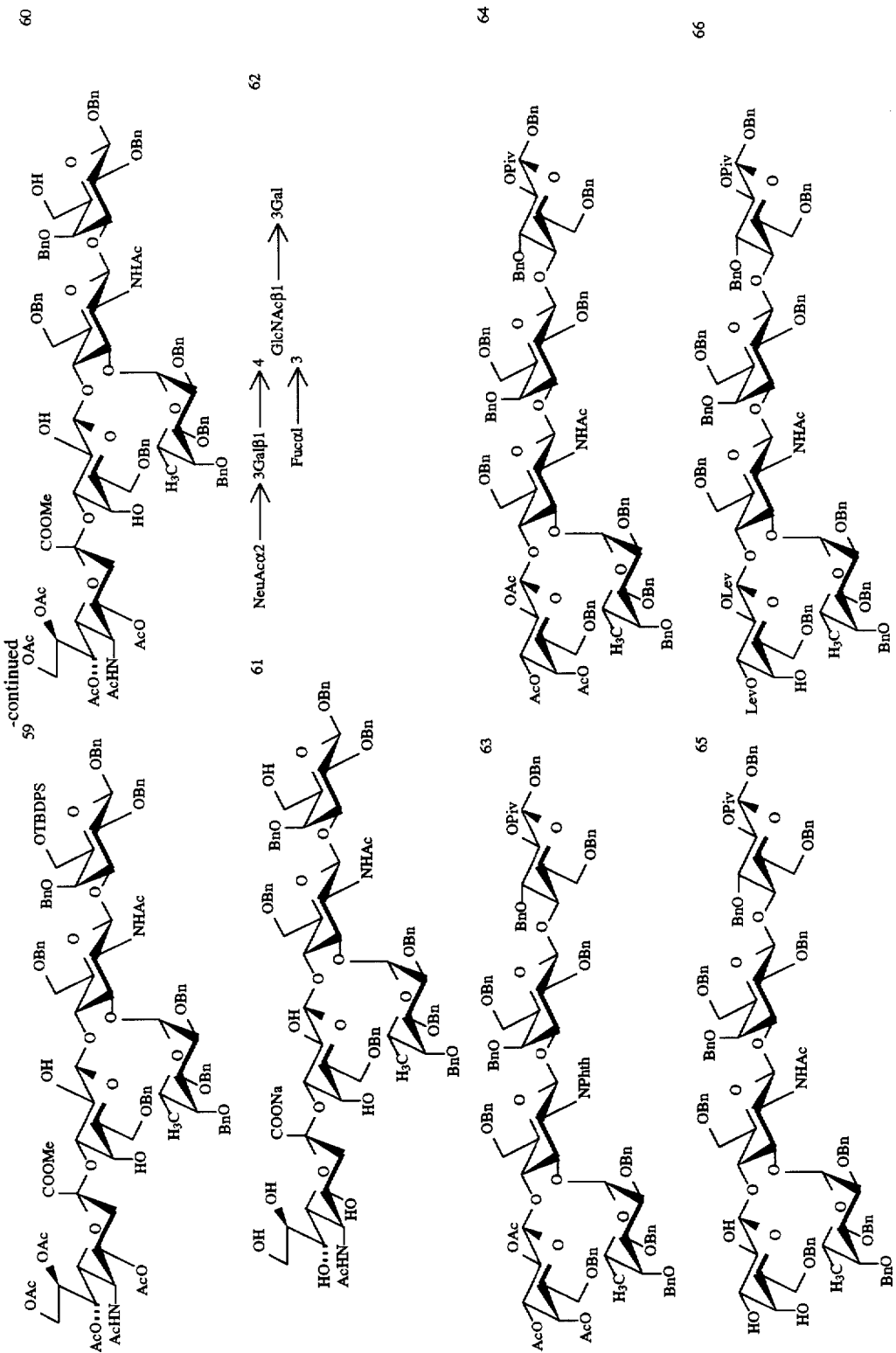

-continued

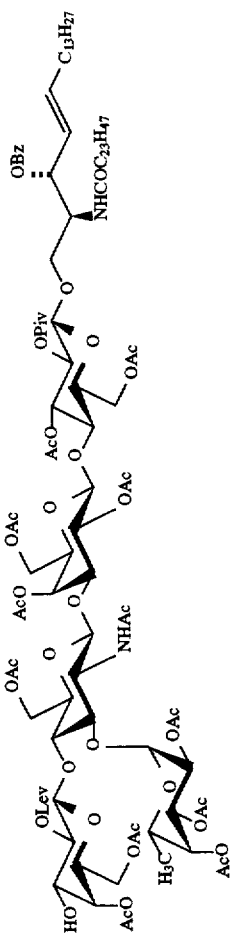
73
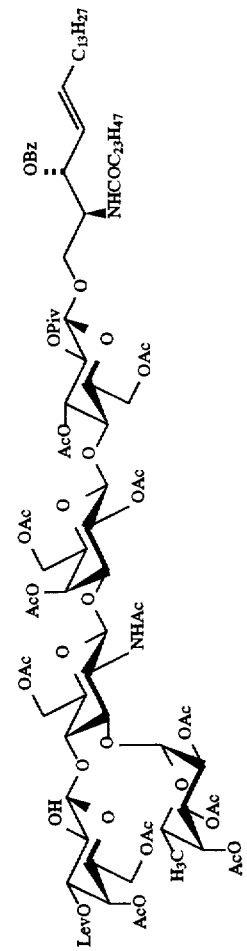
74
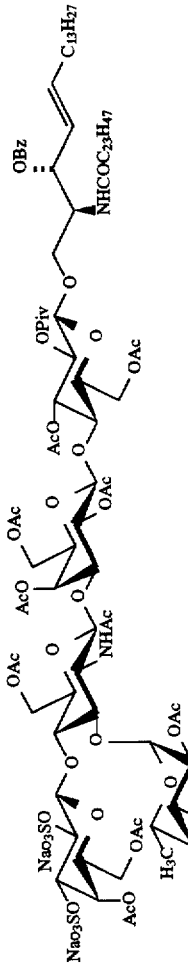
75
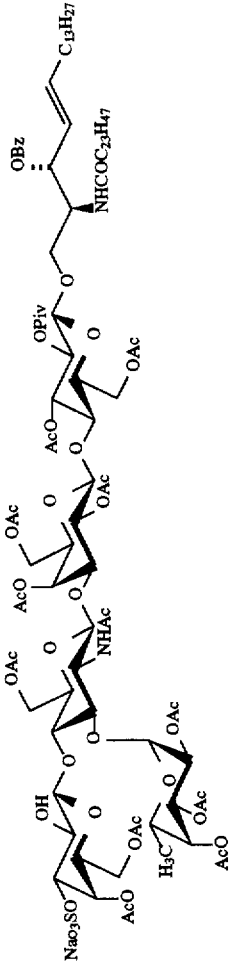
76
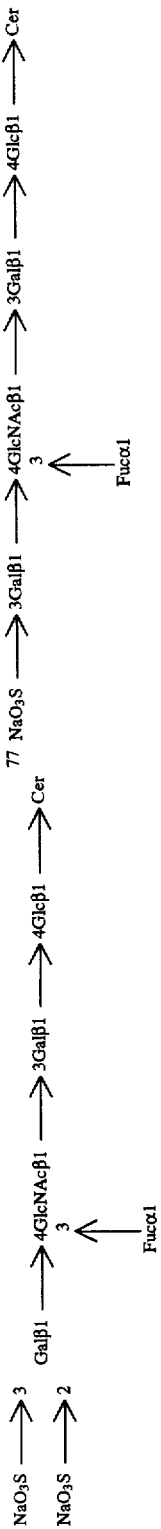
77
78

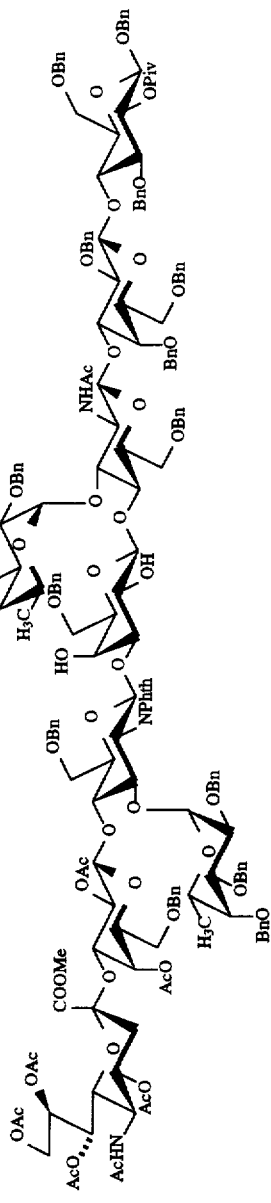
79
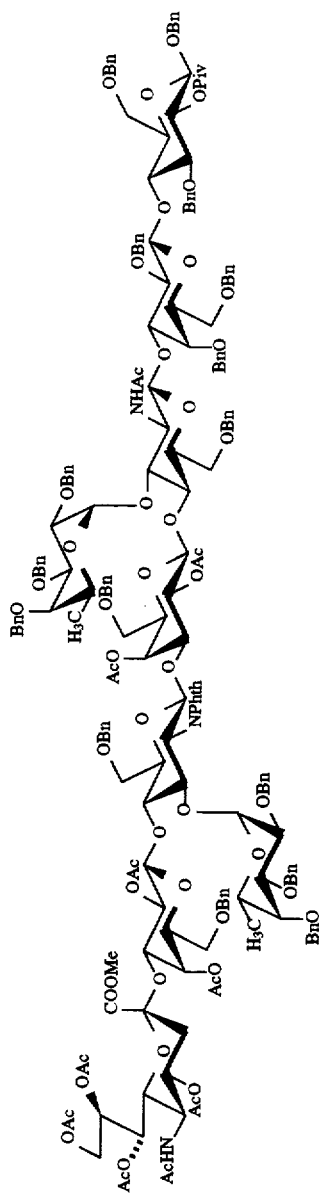
80
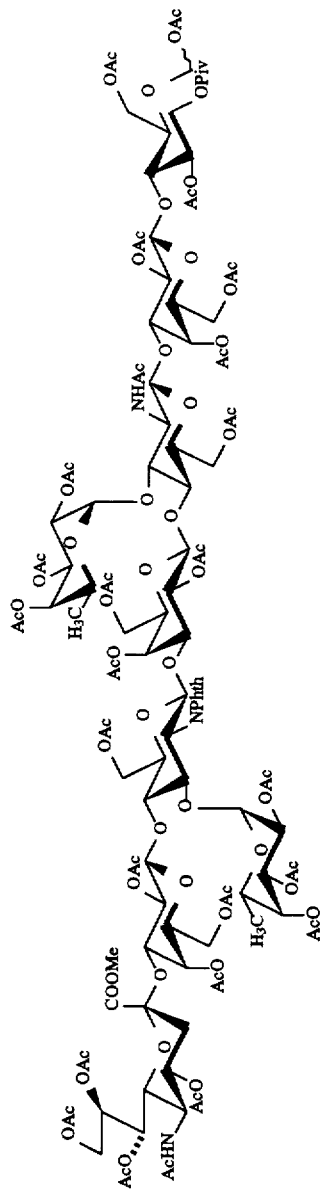
81

-continued
82
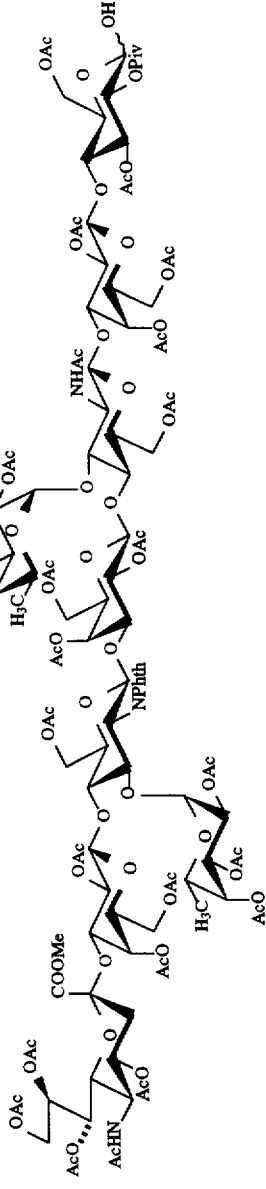
83
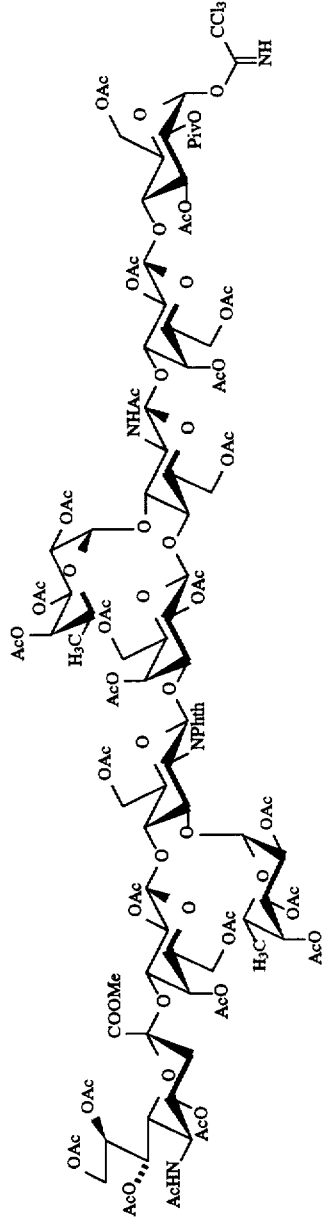
84
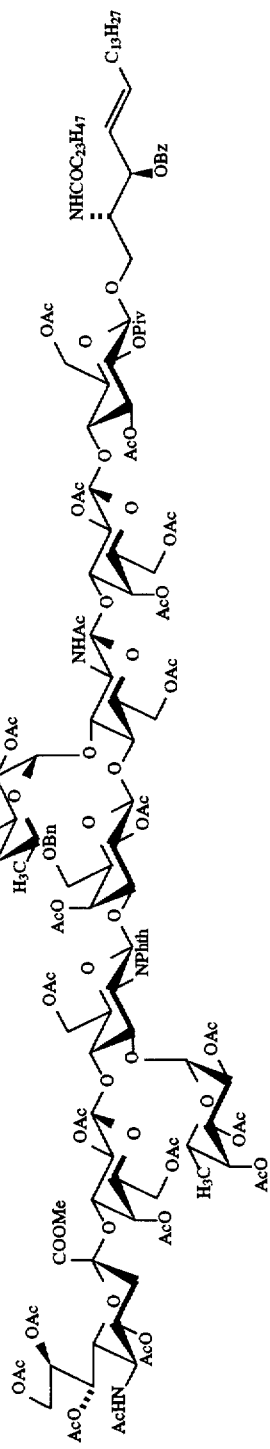

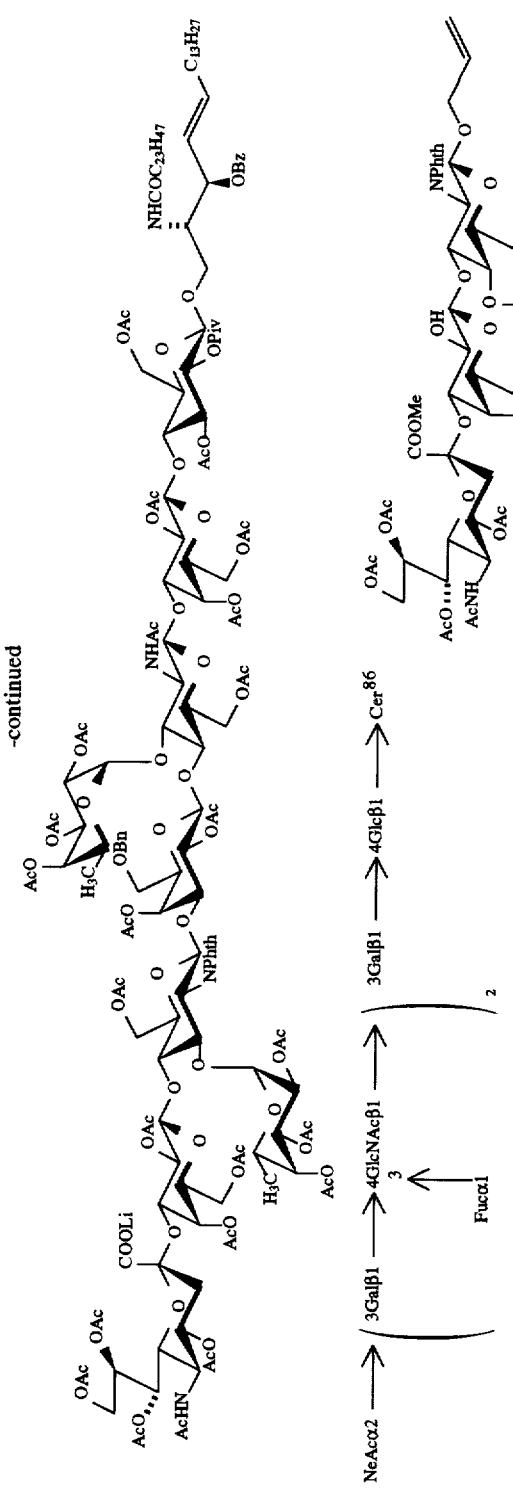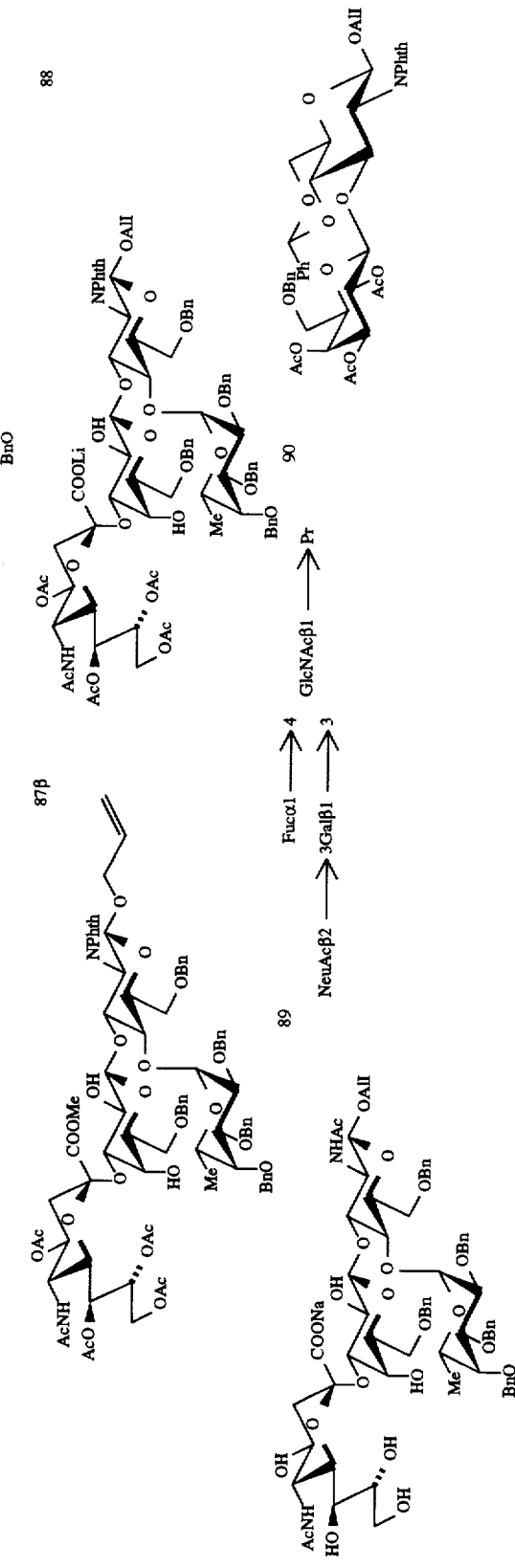

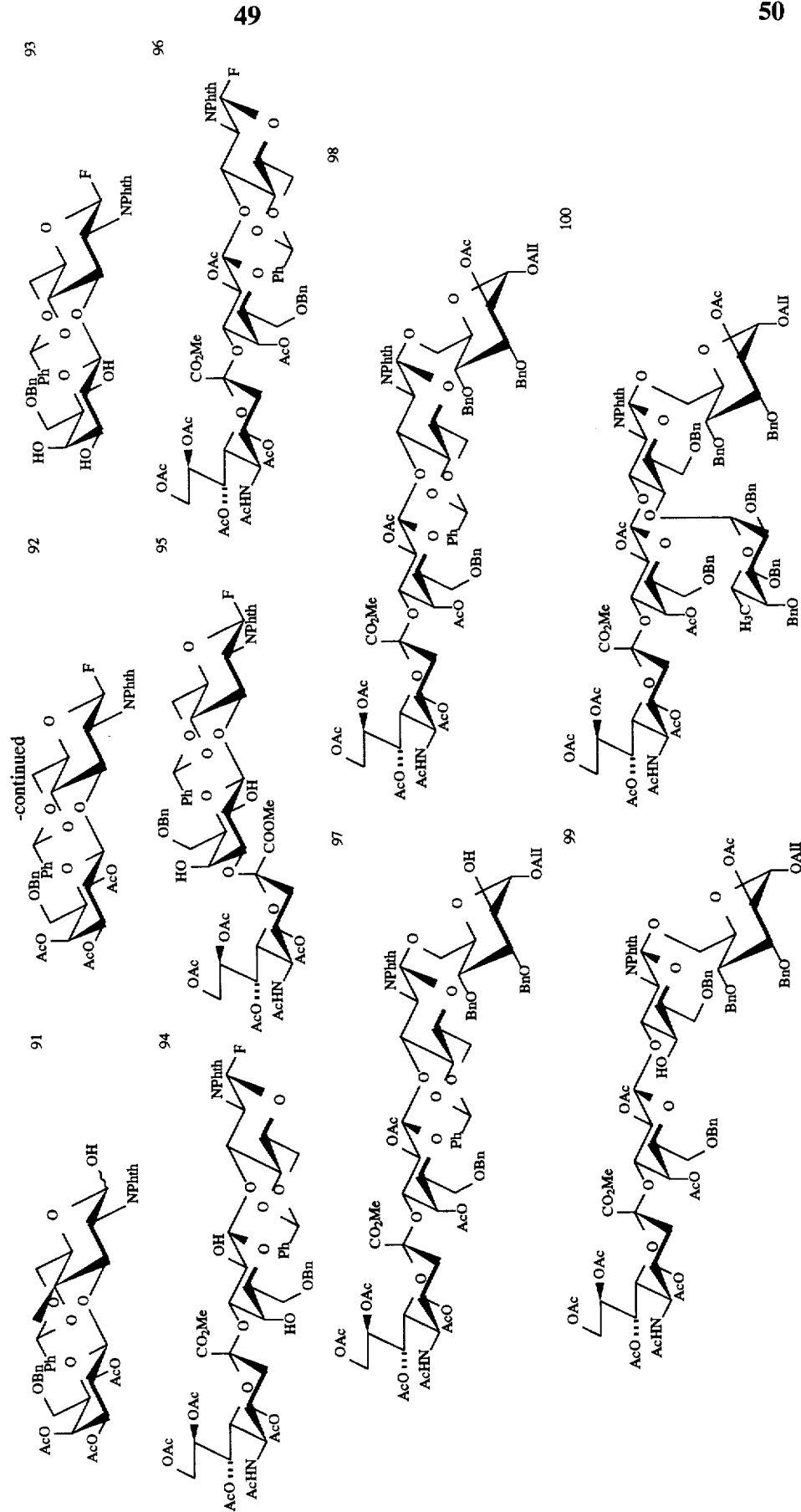

-continued
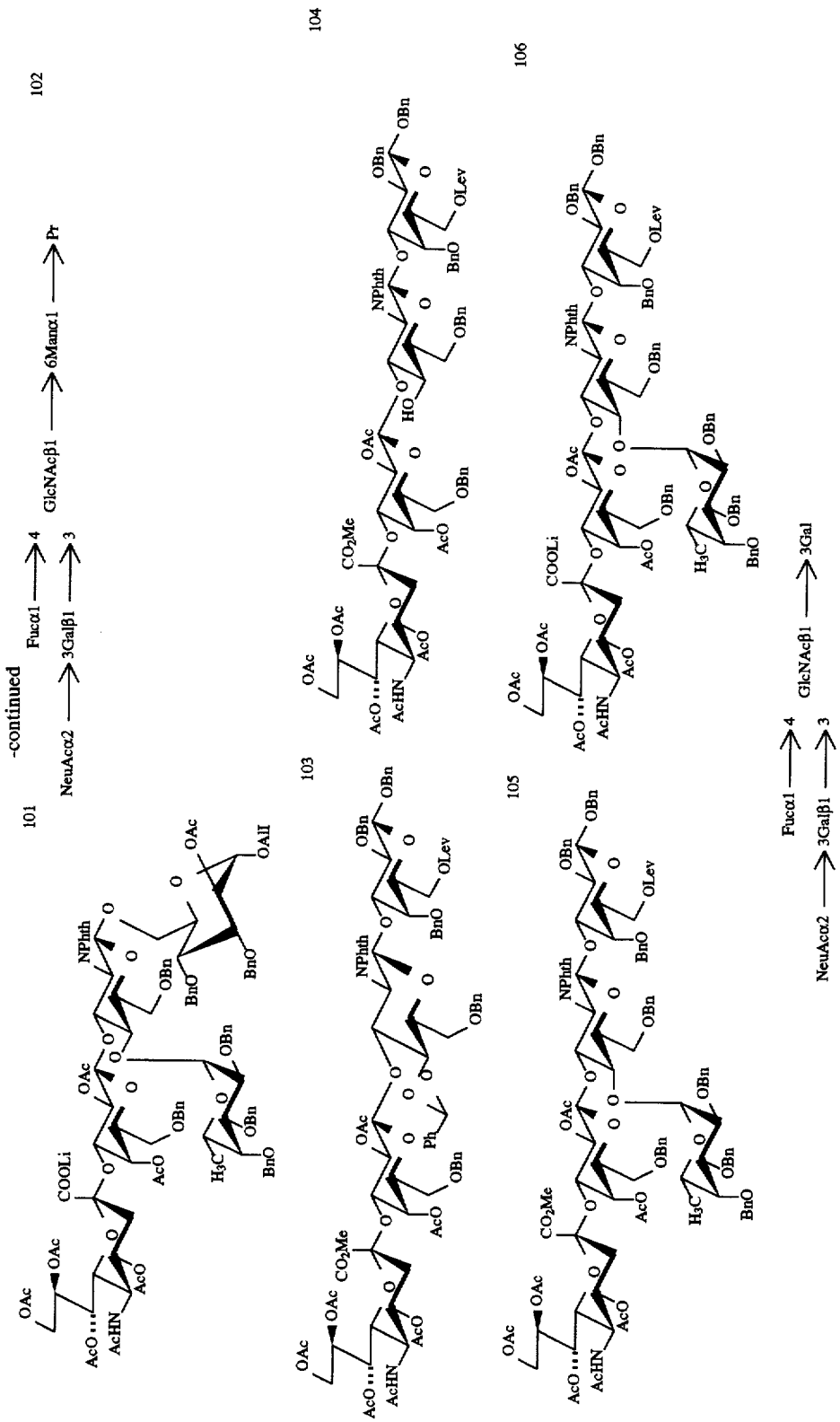

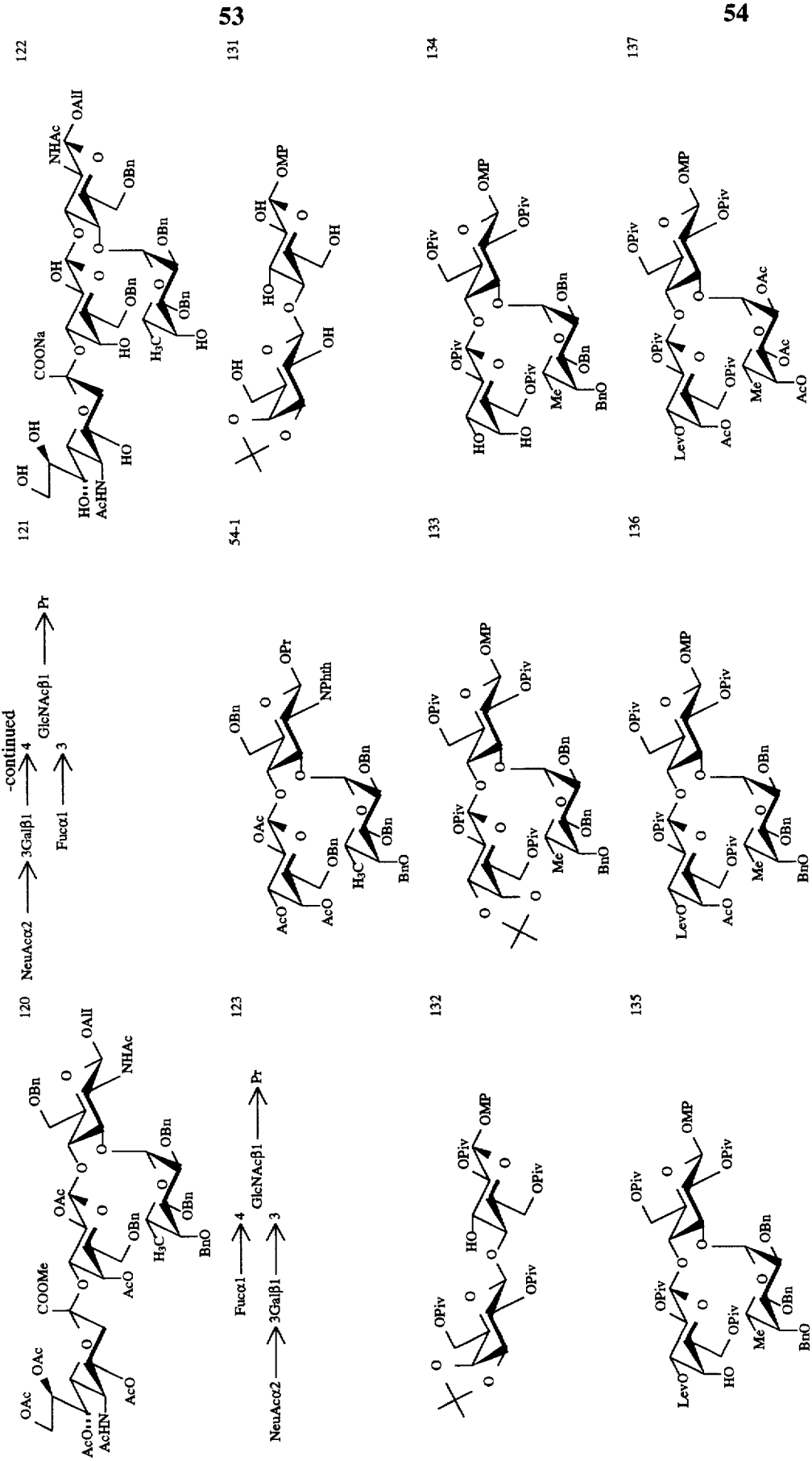

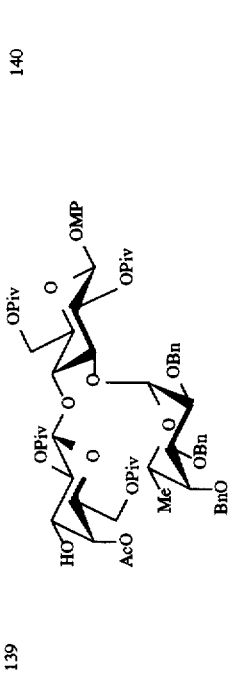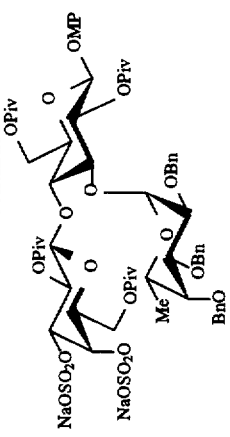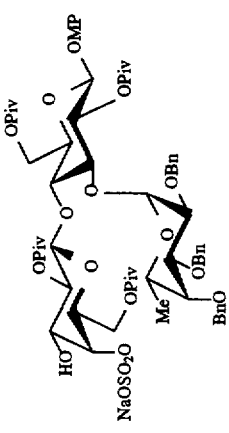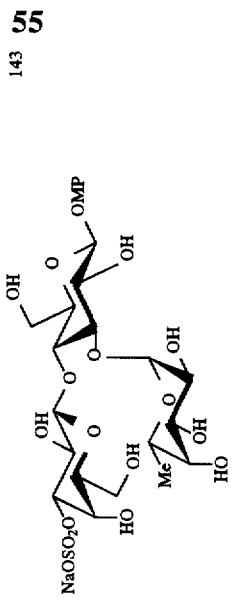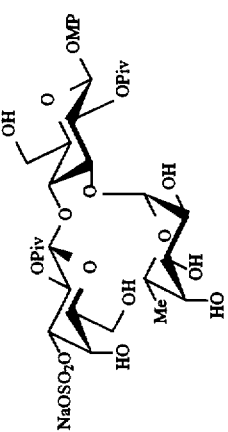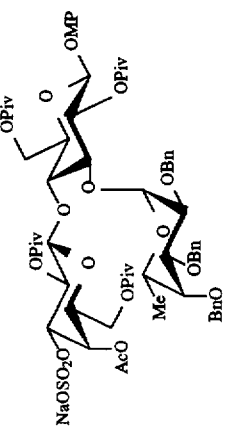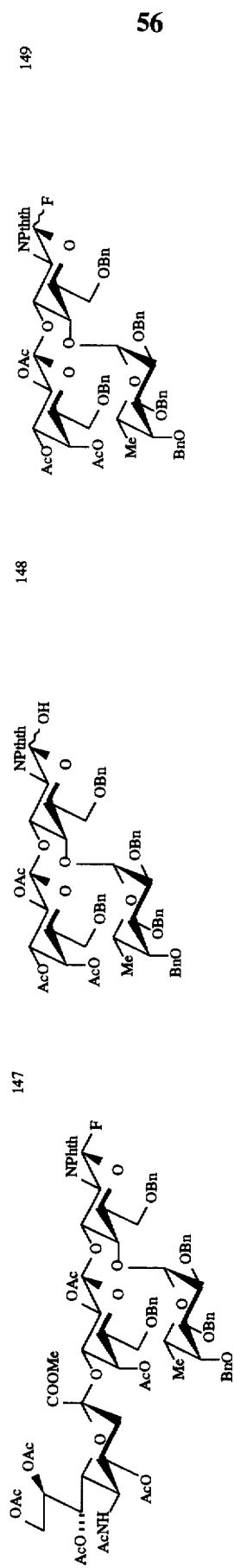

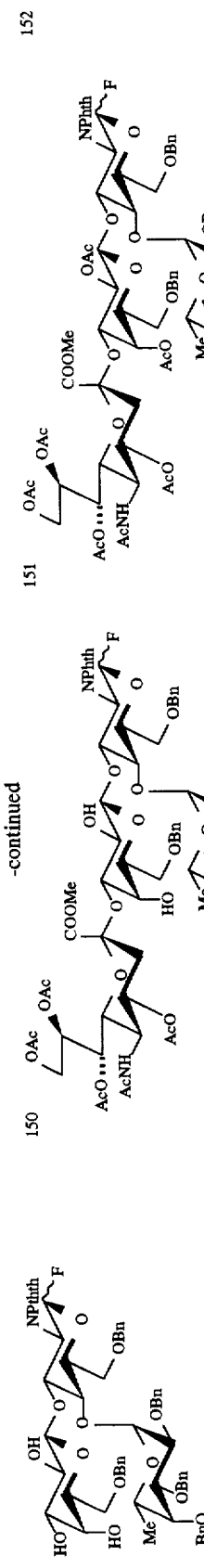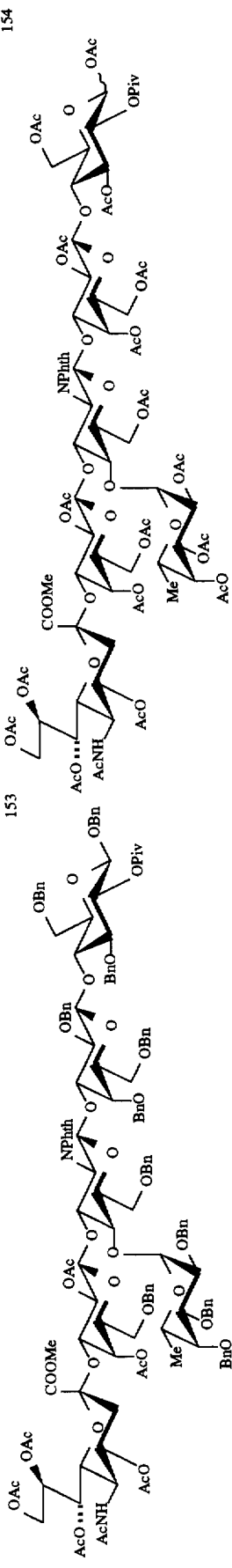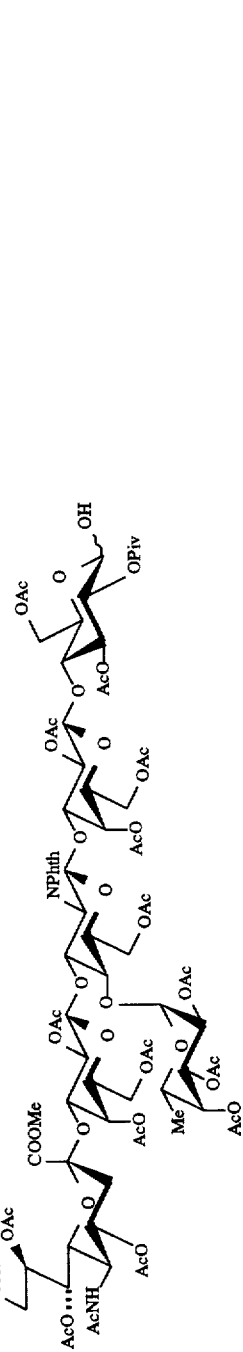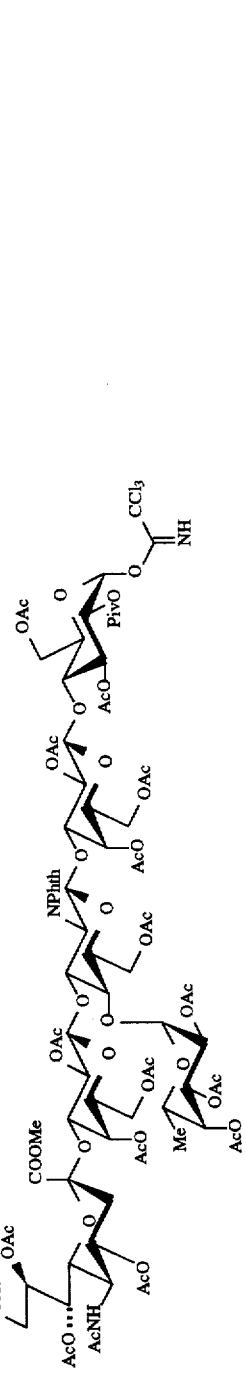

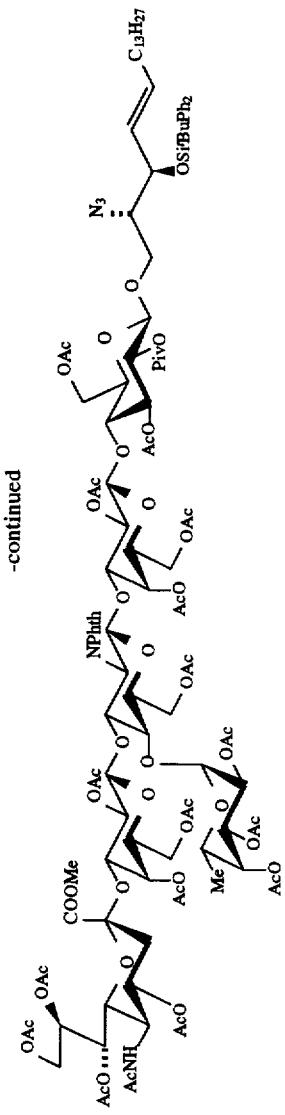
157
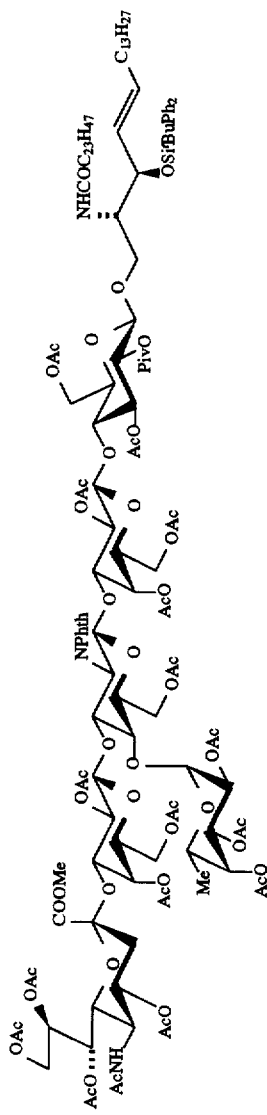
158
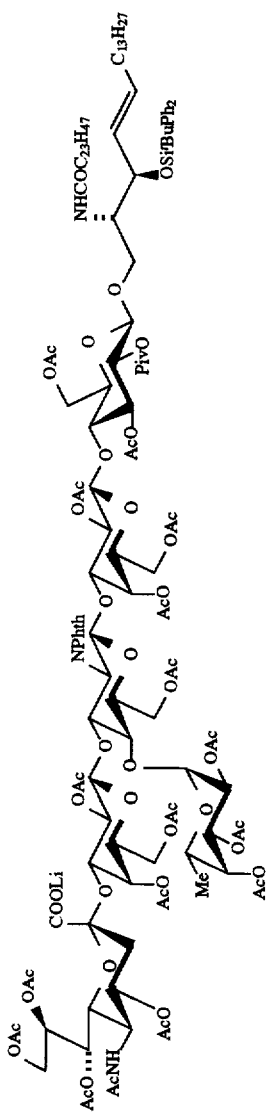
159
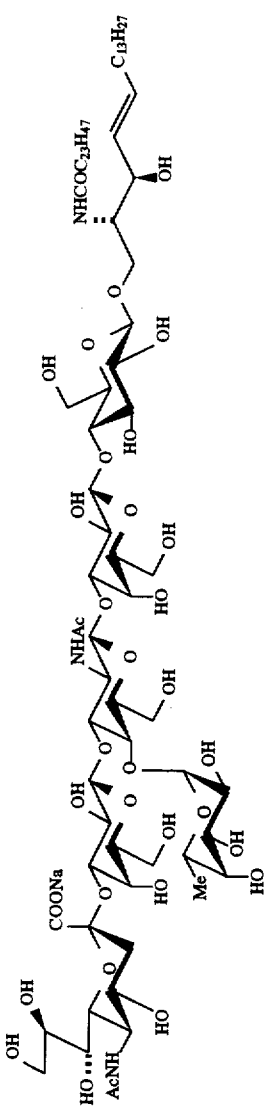
160

-continued
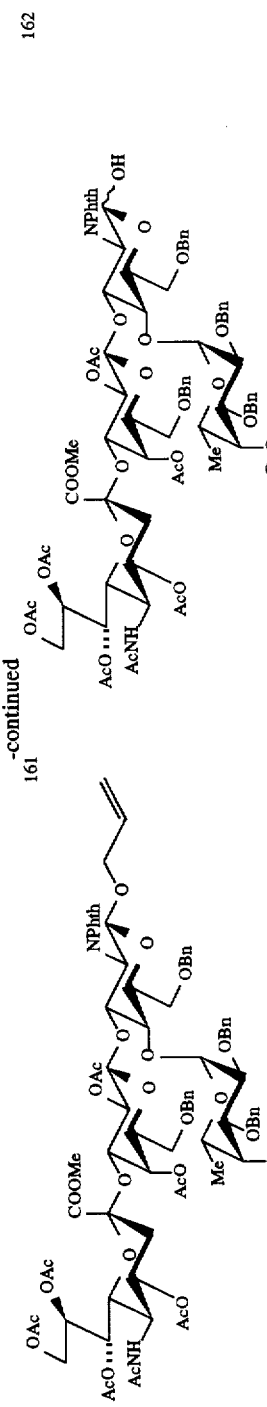
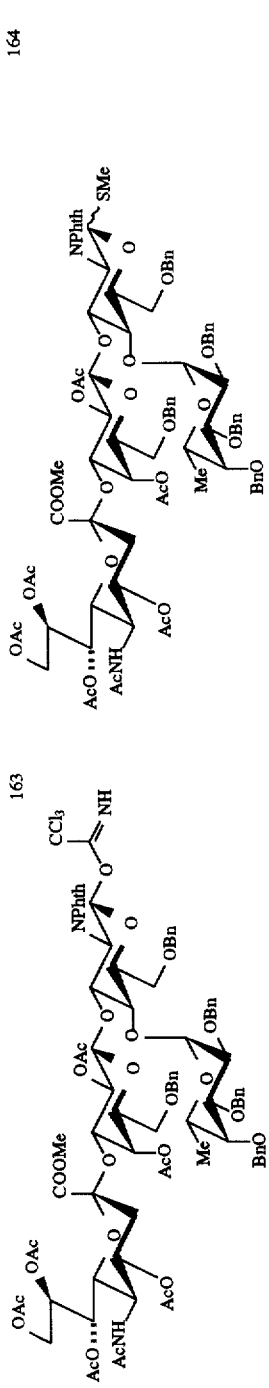
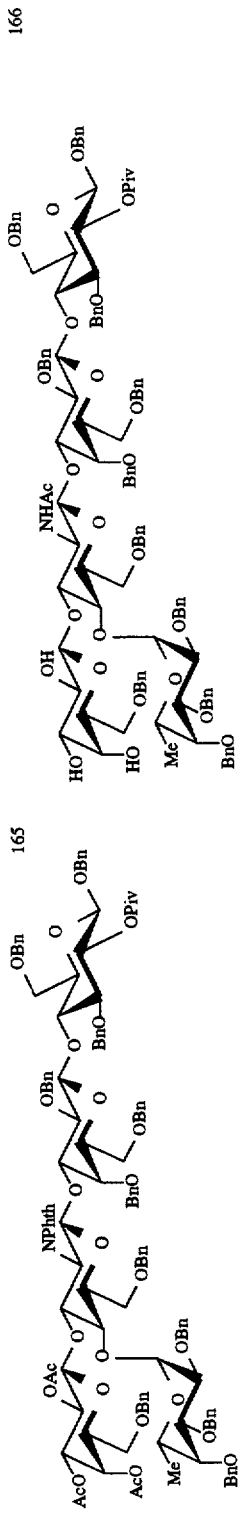
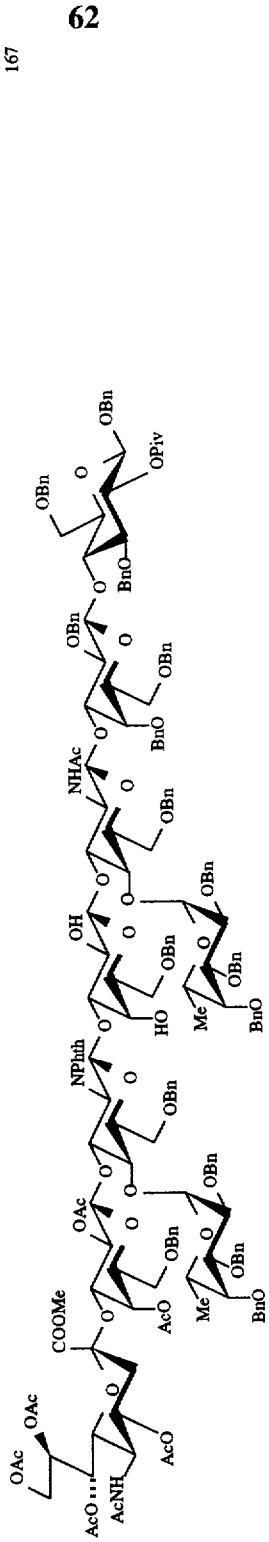

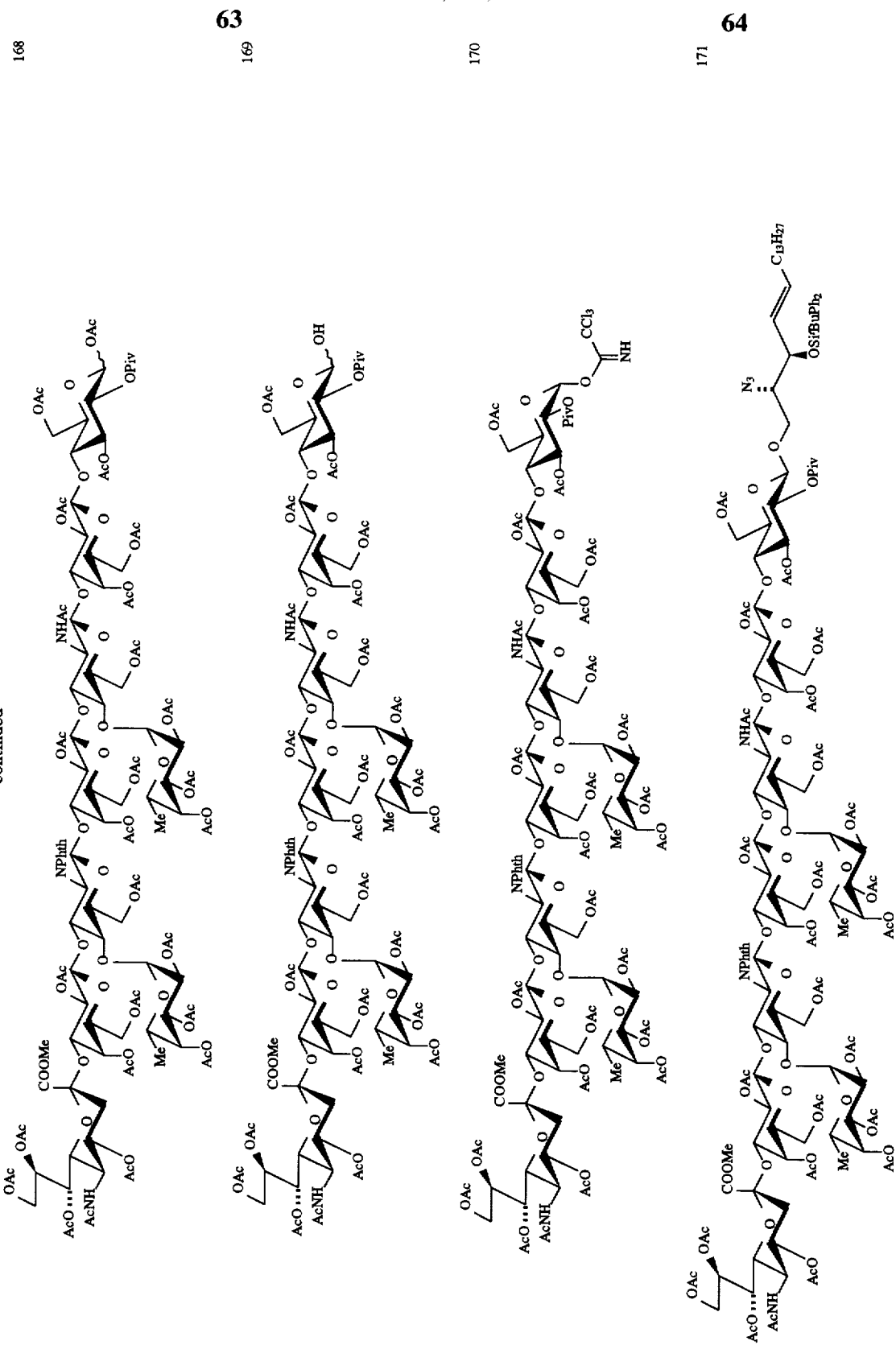

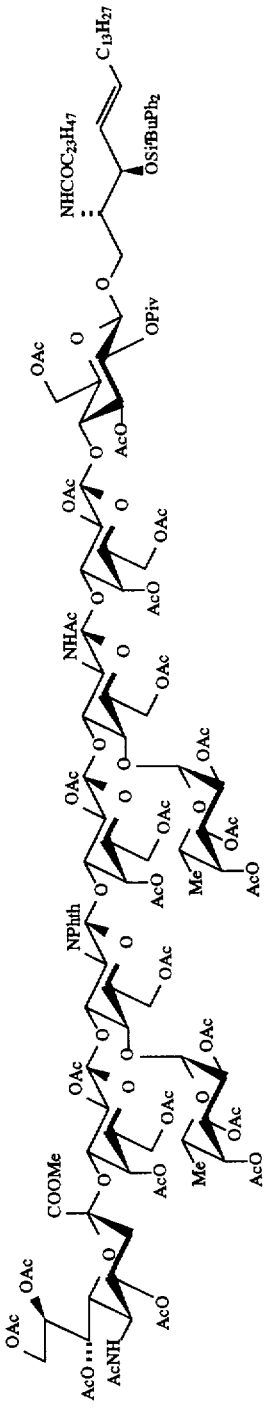
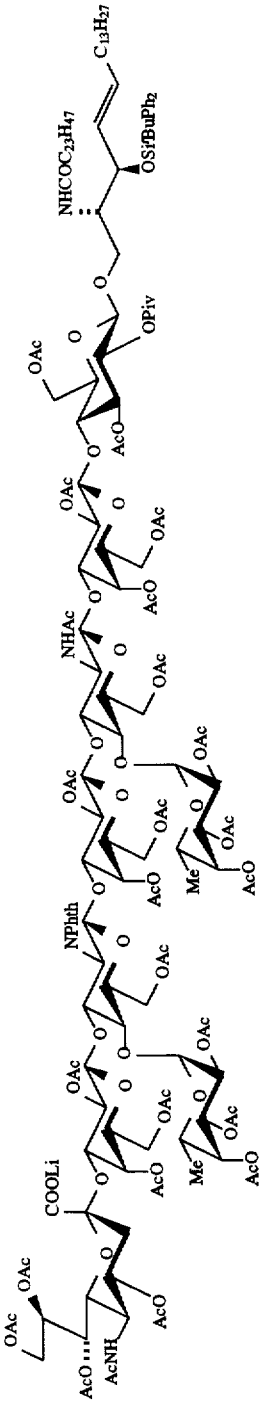
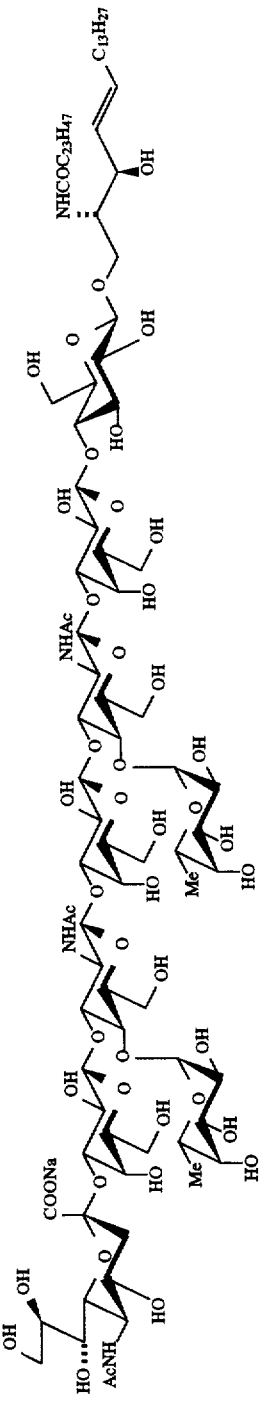
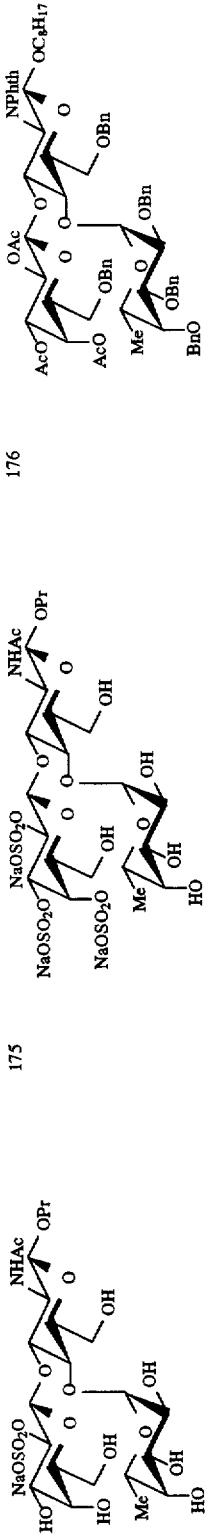

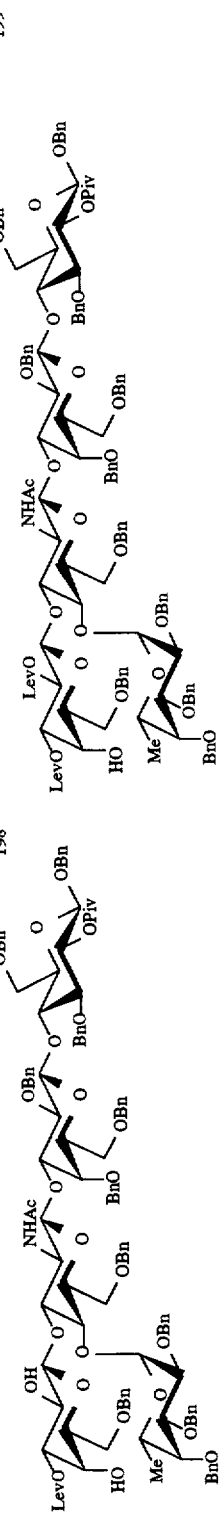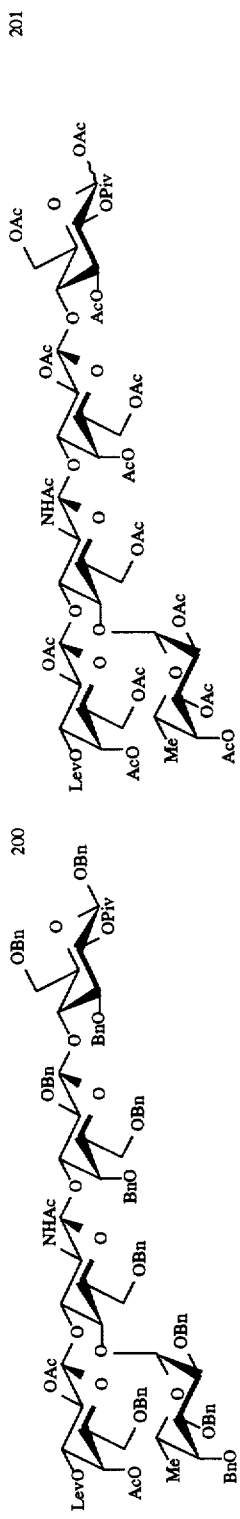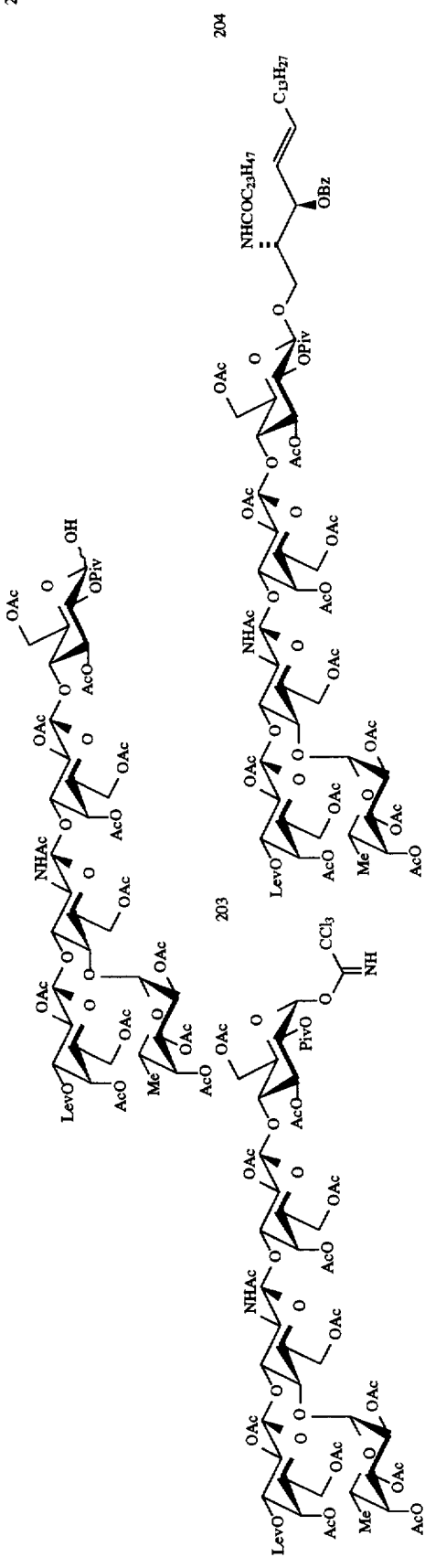

71 72
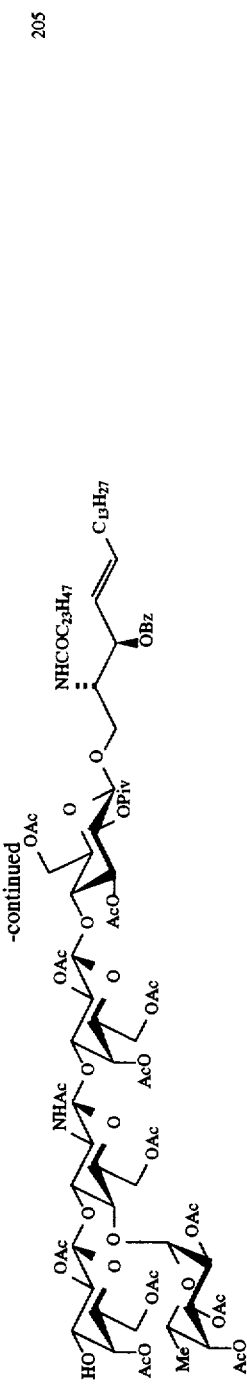
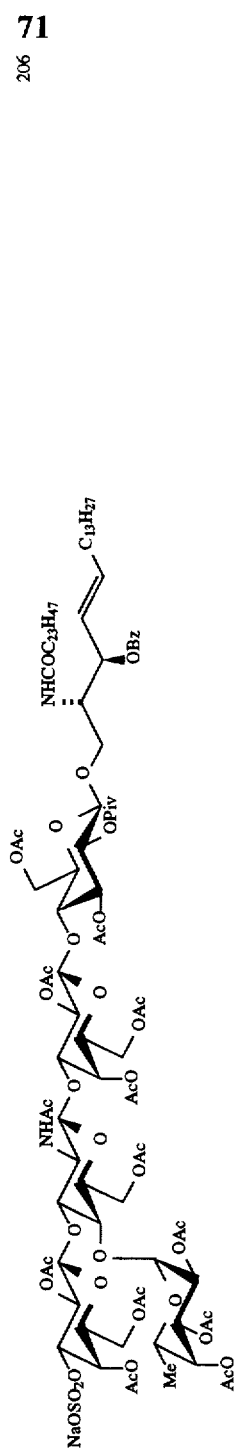
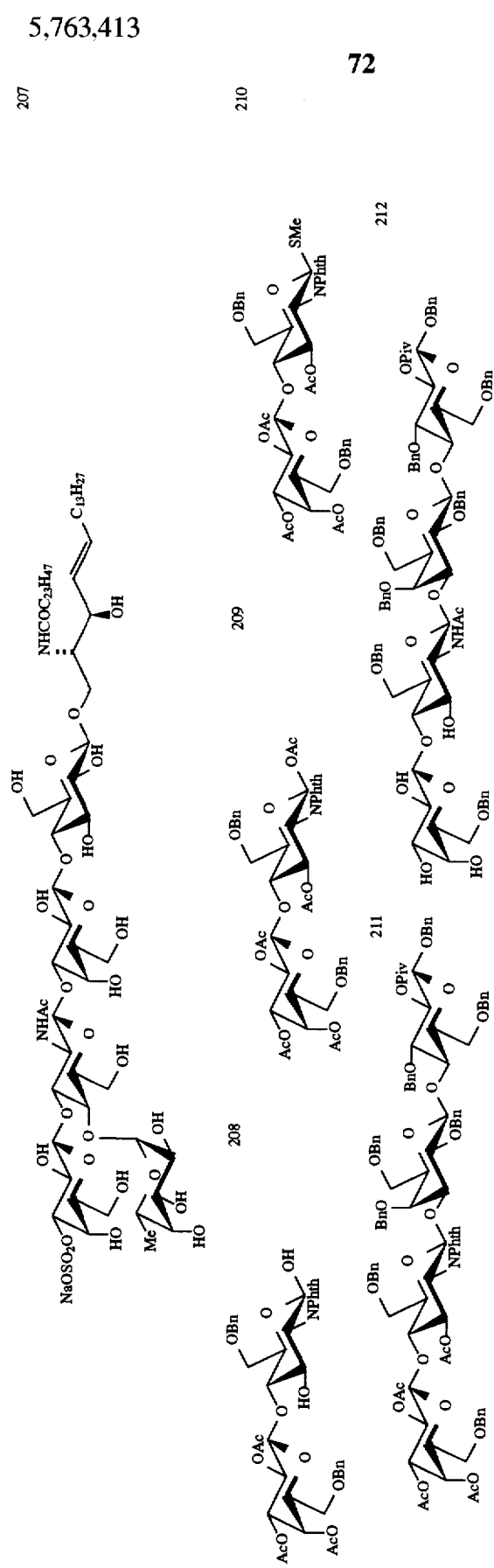

73
74
213
214
215
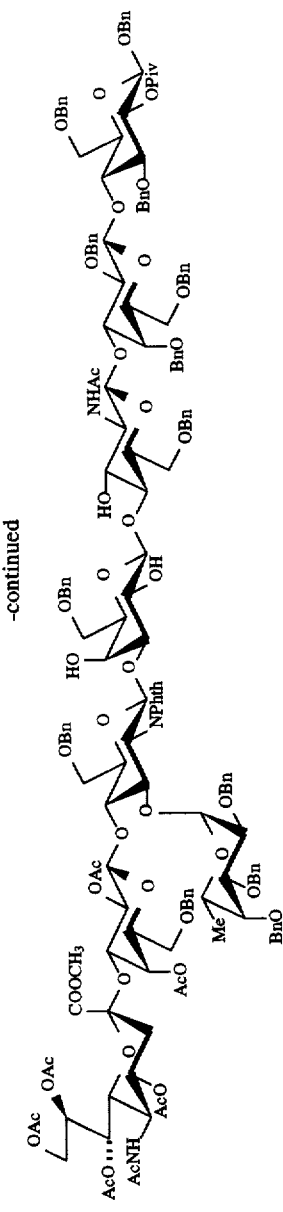
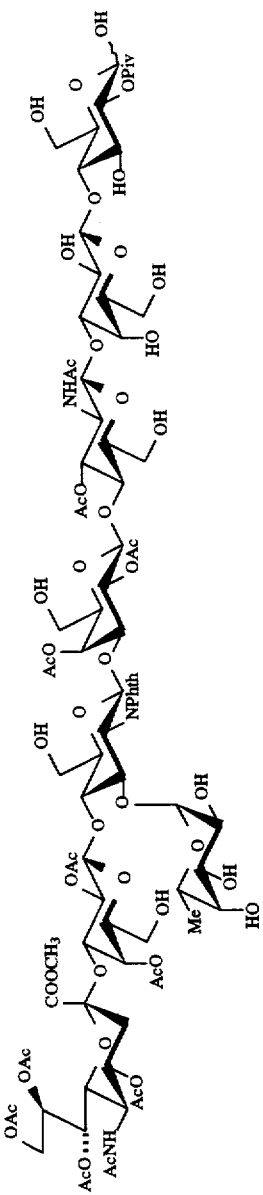
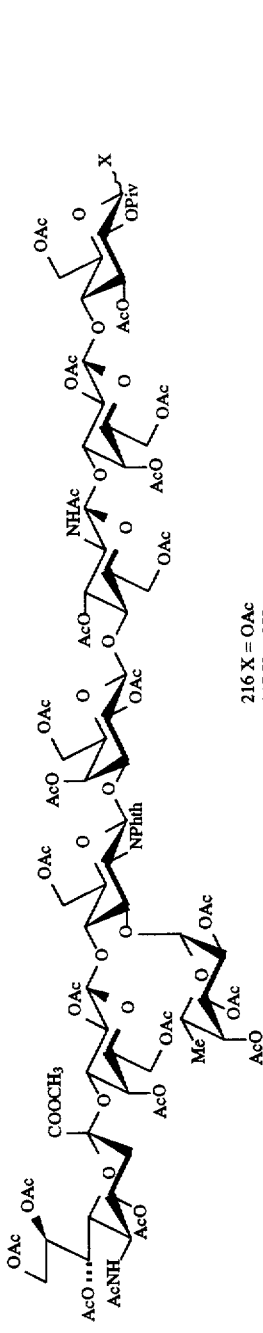
216 X = OAc
217 X = OH
218 X = OC(NH)CCl₃

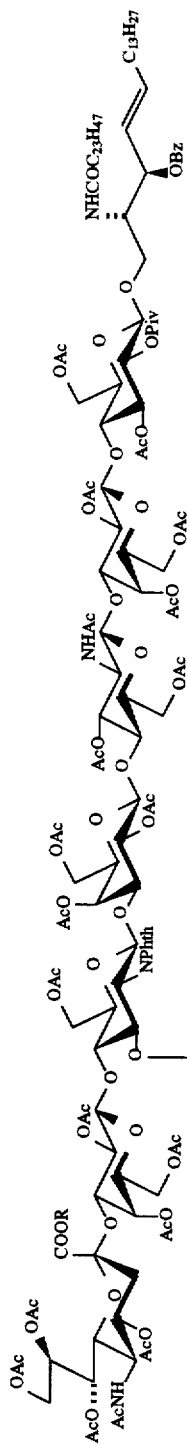
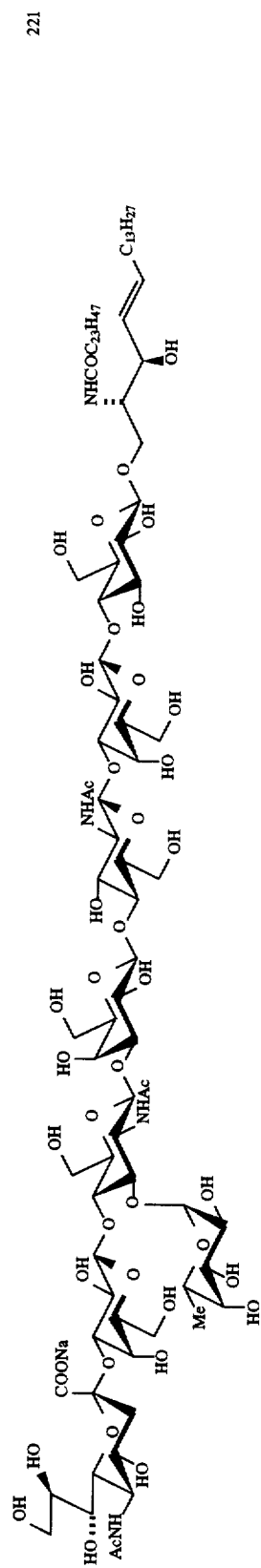
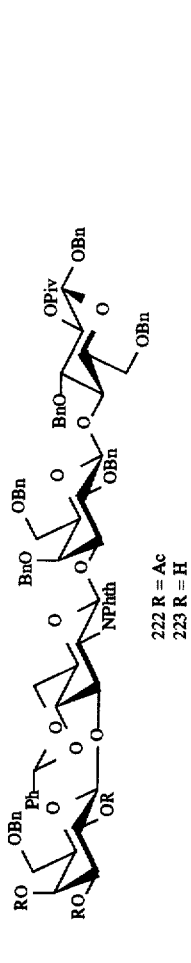
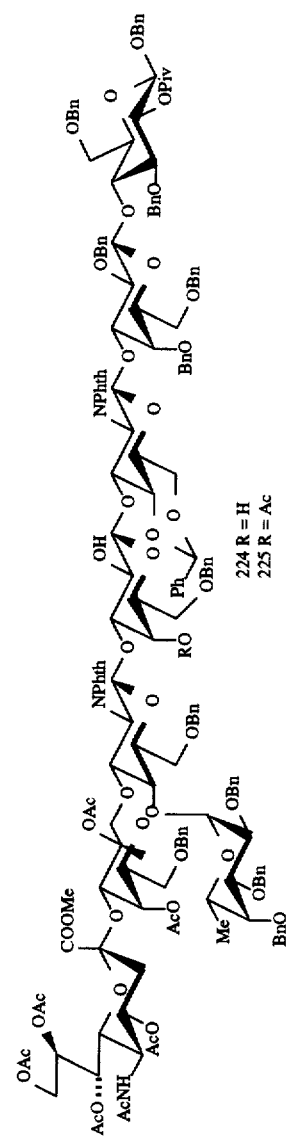

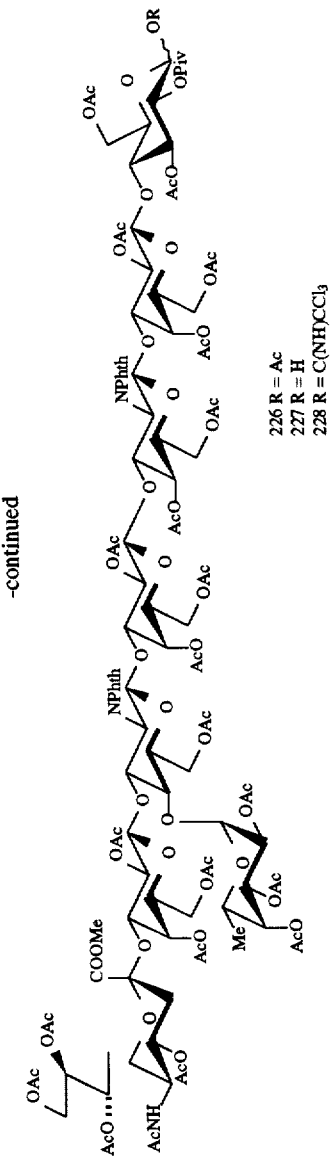
229
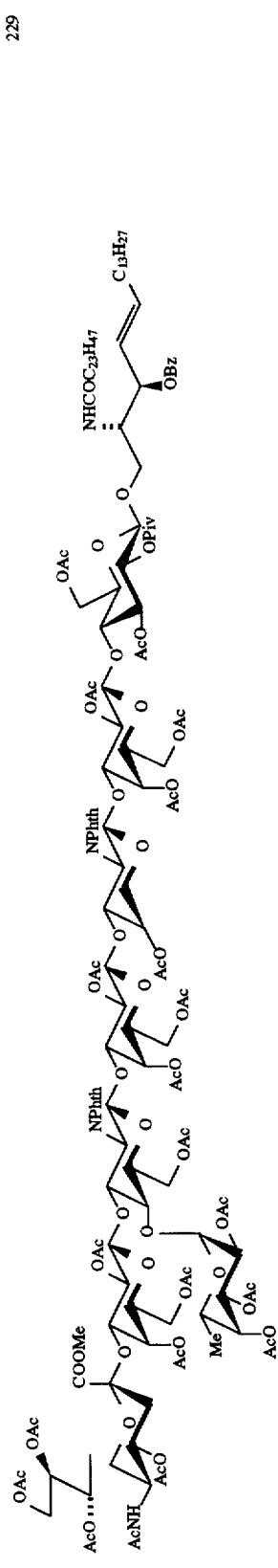
230
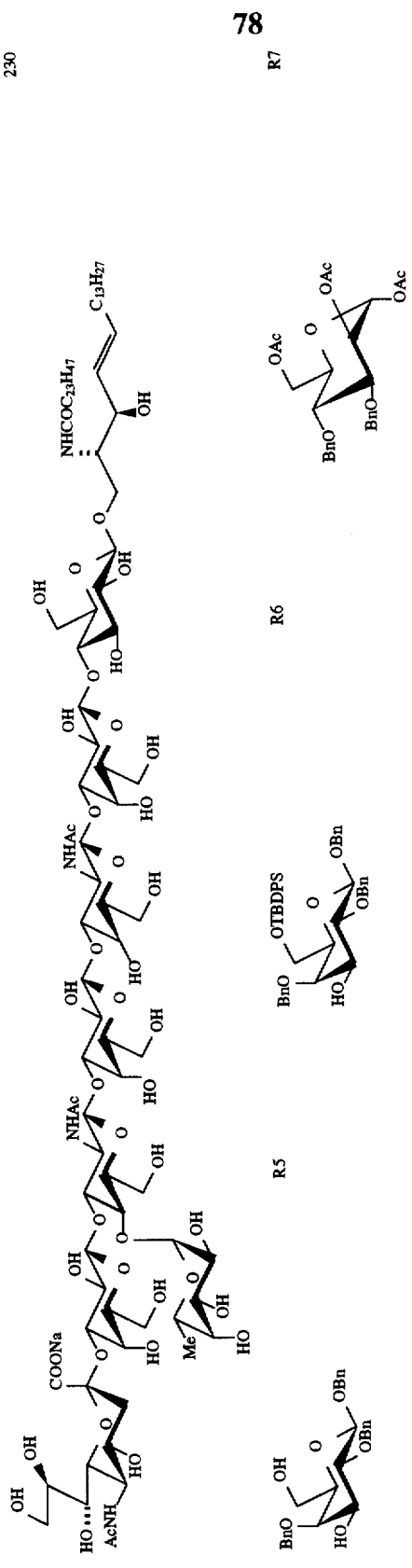

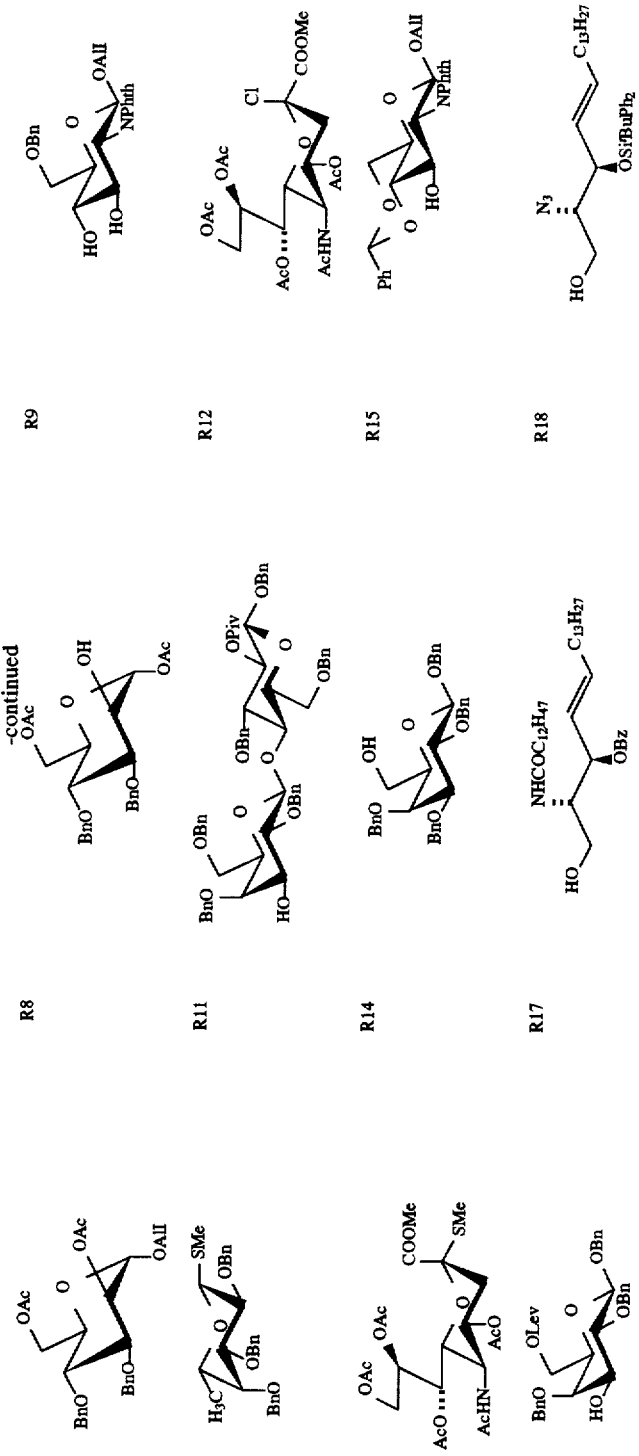

The following is illustrated the method of production of compounds in this invention. At first, the starting material is explained. Compound R4, R5, R7, R10, R11, R12, R13 and R14 are described following references.

R4 J. Carbohydr. Chem., 9(2): 333–343 (1990)

R5 Carbohydr. Res., 101: 263 (1982)

R7 Pure & Appl. Chem., 56: 779–795 (1984)

R10 Carbohydr. Res., 167: 197 (1987) T. Ogawa

R11 Carbohydr. Res., 167: 197 (1987) T. Ogawa

R12 Tetrahedron Letters, 29: 4097 (1988) T. Ogawa

R13 Chem. Ber., 99: 611 (1966)

R14 J. Carbohydr. Chem., 7: 501 (1988)

[Synthesis of Compound R6]

To compound R5 (1.0 g, 2.220 mmol) in DMF (10 ml) was added t-buthyldiphenylchrolosilane (793 mg, 2.886 mmol) and imidazole (363 mg, 5.328 mmol) and the mixture was stirred at 20° C. for 6 h. After the reaction mixture was diluted with $H_2O$ and ether, the organic phase was washed with $NaHCO_3$ and saturated NaCl solution. The washing was dried over $MgSO_4$ and evaporated in vacuo. The residue was purified on a silica gel column chromatography (C-300, 100 g, toluene:ethyl acetate=6:1).

[Compound R6]

1.500 g (98%)

Rf=0.84 (toluene:ethyl acetate=3:1) 500 MHz, 1H—NMR ($CDCl_3$, TMS) $\delta_H$; 1.073 (s, 9H, tBu), 3.485 (t, 1H, J=5.7, 7.0 Hz, H-6), 3.960 (d, 1H, J=1.5 Hz, H-4), 4.390 (d, 1H, J=7.3 Hz, H-1).

Elementary analysis. Theoretical value C; 74.86 H; 7.16 Found value C; 74.90 H; 7.15

[Synthesis of Compound R8]

After allyl alcohol (1.34 g, 0.023 mol) was added to the suspension of MS4A (5.7 g) and compound R7 (5.3 g, 0.011 mol) in 1,2-dichloroethane (114 ml), to the mixture was dropped TMS—$OSO_2CF_3$ (5.11 g, 0.023 mol) at 0° C. and stirred for 100 minutes. The reaction mixture was filtered through celite and the filtrate was diluted with chloroform. After the mixture was washed with $NaHCO_3$ and saturated NaCl solution, the washing was dried over $MgSO_4$ and the solvent was evaporated in vacuo. The residue was purified by silica gel C-300 column chromatography with toluene-ethyl acetate (3:1) as a elution solvent to isolate 4.3 g of compound R8 (77% of yield) as a colorless and solid material.

[Compound R8]

Rf 0.41 (5:1 toluene-ethyl acetate) $^1$H—NMR ($CDCl_3$) $\delta$:5.87 (1H, m, C$\underline{H}$=$CH_2$, 5.39 (1H, dd, J=3.3, 1.8 Hz;H-2), 4.90 (1H, d, J=10.6 Hz, C$\underline{H_2}$—Ph), 4.86 (1H, d, J=1.8 Hz, H-1), 4.71 (1H, d, J=11 Hz, C$\underline{H_2}$—Ph), 4.55 (1H, d, J=10.6 Hz, C$\underline{H_2}$Ph), 4.54(1H, d, J=11 Hz, C$\underline{H_2}$Ph).

[Synthesis of Compound R9]

To compound R8 (4.08 g, 0.0084 mol) in dried methanol (10 ml) was added 28% MeONa (0.1 ml) and the mixture was stirred for 3.5 h. Reaction mixture was neutralized by Dowex 50 WX 8 (H+ type), the solvent was evaporated to obtain 3.39 g of compound R9 (quantitative yield) as a yellow syrup-like material.

[Compound R9]

Rf 0.36 (2:5 toluene-ethyl acetate) $^1$H—NMR ($CDCl_3$) $\delta$: 7.35~7.25 (10 H, m, Ph), 5.86 (1H, m, C$\underline{H}$=$CH_2$), 4.92 (1H, s, H-1), 4.88 (1H, d, J=11 Hz, C$\underline{H_2}$Ph), 4.70 (2H, s, C $\underline{H_2}$Ph), 4.66 (1H, d, J=11 Hz, C$\underline{H_2}$Ph), 4.05 (1H, s, H-2)

[Synthesis of compound R15]

Benzylgalactoside (28 g, 31 mmol) synthesized by the method of A. Lipta'k (Acta Chem. Acad. Sci. Hung., 1979, 101: 81–92) was dissolved in pyridine (200 ml). To the mixture was added TrCl (13 g, 46.5 mmol) and a catalytic amount of dimethylaminopyridine and stirred at 20° C. for 18 h. The reaction mixture was treated by the ordinary manner. The residue in DMF (200 ml) was added 50% NaOH (5.19 g, 108 mmol) with stirring under cooling. To the mixture was added benzylbromide (12.9 ml, 108 mmol) and stirred at 20° C. for 18 h. After the reaction mixture was treated by the ordinary way, the reaction mixture was dissolved in methanol (100 ml). To the mixture was added trifluoroacetic acid (50 ml) and stirred at 20° C. for 2 h. The reaction mixture was treated by the ordinary manner to obtained 30 g of compound R15 (51% of yield on 3 steps).

[Compound R15]

Elementary analysis. Theoretical value C; 75.5%, H; 6.7% Found value C; 75.1%, H; 6.8%

[Synthesis of Compound R16]

Allyl 2-deoxy-2-N-phthaloyl-β-D-glucopyranoside was synthesized by benzylidenation with benzaldehyde.

[Synthesis of Sulfated, Acetylation Le$^x$ Associated Compounds 2~18]

The compounds 2~18 can be synthesized by the following processes.

R4+R10 → glycosylation → 1 (Reference 1)

1+R11 → glycosylation → 2 (Example 1)

2 → deacetylation → 3 (Example 2)

2 → dephthaloylation → acetylation → 4 (Example 3)

4 → acetylation → 5 (Example 4)

2 → 54a → deacetylation → 6 (Example 5)

6 → levulinoylation → 7a, b, c (Example 6)

7a → acetylation → 8 (Example 7)

8 → sulfation → 9 (Example 8)

9 → debenzylation → 10 (Example 9)

5 → sulfation → 11 (Example 10)

11 → debenzylation → 12 (Example 11)

5 → acetyl acid formation → 13a, b, c, 14 (Example 12)

13a → acetylation → 15 (Example 13)

14 → acetylation → 16 (Example 13)

13a → debenzylation → 17 (Example 14)

16 → debenzylation → 18 (Example 15)

[Synthesis of Sulfated, Acetylated Le$^a$ Associated Compounds 22~32]

The compounds 22~32 can be synthesized by the following processes.

R14 +R16 → glycosylation → 20 (Reference 2)

20 → debenzylidenation → 21 (Reference 3)

21 +R11 → glycosylation → 22α, β (Example 16)

22α →deacetylation → 23 (Example 17)

22α →dephthaloylation → acetylation → 24 (Example 18)

24 → sulfation → 25a, b, c (Example 19)

25a → debenzylation → 26 (Example 20)

24 → acetyl acid formation → 27~29 (Example 21)

27 → debenzylation → 30 (Example 22)

28 → debenzylation → 31 (Example 23)

29 → debenzylation → 32 (Example 24)

[Synthesis of Sialyl Le$^x$ Associated Compounds 33~62, 120~123]

The compounds 33~62, 120~123 can be synthesized by the following processes.

5+R13 → glycosylation → 33, 35 (Example 25)
3+R13 → glycosylation → 34, 36 (Example 26)
36 → acetylation → 37 (Example 27)
33 → acetylation → 38 (Example 28)
38 → deacetylation → 39 (Example 29)
39 → debenzylation → 40 (Example 30)
37 → deallylation → 41 (Example 31)
41 → imidation → 42 (Example 32)
42 → ceramidation → 43 (Example 33)
43 → lithiation → 44 (Example 34)
44 → deacetylation → 45 (Example 35)
45 → debenzylation → 46 (Example 36)
42+R9 → glycosylation → 47a (Example 37)
47a → lithiation → 47b (Example 38)
47b → deacetylation → 48 (Example 39)
48 → debenzylation → 49 (Example 40)
42+R15 → glycosylation → 50 (Example 41)
50 → lithiation → 51 (Example 42)
51 → deacetylation → 52 (Example 43)
52 → debenzylation → 53 (Example 44)
2 → deallylation → 54b (Example 45)
54b → fluorination → 55 (Example 46)
55 → imidation → 56 (Example 47)
55+R6 → glycosylation → 57 (Example 48)
57 → dephthaloylation → acetylation → 58 (Example 49)
58+R14 → glycosylation → 59 (Example 50)
59 → desilylation → 60 (Example 51)
60 → deacetylation → 61 (Example 52)
61 → debenzylation → 62 (Example 53)
35 → acetylation → 120 (Example 88)
120 → deprotection → 121 (Example 89)
34 → acetylation → 122 (Example 90)
122 → deprotection → 123 (Example 91)
131 → pivaloylation → 132 (Reference 4)
132+R11 → glycosylation → 133 (Example 92)
133 → deisopropylidenate → 134 (Example 93)
134 → levulinoylation → 135 (Example 94)
134 → sulfation → 138+139 (Example 95)
135 → acetylation → 136 (Example 96)
136 → debenzylation → acetylation → 137 (Example 97)
136 → delevulinoylation → 140 (Example 98)
140 → sulfation → 141 (Example 99)
141 → debenzylation → deacetylation → 142 (Example 100)
142 → depivaloylation → 143 (Example 101)
138 → depivaloylation → 144 (Example 102)
139 → depivaloylation → 145 (Example 103)

[Synthesis of Sialyldimeric Le$^x$ and Sulfated Le$^x$ Associated Compounds 63~86]

The compounds 63~86 can be synthesized by the following processes.

56+R11 → glycosylation → 63 (Example 54)
55+R11 → glycosylation → 63 (Example 55)
63 → dephthaloylation → acetylation → 64, 65 (Example 56)

63 → dephthaloylation → 64 (Example 57)
64 → acetylation → 65 (Example 57)
65 → levulinoylation → 66 (Example 58)
66 → acetylation → 67 (Example 59)
67 → debenzylation → acetylation → 68 (Example 60)
68 → partial deacetylation → 69 (Example 61)
69 → imidation → 70 (Example 62)
70 → ceramidation → 71 (Example 63)
71 → partial delevulinoylation → 72~74 (Example 64)
72 → sulfation → 75 (Example 65)
72 → sulfation → 76 (Example 66)
75 → deprotection → 77 (Example 67)
76 → deprotection → 78 (Example 68)
30+65 → glycosylation → 79 (Example 69)
79 → acetylation → 80 (Example 70)
80 → debenzylation → 80a (Example 71)
80a → acetylation → 81 (Example 72)
81 → partial deacetylation → 82 (Example 73)
82 → imidation → 83 (Example 74)
83 → ceramidation → 84 (Example 75)
84 → lithiation → 85 (Example 76)
85 → deprotection → 86 (Example 77)

[Synthesis of Sialyl Le$^a$ Associated Compounds 87~102, 105~107, 146~147]

The compounds 91~107 can be synthesized by the following processes.

23+R13 → glycosylation → 87 (Example 78)
87 → lithiation → 88 (Example 79)
88 → dephthaloylation → acetylation → 89(Example 80)
89 → debenzylation → 90 (Example 81)
20 → deallylation → 91 (Example 82)
91 → fluorination → 92 (Example 83)
92 → deacetylation → 93 (Example 84)
5+93 → glycosylation → 94, 95 (Example 85)
94 → acetylation → 96 (Example 86)
96+R9 → glycosylation → 97 (Example 87)
97 → acetylation → 98 (Example 104)
98 → benzylidene reductive cleavage → 99 (Example 105)
99+R11 → glycosylation → 100 (Example 106)
100 → lithiation → deacylation → N-acetylation → 101 → debenzylation → 102 (Example 107)
96 → benzylidene reductive cleavage → 146 (Example 108)
146+R11 → glycosylation → 147 (Example 109)
147+R17 → glycosylation → 105 (Example 110)
105 → lithiation → deacylation → N-acetylation → 106 → debenzylation → 107 (Example 111)

[Synthesis of Sialyl Le$^a$ Associate Compounds 148~166]

The compounds 148~166 can be synthesized by the following processes.

22α → deallylation → 148 (Example 112)
148 → fluorination → 149 (Example 113)
149 → acetylation → 150 (Example 114)
150+R14 → glycosylation → 151 (Example 115)
151 → deacetylation → 152 (Example 116)
152+R12 → glycosylation → 153 (Example 117)
153 → debenzylation → acetylation → 154

(Example 118)
    154 → deacetylation → 155 (Example 119)
    155 → imidation → 156 (Example 120)
    156+R19 → ceramidation → 157 (Example 121)
    157 → azido-reduction → 158 (Example 122)
    158 → lithiation → 159 (Example 123)
    159 → deacylation → N-acetylation → desilylation → 160 (Example 124)
    87α → acetylation → 161 (Example 125)
    161 → deallylation → 162 (Example 126)
    162 → imidation → 163 (Example 127)
    163 → thioglycosidation → 164 (Example 128)
    149+R12 → glycosylation → 165 (Example 129)
    165 → deacylation → N-acetylation → 166 (Example 130)

[Synthesis of Sialyldimeric Le$^a$ Associated Compounds 167~174]

The compounds 167~174 can be synthesized by the following processes.

164+166 → glycosylation → 167 (Example 131)
    167 → debenzylation → acetylation → 168 (Example 132)
    168 → deacetylation → 169 (Example 133)
    169 → imidation → 170 (Example 134)
    170+R19 → ceramidation → 171 (Example 135)
    171 → azido-reduction → 172 (Example 136)
    172 → lithiation → 173 (Example 137)
    173 → deacylation → N-acetylation → desilylation → 174 (Example 138)

[Synthesis of Sialyl Le$^a$ Associated Compounds 175~207]

The compounds 175~207 can be synthesized by the following processes.

25b → debenzylation → 175 (Example 139)
    25c → debenzylation → 176 (Example 140)
    149 → alkyl etherification → 177 (Example 141)
    177 → dephthaloylation → acetylation → 178 (Example 142)
    178 → debenzylation → 179 (Example 143)
    22β → dephthaloylation → acetylation → 180 (Example 144)
    180 → deacetylation → 181 (Example 145)
    181 → debenzylation → 182 (Example 146)
    182 → sulfation → 183~187 (Example 147)
    183~187 → debenzylation → 188~192 (Example 148)
    166 → delevulinoylation → 198, 199 (Example 149)
    198 → acetylation → 200 (Example 150)
    201 → debenzylation → acetylation → 201 (Example 151)
    201 → deacetylation → 202 (Example 152)
    202 → imidation → 203 (Example 153)
    203+R18 → ceramidation → 204 (Example 154)
    204 → delevulinoylation → 205 (Example 155)
    205 → sulfation → 206 (Example 156)
    206 → deprotection → 207 (Example 157)
    180 → deallylation → 193 (Example 158)
    193 → imidation → 194 (Example 159)
    194 → alkyl etherification → 195 (Example 160)
    195 → deacetylation → 196 (Example 161)
    196 → debenzylation → 197 (Example 162)

[Synthesis of Intermediates 208~212]

The intermediates 208~212 can be synthesized by the following processes.

1 → deallylation → 208 (Example 163)
    208 → acetylation → 209 (Example 164)
    209 → thioglycosidation → 210 (Example 165)
    210+R12 → glycosylation → 211 (Example 166)
    211 → deacetylation → 212 (Example 167)

[Synthesis of Sialyl Le$^x$ Associated Compounds 213~221]

The compounds 213~221 can be synthesized by the following processes.

212+42 → glycosylation → 213 (Example 168)
    213 → acetylation → 214 (Example 169)
    214 → debenzylation → 215 (Example 170)
    215 → acetylation → 216 (Example 171)
    216 → partial deacetylation → 217 (Example 172)
    217 → imidation → 218 (Example 173)
    218+R18 → ceramidation → 219 (Example 174)
    219 → lithiation → 220 (Example 175)
    220 → deprotection → 221 (Example 176)

[Synthesis of Sialyl Le$^a$ Associated Compounds 222~230]

The compounds 222~230 can be synthesized by the following processes.

92+R12 → glycosylation → 222 (Example 177)
    222 → deacetylation → 223 (Example 178)
    147+223 → glycosylation → 224 (Example 179)
    224 → acetylation → 225 (Example 180)
    225 → debenzylation → acetylation → 22! (Example 181)
    226 → partial deacetylation → 227 (Example 182)
    227 → imidation → 228 (Example 183)
    228+R18 → ceramidation → 229 (Example 184)
    229 → deprotection → 230 (Example 185)

Reagents and conditions suitable for the each synthesizing process of the compounds of this invention will be described below. Each numeral represents the number of the compounds.

[1] Glycosylation R4+R10→1, R4+R16→20, 1→2, 21→22 etc.

Reagents methyltriflate (MeOTf), N-iodosuccinimide (NIS), phenylselenenyl-triflate (PhSeOTf), $CuBr_2$—AgOTf-$nBu_4NBr$, dimethylmethylthiosulfonium-trifluoromethane-sulfonate (DMTST) Solvents $CH_2Cl_2$, $Et_2O$, THF, $CH_3CN$, EtCN, $ClCH_2CH_2Cl$, toluene, $CH_3NO_2$ Time 2 hours~2 days Temperature −20° C.~30° C.

[2] Glycosylation 3+R13→33+36, 5+R13→34+35, 23+R13→87+87α etc.

Reagents $HgBr_2$—$Hg(CN)_2$, AgOTf

Solvents $CH_3CN$, $CH_2Cl_2$, $ClCH_2CH_2Cl$, THF, toluene, $CH_3NO2$, ether

Time 3 hours~4 days

Temperature 0° C.~40° C.

[3] Reductive Cleavage 20→21 etc.

Reagents combination of reductants ($BH_3.NMe_3$, $NaBH_3CN$, $NaBH_4$ etc.) and Lewis acid ($BF_3.Et_2O$, $AlCl_3$, SnCl$_4$, TMSOTf etc.)
  Solvents THF, toluene, ether, CH$_2$Cl$_2$, ClCH$_2$CH$_2$Cl
  Time 30 minutes~8 hours
  Temperature −5° C.~40° C.
[4] Deacylation 2→3, 4→5, 22→23, 38→39, 60→61, 64→65, 120→121 etc.
  Reagents NaOCH$_3$, K$_2$CO$_3$, Na$_2$CO$_3$, Et$_3$N
  Solvents CH$_3$OH, EtOH
  Time 20 minutes~24 hours
  Temperature 0° C.~40° C.
[5] Introducing of Acetic Acid Groups 5→13a, 13b, 14; 24→27, 28, 29 etc.
  Catalysts NaH, DBU, NaOH, KOH,
  Reagents BrCH$_2$CO$_2$Me, ClCH$_2$CO$_2$Me, ICH$_2$CO$_2$Me,
  Solvents DMF, THF, dioxane, DMSO, MeCN
  Time 30 minutes~24 hours
  Temperature 0° C.~40° C.
[6] Acetylation 7a→8, 13a→15, 14→16, 34→38, 36→37, 35→120, 66→67, 79→80 etc.
  Reagents Ac$_2$O—DMAP, AcCl, Ac$_2$O—HClO$_4$, Ac$_2$O
  Solvents pyridine, CH$_2$Cl$_2$, DMF, THF
  Time 1 hour~5 days
  Temperature 0° C.~50° C.
[7] Reductive Debenzylation 11→12, 25→26, 39→40, 48→49, 52→53, 61→62, 67→68, 80→80a, 89→90 etc.
  Catalysts 5~10% Pd—C, 10~20% Pd(OH)$_2$—C, Pt$_2$O
  Solvents CH$_3$OH, CH$_3$OH—H$_2$O, AcOH, EtOAc, CHCl$_3$ and its mixed solvents
  Time 2 hours~50 hours
  Temperature 0° C.~50° C.
[8] Dephthaloylation and N,O— or N-acetylation 2→4, 63→64, 63→65, 22→24, 47→48, 44→45, 51→52, 57→58, 88→89 etc.
  Reagents (dephthaloylation) NH$_2$NH$_2$, NH$_2$—NHCH$_3$, CH$_3$NH$_2$, nBuNH$_2$
  Solvents (dephthaloylation) CH$_3$OH, EtOH
  Time 1 hour~48 hours
  Temperature Room temperature~110° C.
  Reagents (N,O-acetylation) Ac$_2$O—DMAP, AcCl, Ac$_2$O, (N-acetylation) Ac$_2$O, acetoxysuccinimide
  Solvents (N,O-acetylation) pyridine, DMF, (N-acetylation) CH$_3$OH, EtOH, DMF, THF,
  Time 20 minutes~36 hours
  Temperature 0° C.~60° C.
[9] Demethylation 43→44, 46→47, 50→51, 87→88 etc.
  Reagents LiI, NaI, KI
  Solvents pyridine, collidine, picoline
  Time 1 hour~24 hours
  Temperature 40° C.~120° C.
[10] Deallylation 2→54, 37→41, 20→91 etc.
  Reagents Ir complex-I$_2$, PdCl$_2$-AcONa, Ph$_3$PRhCl—I$_2$, Ph$_3$PRhCl—HgCl$_2$—HgO
  Solvents THF, ACOH—H$_2$O, MeOH—H$_2$O, EtOH-benzene-H$_2$O
  Time 1 hour~24 hours
  Temperature 10° C.~80° C.
[11] Imidation of reduced end 41→42, 54→56, 69→70, 82→83 etc.
  Reagents DBU—CCl$_3$CN, NaH—CCl$_3$CN, K$_2$CO$_3$—CCl$_3$CN Solvents ClCH$_2$CH$_2$Cl, CH$_2$Cl$_2$, toluene, benzene
  Time 1 hour~4 hours
  Temperature −5° C.~30° C.
[12] Fluorination of Reduced End 54→55, 91→92 etc.
  Reagents DAST (diethylaminosulfurtrifluoride)
  Solvents ClCH$_2$CH$_2$Cl, CH$_2$Cl$_2$, THF, CH$_3$CN
  Time 20 minutes~3 hours
  Temperature −20° C.~40° C.
[13] Glycosylation by Imidate Group 70→71, 42+65→79, 83→84, 42→R15→50, 42→43, 42+R9→46 etc.
  Reagents BF$_3$—Et$_2$O, TMSOTf
  Solvents CH$_2$Cl$_2$, CHCl$_3$, ClCh$_2$CH$_2$Cl, THF, toluene, CH$_3$CN, EtCN,
  Time 30 minutes~24 hours
  Temperature −40° C.~30° C.
[14] Glycosylation of Fluoride 55→63, 55+R6→57, R9+96→97 etc.
  Reagents TMSOTf, AgOTf—Cp$_2$ZnCl$_2$, AgOTf—Cp$_2$HfCl$_2$, BF$_3$.Et$_2$O, Sn(OTf)$_2$, AgClO$_4$—SnCl$_2$, AgClO$_4$—Cp$_2$HfCl$_2$
  Solvents ClCH$_2$CH$_2$Cl, CH$_2$Cl$_2$, CH$_3$CN, toluene, CH$_3$NO$_2$, THF
  Time 30 minutes~60 hours
  Temperature −50° C.~−20° C.
[15] Hemiacetalization of Reduced End 68→69, 81→82 etc.
  Reagents piperidine acetate, hydrazine acetate
  Solvents THF, CH$_2$Cl$_2$, ClCH$_2$CH$_2$Cl, DMF,
  Time 30 minutes~24 hours
  Temperature 20° C.~60° C.
[16] Selective Delevulinoylation 71→72+73+74, 8→9 etc.
  Reagents hydrazine acetate, piperidene acetate
  Solvents EtOH, EtOH—toluene, DMF
  Time 30 minutes~24 hours
  Temperature −15° C.~40° C.
[17] Sulfation 5→11, 8→9, 72→75, 73→74 etc.
  Reagents trimethylamine sulfurtrioxido, pyridine sulfurtrioxide, piperidine sulfurtrioxide, triethylamine sulfurtrioxide
  Solvents DMF, DMSO, THF
  Time 15 minutes~24 hours
  Temperature 70° C.~120° C.
[18] Regioselective Levulinoylation 6→7a+7b+7c, 65→66 etc.
  Reagents levulinic anhydride and DMAP, levulinoylchloride and DMAP, levulinic-acid-2-chloro-1-methylpyridiumidide-tributylamine, levulinic acid activated ester
  Solvents pyridine, CH$_2$Cl$_2$, ClCH$_2$CH$_2$Cl
  Time 2 hours~24 hours
  Temperature 0° C.~50° C.
[19] Hydrolysis and Reduction 9→10, 15→17, 16→18, 27→30, 28→31, 29→32 etc.
  Reagents (hydrolysis) NaOH, KOH, K$_2$CO$_3$, Et$_3$N, CH$_3$ONa
  Solvents (hydrolysis) MeOH—H$_2$O, H$_2$O, EtOH—H$_2$O
  Time (hydrolysis) 30 minutes~24 hours
  Temperature (hydrolysis) 0° C.~40° C.
  A condition of reductive reaction is the same as [7].

[20] Deacylation 75→77, 76→78 etc.
Reagents NaOH, K$_2$CO$_3$, Na$_2$CO$_3$, Et$_3$N
Solvents THF—MeOH, MeOH,
Time 30 minutes~24 hours
Temperature 0° C.~60° C.
[21] Desilylation 59→60 etc.
Reagents nBu$_4$NF, CF3COOH, CH$_3$COOH, KF
Solvents THF, CH$_2$Cl$_2$, ClCH$_2$CH$_2$Cl,
Time 30 minutes~20 hours
Temperature 0° C.~40° C.

Anti-inflammatory agents of the present invention will be described in the following.

Compounds especially preferred as the active ingredient of anti-inflammatory agents of the present invention are as follows: Compounds 10, 12, 17, 18, 26, 30, 31, 32, 40, 46, 49, 53, 62, 77, 78, 86, 90, 102, 107, 121, 123, 143, 144, 160, 174, 175, 176, 179, 182, 188, 189, 190, 191, 192, 197, 207, 221 and 230.

Anti-inflammatory agents of the present invention are the pharmaceutics comprising said active ingredients, there is no limitation in the dosage form, vehicle to be used and administration form or route, so far as they are capable of producing the desired effect.

The dosage form of anti-inflammatory agents of the present invention may be that for oral or parenteral administration, but preferably the form for oral administration. The dosage form for oral administration includes hard gelatin capsule and soft elastic capsule, tablet, granule, fine granule and powder, and that for parenteral administration includes intravenous injection, intravenous drip infusion and suppository. Generally, oral administration, parenteral administration, especially intravenous injection, preferably isotonic solution or suspension are suitable for the administration of said anti-inflammatory agents. These drugs may be prepared from the lyophilized preparation containing carriers such as mannitol or cyclodextrin prior to use. If necessary, these pharmaceutical preparations may contain the supplement, for example, antiseptic, stabilizer, humectant and/or emulsifier, solubilizing agent, and salt and/or buffering agent to adjust the osmotic pressure.

If necessary, pharmaceutical preparations of the present invention may further include other drugs having different effects, and these preparations themselves may be prepared by the ordinary known method such as mixing, solubilization or lyophilization. Anti-inflammatory agents of the present invention may include said active ingredients, for example, at about 0.1~99.9 weight percent, preferably about 1.0~99.0 weight percent, and in the case of lyophilization up to 100 weight percent. Needless to say, there is no limitation in said mixing range.

As to the administration of pharmaceutical preparations of the present invention, the doctor in charge may select the most suitable dosage regimen and unit dosage depending upon the patient's symptoms. Generally, the unit dosage for the once daily or several times daily administration may be selected usually in the range of about 0.01~1,000 mg for a patient weighing about 50~70 kg, preferably about 0.1~100 mg.

Preferred Embodiments

In the following, the examples of the pharmaceutical preparation, anti-inflammatory activity test and synthesis of the drug of the present invention will be described.

Example of Pharmaceutical Preparation 1 (Tablet)

The following ingredients were homogeneously mixed and formed into tablets containing 100 mg of the mixture by compressing with a tablet machine. Each of said tablet contains 1 mg of the compound of the present invention as the active ingredient.

| Corn starch | 4.8 g |
| Crystalline cellulose | 4.5 g |
| Calcium carboxymethylcellulose | 0.5 g |
| Light anhydrous silicic acid | 0.05 g |
| Magnesium stearate | 0.05 g |
| Compound 26 | 0.1 g |
| Total | 10 g |

Example of Pharmaceutical Preparation 2 (Ampule for Injection)

Compound 123 (1 g) was dissolved in a physiological saline for injection (1,000 ml) and distributed in 1,000 ampules.

Example of Test 1 (Simple Acute Toxicity Test)

The simple acute toxicity test was carried out by an intravenous injection of compounds of the present invention.

Into the tail vein of male mice of ddY strain weighing 18~20 g which have been kept under the conditions at the temperature of 23°±1° C. and in the humidity of 55 ±7% were injected a solution of the compound of the present invention dissolved in the physiological saline containing the desired dose per 20 g body weighing 0.2 ml. Two dosages of which were 50 mg/kg and 500 mg/kg body weight were used. Results are shown in Table 20. In the case of compounds 77, 78 and 86, no mortality was observed with the administration of 50 mg/kg, and in the cases of other compounds no mortality with the dose of 500 mg/kg.

TABLE 20

| Test compound | Mortality (%) | |
| --- | --- | --- |
|  | 50 mg/kg | 500 mg/kg |
| Compound 10 | 0/3 | 0/3 |
| Compound 12 | 0/3 | 0/3 |
| Compound 17 | 0/3 | 0/3 |
| Compound 18 | 0/3 | 0/3 |
| Compound 26 | 0/3 | 0/3 |
| Compound 30 | 0/3 | 0/3 |
| Compound 31 | 0/3 | 0/3 |
| Compound 32 | 0/3 | 0/3 |
| Compound 40 | 0/3 | 0/3 |
| Compound 46 | 0/3 | 0/3 |
| Compound 49 | 0/3 | 0/3 |
| Compound 53 | 0/3 | 0/3 |
| Compound 62 | 0/3 | 0/3 |
| Compound 77 | 0/3 |  |
| Compound 78 | 0/3 |  |
| Compound 86 | 0/3 |  |
| Compound 90 | 0/3 | 0/3 |
| Compound 121 | 0/3 | 0/3 |
| Compound 123 | 0/3 | 0/3 |

Example of Test 2 (Anti-inflammatory Activity Test)

(1) Experimental Animal

Male guinea pigs of the Hartley strain weighing 200~250 g were used.

(2) Experimental Materials

The anti-ovalbumin rabbit serum (PCA titer=1/80,000) and ovalbumin were used as the antiserum and antigen, respectively.

(3) Experimental Method

The passive Arthus reaction was performed according to the method of Katayama et al. [Katayama, S. et al., Arzeim-Forsch., 31, 1196 (1981)]. That is, guinea pigs were sensitized by an intravenous injection of said anti-ovalbumin rabbit serum (2.5 ml/kg). Thirty minutes after the injection, the Arthus reaction was induced by the intradermal injection of an antigen solution (0.05 ml) containing 0.10 mg of ovalbumin to the abdomen shaved the day before. Two hours after the antigen challenge, the area of intradermal bleeding was measured and used as the index representing the grade of inflammatory reaction. Test compounds were intravenously injected 30 min before the antigen injection. Four guinea pigs per each group were used.

(4) Experimental Results

Table 21 shows the percent of inhibitory effect of each compound on the passive Arthus reaction. The percent inhibi- is expressed as the bleeding area of the challenged site (%) of the animal group injected with each compound relative to that (100%) of the group administered with the physiological saline. All compounds tested showed the anti-inflammatory effect.

(5) Judgement

Said results of the Arthus reaction experiment in Table 21 indicate that compounds of the present invention have the inhibitory effect on the Type III allergic reaction. Arthus reaction is an experimental inflammatory reaction which is observed with the dermal edema and bleeding, exemplified by such typical diseases as systemic lupus erythematosus, immune complex glomerulonephritis and serum sickness.

Example of Test 3

(Anti-inflammatory Activity Test)

The anti-inflammatory activity test of compounds of the present invention was similarly carried out as in the case of Example of Test 2. Results are shown in Table 22.

TABLE 21

| Test Compound | Percent inhibition (%) | | |
|---|---|---|---|
| | 0.1 mg/kg | 1 mg/kg | 3 mg/kg |
| Compound 10 | | 25.5 ± 17.4 | 64.8 ± 3.4 |
| Compound 12 | | 45.3 ± 6.7 | 67.8 ± 5.2 |
| Compound 17 | | 45.5 ± 3.5 | 14.9 ± 14.5 |
| Compound 18 | | 75.7 ± 3.9 | 60.8 ± 9.8 |
| Compound 26 | | 75.5 ± 1.6 | 77.3 ± 8.0 |
| Compound 30 | | 21.0 ± 5.9 | 15.4 ± 5.3 |
| Compound 31 | | 74.5 ± 6.7 | 15.9 ± 6.4 |
| Compound 32 | | 61.0 ± 4.2 | 57.4 ± 8.7 |
| Compound 40 | | 47.3 ± 7.4 | 63.5 ± 8.3 |
| Compound 46 | | 25.6 ± 11.3 | 74.4 ± 16.3 |
| Compound 49 | | 38.4 ± 5.1 | 39.3 ± 4.1 |
| Compound 53 | | 44.8 ± 15.0 | 58.7 ± 9.5 |
| Compound 62 | | 41.9 ± 8.9 | 57.4 ± 7.3 |
| Compound 77 | 40.4 ± 5.1 | | |
| Compound 78 | 32.5 ± 7.3 | | |
| Compound 86 | 37.2 ± 10.5 | | |
| Compound 90 | | 65.4 ± 8.5 | 69.6 ± 6.3 |
| Compound 121 | | 42.1 ± 8.3 | 59.8 ± 5.3 |
| Compound 123 | | 76.8 ± 12.0 | 84.5 ± 5.1 |

TABLE 22

| Test | Percent Inhibition (%) | | | |
|---|---|---|---|---|
| | 0.001 | 0.01 mg/kg | 0.1 mg/kg | 1 mg/kg |
| Compound 102 | 25.6 ± 13.7 | 31.5 ± 7.7 | 31.7 ± 12.8 | |
| Compound 107 | 30.7 ± 19.4 | 46.6 ± 15.9 | 48.1 ± 16.4 | |
| Compound 142 | | −3.3 ± 2.7 | 57.6 ± 12.6 | 84.8 ± 4.6 |
| Compound 143 | | 84.1 ± 5.2 | 52.5 ± 12.2 | 70.1 ± 1.8 |
| Compound 144 | | −15.2 ± 6.7 | 22.0 ± 30.1 | 23.9 ± 14.7 |
| Compound 175 | | 44.6 ± 20.1 | 62.5 ± 16.1 | 67.1 ± 4.4 |
| Compound 176 | | 57.5 ± 14.7 | 83.9 ± 10.1 | 92.4 ± 3.8 |
| Compound 188 | 84.2 ± 5.4 | 57.2 ± 14.5 | 86.2 ± 1.7 | |
| Compound 189 | 90.9 ± 4.0 | 73.6 ± 8.9 | 59.8 ± 9.7 | |
| Compound 190 | 12.7 ± 6.3 | 79.3 ± 4.7 | 76.9 ± 4.1 | |
| Compound 191, 192 | 82.1 ± 1.7 | 78.4 ± 5.6 | 88.0 ± 2.5 | |
| Compound 197 | 53.7 ± 15.4 | 77.6 ± 7.4 | 87.5 ± 3.0 | |

Example of Test 4

(Effect on the Adhesion of Cultured Cells Mediated by a Adhesion Molecule)

Experimental Materials and Methods (1) Test compounds

Compound 77

Compound 78

Compound 86

Compound 160

Compound 207

Compound 221

(2) Experimental methods and materials

HUVECs (Human umbilical vein endothelial cells: KURABO) were suspended in E-GM UV medium at the concentration of $5 \times 10^3$ cells/ml, 100-µl each aliquot thereof was distributed into a 96-well microplate and incubated in a 5% $CO_2$ containing air at 37° C. with the medium being replaced fresh 24 h later. The culture was continued for another 5 days, and the following experiment was performed after the confluent growth of the cells was confirmed.

In order to express ELAM-1 on HUVEC monolayers, IL-1β (IL-1β, Human, Recombinant: Genzym) was added to said culture (final concentration, 10 units/ml) and incubated for 4 h, then the test compound (final concentration, 10 µg/ml) containing liposome prepared with lecithin and cholesterol was added and further incubated or 1 h. Then human promyelocytic leukemia cell line HL-6 which had been cultured was added to said culture at the final concentration of $5 \times 10^5$ cells/ml and incubated for 15 min. After washing said culture with the culture medium 3 times to remove the non-adhering HL-60 cells, said culture was gently stirred overnight to strip HL-60 cells adhering to HUVEC monolayers and count. Percent inhibition of adhesion (%) was calculated from the following equation [Margaret, J. et al., Proc. Natl. Acad. Sci. USA, 88, 6224 (1991)].

Percent inhibition of adhesion (%) =

$$\left(1 - \frac{\text{Cell numbers at the time of test compound addition}}{\text{Cell numbers of the control culture}}\right) \times 100$$

(Results)

Results are shown in Table 23, which shows the percent inhibition by each test compound of adhesion of HL-60 cells to HUVEC monolayers. Liposomes (PC+CL: which contained no test compound) showed almost no inhibitory effect, while those containing test compound all showed the inhibitory effect.

TABLE 23

Adhesion Inhibitory activity of test compound

| Test compound | Adhesion inhibitory activity (%) |
|---|---|
| PC + CL | 1.9 ± 1.6 |
| Compound 77 | 21.0 ± 15.0 |
| Compound 78 | 20.7 ± 3.7 |
| Compound 86 | 38.0 ± 10.6 |
| Compound 160 | 49.0 ± 5.1 |
| Compound 207 | 43.8 ± 1.9 |
| Compound 221 | 32.9 ± 4.5 |

(Judgement)

From said results it became evident that those compounds have the activity to inhibit the adhesion of leukocytes to the endothelial cells. Results also indicate that these compounds may be useful as the therapeutics for various inflammatory diseases exemplified by the tumor metastasis or chronic articular rheumatism wherein the cell surface carbohydrate chain play an important role.

Related Example 1

(Synthesis of Compound 1)

To activated MS-4A (8 g) was added compound R10 (2.885 g, 6.56 mmol) and compound R4 (3.360 g, 7.48 mmol) in diethylether (10 ml) under Ar. To this mixture was added MeOTf (1.309 ml, 11.56 mmol) at −15° C. under stirring and further stirred overnight. After Et$_3$N (2 ml) was added to this reaction mixture, the mixture was diluted with EtOAc and filtered through celite into the container with NaHCO$_3$ solution. The filterate was washed with saturated NaCl solution, dried over anhydrous MgSO$_4$, filtered, and then evaporated in vacuo. The residue was purified with silica gel-column chromatography (c-300, 400 g, toluene:EtOAc=4:1).

[Compound 1]

3.627 g (68%)

Rf=0.44 (toluene:EtOAc=2:1)

$[\alpha]_D^{27}$ −4.8° (C=0.5, CHCl$_3$)

500 MHz $^1$H—NMR (CDCl$_3$, TMS) $\delta_H$; 1.968, 1.992, 2.030 (3S, 3H×3, Ac), 3.635 (m, 1H, H-5a), 3.840 (t, 1H, J=6.2 Hz, H-5b), 4.224 (dd, 1H, J=8.8, 10.6 Hz, H-2a), 4.309 (d, 1H, J=7.7 Hz, CH$_2$Ph), 4.494 (d, 1H, J=7.7 Hz, H-1b), 4.533 (d, 1H, J=12.5 Hz, CH$_2$Ph), 4.739 (d, 1H, J=12.5 Hz, CH$_2$Ph), 4.927 (dd, 1H, J=3.3, 10.6 Hz, H-3b), 5.163 (dd, 1H, J=8.1, 10.3 Hz, H-2b), 5.205 (d, 1H, J=8.4 Hz, H-1a), 5.366 (bd, 1H, J=3.7 Hz, H-4b), 5.730 (m, 1H, CH$_2$CH=CH$_2$).

Example 1

(Synthesis of Compound 2)

To activated MS-4A (600 mg) was added compound 1 (100 mg, 0.12 mmol) and compound R11 (68.6 mg, 0.15 mmol) in diethylether (5 ml) under the argon gas. To this mixture was added MeOTf (35 μl) at −20° C. and stirred at 0° for 3 h. After the mixture was stood overnight at −10° C., this reaction mixture was basified by the addition of Et$_3$N and then diluted with EtOAc. The reaction solution was filtered through celite into the container with NaHCO$_3$ solution. The filtrate was washed with saturated NaCl solution, this washing was dried over anhydrous MgSO$_4$. This mixture was filtered, and then evaporated in vacuo. The resulting residue was purified by silica gel-column chromatography (c-300, 400 g, toluene:EtOAc=4:1).

[Compound 2]

144.5 mg (94.3%)

R=0.35 (toluene:EtOAc=3:1)

$[\alpha]_D^{28}$ −11.1° (C=0.4, CHCl$_3$)

500 MHz $^1$H—NMR (CDCl$_3$, TMS) $\delta$H; 1.264 (d, 3H, J=9.2 Hz, H-6c), 1.768, 1.948, 2.001 (3s, 9H, Ac×3), 4.144 (t, 1H, J=9.5 Hz, H-2b), 4.179 (d, 1H, J=12.5 Hz, CH$_2$Ph), 4.365 (d, 1H, J=12.1 Hz, CH$_2$Ph), 4.400 (d, 1H, J=12.1 Hz, CH$_2$Ph), 4.421 (dd, 1H, J=8.4, 10.6 Hz, H-2a), 4.458 (d, 1H, J=11.4 Hz, CH$_2$Ph), 4.486 (d, 1H, J=12.1 Hz, CH$_2$Ph), 4.550 (d, 1H, J=11.7 Hz, CH$_2$Ph), 4.678 (d, 1H, J=8.1 Hz, H-1b), 4.710 (dd, 1H, J=9.2, 10.6 Hz, H-3a), 4.781 (dd, 1H, J=3.7, 10.3 Hz, H-3b), 4.978 (d, 1H, J=10.3 Hz, CH$_2$Ph), 5.091 (d, 1H, J=8.8 Hz, H-1a), 5.366 (bd, 1H, J=2.6 Hz, H-4b), 5.635 (m, 1H, CH$_2$CH=CH$_2$).

Example 2

(Synthesis of Compound 3)

Compound 2 (4.754 g, 3.706 mmol) was dissolved in dried methanol (50 ml) and added to the catalytic amount of 28% sodium methoxide. This mixture was stirred at 25° C. for 6 h. The reaction solution was evaporated in vacuo. The residue was purified by Sephadex column chromatography (LH-20; MeOH) followed by silica gel column chromatography (C-300, 250 g, CHCl$_3$:methanol=20:1).

[Compound 3]

3.536 g (86.8%)

Rf=0.61 (CHCl$_3$:methanol=12:1)

$[\alpha]_D^{26}$ −13.2° (c=0.3, CHCl$_3$)

500 MHz $^1$H—NMR (CD$_3$OD TMS) $\delta_H$; 1.126 (d, 3H, J=6.6 Hz, H-6c), 3.521 (dd, 1H, J=7.7, 9.5 Hz, H-2b), 3.651 (dd, 1H, J=3.3, 10.3 Hz, H-3b), 3.873 (dd, 1H, J=1.5, 11.0 Hz, H-2c), 4.103 (dd, 1H, J=3.3, 11.0 Hz, H-3c), 4.184 (d, 1H, J=12.5 Hz, CH$_2$Ph), 4.290 (dd, 1H, J=8.4, 10.6 Hz, H-3a), 5.129 (d,1H, J=8.4 Hz, H-1a), 5.660 (m, 1H, CH$_2$CH=CH$_2$).

Example 3

(Synthesis of Compound 4)

Compound 2 (1.028 g, 0.825 mmol) in methylamine (20 ml) was stirred at 20° C. for 42 h. After the reaction solution was evaporated in vacuo, the residue was dissolved in pyridine (10 ml) and acetic anhydride (10 ml) and this mixture stirred at 20° C. for 18 h. The reaction mixture was evaporated in vacuo. The residue was purified by silica gel column chromatography (C-300, 100 g, toluene:ethyl acetate=3:2) and Sephadex LH-20 column chromatography (methanol).

[Compound 4]

687.2 mg (71.9%)

Rf=0.41 (toluene:ethyl acetate=1:1)

$[\alpha]_D^{26}$ −54.5° (c=0.2, CHCl$_3$)

500 MHz, $^1$H—NMR (CDCl$_3$, TMS) $\delta_H$; 1.074 (d, 3H, J=6.6 Hz, H-6c), 1.825, 1.910, 1.965, 2.012 (4S, 12H, Ac×4), 3.386 (t, 1H, J=8.1 Hz, H-6b), 4.512 (d, 1H, J=8.1 Hz, H-1b), 4.898 (dd, 1H, J=3.7, 10.6 Hz, H-3b), 5.043 (dd, 1H, J=8.1, 10.6 Hz, H-2b), 5.094 (d, 1H, J=3.3 Hz, H-1c), 5.419 (d, 1H, J=3.7 Hz, H-4b), 5.801 (m, 1H, CH$_2$CH=CH$_2$), 6.010 (d, 1H, J=8.4 Hz, NH), 7.15~7.37 (m, 25H, CH$_2$Ph).

Example 4

(Synthesis of Compound 5)

To compound 4 (600 mg, 0.518 mmol) in methanol (30 ml) was added a catalytic amount of sodium methoxide and this mixture was stirred at 20° C. for 3 h. The reaction mixture was evaporated in vacuo. The resulting residue was purified by Sephadex column chromatography (LH-20; methanol).

[Compound 5]

535 mg (100%)

Rf=0.16 (toluene:MeOH=10:1)

$[\alpha]_D^{27}$ −55.10 (c=0.2, CH$_3$OH)

500 MHz, $^1$H—NMR (CD$_3$OD, TMS) $\delta_H$; 1.145 (d, 3H, J=6.2 Hz, H-6c) 1.926 (s, 3H, NHCOCH$_3$), 4.404 (d, 1H, J=7.7 Hz, H-1a or H-1b), 5.282 (d, 1H, J=3.7 Hz, H-1c), 5.871 (m, 1H, CH$_2$CH=CH$_2$), 7.16~7.37 (m, 25H, CH$_2$Ph).

Example 5

(Synthesis of Compound 6)

(1) The mixture of compound 2 (645 mg, 0.523 mmol), H$_2$ activated-Ir complex (123 mg, 0.1 mmol) and THF (15 ml) was stirred at room temperature for 14 h. After the evaporation of the solvent, THF (30 ml), H$_2$O (10 ml) and I2 (398 mg, 1.6 mmol) was added to the residue and the mixture was stirred at room temperature for 1 h. After the dilution with ethyl acetate, this mixture was washed with saturated Na$_2$S$_2$O$_3$ solution followed by with saturated NaCl solution. The organic phase was dried over MgSO$_4$. After the evaporation of the solvent, the residue was purified by silica gel column chromatography (hexane/ethyl acetate=1:1) to yield 513 mg of compound 54a (79.5%) and 112 mg of compound 54 (18%).

[Compound 54a]

Rf=0.54 (hexane/ethyl acetate=1:1)

500 MHz, $^1$H—NMR (CD$_3$OD, TMS) $\delta_H$; 7.80~6.98 (m, 29H, Ph), 5.367 (d, 1H, J=3.3 Hz, H-4b), 5.045 (d, 1H, 7=8.5 Hz, H-1a), 4.988 (dd, 1H, J=8.4, 10.2 Hz, H-2b), 4.830 (d, 1H, J=3.3 Hz, H-1c), 4.674 (d, 1H, J=8.0 Hz, H-1b), 2.000, 1.948, 1.769 (3s, 9H, 3×Ac), 1.173 (d, 3H, J=6.2 Hz, H-6c), 0.609 (t, 3H, J=7.3 Hz, —CH$_2$CH$_3$).

(2) The mixture of compound 54a (458 mg, 0.37 mmol), ethanol (18 ml) and H$_2$NNH.H$_2$O (2 ml) was refluxed for 28 h. After the evaporation of the solvent, the mixture was purified by LH-20 column chromatography to yield aminoderivative of compound 54a. To this product was added methanol (10 ml) and Ac$_2$0 (2 ml) and this mixture was stirred at room temperature for 30 minutes. After the evaporation of the solvent, the resulting residue was purified by silica gel column chromatography (CHCl$_3$/methanol=20:1) to yield 310 mg of compound 6 (82%).

[Compound 6]

Rf=0.43 (CHCl$_3$/methanol=15:1)

500 MHz, $^1$H—NMR (CD$_3$OD, TMS) $\delta_H$; 7.50~7.22 (m, 25H, Ph), 5.919 (d, 1H, J=7.0 Hz, NH), 5.132 (d, 1H, J=3.7 Hz, H-1c), 4.764 (d, 1H, J=7.7 Hz, H-1a), 4.510 (d, 1H, J=7.3 Hz, H-1b), 1.641 (s, 3H, Ac), 1.123 (d, 3H, J=6.2 Hz, H-6c), 0.840 (t, 3H, J=7.3 Hz, CH$_2$CH$_3$).

Example 6

(Synthesis of Compound 7)

The mixture of compound 6 (102 mg, 0.1 mmol), LeV$_2$O/ClCH$_2$CH$_2$Cl (1N solution, 0.5 mmol), pyridine (5 ml) and the catalytic amount of 4-DMAP was stirred for 15 h. After quenching with methanol, the solvent was evaporated. The residue was filtered by LH-20 (MeOH) and the solvent was evaporated in vacuo. Purification of the residue by silica gel column chromatography (ethyl acetate:toluene=4:1) yielded 45 mg of compound 7a (40%), 10 mg of compound 7b (8%) and 12 mg of compound 7c (10%) and recovered 25 mg of compound 6 (25%).

[Compound 7a]

Rf=0.19 (AcOEt/toluene=5:1)

$\delta_H$ 7.46~7.20 (m, 25H, aromatic H), 5.892 (d, 1H, J=8.3 Hz, NH), 5.129 (d, 1H, J=3.7 Hz, H-1c), 4.777 (d, 1H, J=7.7 Hz, H-1a), 4.562 (d, 1H, J=7.7 Hz, H-1b), 2.90~2.50 (m, 4H, —CH$_2$CH$_2$—), 2.179 (s, 3H, Me), 1.635 (s, 3H, NHAc), 1.133 (d, 3H, J=6.2 Hz, H-6c), 0.838 (t, 3H, J=7.3 Hz, Me).

[Compound 7b]

Rf=0.28 (AcOEt/toluene=5:1)

$\delta_H$ 7.42~7.20 (m, 25H, aromatic H), 5.916 (d, 1H, J=7.7 Hz, NH), 5.112 (d, 1H, J=3.7 Hz, H-1c), 4.914 (dd, 1H, J=8.0, 9.5 Hz, H-2b), 2.90~2.48 (m, 4H, —CH$_2$CH$_2$—), 2.181 (s, 3H, Me), 1.735 (s, 3H, NHAC), 1.082 (d, 3H, J=6.2 Hz, H-6c), 0.831 (t, 3H, J=7.3 Hz, Me).

[Compound 7c]

Rf=0.38 (AcOEt/toluene=5:1)

$\delta_H$ 7.39~7.20 (m, 25H, aromatic H), 5.867 (d, 1H, J=7.7 Hz, NHAC), 5.180 (dd, 1H, J=8.0, 10.2 Hz, H-2b) 5.080 (d, 1H, J=3.6 Hz, H-1c), 4.803 (d, 1H, J=8.5 Hz, H-1a), 4.742 (dd, 1H, J=3.7, 10.2 Hz, H-3b), 4.525 (d, 1H, J=8.0 Hz, H-1b), 2.85~2.40 (m, 8H, 2×—CH$_2$CH$_2$—), 2.183, 2.167 (2s, 6H, 2×Me), 1.613 (s, 3H, NH Ac), 1.106 (d, 3H, J=6.6 Hz, H-6c), 0.880 (t, 3H, J=7.3 Hz, Me).

$[\alpha]_D^{22}$ −23.4° (c=1.47, CHCl$_3$)

Example 7

(Synthesis of Compound 8)

The mixture of compound 7 (40 mg, 0.036 mmol), pyridine (2 ml), Ac$_2$O (2 ml) and the catalytic amount of 4-DMAP was stirred at room temperature for 15 h. After the solvent was evaporated with toluene, the mixture was purified by silica gel column chromatography (AcOEt/toluene=5:1) to yield quantitatively 43 mg of compound 8.

[Compound 8]

Rf=0.59 (AcOEt/toluene=5:1)

$\delta_H$ 7.41~7.16 (m, 25H, aromatic H), 5.906 (d, 1H, J=8.0 Hz, NHAc), 5.381 (d, 1H, J=3.2 Hz, H-4b), 5.082 (d, 1H, J=3.7 Hz, H-1c), 5.019 (dd, 1H, J=8.0, 10.2 Hz, H-2b), 4.862 (dd, 1H, J=3.3, 10.2 Hz, H-3b), 4.539 (d, 1H, J=8.4 Hz, H-1b), 2.81~2.50 (m, 4H, —CH$_2$CH$_2$—), 2.162, 2.042, 1.878, 1.775 (4S, 12H, 3×Ac, Me), 1.098 (d, 3H, J=6.2 Hz, H-6c), 0.841 (t, 3H, J=7.3 Hz, Me)

Example 8

(Synthesis of Compound 9)

The mixture of compound 8 (41 mg, 0.034 mmol), H$_2$NNH$_2$¥ACOH (16 mg, 0.17 mmol) and ethanol (2 ml) was stirred for 1 h at room temperature and this mixture was purified by LH-20 (methanol) to obtain 31 mg of the delevulinoylated derivative (82%). A portion (28 mg, 0.025 mmol) of this product, Me$_3$N.SO$_3$ (44 mg, 0.32 mmol) and DMF (0.8 ml) was stirred at 90° C. for 2 h. After passed through LH-20 (methanol), this reaction mixture was subjected to ion-exchange by Dowex (CHCl$_3$ methanol=1:1) and finally purified by silica gel column chromatography (CHCl$_3$:methanol=4:1) to yield 27 mg of compound 9 (88%).

[Compound 9]

Rf=0.56 (CHCl$_3$/MeOH=6:1)

$[\alpha]_D^{22}$–47.6° (C=1.8, CHCl$_3$)

$\delta_H$ (CD$_3$OD) 7.42~7.14 (m, 25H, aromatic H), 5.585 (d, 1H, J=3.7 Hz, H-4b), 5.317 (d, 1H, J=2.6 Hz, H-1c), 4.986 (dd, 1H, J=8.0, 10.3 Hz, H-2b), 4.370 (dd, 1H, J=3.7, 10.3 Hz, H-3b), 2.066, 1.958, 1.945 (3S, 9H, 3×Ac), 1.200 (d, 3H, J=6.6 Hz, H-6c), 0.903 (t, 3H, J=7.3 Hz, Me)

Example 9

(Synthesis of Compound 10)

The mixture of compound 9 (26 mg, 22 μmol), 20% Pd(OH)$_2$—C (26 mg) and methanol-H$_2$O (4:1) (2 ml) was hydrogenated at room temperature. After removed the catalyst by filtration, to the filtrates was added 1N NaOH (0.3 and this mixture was stirred at room temperature for 2 h. The reaction mixture was purified by LH-20 (methanol) to obtain quantitatively 7.4 mg of compound 10.

[Compound 10]

Rf=0.48 (nBuOH:EtOH:H$_2$O=2:1:1)

$\delta_H$ (CD$_3$OD) 5.036 (d, 1H, J=4.0 Hz, H-1c), 4.562 (d, 1H, J=7.7 Hz, H-1b), 4.439 (d, 1H, J=8.1 Hz, H-1a), 4.225 (dd, 1H, J=3.3, 9.5 Hz, H-3b), 4.216 (d, 1H, J=3.3 Hz, H-4b), 1.958 (s, 3H, NHAc), 1.166 (d, 3H, J=6.6 Hz, H-6c), 0.907 (t, 3H, J=7.4 Hz, Me)

Example 10

(Synthesis of Compound 11)

A mixture of compound 5 (23 mg, 23 μmol), Me$_3$N.SO$_3$ (31 mg, 0.22 mmol) and dried DMF (1 ml) was stirred at 90° C. for 40 minutes. The reaction mixture was passed through LH-20 (CHCl$_3$:methanol=1:1), and then subjected to ion-exchange with Dowex (MeOH:H$_2$O=8:1). Thus obtained mixture was purified by separation with preparative TLC (CHCl$_3$/methanol=2:1) followed by LH-20(CHCl$_3$/methanol=1:1) to yield 5.4 mg of compound 11 (18%).

[Compound 11]

Rf=0.26 (CHCl$_3$:methanol=2:1)

$\delta_H$ (CD$_3$OD:CDCl$_3$=1:1) 7.50~7.15 (m, 25H, aromatic H) 5.868 (m, H, —O—CH$_2$—CH=), 5.073 (d, 1H, J=2.6 Hz, H-4b), 4.637 (d, 1H, J=8.1 Hz, H-1b), 1.939 (s, 3H, NH Ac), 1.285 (d, 3H, J=5.9 Hz, H-6c)

Example 11

(Synthesis of Compound 12)

A mixture of compound 11 (5 mg, 3.8 μmol), methanol-H$_2$O (4:1) (2 ml) and 20% Pd(OH)$_2$—C (8 mg) was hydrogenated at room temperature. After the catalyst was removed by filtration, the solvent was evaporated in vacuo. The resulting residue was purified by LH-20 (methanol) to yield 3 mg of compound 12 (91%).

[Compound 12]

Rf=0.39 (nBuOH:ethanol:H$_2$O=2:1:1)

$\delta_H$ (CD$_3$OD) 5.076 (d, 1H, J=2 h, H-4b), 5.041 (d, 1H, J=3.7 Hz, H-1c), 4.727 (d, 1H, J=7.3 Hz, H-1b), 4.426 (d, 1H, J=8.4 Hz, H-1a), 4.423 (t, 1H, J=12.5 Hz, H-2b), 4.069 (dd, 1H, J=2.9, 12.5 Hz, H-3b), 1.951 (s, 3H, CO$_2$Me), 1.557 (m, 2H, —CH$_2$—), 1.280 (d, 3H, J=6.6 Hz, H-6c), 0.903 (t, 3H, J=7.3 Hz, CH$_3$)

Example 12

(Synthesis of Compound 13 and 14)

A solution of compound 5 (160 mg, 157 μmol) in DMF (5 ml) was mixed with 60% NaH (31 mg, 775 μmol) under stirring and further stirred for 15 minutes. To the mixture was added methyl bromoacetate (60 μl, 634 μmol). After stirring at 0° C. to room temperature for 2 h, methanol was added to the mixture to quench the excess NaH. The solvent was evaporated, the resulting residue was extracted with AcOEt and then washed with saturated NaHCO$_3$ solution, followed by saturated NaCl solution. After the organic phase was dried over MgSO$_4$, the solvent was evaporated. Purification of the resulting residue by silica gel column chromatography (AcOEt/toluene=3:1) yielded 81 mg of compound 13a (47%), 46 mg of compound 14 (25%) and 10 mg of compound 13b (6%).

[Compound 13a]

Rf=0.28 (AcOEt/toluene=4:1)

$[\alpha]_D^{22}$–42.4° (C=0.5, CHCl$_3$)

| C$_{61}$H$_{73}$NO$_{17}$ · H$_2$O | C (%) | H (%) | N (%) |
|---|---|---|---|
| Theoretical value | 65.99 | 6.76 | 1.26 |
| Found value | 66.34 | 6.72 | 1.14 |

$\delta_H$ 7.42~7.15 (m, aromatic H, 25H), 5.870 (d, 1H, J=7.0 Hz, NH), 5.825 (m, 1H, —O—CH$_2$—CH=), 5.109 (d, 1H, J=2.2 Hz, H-1c), 4.380 (d, 1H, J=17.6 Hz, —CH$_2$CO$_2$Me), 4.237 (d, 1H, J=17.6 Hz, —CH$_2$CO$_2$Me), 3.771 (s, 3H, CO$_2$Me), 3.183 (dd, 1H, J=3.3, 9.6 Hz, H-3b), 1.653 (s, 3H, NHAc), 1.106 (d, 3H, J=6.6 Hz, H-6c).

[Compound 14]

Rf=0.38 (AcOEt/toluene=2:1)

δH 7.40~7.20 (m, aromatic H, 25H), 5.850 (m, 1H, —O—CH$_2$—C$\underline{H}$=), 5.742 (d, 1H, J=7.0 Hz, N$\underline{H}$), 5.086 (d, 1H, J=7.7 Hz, H-1a), 5.026 (d, 1H, J=3.7 Hz, H-1c), 3.767, 3.731 (2S, 6H, 2×CO$_2$M$\underline{e}$), 1.649 (s, 3H, NHA$\underline{c}$), 1.106 (d, 3H, J=6.6 Hz, H-6c).

[Compound 13b]

Rf=0.44 (AcOEt/toluene=2:1)

[α]$_D^{22}$-20.9° (c=0.33, CHCl$_3$)

δ$_H$ 7.40~7.20 (m, aromatic H, 25H), 5.849 (m, 1H, —O—CH$_2$—C$\underline{H}$=), 5.703 (d, 1H, J=6.6 Hz, N$\underline{H}$), 4.928 (d, 1H, J=4.0 Hz, H-1c), 3.770 (s, 3H, CO$_2$M$\underline{e}$), 3.183 (t, 1H, J=8.4 Hz, H-2b), 1.624 (s, 3H, Ac), 1.014 (d, 3H, J=6.6 Hz, H-6c).

Example 13

(Synthesis of Compound 15 and 16)

A mixture of compound 13a (8.5 mg, 7.8 μmol), pyridine (1 ml), Ac$_2$O (1 ml) and a catalytic amount of 4-DMAP was stirred for 2 h at room temperature. The solvent was evaporated. The resulting residue was purified by silica gel column chromatography (AcOEt/toluene=3:1) to yield 7.4 mg of compound 15 (84%).

[Compound 15]

Rf=0.43 (AcOEt/toluene=3:1)

δ$_H$ 7.40~7.16 (m, 25H, aromatic H), 6.050 (d, 1H, J=8.5 Hz, N$\underline{H}$), 5.798 (m, 1H, —O—CH$_2$—C$\underline{H}$=), 5.470 (d, 1H, J=3.3 Hz, H-4b), 5.117 (d, 1H, J=4.1 Hz, H-1c), 4.968 (dd, 1H, J=8.4, 9.9 Hz, H-2b), 4.121 (d, 1H, J=16.9 Hz, —C$\underline{H}_2$CO$_2$Me), 4.065 (d, 1H, J=16.9 Hz, —C$\underline{H}_2$CO$_2$Me), 3.728 (s, 3H, CO$_2$M$\underline{e}$), 2.098, 1.954, 1.842 (3S, 9H, 3×Ac), 1.065 (d, 3H, J=6.2 Hz, H-6c)

Compound 14 (44 mg, 19 μmol) was subjected to acetylation as a previous manner and the reaction mixture was purified by silica gel column chromatography (AcOEt/toluene=2:1) to yield 34 mg of compound 16 (75%).

[Compound 16]

Rf=0.43 (AcOEt/toluene=2:1)

δ$_H$ 7.40~7.15 (m, 25H, aromatic H), 5.892 (d, 1H, J=7.3 Hz, N$\underline{H}$), 5.831 (m, 1H, —O—CH$_2$—C$\underline{H}$=), 5.401 (d, 1H, J=2.9 Hz, H-4b), 5.088 (d, 1H, J=3.7 Hz, H-1c), 5.002 (d, 1H, J=7.2 Hz, H-1a), 3.723, 3.715 (2S, 6H, 2×CO$_2$M$\underline{e}$), 1.859, 1.691 (2S, 6H, 2×NHA$\underline{c}$), 1.080 (d, 3H, J=6.6 Hz, H-6c)

Example 14

(Synthesis of Compound 17)

A mixture of compound 13 (14 mg, 12.8 μmol), 20% Pd(OH)2 (20 mg) and MeOH—H$_2$O (4:1) (30 ml) was hydrogenated at room temperature. After the removal of the catalyst, the filtrate was evaporated. To the residue was added 0.1N NaOH (250 μl) and methanol (500 μl) and stirred for 1 h at room temperature. Purification of the mixture through LH-20 (methanol) yielded 8.3 mg of compound 17 (99%).

[Compound 17]

Rf=0.30 (nBuOH/EtOH/H$_2$O=2:1:1)

δ$_H$ (CD$_3$OD) 5.034 (d, 1H, J=3.7 Hz, H-1c), 4.484 (d, 1H, J=7.7 Hz, H-1b), 4.432 (d, 1H, J=7.7 Hz, H-1a), 4.049 (d, 1H, J=16.1 Hz, —C$\underline{H}_2$CO$_2$Na), 4.006 (d, 1H, J=16.1 Hz, —C$\underline{H}_2$CO$_2$Na), 3.927 (d, 1H, J=3.0 Hz, H-4b), 3.267 (dd, 1H, J=3.0, 9.6 Hz, H-3b), 1.952 (s, 3H, NHA$\underline{c}$), 1.559 (m, 2H, —CH$_2$—), 1.173 (d, 3H, J=6.2 Hz, H-6c), 0.907 (t, 3H, J=7.3 Hz, C$\underline{H}_3$)

Example 15

(Synthesis of Compound 18)

A solution of compound 16 (20 mg, 16 μmol) dissolved in methanol (1 ml) and 0.1N NaOH (0.5 ml) was stirred for 1 h at room temperature and then hydrogenated by addition of 10% Pd—C (20 mg) at room temperature overnight. The removal of the catalyst, the filtrate was evaporated. To the residue was added methanol (2.8 ml), H$_2$O (0.2 ml) and 20% Pd(OH)$_2$ (25 mg) and the mixture was further hydrogenated for 42 h. After the catalyst was removed, the filtrate was evaporated in vacuo. The residue was passed through LH-20 (methanol) and then purified by preparative TLC to yield 7.5 mg of compound 18 (66%).

[Compound 18]

Rf=0.27 (nBuOH/EtOH/H$_2$O=2:1:1)

δ$_H$ (CD$_3$OD) 5.043 (d, 1H, J=3.7 Hz, H-1c), 4.619 (d, 1H, J=7.3 Hz, H-1b), 4.412 (d, 1H, J=8.4 Hz, H-1a), 4.352 (d, 1H, J=15.2 Hz, —C$\underline{H}_2$CO$_2$Na), 4.142 (d, 1H, J=15.2 Hz, —C$\underline{H}_2$CO$_2$Na), 1.956 (s, 1H, NHA$\underline{C}$), 1.557 (m, 1H, —C$\underline{H}_2$—), 1.212 (d, 3H, J=6.2 Hz, H-6c), 0.905 (t, 3H, J=7.0 Hz, CH$_3$)

Related Example 2

(Synthesis of Compound 20)

After compound R14 (11.99 g, 28.11 mmol) and compound R16 (8.20 g, 18.74 mmol) was dissolved in CH$_2$Cl$_2$ (188 ml) in the presence of MS4A (32.8 g), to this mixture was added MeOTf (3.4 ml, 30.04 mmol) and stirred under cooling. After the mixture was stood for 16.5 h, MeOTf (680 ml, 6.01 mmol) was further added to the mixture and stirred for 24 h. After the removal of MS by filtration through celite, the mixture was extracted with CHCl$_3$. This mixture was washed with NaHCO$_3$ solution and brine and then dried over MgSO$_4$. After the removal of MgSO$_4$ by filtration, the solvent was evaporated and then purified by silica gel column chromatography (PhMe:AcOEt=3:1) to yield 13.58 g of compound 20 (88.8%)

[Compound 20]

Rf 0.38 (PhMe:AcOEt=3:1), [α]$_D$-20.9° (C1.0, CHCl$_3$
$^1$H—NMR (CDCl$_3$) δ1.543 (3H, s, Ac), 1.836 (3H, s, Ac), 1.987 (3H, s, Ac), 3.283 (1H, dd, J$_{66}$=9.0 Hz, J$_{65}$=5.5 Hz, H6-b), 3.342 (1H, dd, J$_{6'6}$=9.5 Hz, J$_{6'5}$=7.0 Hz, H6'-b), 3.490 (1H, brt, J$_{56}$=J$_{56}$=6.5 Hz, H5-b), 3.603 (1H, dt, J$_{56}$=4.5 Hz, J$_{54}$=9.5 Hz, H5-a), 3.806 (2H, m, H4-a and H6-a), 4.002 (1H, tdd, J=1.5, 6.5, 13.0 Hz, H3-All), 4.193 (1H, d, J=11.5 Hz, CH$_2$Ph), 4.253 (1H, tdd, J=1.5, 4.0, 13.5 Hz, H3'-All), 4.339 (1H, dd, J$_{21}$=8.5, J$_{23}$=10.5 Hz, H2-a), 4.342 (1H, dd, J$_{6'5}$=5.0, J$_{6'6}$=10.5 Hz, H6'-a), 4.388 (1H, d, J=11.5 Hz, CH$_2$Ph), 4.547 (1H, d, J$_{12}$=8.5 Hz, H1-b), 4.736 (1H, dd, J$_{34}$=9.0, J$_{32}$=10.5 Hz, H3-a), 4.755 (1H, dd, J$_{34}$=3.0, J$_{32}$=10.5 Hz, H3-b), 4.959 (1H, dd, J$_{21}$=8.0, J$_{23}$=10.0 Hz, H2-b), 5.019 (1H, dd, J=1.5, 10.5 Hz, H1$_{cis}$-All), 5.105 (1H, dd, J=1.5, 17.0 Hz, H1$_{trans}$-All), 5.183 (1H, d, J$_{12}$=8.5 Hz, H1-a), 5.275 (1H, d, J$_{43}$=3.0 Hz, H4-b), 5.499 (1H, s, CHPh), 5.650 (1H, m, H2-All), 7.14~7.19 (4H, m, Ph), 7.24~7.36 (4H, m, Ph), 7.44~7.46 (2H, m, Ph), 7.75~7.78 (2H, m, Phth), 7.87 (2H, m, Phth).

Related Example 3

(Synthesis of Compound 21)

To a solution of compound 20 (6.0 g, 7.5 mmol) and BH$_3$.N Me$_3$ (1.07 g, 14.67 mmol) dissolved in THF (30 ml) was added TMSOTf (1.33 ml, 7.33 mmol) and the mixture was stirred under cooling. After the extraction with AcOEt, the mixture was washed with NaHCO$_3$ solution and brine and dried over MgSO$_4$. After the removal of MgSO$_4$, the solvent was evaporated and the residue was purified by silica gel column chromatography (PhMe:AcOEt=3:1) to yield 5.37 g of compound 21 (89.3%).

[Compound 21]

Rf 0.24 (PhMe:AcOEt=3:1), [α]$_D$–16.9° (C1.0, CHCl$_3$) $^1$H—NMR (CDCl$_3$) δ1.399 (3H, s, Ac), 1.867 (3H, s, Ac), 2.041 (3H, s, Ac), 3.447 (1H, dd, J$_{65}$=7.5, J$_{66}$=9.5 Hz, H6-b), 3.531 (1H, dd, J$_{6'5}$=7.5, J$_{6'6}$=9.5 Hz, H6'-b), 3.605~3.685 (2H, m, H4-a and H6-a), 3.729 (1H, dd, J$_{6'5}$=5.5, J$_{6'6}$=11.0 Hz, H6'-a), 3.858~3.892 (2H, m, H5-a and H5-b), 4.001 (1H, tdd, J=1.5, 6.5, 13.0 Hz, H3-All), 4.242 (1H, d, J=2.0 Hz, OH4-a), 4.257 (1H, tdd, J=1.5, 2.0, 15.0 Hz, H3'-All), 4.273 (1H, dd, J$_{21}$=9.0, J$_{23}$=11.0 Hz, H2-a), 4.417 (1H, d, J=11.0, CH$_2$Ph), 4.420 (1H, d, J$_{12}$=8.0 Hz, H1-b), 4.486 (1H, dd, J$_{34}$=8.0, J$_{32}$=11.0 Hz, H3-a), 4.529 (1H, d, J=12.0 Hz, CH$_2$Ph), 4.620 (2H, s, CH$_2$Ph), 4.809 (1H, dd, J$_{34}$=3.0, J$_{32}$=10.0 Hz, H3-b), 4.991 (1H, dd, J=1.5, 10.5 Hz, H1$_{cis}$-All), 5.061 (1H, d, J$_{12}$=8.5 Hz, H1-a), 5.074 (1H, dd, J=1.5; 17.5 Hz, H1$_{trans}$-All), 5.106 (1H, dd, J$_{21}$=8.0, J$_{23}$=10.5 Hz, H2-b), 5.309 (1H, d, J$_{43}$=2.5 Hz, H4-b), 5.625~5.702 (1H, m, H2-All), 7.261~7.376 (10H, m, Ph), 7.763 (2H, dd, J=3.0, 5.5 Hz, Phth), 7.872 (2H, dd, J=3.0, 5.5 Hz, Phth).

Example 16

(Synthesis of Compound 22α and 22β)

To a solution of compound 21 (4.09 g, 5.00 mol) and compound R11 (4.65 g, 10.01 mmol) dissolved in CH$_3$CN (50 ml) in the presence of MS3A (16 g) was added MeOTf (1.1 ml, 10.03 mmol) and this mixture was stirred under cooling. After the removal of MS by filtration through celite, the mixture was extracted with AcOEt and washed with NaHCO$_3$ solution and brine. This washing was dried over MgSO$_4$. After the removal of MgSO$_4$ by filtration, the solvent was evaporated and the residue was purified by silica gel column chromatography (PhMe:AcOEt=3:1) to yield 4.68 g of compound 22 (75.8%).

[Compound 22α]

Rf 0.45 (PhMe:AcOEt=3:1), [α]$_D$–29.10 (C1.0, CHCl$_3$) $^1$H—NMR (CDCl$_3$) δ1.281 (3H, d, J=6.5 Hz, H-6c), 1.678 (3H, s, Ac), 1.841 (3H, s, Ac), 1.989 (3H, s, Ac), 3.338 (1H, t, J$_{56}$=J$_{56}$=8.0 Hz, H5-b), 3.521 (1H, td, J$_{56}$=J$_{56}$=2.0, J$_{54}$=7.5 Hz, H5-a), 3.581~3.640 (3H, m, H6-a, H6-b and H4-c), 3.89~3.955 (3H, m, H6'-b, H3-c and H-All), 3.986 (1H, t, J$_{43}$=J$_{45}$=9.5 Hz, H4-a), 4.122 (1H, dd, J$_{21}$=4.0, J$_{23}$=10.0 Hz, H2-c), 4.187 (1H, tdd, J=1.5, 5.0, 13.0, H3'-All), 4.194 (1H, d, J$_{12}$=7.5 Hz, H1-b) 4.255 (1H, d, J=12.0 Hz, CH$_2$Ph), 4.276 (1H, dd, J$_{21}$=8.5, J$_{23}$=10.5 Hz, H2-a), 4.427 (1H, dd, J$_{34}$=3.5, J$_{32}$=10.5 Hz, H3-b), 4.445 (2H, s, CH$_2$Ph), 4.463 (1H, dd, J$_{6'5}$=5.5, J$_{6'6}$=12.5 Hz, H6'-a), 4.590 (1H, d, J=11.0 Hz, CH$_2$Ph), 4.630 (1H, d, J=11.5 Hz, CH$_2$Ph), 4.695 (1H, d, J=11.0 Hz, CH$_2$Ph), 4.71 (1H, m, H5-c), 4.734 (1H, d, J=12.5 Hz, CH$_2$Ph), 4.790 (1H, dd, J$_{34}$=90, J$_{32}$=10.5 Hz, H3-a), 4.812 (1H, d, J=11.0 Hz, CH$_2$Ph), 4.952 (1H, d, J$_{12}$=9.0 Hz, H1-a), 4.980 (1H, dd, J$_{21}$=8.0, J$_{23}$=10.5 Hz, H2-b), 4.95 (3H, m, H1$_{cis}$-All, CH$_2$Ph), 5.029 (1H, ddd, J=1.5, 3.0, 17.5 Hz, H1$_{trans}$-All), 5.159 (1H, d, J$_{12}$=4.0 Hz, H1-c), 5.339 (1H, d, J$_{43}$=3.0 Hz, H4-b), 5.626 (1H, m, H2-All), 7.108~7.408 (25H, m, Ph), 7.789 (2H, dd, J=3.0, 5.5 Hz, Phth), 7.871 (2H, dd, J=3.0, 5.5 Hz, Phth)

[Compound 22β]

Rf 0.48 (PhMe:AcOEt=3:1) $^1$H—NMR (CDCl$_3$) δ1.020 (3H, d, J=6.0 Hz, H-6c), 1.820 (3H, s, Ac), 1.872 (3H, s, Ac), 1.907 (3H, s, Ac), 3.186 (1H, q, J=6.5 Hz, H-5c), 3.989 (1H, br.dd, J=6.5, 13.0 Hz, OCH$_2$CH=CH$_2$), 4.064 (1H, d, J=9.5 Hz, H-1c), 4.118 (1H, d, J=11.5 Hz, CH$_2$Ph), 4.539 (1H, d, J=12.5 Hz, CH$_2$Ph), 4.587 (1H, d, J=12.0 Hz, CH$_2$Ph), 4.598 (1H, d, J=11.5 Hz, CH$_2$Ph), 4.666 (1H, d, J=12.5 Hz, CH$_2$Ph), 4.698 (1H, d, J=12.5 Hz, CH$_2$Ph), 4.767 (1H, d, J=11.5 Hz, CH$_2$Ph), 4.808 (1H, dd, J=8.0, 10.5 Hz, H-2b), 4.923 (1H, d, J=8.0 Hz, H-1a), 4.976 (1H, dd, J=2.0, 10.5 Hz, OCH$_2$CH=CH$_2$ cis), 5.056 (1H, dd, J=1.5, 17.5 Hz, OCH$_2$CH=CH$_2$ trans), 5.121 (1H, d, J=8.5 Hz, H-1b), 5.180 (1H, d, J=3.5 Hz, H-4b), 5.61–5.67 (1H, m, OCH$_2$CH=CH$_2$), 7.14–7.40 (25H, m, Ph×5), 7.74–7.87 (4H, m, Phth)

Example 17

(Synthesis of Compound 23)

To a solution of compound 22 (143.1 mg, 115.9 μmol) dissolved in methanol (2 ml) was added 28% NaOMe—MeOH solution (7.1 ml, 34.8 μmol) and stirred for 7.5 h at room temperature. After the evaporation of the solvent, purification of the residue through LH-20 (methanol) and silica gel column chromatography (CHCl$_3$:methanol=19:1) yielded 86.5 mg of compound 23 (67.3%).

[Compound 23]

Rf 0.59 (CHCl$_3$:MeOH=19:1), [α]$_D$–46.6° (C1.0, CHCl$_3$) $^1$H—NMR (CDCl$_3$) δ1.098 (3H, d, J=7.0 Hz, H-6c), 3.417 (2H, m, H2-b and H6-a), 4.039 (1H, d, J$_{12}$=7.5H, H1-b), 4.049 (1H, dd, J$_{12}$=3.5, J$_{23}$=10.0 Hz, H2-c), 4.216 (1H, tdd, J=1.5, 5.0, 13.0 Hz, H-3All), 4.331 (1H, dd, J$_{12}$=8.5, J$_{23}$=11.0 Hz, H2-a), 4.55 (1H, m, H5-c), 4.569 (1H, d, J=11.5 Hz, CH$_2$Ph), 4.614 (1H, d, J=11.5 Hz, CH$_2$Ph), 4.692 (1H, d, J=11.5 Hz, CH$_2$Ph), 4.730 (1H, d, J=11.5 Hz, CH$_2$Ph), 4.915 (1H, d, J=11.5 Hz, CH$_2$Ph), 4.990 (1H, dd, J=1.5, 10.5 Hz, H1$_{cis}$-All), 5.049 (1H, d, J$_{12}$=8.5 Hz, H1-a), 5.060 (1H, dd, J=1.5, 17.0 Hz, H1$_{trans}$-All), 5.134 (1H, d, J$_{12}$=3.5 Hz, H1-c), 5.65 (1H, m, H2-All), 7.2~7.4 (25H, m, Ph), 7.679 (2H, dd, J=3.0, 5.5 Hz, Phth), 7.778 (2H, dd, J=3.0, 5.5 Hz, Phth).

Example 18

(Synthesis of Compound 24)

To compound 22α (308.4 mg, 249.8 μmol) in ethanol (6.6 ml) was added MeNHNH$_2$ (13.2 ml, 250.4 mmol) and stirred at 75° C. for 17.5 h. After ethanol and MeNHNH$_2$ were evaporated in vacuo, Ac$_2$O (1.5 ml) and methanol (3.0 ml) were added to the mixture and stirred for 24 h at room temperature. After the evaporation of Ac₂O and methanol in vacuo, purification of the residue by silica gel column chromatography (CHCl₃:methanol=19:1) yielded 249.0 mg of compound 24 (97.7%).

[Compound 24]

Rf 0.27 (CHCl₃:MeOH=19:1), [α]$_D$–62.2° (C1.0, CHCl₃) ¹H—NMR (CD₃OD) 1.198 (3H, d, J=6.5 Hz, H-6c) 1.929 (3H, s, Ac), 3.393 (1H, ddd, J$_{56}$=2.5, J$_{56'}$=3.0, J$_{54}$=9.0 Hz, H5-a), 3.433 (1H, dd, J$_{34}$=3.5, J$_{32}$=9.5 Hz, H-b), 3.530 (1H, dd, J$_{21}$=8.0, J$_{23}$=9.5 Hz, H2-b), 3.794 (1H, t, J$_{43}$=J$_{45}$=9.0 Hz, H4-a), 3.842 (1H, d, J$_{43}$=3.0, H4-b), 3.930 (1H, dd, J$_{21}$=4.0, J$_{23}$=6.5 Hz, H2-c), 3.945 (1H, t, J$_{32}$=J$_{34}$=9.5 Hz, H3-a), 4.026 (1H, tdd, J=1.5, 5.5, 13.0 Hz, H3-All), 4.266 (1H, tdd, J=1.5, 5.0, 13.0 Hz, H3'-All), 4.370 (1H, d, J=12.0 Hz, CH₂Ph), 4.434 (1H, d, J$_{12}$=9.0 Hz, H1-b), 4.436 (1H, d, J$_{12}$=7.5 Hz, H1-a), 4.482 (1H, d, J=11.0 Hz, CH₂Ph), 4.501 (2H, S, CH₂Ph), 4.513 (1H, d, J=12.0 Hz, CH₂Ph), 4.607 (1H, d, J=11.0 Hz, CH₂Ph), 4.626 (1H, d, J=12.0 Hz, CH₂Ph), 4.710 (1H, d, J=11.5 Hz, CH₂Ph), 4.719 (1H, d, J=12.0 Hz, CH₂Ph), 4.880 (1H, d, J=11.5 Hz, CH₂Ph), 5.039 (1H, d, J$_{12}$=3.5 Hz, H1-c), 5.126 (1H, tdd, J=1.5, 2.0, 10.5 Hz, H1$_{cis}$-All), 5.243 (1H, tdd, J=1.5, 2.0, 17.5 Hz, H1$_{trans}$-All), 5.885 (1H, m, H2-All), 7.167–7.361 (25H, m, Ph).

Example 19

(Synthesis of Compound 25)

Compound 24 (48.5 mg, 47.5 μmol) and Et₃N¥SO₃ (17.2 mg, 94.9 μmol) were dissolved in DMF (3 ml) and stirred for 2 h at 90° C. The reaction mixture was subjected to LH20 gel filtration (CHCl₃:MeOH=1:1) and then converted to the sodium salt with Dowex 50 (Na+ type) (CHCl₃:MeOH=1:1). Purification of the reaction mixture by silica gel column chromatography (CHCl₃:MeOH=10:1) yielded 23.3 mg of compound 25a (43.7%), 1.6 mg of compound 25b (3%) and 2.6 mg of compound 25c (4.1%).

[Compound 25a]

Rf 0.53 (CHCl₃:MeOH=5:1), [α]$_D$–63.5° (c0.92, CHCl₃) ¹H—NMR (CD₃OD) δ1.181 (3H, d, J=6.5 Hz, H-6c), 1.957 (3H, s, Ac), 3.700 (1H, dd, J$_{21}$=7.5, J$_{23}$=9.5 Hz, H2-b), 3.784 (1H, t, J$_{43}$=J$_{45}$=9.0 Hz, H4-a), 3.930 (1H, d, J$_{43}$=3.5 Hz, H4-c), 3.984 (1H, t, J$_{32}$=J$_{34}$=9.5 Hz, H3-a), 4.060 (1H, dd, J$_{34}$=3.0, J$_{32}$=10.0 Hz, H-c), 4.185 (1H, dd, J$_{34}$=3.5, J$_{32}$=10.0 Hz, H3-b), 4.279 (1H, d, J$_{43}$=3.0 Hz, H4-b), 4.355 (1H, d, J=12.0 Hz, CH₂Ph), 4.420 (1H, d, J$_{12}$=8.0 Hz, H1-a), 4.473 (1H, d, J=12.0 Hz, CH₂Ph), 4.505 (1H, d, J=12.0 Hz, CH₂Ph), 4.512 (1H, d, J=12.0 Hz, CH₂Ph), 4.539 (1H, d, J$_{12}$=7.5 Hz, H1-b), 4.607 (1H, d, J=11.5 Hz, CH₂Ph), 4.701 (1H, d, J=11.5 Hz, CH₂Ph), 4.716 (1H, d, J=11.5 Hz, C H₂Ph), 4.871 (1H, d, J=11.5 Hz, CH₂Ph), 5.034 (1H, d, J$_{12}$=3.5 Hz, H1-c), 5.126 (1H, dd, J=1.5, 10.5 Hz, H1$_{cis}$-All), 5.242 (1H, dd, J=1.5, 17.5 Hz, H1$_{trans}$-All), 5.864 (1H, m, H2-All), 7.148–7.362 (25H, m, Ph)

[Compound 25b]

¹H—NMR (CD₃OD) 1.266 (3H, d, J=6.5 Hz, H-6c), 2.009 (3H, s, Ac), 3.677 (1H, dd, J=3.5, 9.5 Hz, H-3b), 4.033 (1H, tdd, J=1.5, 6.0, 13.0 Hz, OCH₂CH=CH₂), 4.060 (1H, dd, J=2.0, 10.0 Hz, H-3c), 4.257 (1H, tdd, J=1.5, 5.5, 13.0 Hz, OCH₂CH=CH₂) 4.335 (1H, d, J=12.0 Hz, OCH₂Ph), 4.413 (1H, dd, J=8.0, 9.5 Hz, H-2b), 4.536 (1H, d, J=8.0 Hz, H-1b), 4.611 (1H, d, J=11.5 Hz, OCH₂Ph), 4.622 (1H, d, J=11.5 Hz, OCH₂Ph), 4.708 (1H, d, J=11.5 Hz, OCH₂Ph), 4.719 (1H, d, J=11.5 Hz, OCH₂Ph), 4.965 (1H, q, H=6.5 Hz, H-5c), 5.022 (1H, d, J=4.0 Hz, H-1c), 5.129 (1H, ddd, J=1.0, 1.5, 10.5 Hz, OCH₂CH=CH₂ cis), 5.240 (1H, ddd, J=1.0, 1.5, 17.0 Hz, OCH₂CH=CH₂ trans), 5.85 (1H, m, OCH₂CH=CH₂), 7.15–7.36 (25H, m, Ph×5)

[Compound 25c]

¹H—NMR (CD₃OD) δ1.441 (3H, d, J=6.0 Hz, H-6c), 2.085 (3H, s, Ac), 3.938 (1H, dd, J=3.5, 10.0 Hz, H-2c), 4.023 (1H, br.dd, J=6.0, 13.0 Hz, OCH₂CH=CH₂), 4.078 (1H, dd, J=2.5, 10.0 Hz, H-3c), 4.248 (1H, br.dd, J=5.0, 13.0 Hz, OCH₂CH=CH₂), 4.328 (1H, d, J=11.5 Hz, OCH₂Ph), 4.471 (1H, dd, J=3.0, 9.0 Hz, H-3b), 4.488 (1H, d, J=2.0 Hz, H-4c), 4.502 (1H, d, J=12.0 Hz, OCH₂Ph), 4.517 (1H, d, J=11.5 Hz, OCH₂Ph), 4.600 (1H, dd, J=7.5, 9.5 Hz, H-2b), 4.625 (1H, d, J=11.5 Hz, OCH₂Ph), 4.691 (1H, d, J=7.5 Hz, H-1b), 4.720 (1H, d, J=11.5 Hz, OCH₂Ph), 4.785 (1H, d, J=11.5 Hz, OCH₂Ph), 4.960 (1H, q, J=7.5 Hz, H-5c), 5.019 (1H, d, J=3.5 Hz, H-1c), 5.126 (1H, br.dd, J=1.0, 10.5 Hz, OCH₂CH=CH₂ cis), 5.163 (1H, d, J=3.0 Hz, H-4b), 5.234 (1H, br.dd, J=2.0, 17.5 Hz, OCH₂CH=CH₂ trans), 5.85 (1H, m, OCH₂CH=CH₂), 7.13–7.38 (25H, m, Ph×5).

Example 20

(Synthesis of Compound 26)

Compound 25 (28.1 mg, 25.0 μmol) was dissolved in a solution of methanol (1.6 ml) and H₂O (0.4 ml) and stirred with 20% Pd(OH)₂—C (28 mg) under H₂ for 3 h. After the removal of 20% Pd(OH)₂—C by filtration through celite, the mixture was purified by LH-20 gel filtration (MeOH) to yield 16.9 mg of compound 26 (quantitative).

[Compound 26]

Rf 0.44 (nBuOH:EtOH:H₂O=2:1:1),

[α]$_D$–63.40 (C 1.14, MeOH)

¹H—NMR (CD₃OD) 0.908 (3H, t, J=7.5 Hz, OCH₂CH₂CH₃), 1.169 (3H, d, J=6.5 Hz, H-6c), 1.559 (2H, m, OCH₂CH₂CH₃), 1.974 (3H, s, Ac), 3.394 (1H, td, J$_{56}$=J$_{56}$'=2.5, J$_{54}$=9.5 Hz, H5-a), 3.427 (1H, td, J=6.5, 9.5 Hz, OCH₂CH₂CH₃), 3.667 (1H, dd, J$_{21}$=7.5, J$_{23}$=9.5, H2-b), 3.818 (1H, td, J=0.5, 9.5 Hz, OCH₂CH₂CH₃), 4.015 (1H, t, J$_{32}$=J$_{34}$=10.0 Hz, H3-a), 4.148 (1H, dd, J$_{34}$=3.0, J$_{32}$=9.5 Hz, H3-b), 4.203 (1H, d, J$_{43}$=3.0 Hz, H4-b), 4.470 (1H, d, J$_{12}$=8.5 Hz, H1-a), 4.492 (1H, d, J$_{12}$=7.5 Hz, H1-b), 5.040 (1H, d, J$_{12}$=4.0 Hz, H1-c)

Example 21

(Synthesis of Compound 27, 28 and 29)

To compound 24 (101.3 mg, 99.3 μmol) and 60% NaH (7.9 mg, 197.5 μmol) in DMF (5 ml) was added BrCH₂COOMe (18.8 μl, 198.6 μmol) and stirred at 0° C. for 1.5 h. After methanol (5 ml) was added to the mixture, the resulting mixture was extracted with AcOEt, washed with NaHCO₃ solution and brine and dried over MgSO₄. After the removal of MgSO₄, the solvent was evaporated. Purification of the resulting residue with LH-20 gel filtration (MeOH) and HPLC (CHCl₃:MeOH=50:1) yielded 27.7 mg of compound 28 (23.9%), 22.6 mg of compound 27 (20.8%) and 18.4 mg of compound 29 (16.9%).

[Compound 28]

Rf 0.77 (CHCl₃:MeOH=19:1), [α]$_D$–42.1° (c 1.51, CHCl₃) ¹H—NMR (CDCl₃) δ1.109 (3H, d, J=6.5 Hz, H-6c), 1.852 (3H, s, Ac), 3.168 (1H, brdd, H2-a), 3.301 (1H, dd, $J_{34}=3.0$, $J_{32}=9.0$ Hz, H3-b), 3.382 (1H, brs, OH4-b), 3.443 (1H, dd, $J_{21}=8.0$, $J_{23}=9.0$ Hz, H2-b), 3.700 (1H, brs, H4-c), 3.837 (1H, t, $J_{43}=J_{45}=8.0$ Hz, H4-a), 4.004 (1H, brs, H4-b), 4.036 (1H, dd, $J_{21}=3.5$, $J_{23}=10.5$ Hz, H2-c), 4.081 (1H, tdd, J=1.5, 5.5, 13.0 Hz, H3-All), 4.159 (1H, d, J=17.5 Hz, CH$_2$COOMe), 4.277 (1H, tdd, J=1.5, 5.5, 13.0 Hz, H3'-All), 4.331 (1H, t, $J_{32}=J_{34}=8.0$ Hz, H3-a), 4.338 (1H, d, J=16.0 Hz, CH$_2$COOMe), 4.431 (1H, d, J=12.0 Hz, CH$_2$Ph), 4.438 (2H, s, CH$_2$Ph), 4.446 (1H, d, $J_{12}=7.5$ Hz, H1-b), 4.454 (1H, d, J=15.5 Hz, CH$_2$COOMe), 4.460 (1H, d, J=17.0 Hz, CH$_2$COOMe), 4.465 (1H, d, J=12.0 Hz, CH$_2$Ph), 4.591 (1H, d, J=11.5 Hz, CH$_2$Ph), 4.601 (1H, d, J=11.5 Hz, CH$_2$Ph), 4.658 (1H, d, J=11.5 Hz, CH$_2$Ph), 4.695 (1H, d, J=11.5 Hz, CH$_2$Ph), 4.928 (1H, d, J=12.0 Hz, CH$_2$Ph), 5.108 (1H, d, $J_{12}=3.5$ Hz, H1-c), 5.112 (1H, d, $J_{12}=7.5$ Hz, H1-a), 5.143 (1H, dd, J=1.5, 2.0, 10.0 Hz, H1$_{cis}$-All), 5.249 (1H, ddd, J=1.5, 2.0, 17.0 Hz, H1$_{trans}$-All), 5.895 (1H, m, H2-All), 7.22-7.36 (26H, m, NHAc, Ph)

[Compound 27]

Rf 0.68 (CHCl$_3$:MeOH=19:1), [α]$_D$-66.70 (c 0.34, CHCl$_3$) $^1$H—NMR (CDCl$_3$) δ1.111 (3H, d, J=6.0 Hz, H-6c), 1.516 (3H, s, Ac), 3.379 (1H, dd, $J_{34}=3.0$, $J_{32}=10.0$ Hz, H3-b), 3.599 (1H, brd, $J_{43}=2.0$ Hz, H4-c), 3.815 (1H, dd, $J_{34}=2.5$, $J_{32}=10.0$ Hz, H3-c), 3.877 (1H, dd, J=6.0, 11.0 Hz, H5-c), 3.967 (1H, d, $J_{43}=3.0$ Hz, H4-b), 4.058 (1H, dd, $J_{21}=4.0$, $J_{23}=10.5$ Hz, H2-c), 4.141 (1H, tdd, J=1.5, 6.0, 12.5 Hz, H3-All), 4.272 (1H, d, J=17.5 Hz, CH$_2$COOMe), 4.324 (1H, tdd, J=1.5, 5.5, 13.0 Hz, H3'-All), 4.390 (1H, d, $J_{12}=7.5$ Hz, H1-b), 4.408 (1H, d, J=11.0 Hz, CH$_2$Ph), 4.452 (1H, d, J=12.0 Hz, CH$_2$Ph), 4.543 (1H, d, J=17.0 Hz, CH$_2$COOMe), 4.552 (2H, S, CH$_2$Ph), 4.596 (1H, d, J=11.5 Hz, CH$_2$Ph), 4.634 (1H, d, J=11.0 Hz, CH$_2$Ph), 4.687 (1H, d, J=11.5 Hz, CH$_2$Ph), 4.714 (1H, d, J=11.0 Hz, CH$_2$Ph), 4.750 (1H, d, J=11.5 Hz, CH$_2$Ph), 4.946 (1H, d, J=11.0 Hz, CH$_2$Ph), 5.026 (1H, brd, J=4.0 Hz, H1-a), 5.145 (1H, d, $J_{12}=3.5$ Hz, H1-c), 5.207 (1H, dd, J=1.5, 10.5 Hz, H1$_{cis}$-All), 5.281 (1H, dd, J=1.5, 17.0 Hz, H1$_{trans}$-All), 5.85~5.92 (1H, m, H2-All), 7.058 (1H, d, J=8.0 Hz, NHAC), 7.22~7.35 (25H, m, Ph)

[Compound 29]

Rf 0.61 (CHCl$_3$:MeOH=19:1), [α]$_D$-51.4° (c 1.03, CHCl$_3$) $^1$H—NMR (CDCl$_3$) δ1.037 (3H, d, J=6.0 Hz, H-6c), 1.669 (3H, s, Ac), 3.238 (1H, dd, $J_{21}=7.5$, $J_{23}=9.5$ Hz, H2-b), 3.633 (1H, dd, $J_{34}=3.5$, $J_{32}=9.0$ Hz, H3-b), 3.823 (1H, dd, $J_{34}=3.0$, $J_{32}=10.0$ Hz, H3-c), 4.000 (1H, d, $J_{43}=3.5$ Hz, H4-b), 4.173 (1H, brq, J=7.0 Hz, H5-c), 4.310 (1H, tdd, J=1.5, 5.5, 12.5 Hz, H3-All), 4.358 (1H, d, J=18.0 Hz, CH$_2$COOMe), 4.464 (2H, s, CH$_2$Ph), 4.450 (1H, d, J=17.0 Hz, CH$_2$COOMe), 4.460 (1H, d, J=12.0 Hz, CH$_2$Ph), 4.475 (1H, d, J=11.0 Hz, CH$_2$Ph), 4.518 (1H, d, $J_{12}=7.5$ Hz, H1-b), 4.582 (1H, d, J=11.5 Hz, CH$_2$Ph), 4.626 (1H, d, J=11.0 Hz, CH$_2$Ph), 4.663 (1H, d, J=11.5 Hz, CH$_2$Ph), 4.668 (1H, d, $J_{12}=7.5$ Hz, H1-a), 4.711 (1H, d, J=11.0 Hz, CH$_2$Ph), 4.716 (1H, d, J=11.0 Hz, CH$_2$Ph), 4.931 (1H, d, J=11.5 Hz, CH$_2$Ph), 5.150 (1H, dd, J=1.5, 10.0 Hz, H1$_{cis}$-All), 5.189 (1H, d, $J_{12}=3.5$ Hz, H1-c), 5.252 (1H, dd, J=1.5, 16.5 Hz, H1$_{trans}$-All), 5.83~5.91 (1H, m, H2-All), 6.523 (1H, d, J=9.5 Hz, NHAc), 7.2~7.4 (25H, m, Ph).

Example 22

(Synthesis of Compound 30)

Compound 27 (13.9 mg, 12.7 µmol) was dissolved in a solvent of methanol (0.6 ml) and H$_2$O (0.15 ml) and stirred in the presence of 20% Pd(OH)$_2$—C (14 mg) under H$_2$ gas for 3 h. After the removal of Pd(OH)$_2$—C by filtration through celite, the solvent was evaporated. To the condensed residue dissolved in methanol (1 ml) and H$_2$O (2 ml) was added 1N—NaOH solution (30 µl), and stirred for 15 minutes. After the solvent was evaporated, the residue was purified by G-10 gel column chromatography (H$_2$O) and LH-20 (MeOH) to yield 7.9 mg of compound 30 (95.3%).

[Compound 30]

Rf 0.35 (nBuOH:EtOH:H$_2$O=2:1:1)

[α]$_D$-77.20 (c 0.53, MeOH)

$^1$H—NMR (CD$_3$OD) 0.908 (3H, t, J=7.5 Hz, OCH$_2$CH$_2$CH$_3$), 1.181 (3H, d, J=6.5 Hz, H-6c), 1.559 (2H, m, OCH$_2$CH$_2$CH$_3$), 3.222 (1H, dd, $J_{34}=3.5$, $J_{32}=10.0$ Hz, H3-b), 3.631 (1H, dd, $J_{21}=8.0$, $J_{23}=9.5$ Hz, H2-b), 3.913 (1H, d, $J_{43}=3.0$ Hz, H4-b), 3.967 (1H, d, J=16.0 Hz, CH$_2$COONa), 4.012 (1H, t, $J_{32}=J_{34}=10.0$ Hz, H3-a), 4.103 (1H, d, J=16.5 Hz, CH$_2$COONa), 4.412 (1H, d, $J_{12}=7.5$ Hz, H1-b), 4.493 (1H, d, $J_{12}=8.5$ Hz, H1-a), 5.037 (1H, d, $J_{12}=4.5$ Hz, H1-c)

Example 23

(Synthesis of Compound 31)

Compound 28 (22.6 mg, 19.4 µmol) dissolved in methanol (0.8 ml) and H$_2$O (0.2 ml) was stirred with 20% Pd(OH)$_2$—C (23 mg) under H$_2$ for 3 h. After the removal of Pd(OH)$_2$—C by filtration through celite, the solvent was evaporated. To the condensed residue dissolved in methanol (2 ml) and H$_2$O (4 ml) was added 1N—NaOH solution (100 µl) and stirred for 15 minutes. After the solvent was evaporated to dryness, the residue was purified by G-10 (H$_2$O) and LH-20 (MeOH) to yield 14.0 mg of compound 31 (99.0%).

[Compound 31]

Rf 0.22 (nBuOH:EtOH:H$_2$O=2:1:1)

[α]$_D$-46.70 (c 0.59, MeOH)

$^1$H—NMR (CD$_3$OD) 0.904 (3H, t, J=7.5 Hz, OCH$_2$CH$_2$CH$_3$), 1.205 (3H, d, J=6.5 Hz, H-6c), 1.549 (2H, m, OCH$_2$CH$_2$CH$_3$), 1.979 (3H, s, Ac), 4.007 (1H, d, J=15.5 Hz, CH$_2$COONa), 4.044 (1H, d, J=15.5 Hz, CH$_2$COONa), 4.224 (1H, d, J=15.0 Hz, CH$_2$COONa), 4.318 (1H, d, J=15.0 Hz, CH$_2$COONa), 4.526 (1H, d, J=7.0 Hz, H1-b), 4.691 (1H, brs, H1-a), 5.024 (1H, d, J=4.0 Hz, H1-c)

Example 24

(Synthesis of Compound 32)

Compound 29 (13.1 mg, 1 2.0 µmol) in methanol (0.6 ml) and H$_2$O (0.15 ml) was stirred with 20% Pd(OH)$_2$—C (14 mg) under H$_2$ for 3 h. After Pd(OH)$_2$—C was removed by filtration through celite, the solvent was evaporated to dryness. The condensed residue dissolved in methanol (1 ml) and H$_2$O (2 ml) was added 1N—NaOH solution (30 µl), and stirred for 15 minutes. After the solvent was evaporated to dryness, the residue was purified by G-10 (H$_2$O) and LH-20 (MeOH) to yield 6.70 mg of compound 32 (85.7%).

[Compound 32]

Rf 0.43 (nBuOH:EtOH:H$_2$O=2:1:1), [α]$_D^{32}$-48.1° (c 0.45, MeOH)

$^1$H—NMR (CD$_3$OD) 0.908 (3H, t, J=7.5 Hz, OCH$_2$CH$_2$CH$_3$), 1.142 (3H, d, J=6.5 Hz, H-6c), 1.557 (2H, m, OCH$_2$CH$_2$CH$_3$), 1.950 (3H, s, Ac), 3.30 (H2-b, overlapping with CD$_3$OD), 3.500 (1H, dd, J$_{34}$=3.0, J$_{32}$=9.5 Hz, H3-b), 3.724 (1H, dd, J$_{21}$=4.0, J$_{23}$=10.0 Hz, H2-c), 3.808 (1H, d, J$_{43}$=2.0 Hz, H4-b), 4.111 (1H, d, J=17.5 Hz, CH$_2$COONa), 4.198 (1H, d, J=17.5 Hz, CH$_2$COONa), 4.421 (1H, d, J$_{12}$=8.0 Hz, H1-a), 4.535 (1H, d, J$_{12}$=8.0 Hz, H1-b), 5.016 (1H, d, J$_{12}$=4.0 Hz, H1-c)

Example 25

(Synthesis of Compound 33 (β-epimer) and 35 (α-epimer))

Activated MS-4A (600 mg) was added to a solution of compound 5 (100 mg, 0.097 mmol) in acetonitrile (1.5 ml) with HgBr$_2$—Hg(CN)$_2$ (1:1) (361 mg, 0.580 mmol) by stirring under the argon gas for 1 h. compound R13 (148 mg, 0.290 mmol) in acetonitrile (1.5 ml) was added to the mixture and stirred at 25° C. for 18 h. The reaction mixture was diluted with ethyl acetate and filtered through celite. After the organic phase was washed with NaHCO$_3$ solution followed by saturated NaCl solution, the organic layer was dried over anhydrous MgSO$_4$ and evaporated. The residue was purified by S-X3 (Bio-Rad) (toluene) and robber column (toluene:MeOH=20:1) to obtain compound 33 and 35.

[Compound 35 (α-epimer)]

31.8 mg (21.8%)

[α]$_D{}^{30}$−34.1° (c=0.1, CHCl$_3$)

500 MHz, $^1$H—NMR (CDCl$_3$, TMS) δ$_H$; 1.115 (d, 3H, J=6.6 Hz, H-6d), 1.680, 1.896, 1.983, 2.033, 2.085, 2.098 (6S, 18H, Ac×6), 2.534 (d, 1H, J=3.7 Hz, OH), 2.679 (dd, 1H, J=4.4, 13.2 Hz, H-3ceq), 3.128 (s, 1H, OH), 3.772 (s, 3H, OCH$_3$), 4.843 (d, 1H, J=11.4 Hz, CH$_2$Ph), 4.915 (d, 1H, J=11.7 Hz, CH$_2$Ph), 4.965 (m, 1H, H-4c), 5.312 (dd, 1H, J=1.8, 8.8 Hz, H-7c), 5.418 (m, 1H, H-8c), 5.806 (m, 1H, CH$_2$CH=CH$_2$), 5.997 (d, 1H, J=7.7 Hz, NH).

[Compound 33 (β-epimer)]

15.7 mg (15.2%)

[α]$_D{}^{25}$−41.8° (c=0.9, CHCl$_3$)

500 MHz, $^1$H—NMR (CDCl$_3$, TMS) δ$_H$; 1.128 (d, 3H, J=6.2 Hz, H-6d), 1.677, 1.854, 1.929, 2.004, 2.010, 2.133 (6S, 18H, Ac×6), 2.605 (dd, 1H, J=4.8, 13.2 Hz, H-3ceq), 3.757 (s, 3H, OCH$_3$), 5.191 (m, 1H, H-4c), 5.376 (t, 1H, J=2.9 Hz, H-7c), 5.400 (m, 1H, H-8c), 5.643 (d, 1H, J=10.3 Hz, NH), 5.795 (m, 1H, CH$_2$C H=CH$_2$), 6.089 (d, 1H, J=7.3 Hz, NH).

Example 26

(Synthesis of Compound 34 (β-epimer) and 36 (α-epimer))

Activated MS-4A (10 g) was mixed to compound 3 (2.278 g, 2.055 mmol) in acetonitrile (30 ml) with HgBr$_2$—Hg(CN)$_2$ (1:1) (7.664 g) by stirring under the argon gas for 1 h. To the mixture was added compound R13 (3.144 g, 6.166 mmol) in acetonitrile (30 ml) and stirred at 25° C. for 2 days. The reaction mixture was diluted with ethyl acetate, and filtered through celite. The organic phase was washed with NaHCO$_3$ solution followed by saturated NaCl solution, and dried over anhydrous MgSO$_4$. After the mixture was evaporated to dryness, the residue was purified by S-X3 (Bio-Rad) (toluene) and robber column (toluene:MeOH=10:1).

[Compound 36(α-epimer)]

1.341 g (41.2%)

Rf=0.14 (toluene:MeOH=10:1)

[α]$_D{}^{24}$−4.9° (c=0.3, CHCl$_3$)

500 MHz, $^1$H—NMR (CDCl$_3$, TMS) δ$_H$; 1.066 (d, 3H, J=6.6 Hz, H-6d), 1.901, 1.999, 2.036, 2.099, 2.110 (5S, 15H, Ac×5), 2.430 (d, 1H, J=4.0 Hz, OH), 2.671 (dd, 1H, J=4.8, 13.2 Hz, H-3ceq), 3.152 (d, 1H, J=1.1 Hz, OH), 3.753 (s, 3H, COOCH$_3$), 4.056 (dd, 1H, J=5.1, 12.5 Hz, H-9b), 4.458 (d, 1H, J=12.1 Hz, CH$_2$Ph), 4.659 (d, 1H, J=7.3 Hz, H-1b), 4.919 (d, 1H, J=3.0 Hz, H-1d), 4.954 (m, 1H, H-4c), 5.175 (d, 1H, J=8.8 Hz, H-1a), 5.327 (dd, 1H, J=1.8, 8.8 Hz, H-7c), 5.447 (m, 1H, H-8c), 5.671 (m, 1H, CH$_2$CH=CH$_2$)

[Compound 34 (β-epimer)]

615 mg (18.9%)

Rf=0.19 (toluene:MeOH=10:1)

500 MHz, $^1$H—NMR (CDCl$_3$, TMS) δ$_H$; 1.076 (d, 3H, J=6.6 Hz, H-6d), 1.822, 1.938, 1.967, 2.005, 2.123 (5S, 15H, Ac×5), 2.353 (s, 1H, OH), 2.599 (dd, 1H, J=4.4, 13.6 Hz, H-3ceq), 3.138 (d, 1H, J=4.0 Hz, OH), 3.707 (s, 3H, OCH$_3$), 5.188 (d, 1H, J=8.8 Hz, H-1a), 5.242 (m, 1H, H-8c), 5.349 (m, 1H, H-4c), 5.356 (dd, 1H, J=2.2, 4.0 Hz, H-7c), 5.452 (d, 1H, J=9.9 Hz, NH), 5.695 (m, 1H, CH$_2$CH=CH$_2$).

Example 27

(Synthesis of Compound 37)

Compound 36 (1.264 g, 0.799 mmol) was dissolved in pyridine (10 ml) and acetic anhydride (10 ml) by stirring at 25° C. for 2 days. To the mixture was added dimethylaminopyridine (50 mg) and stirred for 5 h. The reaction mixture was evaporated and the resulting residue was purified by silica gel column chromatography (C-300, 100 g, toluene:methanol=9:1) and Sephadex LH-20 (methanol).

[Compound 37]

1.154 g (86.7%)

Rf=0.25 (toluene:MeOH=9:1)

[α]$_D{}^{24}$−9.1° (c=0.2, CHCl$_3$)

500 MHz, $^1$H—NMR (CDCl$_3$, TMS) δ$_H$; 1.207 (d, 3H, J=6.2 Hz, H-6d), 1.784, 1.854, 1.996, 2.004, 2.059, 2.081, 2.224 (7S, 21H, Ac×7), 2.542 (dd, 1H, J=4.8, 12.5 Hz, H-3ceq), 4.908 (m, 1H, H-4c), 5.058 (d, 1H, J=3.3 Hz, H-4b), 5.119 (d, 1H, J=8.4 Hz, H-1a), 5.391 (dd, 1H, J=2.6, 9.5 Hz, H-7c), 5.580 (m, 1H, H-8c), 5.640 (m, 1H, CH$_2$C H=CH$_2$).

Example 28

(Synthesis of Compound 38)

To compound 33 (134.6 mg, 0.089 mmol) in pyridine (5 ml) and acetic anhydride (5 ml) was added a catalytic amount of dimethylaminopyridine and this mixture was stirred at 25° C. for 18 h. After the reaction mixture was evaporated, the residue was purified by silica gel column chromatography (C-300, 30 g, toluene:methanol=10:1) followed by Sephadex LH-20 (methanol).

109

[Compound 38]

103.4 mg (72.8%)

Rf=0.21 (toluene:Methanol=10:1)

$[\alpha]_D^{24}$ −44.7° (c=0.1, CHCl$_3$)

500 MHz, $^1$H—NMR (CDCl$_3$, TMS) $\delta_H$; 1.139 (d, 3H, J=6.3 Hz, H-6d), 1.784 (t, 1H, J=13.2 Hz, H-3cax), 1.879, 1.922, 1.962, 1.989, 1.999, 2.076, 2.147, 2.175 (8S, 24H, Ac×8), 2.480 (dd, 1H, J=4.8, 13.6 Hz, H-3ceq), 4.382 (d, 1H, J=12.1 Hz, CH$_2$Ph), 4.406 (d, 1H, J=12.1 Hz, CH$_2$Ph), 4.514 (d, 1H, J=8.1 Hz, H-1b), 4.917 (d, 1H, J=11.7 Hz, CH$_2$Ph), 5.031 (m, 1H, H-4c), 5.316 (td, 1H, J=2.6, 9.5 Hz, H-8c), 5.386 (t, 1H, J=2.2 Hz, H-7c), 5.414 (d, 1H, J=2.9 Hz, H-4b), 5.676 (d, 1H, J=10.3 Hz, NH), 5.767 (m, 1H, CH$_2$CH=CH$_2$), 6.297 (d, 1H, J=8.8 Hz, NH)

Example 29

(Synthesis of Compound 39)

To compound 38 (83 mg, 0.052 mmol) in dried methanol (5 ml) was added a catalytic amount of sodium methoxide and the mixture was stirred at 20° C. for 5 h. Then the mixture was evaporated. The resulting residue was dissolved in methanol (8 ml) and H$_2$O (1 ml) and the mixture was stirred at 20° C. for 18 h. The reaction mixture was evaporated, and the residue was purified by Sephadex LH-20 column chromatography (methanol).

[Compound 39]

68.2 mg (97.1%)

Rf=0.58 (BuOH:EtOH:H$_2$O=2:1:1)

$[\alpha]_D^{22}$ −48.2° (c=0.1, CHCl$_3$)

500 MHz, $^1$H—NMR (CD$_3$OD, TMS) $\delta_H$; 1.156 (d, 3H, J=6.2 Hz, CH$_3$), 1.926, 1.977 (2S, 6H, Ac×2), 2.418 (dd, 1H, J=4.8, 12.5 Hz, H-3ceq), 3.044 (t, 1H, J=6.2 Hz, H-6b), 4.330 (d, 1H, J=7.7 Hz, H-1b), 4.507 (d, 1H, J=12.1 Hz, CH$_2$Ph), 4.535 (d, 1H, J=11.4 Hz, CH$_2$Ph), 4.639 (d, 1H, J=11.7 Hz, CH$_2$Ph), 4.643 (d, 1H, J=11.7 Hz, CH$_2$Ph), 4.695 (d, 1H, J=11.7 Hz, CH$_2$Ph), 2.606 (d, 1H, J=11.7 Hz, CH$_2$Ph), 5.298 (d, 1H, J=3.7 Hz, H-1d), 5.870 (m, 1H, CH$_2$CH=CH$_2$)

Example 30

(Synthesis of Compound 40)

To compound 39 (60.9 mg, 0.045 mmol) in methanol (8 ml) was added 10% Pd—C (60 mg) and the mixture was catalytically reduced at 20° C. for 18 h. After the reaction mixture was filtered through chromatodisc, the solvent was evaporated. The resulting residue was purified by Sephadex LH-20 column chromatography (methanol).

[Compound 40]

40.6 mg (99.3%)

Rf=0.44 (BuOH:EtOH:H$_2$O=2:1:1)

$[\alpha]_D^{24}$ −54.8° (c=0.2, CH$_3$OH)

500 MHz, $^1$H—NMR (CD$_3$OD, TMS) $\delta_H$; 0.903 (t, 3H, J=7.3 Hz, CH$_2$CH$_3$), 1.188 (d, 3H, J=6.6 Hz, H-6d), 1.643 (t, 1H, J=12.5 Hz, H-3cax), 1.946, 1.972 (2S, 6H, Ac×2), 2.402 (dd, 1H, J=4.8, 12.5 Hz, H-3ceq), 4.230 (m, 1H, H-4c), 4.409 (d, 1H, J=8.1 Hz, H-1a), 4.472 (d, 1H, J=7.7 Hz, H-1b), 5.035 (d, 1H, J=4.0 Hz, H-1d).

Example 31

(Synthesis of Compound 41)

H$_2$ activated-Iridium complex (10.6 mg) in tetrahydrofuran (5 ml) was added to compound 37 (150 mg, 0.09 mmol) in tetrahydrofuran (5 ml) and the mixture was stirred for 1.5 h at room temperature. Then the mixture was further stirred with adding H$_2$O (2.3 ml) and I$_2$ (135.5 mg). After the dilution with CHCl$_3$ the mixture was washed with sodium thiosulfate (Na$_2$S$_2$O$_3$.5H$_2$O) solution, NaHCO$_3$ solution, NaCl solution. After the mixture was dried over MgSO$_4$, the solvent was evaporated to dryness. The resulting residue was purified by silica gel column chromatography (WAKO-gel) C-300, toluene:methanol=5:1) to obtain 122.2 mg of compound 41 (83.5%).

[Compound 41]

Rf 0.37 (toluene:MeOH=5:1)

NMR CDCl$_3$ TMS $\delta_H$ 5.579 (1H, m, H-8c), 5.389 (1H, dd, J=2.9, 9.5 Hz, H-7c), 5.267 (1H, t, J=8.6 Hz, H-3a), 5.065 (1H, d, J=3.3 Hz, H-4b), 4.872 (1H, d, J=3.7 Hz, H-1d), 4.640 (1H, q, J=6.6 Hz, H-5d), 3.831 (3H, s, OMe), 2.540 (1H, dd, J=12.8, 4.8 Hz, H-3cq), 2.227, 2.066, 2.066, 2.006, 1.984, 1.854, 1.783 (7S, 21H, 7Ac), 1.224 (3H, d, J=6.6 Hz, H-6d)

Example 32

(Synthesis of Compound 42)

Compound 41 (245.7 mg, 0.151 mmol) in 1,2-dichloroethane (2 ml) was stirred at 0° C. under Ar. Trichloroacetonitrile (236.1 µl, 2.35 mmol), 1,8-diazabicyclo[5.4.0]-7-undecene (16.2 µl, 0.106 mmol) were added to the mixture and stirred for 2 h. The resulting mixture was purified by silica gel column chromatography (WAKO-gel C-300, toluene:ethyl acetate=1:3) to obtain 213.9 mg of compound 42 (80.0%).

[Compound 42]

Rf 0.33 (CHCl$_3$:acetone 3:1)

NMR CDCl$_3$, TMS.

$\delta_H$ 8.518 (s, 1H, NH), 6.394 (d, 1H, J=8.8 Hz, H-1a), 5.577 (m, 1H, H-8c), 5.388 (dd, 1H, H-7c), 4.887 (d, 1H, J=4.03 H-1d), 4.842 (dd, 1H, J=10.6, 8.4 Hz, H-2a), 4.680 (dd, 1H, J=10.6, 8.8 Hz, H-2b), 3.822 (s, 3H, OMe), 2.233, 2.080, 2.071, 2.007, 1.986, 1.795, 1.855 (7S, 21H, 7Ac)

Example 33

(Synthesis of Compound 43)

Compound 42 (358 mg, 0.202 mmol) in chloroform (4 ml) and compound R18 (305 mg, 0.404 mmol) was added to activated MS4A (2 g) under Ar. After the addition of BF$_3$.Et$_2$O (40 µl, 0.330 mmol) at 5° C. with stirring, the mixture was further stirred for 18 h. The reaction mixture was diluted with CHCl$_3$ and filtered through celite into the container with NaHCO$_3$ solution. The organic phase was washed with saturated NaCl solution, dried over anhydrous MgSO$_4$ and evaporated to dryness. The residue was purified by silica gel column chromatography (C-300, 120 g, CHCl$_3$:acetone=8:1 followed by 6:1).

[Compound 43]

262.8 mg (55%)

Rf=0.45 (CHCl$_3$:acetone=4:1)

500 MHz, $^1$H—NMR (CDCl$_3$, TMS) $\delta_H$; 0.878 (t, 6H, J=6.6 Hz, 2CH$_2$CH$_3$), 1.691 (t, 1H, J=12.5 Hz, H-3cax), 1.847, 2.000, 2.007, 2.033, 2.049, 2.126, 2.141 (7S, 21H, Ac×7), 2.564 (dd, 1H, J=4.4, 12.5 Hz, H-3ceq), 3.816 (s, 3H, OCH$_3$), 3.904 (dd, 1H, J=6.6, 12.5 Hz, H-9c), 4.749 (d, 1H, J=8.1 Hz, H-1b), 4.857 (m, 1H, H-4c), 4.889 (d, 1H, J=3.6 Hz, H-1d), 5.177 (d, 1H, J=8.8 Hz, H-1a), 5.328 (dd, 1H, J=2.9, 9.2 Hz, H-7c), 5.367 (dd, 1H, J=7.3, 15.0 Hz, H-4Cer), 5.444 (t, 1H, J=6.6 Hz, H-3Cer), 5.535 (m, 1H, H-8c), 5.673 (dt, 1H, J=12.1, 6.6 Hz, H-5Cer), 5.687 (d, 1H, J=9.2 Hz, NH).

Example 34

(Synthesis of Compound 44)

To dried LiI (66.4 mg, 4969 mol) was added compound 43 (196 mg, 839 mol) in pyridine (2 ml) and the mixture was stirred at 110° C. for 18 h. The reaction mixture was purified by Sephadex LH-20 (methanol) followed by silica gel column chromatography (C-300, 50 g, CHCl$_3$:acetone= 20:1, then 10:1)

[Compound 44]

167.4 mg (85.7%)

Rf=0.58 (CHCl$_3$:MeOH=7:1)

500 MHz, $^1$H—NMR (CDCl$_3$, TMS) $\delta_H$; 0.882 (t, 6H, J=6.6 Hz, CH$_2$CH$_3$×2), 1.809, 1.979, 2.003, 2.041, 2.069, 2.088, 2.167 (7S, 21H, Ac×7), 2.568 (dd, 1H, J=4.8, 12.5 Hz, H-3ceq), 4.533 (d, 1H, J=3.7 Hz, H-1d), 4.812 (d, 1H, J=7.7 Hz, H-1b), 5.193 (d, 1H, J=8.4 Hz, H-1a), 5.325 (dd, 1H, J=1.8, 8.1 Hz, H-7c), 5.368 (dd, 1H, J=7.3, 15.4 Hz, H-4Cer), 5.461 (t, 1H, J=7.3 Hz, H-3Cer), 5.529 (m, 1H, H-8c), 5.708 (dt, 1H, J=15.4, 7.4 Hz, H-5Cer).

Example 35

(Synthesis of Compound 45)

To compound 44 (166 mg, 71 μmol) in ethanol (4 ml) was added methylhydrazine (10 ml) and the mixture was stirred at 90° C. for 18 h. The reaction mixture was evaporated and purified by Sephadex LH-20 (methanol). To the residue dissolved in a solution (10:1) of methanol and CHCl$_3$ was added a small amount of acetic anhydride and the mixture was stirred at 20° C. for 30 minutes. After the reaction mixture was basified by addition of NaOH, the mixture was purified by Sephadex LH-20 (chloroform:methanol=1:3)

[Compound 45]

93.1 mg (68.2%)

Rf=0.61 (CHCl$_3$:MeOH=3:1)

500 MHz, $^1$H—NMR (CDCl$_3$/CD$_3$OD=⅓, TMS) $\delta_H$; 0.887 (t, 6H, J=6.2 Hz, CH$_2$CH$_3$×2), 1.987, 2.025 (2S, 6H, Ac×2), 5.439 (dd, 1H, J=7.3, 15.0 Hz, H-4Cer), 5.694 (dt, 1H, J=14.7, 7.3 Hz, H-5Cer).

Example 36

(Synthesis of Compound 46)

To compound 45 (92 mg, 47.59 mol) in the solution of methanol (3 ml), CHCl$_3$ (1 ml) and H$_2$O (0.5 ml) was added 20% Pd(OH)$_2$—C (92 mg) and the mixture was hydrogenated at 0° C. for 18 h. The reaction mixture was subjected to chromatodisc and then purified by Sephadex LH-20 column chromatography (CHCl$_3$:methanol=1:3).

[Compound 46]

61.1 mg (87%)

Rf=0.60 (BuOH:EtOH:H$_2$O=2:1:1)

500 MHz, $^1$H—NMR (CDCl$_3$/CD$_3$OD=⅓, TMS) $\delta_H$; 0.890 (t, 6H, J=6.6 Hz, CH$_2$CH$_3$×2), 1.235 (d, 3H, J=7.0 Hz, H-6d), 2.000, 2.034 (2S, 6H, Ac×2), 2.855 (dd, 1H, J=4.2, 12.6 Hz, H-3ceq), 4.324 (d, 1H, J=8.6 Hz, H-1b or H-1a), 4.423 (d, 1H, J=7.70, H-1a or H-1b), 4.650 (bs, 1H, H-1d).

Example 37

(Synthesis of Compound 47a)

To compound 42 (92.7 mg, 0.052 mmol) and compound R9 (41.9 mg, 0.105 mmol) in acetonitrile (1.5 ml) was added 0.1M—TMSOTf (130 μl) under the argon gas with activated MS-4A and 3A (1:1) (200 mg) and the mixture was stirred at −40° C. for 2 h and further at −25° C. for 1 h. After the reaction mixture was basified by the addition of triethylamine, the mixture was diluted with CHCl$_3$ and filtered through celite into the container with NaHCO$_3$ solution. After the organic phase was washed with H$_2$O followed by saturated NaCl solution, the mixture was dried over anhydrous MgSO$_4$ and evaporated in vacuo. The residue was purified by Bio-Rad S-X3 (toluene) and silica gel column chromatography (C-300, 20 g, toluene-ethyl acetate=1:3).

[Compound 47a]

88.8 mg (84.4%)

Rf=0.50 (CHCl$_3$:MeOH=24:1)

500 MHz, $^1$H—NMR (CDCl$_3$, TMS) $\delta_H$; 1.203 (d, 3H, J=6.2 Hz, H-6e), 1.712 (t, 1H, J=12.4 Hz, H-3dax), 1.785, 1.854, 1.988, 2.006, 2.057, 2.084, 2.224 (7S, 21H, Ac×7), 542 (dd, 1H, J=4.8, 12.8 Hz, H-3deq), 3.287 (t, 1H, J=9.2 Hz, H-6c), 3.831 (s, 3H, OCH$_3$), 4.170 (d, 1H, J=12.5 Hz, CH$_2$Ph), 4.230 (d, 1H, J=11.7 Hz, CH$_2$Ph), 4.361, 4.400 (2d, 2H, J=12.1 Hz, CH$_2$Ph), 4.434 (d, 1H, J=11.4 Hz, CH$_2$Ph), 4.435 (dd, 1H, J=8.4 Hz, H-2b), 4.900 (d, 1H, J=8.4 Hz, H-1c), 5.034 (d, 1H, J=10.3 Hz, NH), 5.058 (d, 1H, J=3.3 Hz, H-1e), 5.131 (d, 1H, J=8.4 Hz, H-1b), 5.390 (dd, 1H, J=2.2, 9.1 Hz, H-7d), 5.571 (m, 1H, H-8d), 5.720 (m, 1H, CH$_2$CH=CH$_2$).

Example 38

(Synthesis of Compound 47b)

To LiI (66.4 mg, 0.496 mmol) dried at 120° C. for 4 h was added compound 47a (55 mg, 0.027 mmol) in pyridine (1 ml) and the mixture was stirred at 110° C. for 18 h. The reaction mixture was purified by Sephadex LH-20 (methanol).

[Compound 47b]

51.5 mg (94.0%)

Rf=0.07 (CHCl$_3$:MeOH=24:1)

500 MHz, $^1$H—NMR (CD$_3$OD, TMS) $\delta_H$; 1.213 (d, 3H, J=6.6 Hz, H-6e), 1.795, 1.878, 1.929, 1.971, 1.989, 2.061, 2.286 (7S, 21H, Ac×7), 2.585 (dd, 1H, J=4.6, 12.5 Hz, H-3deq), 4.396 (d, 1H, J=6.6 Hz, H-1b or H-1c), 4.420 (d, 1H, J=1.5 Hz, H-1a), 4.470 (d, 1H, J=11.4 Hz, CH$_2$Ph), 4.502 (d, 1H, J=12.1 Hz, CH$_2$Ph), 4.533 (d, 1H, J=11.4 Hz, CH$_2$Ph), 4.539 (d, 1H, J=10.6 Hz, CH$_2$Ph), 4.573 (d, 1H, J=12.4 Hz, CH$_2$Ph), 5.665 (m, 1H, H-8d), 5.735 (m, 1H, CH$_2$CH=CH$_2$)

Example 39

(Synthesis of Compound 48)

To compound 47 (51 mg, 0.025 mmol) in ethanol (3 ml) was added methylhydradine (1 ml) and the mixture was stirred at 80° C. for 18 h. After evaporated in vacuo, the reaction mixture was further coevaporated by the addition of toluene. The residue was purified by Sephadex LH-20 column chromatography (methanol) to obtain 37.4 mg of a product. Then, to the product dissolved in methanol (2 ml) was added acetic anhydride (0.5 ml) and the mixture was stirred at 20° C. for 1 h. After the reaction mixture was basified by the addition of NaOH, this mixture was purified by Sephadex LH-20 (methanol).

[Compound 48]

35.5 mg (78.9%)

Rf=0.43 ($CHCl_3$:MeOH=3:1; nynhydrin(-))

500 MHz, $^1$H—NMR ($CD_3OD$, TMS) $\delta_H$; 1.125 (d, 3H, J=6.6 Hz, H-6e), 1.732 (t, 1H, J=12.2 Hz, H-3dax), 1.877, 1.984 (2S, 6H, Ac×2), 2.901 (dd, 1H, J=4.4, 12.5 Hz, H-3deq), 4.312 (d, 1H, J=12.1 Hz, $CH_2Ph$), 4.371 (d, 1H, J=11.4 Hz, $CH_2Ph$), 4.475 (d, 1H, J=8.1 Hz, H-1b or H-1c), 4.568, 4.596 (2d, 2H, J=12.1 Hz, $CH_2Ph$), 5.261 (d, 1H, J=3.3 Hz, H-1e), 5.890 (m, 1H, $CH_2CH=CH_2$)

Example 40

(Synthesis of Compound 49)

To compound 48 (34 mg, 0.019 mmol) in methanol (4 ml) and $H_2O$ (1 ml) was added 10% Pd—C (35 mg) and hydrogenated at 20° C. for 18 h. The reaction mixture was filtered through chromatodisc and the solvent was evaporated in vacuo. The residue was purified by Sephadex LH-20 (methanol).

[Compound 49]

20.2 mg (100%)

Rf=0.07 (ethyl acetate:EtOH:$H_2O$=5:2:1)

500 MHz, $^1$H—NMR ($CD_3OD$) $\delta_H$; 0.946 (t, 3H, J=7.7 Hz, $CH_2CH_3$), 1.156 (d, 3H, J=6.6 Hz, H-6e), 1.715 (t, 1H, J=12.1 Hz, H-3dax), 1.951, 2.004 (2S, 6H, Ac×2), 2.873 (dd, 1H, J=4.1, 12.5 Hz, H-3deq), 4.485 (d, 1H, J=7.0 Hz, H-1b or H-1c), 4.500 (d, 1H, J=7.7 Hz, H-1c or H-1b), 4.683 (d, 1H, J=1.5 Hz, H-1a), 5.031 (d, 1H, J=4.0 Hz, H-1e).

Example 41

(Synthesis of Compound 50)

Compound 42 (230 mg, 130 μmol) and compound R15 (140.6 mg, 260 μmol) in dichloromethane (4 ml) was added to activated MS-4A (400 mg) and the mixture was stirred for 1 h under Ar. To this mixture was further added $BF_3.Et_2O$ (40 μl, 330μmol) at 0° C. and stirred for 18 h at the same temperature (0° C.). The reaction mixture was diluted with ethyl acetate and filtered through celite. After the organic phase was washed with $NaHCO_3$ solution followed by saturated NaCl solution, the washing was dried over anhydrous $MgSO_4$ and the solvent was evaporated in vacuo. The residue was purified by silica gel column chromatography (C-300, 60 g, $CHCl_3$:acetone=7:1).

[Compound 50]

184 mg (65.9%)

Rf=0.29 (toluene:methanol=9:1)

500 MHz, $^1$H—NMR ($CD_3OD$, TMS) $\delta_H$; 1.209 (d, 3H, J=6.6 Hz, H-6e), 1.713 (t, 1H, J=12.8 Hz, H-3dax), 1.778, 1.857, 1.995, 2.007, 2.057, 2.075, 2.220 (7S, 21H, Ac×7), 2.537 (dd, 1H, J=4.8, 12.8 Hz, H-3deq), 3.826 (s, 3H, $OCH_3$), 4.264 (d, 1H, J=7.7 Hz, H-1a or H-1b), 4.330 (d, 1H, J=8.1 Hz, H-1b or H-1a), 4.862 (d, 1H, J=3.7 Hz, H-1e), 4.914 (m, 1H, H-4d), 5.051 (d, 1H, J=4.0 Hz, H-4c), 5.150 (d, 1H, J=8.4 Hz, NH), 5.388 (dd, 1H, J=2.6, 9.2 Hz, H-7d), 5.579 (m, 1H, H-8d), 7.00–7.37 (m, 45H, Ph), 7.50 (m, 3H, Ph), 7.71 (m, 1H, Ph).

Example 42

(Synthesis of Compound 51)

To dried LiI (198 mg, 1.479 mmol) was added compound 50 (176.5 mg, 0.082 mmol) in pyridine (2 ml) and the mixture was stirred at 105° C. for 18 h. The reaction mixture was purified by Sephadex LH-20 (methanol).

[Compound 51]

155 mg (88.2%)

Rf=0.19 ($CHCl_3$:MeOH=24:1)

500 MHz, $^1$H—NMR ($CD_3OD$, TMS) $\delta_H$; 1.220 (d, 3H, J=6.6 Hz, H-6e), 1.403 (t, 1H, J=12.4 Hz, H-3dax), 1.798, 1.880, 1.935, 1.969, 1.997, 2.052 (7S, 21H, Ac×7), 2.556 (dd, 1H, J=4.5, 12.4 Hz, H-3deq), 4.309 (d, 1H, J=7.69 Hz, H-1a or H-1b), 5.101 (m, 1H, H-4d), 5.200 (d, 1H, J=8.4 Hz, H-1b), 5.365 (d, 1H, J=2.2 Hz, H-4c), 5.389 (dd, 1H, J=2.6, 9.2 Hz, H-7d), 5.667 (m, 1H, H-8d), 7.36–6.80 (m, 40H, $CH_2Ph$)

Example 43

(Synthesis of Compound 52)

To compound 51 (150 mg, 70 μmol) in ethanol (5 ml) was added methylhydradine (20 ml) at 80° C. for 18 h. The reaction mixture was evaporated in vacuo and purified by Sephadex LH-20 column chromatography (methanol). To the residue dissolved in methanol (1 ml) was added acetic anhydride (0.5 ml) and stirred at 20° C. for 15 minutes. The mixture was basified by adding NaOH solution and then purified by Sephadex LH-20 (methanol).

[Compound 52]

125 mg (98.3%)

Rf=0.12 ($CHCl_3$:MeOH=6:1)

500 MHz, $^1$H—NMR ($CD_3OD$, TMS) $\delta_H$; 1.133 (d, 3H, J=6.2 Hz, H-6e), 1.735 (t, 1H, J=12.8 Hz, H-3dax), 1.915, 2.015 (2S, 6H, Ac×2), 2.903 (dd, 1H, J=4.8, 12.8 Hz, H-3deq), 5.303 (d, 1H, J=3.7 Hz, H-1e), 7.098–7.369 (m, 45H, Ph).

Example 44

(Synthesis of Compound 53)

To compound 52 (125 mg, 68.89 mol) in $H_2O$ (1 ml) and methanol (4 ml) was added 20% Pd(OH)$_2$—C and hydrogenated at 20° C. for 18 h. The reaction mixture was filtered through chromatodisc 25A and the filtrate was purified by Sephadex G-10 column chromatography ($H_2O$).

115

[Compound 53]

46.8 mg (66.7%)

Rf=0.18 (BuOH:EtOH:H$_2$O=2:1:1)

500 MHz, $^1$H—NMR (CD$_3$OD TMS) $\delta_H$; 1.154 (d, 3H, J=6.6 Hz, H-6e), 1.715 (t, 1H, J=12.5 Hz, H-3dax), 1.963, 1.971 (2S, 3H, Ac), 2.004 (s, 3H, Ac), 2.873 (dd, 1H, J=4.0, 12.5 Hz, H-3deq), 4.398 (d, 0.6H, J=7.3 Hz, H-1b β), 4.450 (d, 0.4H, J=8.1 Hz, H-1bα), 4.491 (d, 1H, J=7.7 Hz, H-1c), 4.934 (d, 0.4H, J=5.0 Hz, H-1aα), 5.031 (d, 0.6H, J=4.0 Hz, H-1eβ), 5.112 (d, 0.4H, J=3.0 Hz, H-1eα).

Example 45

(Synthesis of Compound 54)

To H$_2$ activated-iridium complex ([Ir(COD)(PMePh$_2$)$_2$] PF$_6$) in THF (41 ml, 0.1 eq) was added compound 2 (1.0 g, 0.81 mmol) and this mixture was stirred for 1 h. Then, to the mixture was added H$_2$O (20.5 ml) and I$_2$ (1219 mg) and further stirred for 1 h. After diluted with CHCl$_3$, the mixture was washed with N$_2$S$_2$O$_3$ solution, saturated NaHCO$_3$ solution and then saturated NaCl solution. After the organic phase was dried over MgSO$_4$, the solvent was evaporated. The residue was purified by silica gel column chromatography (toluene/ethyl acetate=2:1) to obtain 784.5 mg of compound 54 (81%). Intermediate Rf 0.36, 0.48 (toluene:ethyl acetate=3:1)

[Compound 54]

Rf 0.07 (toluene:ethyl acetate=3:1)
NMR CDCl$_3$ TMS $\delta_H$ 5.366 (1H, d, J=3.3 Hz, H-4b), 5.250 (1H, t, J=8.8 Hz, H-3a), 4.981 (1H, dd, J=8.1 Hz, 10.6 Hz, H-4a), 4.631 (1H, d, J=8.4 Hz, H-1b), 4.282 (1H, dd, J=8.8 Hz, 10.6 Hz, H-2a), 1.990, 1.948, 1.765 (3S, 9H, 3Ac), 1.176 (3H, d, J=6.2 Hz, H-6c)

Example 46

(Synthesis of Compound 55)

Compound 54 (2.34 g, 1.96 mmol) in 1,2-dichloroethane (8 ml) was stirred at −15° C. To the solution was added diethylaminosulfur trifluoride (DAST) (1.0 ml, 4 eq) and stirred for 40 minutes. After diluted with ethyl acetate, the mixture was washed with saturated NaHCO$_3$ solution followed by saturated NaCl solution. After the organic phase was dried over MgSO$_4$, the solvent was evaporated and the resulting residue was purified by silica gel column chromatography (toluene:ethyl acetate=2:1) to yield 2.30 g of compound 55 (98.2%).

[Compound 55]

Rf=0.60 (toluene:etyl acetate=1:1)
NMR CDCl$_3$, TMS $\delta_H$ 1.153 (d, J=6.22 Hz, H-5c (β)), 1.222 (d, J=6.59 Hz, H-5c (α)) 1.754, 1.777, 1.951, 1.956, 1.997, 2.004 (6S, 18H, Ac (α, β)), 4.658 (d, J=8.1 Hz, H-1b), 4.714 (dd, J=8.8 Hz, J=10.6 Hz, H-4a), 4.987 (dd, J=8.1 Hz, J=9.9 Hz, H-2b (β)), 5.360 (d, J=3.3 Hz, H-4b (β)), 5.375 (d, J=3.7 Hz, H-4b (α)), 5.822 (dd, J=7.7 Hz, 54.6 Hz, H-1a (β))

Example 47

(Synthesis of Compound 56)

Compound 54 (261.2 mg, 0.22 mmol) in 1,2-dichloroethane (4 ml) was stirred at 0° C. To the solution

116 was added 1,8-diazabicyclo[5,4,0]-7-undecene (DBU) (23 μl, 0.7 eq) and CCl$_3$CN (319 μl, 15 eq) and the mixture was stirred for 2 h. The mixture was purified by silica gel column chromatography (toluene:ethyl acetate=3:1) to yield 228 mg of compound 56 (77.7%).

[Compound 56]

Rf=0.60 (toluene:ethyl acetate=1:1)

[α]$_D^{23}$6.2° (c=1.00 CHCl$_3$)

nmr CDCl$_3$, TMS $\delta_H$ 6.365 (1H, d, J=8.8 Hz, H-1a), 5.368 (1H, d, J=3.3 Hz, H-4b), 5.001 (1H, dd, J=8.1, 10.3 Hz, H-2b), 4.838 (1H, d, J=3.7 Hz, H-1c), 4.697 (1H, d, J=8.1 Hz, H-1b), 4.594 (1H, q, J=7.0 Hz, H-5c), 2.009, 1.790, 1.779 (3S, 9H, 3Ac), 1.179 (3H, d, J=6.6 Hz, H-6c)

Example 48

(Synthesis of Compound 57)

Compound R6 (603 mg, 0.900 mmol), compound 55 (544 mg, 0.450 mmol) and dichloromethane (4 ml) were added to activated MS-4A (1.5 g) under Ar and the mixture was stirred for 1 h. Then, to this mixture was added CpHfCl$_2$ (512.6 mg, 1.35 mmol) and AgOTf (693.9 mg, 2.7 mmol) in dichloromethane at −20° C. and the mixture was stirred for 1 h. The reaction mixture was diluted with ethyl acetate and filtered through celite into the container with NaHCO$_3$ solution. After the organic phase was washed with saturated NaCl solution, this washing was dried over anhydrous MgSO$_4$ and the solvent was evaporated. The resulting residue was purified by silica gel column chromatography (C-300, 40 g, toluene:ethyl acetate=6:1 and 2:1).

[Compound 57]

98.8 mg (53.0%)

Rf=0.56 (toluene:ethyl acetate=4:1)

500 MHz, $^1$H—NMR (CDCl$_3$, TMS) $\delta_H$; 1.025 (s, 9H, tBu, 1.172 (d, 3H, J=6.6 Hz, H-6d), 1.759, 1.949, 1.991 (3S, 9H, Ac×3), 3.295 (t, 1H, J=8.8 Hz, H-6c), 4.262 (d, 1H, J=7.7 Hz, H-1a), 4.502 (dd, 1H, J=8.4, 10.3 Hz, H-2b), 4.613 (q, 1H, J=7.0 Hz, H-5d), 4.672 (d, 1H, J=8.1 Hz, H-1c), 4.986 (dd, 1H, J=8.8, 10.3 Hz, H-2c), 5.357 (d, 1H, J=3.3 Hz, H-4c), 5.445 (d, 1H, J=8.4 Hz, H-1b), 7.431~6.965 (m, 50H, Ph), 7.591 (d, 2H, J=8.1 Hz, Ph), 7.632 (d, 2H, J=8.1 Hz, Ph).

Example 49

(Synthesis of Compound 58)

To compound 57 (100 mg, 0.054 mmol) in ethanol (6 ml) was added methylhydrazine (20 ml) and stirred at 80° C. for 18 h. The reaction mixture was evaporated, the residue was purified by Sephadex LH-20 column chromatography (methanol). Then, to this purified sample dissolved in methanol (2 ml) was added acetic anhydride (0.2 ml) and the mixture was stirred at 20° C. for 1 h. The reaction mixture was basified by the addition of NaOH and the resulting mixture was purified by Sephadex LH-20 (methanol).

[Compound 58]

83.6 mg (90.9%)

Rf=0.59 (CHCl$_3$:Methanol=18:1)

500 MHz, $^1$H—NMR (CD$_3$OD, TMS) $\delta_H$; 1.025 (s, 9H, t Bu), 1.129 (d, 3H, J=6.6 Hz, H-6d), 1.707 (s, 3H, NHCOC H$_3$), 4.436 (d, 1H, J=8.1 Hz, H-1a), 4.730 (q, 1H, J=7.0 Hz, H-5d), 5.315 (d, 1H, J=3.7 Hz, H-1d), 7.430~7.065 (m, 46H, Ph), 7.598 (d, 2H, J=7.3 Hz, Ph), 7.647 (d, 2H, J=6.6 Hz, Ph).

Example 50

(Synthesis of Compound 59)

Compound 58 (200 mg, 0.117 mmol), compound R14 (SCH$_3$-form of sialic acid) (86.4 mg, 0.175 mmol) and acetonitrile (2 ml) were added to activated MS-4A (500 mg) under Ar and the mixture was stirred for 1 h. Then to this mixture cooled at –40° C. was added AgOTf (157.3 mg, 0.612 mmol) in acetonitrile followed by PhSeCl (117.2 mg, 0.612 mmol) in acetonitrile and the resulting mixture was stirred for 3 h. The reaction mixture was diluted with ethyl acetate and filtered through celite into the container with NaHCO$_3$. After the organic phase was washed with saturated NaCl solution, the washing was dried over anhydrous MgSO$_4$ and the solvent was evaporated. The resulting residue was purified by Bio-Rad S-X3 (toluene) and silica gel column chromatography (C-300, 40 g, toluene:acetone= 2:1).

[Compound 59]

71.3 mg (28.3%)

Rf=0.24 (toluene:acetone=2:1)

500 MHz, $^1$H—NMR (CDCl$_3$, TMS) $\delta_H$; 1.025 (s, 9H, tBu), 1.107 (d, 3H, J=6.2 Hz, H-6e), 2.098, 2.073, 2.038, 1.959, 1.901 (5S, 15H, Ac×5), 2.681 (dd, 1H, J=4.4, 13.2 Hz, H-3deq), 3.764 (s, 3H, OCH3), 4.963 (m, 1H, H-4d), 5.124 (d, 1H, J=3.7 Hz, H-1e), 5.192 (d, 1H, J=9.9 Hz, NH), 5.316 (dd, 1H, J=1.8, 8.8 Hz, H-7d), 5.432 (m, 1H, H-8d), 5.440 (d, 1H, J=7.7 Hz, NH).

Example 51

(Synthesis of Compound 60)

Compound 59 (44 mg, 0.023 mmol) in tetrahydrofuran (2 ml) were added 1M-tetrabuthylammouniumfluoride (139 µl, 0.139 mmol) and acetic acid (20 mg, 0.333 mmol) at 0° C. and the mixture was stirred at 20° C. for 18 h. The reaction mixture was diluted with chloroform, and washed with NaHCO$_3$ solution and saturated NaCl solution. After the washing was dried over anhydrous MgSO$_4$, the solvent was evaporate in vacuo. The resulting residue was purified by TLC (toluene:acetone=1:1).

[Compound 60]

14.3 mg (36.6%)

Rf=0.47 (toluene:acetone=1:1)

$[\alpha]_D^{22}$–12.0° (c=1.0, CHCl$_3$)

500 MHz, $^1$H—NMR (CDCl$_3$, TMS) $\delta_H$; 1.111 (d, 3H, J=6.2 Hz, H-6e), 1.462, 1.900, 1.971, 2.038, 2.074, 2.099 (6S, 18H, Ac×6), 2.694 (dd, 1H, J=4.4, 12.8 Hz, H-3deq), 3.764 (s, 3H, OCH$_3$), 5.185 (d, 1H, J=3.7 Hz, H-1e), 5.220 (d, 1H, J=9.9 Hz, NH), 5.316 (dd, 1H, J=1.8, 9.2 Hz, H-7d), 5.443 (m, 1H, H-8d), 5.543 (d, 1H, J=8.4 Hz, NH), 7.171~7.390 (m, 40H, Ph)

Example 52

(Synthesis of Compound 61)

To compound 60 (14.3 mg, 7.4 µmol) in methanol (2 ml) was added a catalytic amount of CH$_3$ONa and the mixture was stirred at 20° C. for 18 h. After the reaction mixture was evaporated in vacuo, the resulting residue was dissolved in a solution of methanol and H$_2$O (2:1) (2 ml) and the mixture was stirred at 20° C. for 5 h. The residue was purified by Sephadex LH-20 column chromatography (methanol).

[Compound 61]

12.1 mg (92.4%)

Rf=0.19 (CHCl$_3$:Methanol=3:1) $[\alpha]_D^{25}$–25.6 (c=0.5, CH$_3$OH 500 MHz, $^1$H—NMR (CD$_3$OD, TMS) $\delta_H$; 1.114 (d, 3H, J=6.2 Hz, H-6e), 1.721, 2.012 (2S, 6-H, NAc), 2.906 (dd, 1H, J=4.4, 12.8 Hz, H-3deq), 4.454 (d, 1H, J=7.7 Hz, H-1), 5.329 (d, 1H, J=3.7 Hz, H-1e), 7.157~7.384 (m, 40H, Ph).

Example 53

(Synthesis of Compound 62)

To compound 61 (12.1 mg, 6.8 µmol) in methanol (2 ml) and H$_2$O (0.5 ml) was added Pd(OH)$_2$—C (10 mg) and hydrogenated at 20° C. for 18 h. After the reaction mixture was filtered through chromatodisc, the solvent was evaporated in vacuo. The resulting residue was purified by Sephadex G-10 (H$_2$O).

[Compound 62]

7.0 mg (99.7%)

Rf=0.17 (BuOH:EtOH:H$_2$O=2:1:1)

500 MHz, $^1$H—NMR (CD$_3$OD, TMS) $\delta_H$; 1.196 (d, 3H, J=6.6 Hz, H-6e), 1.771 (t, 1H, J=11.7 Hz, H-3dax), 2.038, 2.058 (2s, 6H, Ac×2), 2.851 (dd, 1H, J=4.4, 12.5 Hz, H-3deq), 4.511 (d, 1H, J=7.7 Hz, H-1c), 4.537 (d, 1H, J=7.7 Hz, H-1b), 4.543 (d, 0.5 H, J=7.7 Hz, H-1a β), 5.109 (d, 1H, J=4.0 Hz, H-1e), 5.189 (bs, 0.5H, H-1a α).

Example 54

(Synthesis of Compound 63)

To the mixture of compound 56 (27 mg, 20 µmol) and compound R11 (39 mg, 40 µmol), MS-4A (500 mg) and CH$_3$CN (1 ml) was added trimethylsilyl triflate (1 µl) in CH$_3$CN (100 µl) at –38° C. by stirring and the mixture was further stirred for 1 h. After diluted with ethyl acetate, the mixture was filtered through celite and the filtrate was washed with saturated NaHCO$_3$ solution and saturated NaCl solution. After the organic phase was dried over MgSO$_4$, the solvent was evaporated and the resulting residue was purified by silica gel column chromatography (toluene/ethyl acetate=3:1) to yield 18 mg of compound 63 (42%) and 7 mg of the hemiacetal 54 (29%) was recovered.

[Compound 63]

Rf=0.33 (toluene:ethyl acetate=4:1)

$[\alpha]_D^{22}$–26° (c=0.93, CHCl$_3$)

|                   | C (%) | H (%) | N (%) |
| ----------------- | ----- | ----- | ----- |
| Theoretical value | 70.61 | 6.35  | 0.65  |
| Found value       | 70.40 | 6.36  | 0.61  |

$\delta_H$ 7.90~6.85 (m, 59H, aromatic H), 5.382 (d, 1H, J=3.7 Hz, H-4d), 5.338 (d, 1H, J=8.4 Hz, H-1c), 3.978 (d, 1H, J=2.6 Hz, H-4b), 2.005, 1.951, 1.763 (3s, 9H, 3×Ac), 1.170 (d, 3H, J=6.6 Hz, H-5e), 1.089 (s, 9H, tBu).

Example 55

(Synthesis of Compound 63) (fluorine method)

Compound R11 (1.43 g, 1.48 mmol) in 1,2-dichloroethane (4 ml) was stirred with MS-4A (4 g). To the mixture were added hafnocenedichloride (1.46 g, 3.85 mmol) and silvertrifluoromethanesulfonate (1.98 g, 770 mmol) and stirred at −40° C. for 15 minutes. To the mixture was added compound 55 (2.30 g, 1.93 mmol) and stirred at −40° C. for 4 h. After diluted with ethyl acetate, to the mixture was added triethylamine and washed with saturated NaHCO$_3$ solution followed by saturated NaCl solution. The organic phase was dried over MgSO$_4$ and the solvent was evaporated. The resulting residue was purified by silica gel column chromatography (WAKO-gel C-300, toluene:ethyl acetate=4:1) to obtain 2.38 g of compound 63 (75%).

[Compound 63]

Rf=0.33 (toluene:ethyl acetate=3:1)
Elementary analysis C$_{126}$H$_{135}$O$_{30}$N
Theoretical value
C, 70.61, H, 6.35, N, 0.65
C, 70.36, H, 6.33, N, 0.64
NMR CDCl$_3$ TMS $\delta_H$ 5.382 (d, 1H, J=3.3 Hz, H-4d), 5.335 (d, 1H, J=8.4 Hz, H-1c), 4.703 (d, 1H, J=8.1 Hz, H-1b), 4.612 (q, 1H, J=7.3 Hz, H-5e), 3.977 (d, 1H, J=2.9 Hz, H-4b), 2.007, 1.953, 1.759 (3S, 9H, 3Ac), 1.169 (d, 3H, J=6.59 Hz, H-6e), 1.091 (s, 9H, (CH$_3$)$_3$C).

Example 56

(Synthesis of Compound 65)

After compound 63 (2.25 g, 1.05 mmol) was suspended in ethanol (52 ml), hydrazine hydrate (5.2 ml, 105.3 mmol) was added to this suspension and stirred for 12 h on the oil bath heated at 110° C. After the solvent was evaporated, the residue was purified by LH-20 column chromatography (methanol). Then, methanol (170 ml) and acetic anhydride (21.2 ml) was added to the mixture and the resulting mixture was stirred. After The solvent was evaporated, methanol (52 ml) and NaOMe (112 μl) was added to the mixture and stirred for 1 h at room temperature. After subjected to amberlyst15E, the solvent was evaporated. Purification of the resulting residue by silica gel column chromatography (WAKO-gel C-300, toluene:ethyl acetate (1:6)) yielded 1.92 g of compound 65 (90.4%).

[Compound 65]

Rf=0.30 (THF:hexane=3:2)
Rf=0.29 (ethyl acetate/toluene=3:1)
[α]$_D^{22}$−38.2° (C=1.6, CHCl$_3$)

|  | C (%) | H (%) | N (%) |
|---|---|---|---|
| Theoretical value | 70.60 | 6.86 | 0.58 |
| Found value | 70.97 | 6.74 | 0.73 |

$\delta_H$ 7.40–7.05 (m, 55H, Arom H), 5.542 (d, 1H, J=7.0 Hz, NH), 1.304 (s, 3H, Ac), 1.117 (s, 9H, tBu), 1.100 (d, 3H, J=6.6 Hz, H-5e).

Example 57

(Synthesis of Compound 64 and Compound 65)

The mixture of compound 63 (13 mg, 6 mmol), ethanol (2 ml) and CH$_3$NHNH$_2$ (0.5 ml) was refluxed for 22 h. After the solvent was evaporated, the resulting residue was subjected to LH-20 (methanol) and then the solvent was evaporated to dryness. Pyridine (0.5 ml), Ac$_2$O (0.5 ml) and a catalytic amount of 4-DMAP was added to the residue and the mixture was stirred at room temperature for 1 h. After the solvent was evaporated, the residue was purified by silica gel column chromatography (toluene:AcOEt=1:1) to obtain 10.4 mg of compound 64 (83%). Then, compound 64 (10.4 mg, 5 μmol), methanol (1 ml) and 5.2N CH$_3$ONa (10 μl) were mixed and stirred for 30 minutes at room temperature. After the reaction mixture was neutralized with amberlyst 15, purification by preparative TLC (AcOEt/toluene=3:1) yielded 7 mg of compound 65 (60%).

[Compound 64]

Rf=0.52 (AcOEt/toluene=1:1)

$\delta_H$ 7.42–7.08 (m, 55H, Arom H), 5.498 (d, 1H, J=8.0 Hz, NH), 5.391 (d, 1H, J=3.7 Hz, H-4d), 5.117 (d, 1H, J=3.7 Hz, H-1e), 5.080 (dd, 1H, J=8.1, 9.5 Hz, H-2a), 1.958, 1.957, 1.815, 1.415 (4s, 12H, 4×Ac), 1.124 (s, 3H, tBu).

[Compound 65]

Rf=0.29 (AcOEt/toluene=3:1)
[α]$_D^{22}$−38.2° (c=1.6, CHCl$_3$)

$\delta_H$ 7.40–7.08 (m, 55H, aromatic H), 5.542 (d, 1H, J=7.0 Hz, NH), 1.304 (s, 3H Ac), 1.117 (s, 9H, $^t$Bu), 1.100 (d, 3H, J=6.6 Hz, H-6e).

|  | C (%) | H(%) | N (%) |
|---|---|---|---|
| Theoretical value (C$_{114}$H$_{129}$NO$_{26}$) | 70.97 | 6.74 | 0.73 |
| Found value | 70.60 | 6.86 | 0.58 |

Example 58

(Synthesis of Compound 66)

The mixture of compound 65 (405 mg, 0.21 mmol), LeV$_2$O/Cl CH$_2$CH$_2$Cl (1N solution, 15 ml), pyridine (12 ml) and a catalytic amount of 4-DMAP was stirred for 15 h at room temperature. After the reaction mixture was azeotropically evaporated with toluene, the residue was filtrated with LH-20 (methanol) and the solvent was evaporated to dryness. The residue was purified by silica gel column chromatography (ethyl acetate:toluene=5:3) to obtain 341 mg of compound 66 (76.5%).

[Compound 66]

R=0.43 (ethyl acetate/toluene=5:3)
[α]$_D^{22}$−55.9° (c=0.87, CHCl$_3$)

| C$_{124}$H$_{141}$NO$_{30}$ | C (%) | H (%) | N (%) |
|---|---|---|---|
| Theoretical value | 70.07 | 6.69 | 0.66 |
| Found value | 69.63 | 6.63 | 0.52 |

$\delta_H$ 7.40–7.10 (m, 55H, Arom H), 5.497 (d, 1H, J=8.5 Hz, NH), 5.145 (dd, 1H J=8.1, 10.3 Hz, H-2d), 2.87–2.35 (m, 8H, 2×—CH$_2$CH$_3$—), 2.184, 2.123 (2S, 6H, 2×Me), 1.351 (s, 3H, Ac), 1.121 (s, 9H, tBu).

Example 59

(Synthesis of Compound 67)

The mixture of compound 66 (337 mg, 0.158 mmol), pyridine (10 ml), Ac$_2$O (10 ml) and catalytic amount of 4-DMAP was stirred for 15 h. After the solvent was evaporated by addition of toluene and the resulting residue was purified by silica gel column chromatography (toluene:ethyl acetate=1:1) to yield 335 mg of compound 67 (97.5%).

[Compound 67]

Rf=0.37 (ethyl acetate:toluene=5:3)

$[\alpha]_D^{22}$ −51.9° (c=0.93, $CHCl_3$)

|  | C (%) | H (%) | N (%) |
|---|---|---|---|
| Theoretical value | 69.82 | 6.65 | 0.65 |
| Found value | 69.58 | 6.69 | 0.52 |

$\delta_H$ 7.40~7.08 (m, 55H, aromatic H), 5.472 (d, 1H, J=8.4 Hz, NH), 5.350 (d, 1H, J=4.0 Hz, H-4d), 5.139 (d, 1H, J=3.7 Hz, H-1e), 5.083 (dd, 1H, J=8.1, 9.2 Hz, H-2a), 4.956 (dd, 1H, J=8.0, 10.6 Hz, H-2d), 2.85~2.32 (m, 8H, 2×—$CH_2CH_2$—), 2.166, 2.114 (2s, 6H, 2×Me), 1.782, 1.408 (2S, 6H, 2×Ac), 1.126 (s, 9H, tBu)

Example 60

(Synthesis of Compound 68)

The mixture of compound 67 (335 mg, 0.155 mmol), 20% Pd(OH)$_2$—C (335 mg) and 20% aqueous methanol (30 ml) was hydrogenated at room temperature. After the catalyst was filtered out, the filtrate was evaporated to dryness in vacuo. Pyridine (10 ml), Ac$_2$O (10 ml) and a catalytic amount of 4-DMP was added to the resulting residue and the mixture was stirred overnight. The solvent was evaporated to dryness and the residue was purified by silica gel column chromatography to obtain 234 mg of compound 68 (95%) (β/α=2:1)

[Compound 68]

Rf=0.33 ($CHCl_3$/MeOH=30:1)

$\delta_H$ 6.290 (d, 0.33H, J=3.7 Hz, H-1aα), 5.699 (d, 0.67H, J=8.1 Hz, H-1aβ), 1.179 (d, 0.99H, J=6.6 Hz, H-6eα), 1.126 (d, 2.01H, J=6.6 Hz, H-6eβ).

Example 61

(Synthesis of Compound 69)

The mixture of compound 68 (230 mg, 0.14 mmol), piperidineacetate (142 mg, 0.98 mmol) and dried THF (10 ml) was reacted by standing for 1 h at room temperature followed by shaking with ultrasonic wave for 3 h. After extracted with ethyl acetate, the reaction mixture was washed with saturated NaHCO$_3$ solution and then washed with saturated NaCl solution. After the organic phase was dried over MgSO$_4$, the solvent was evaporated to dryness. The resulting residue was purified by silica gel column chromatography ($CHCl_3$:methanol=35:1) to obtain 164 mg of compound 69 (74%) and collect 41 mg of compound 68 (18%) that mainly contained α-glucoside epimer.

[Compound 69]

R=0.42 (.$CHCl_3$/MeOH=18:1)

| $C_{69}H_{97}NO_{41}$ | C (%) | H (%) | N (%) |
|---|---|---|---|
| Theoretical value | 51.91 | 6.12 | 0.88 |
| Found value | 52.09 | 6.17 | 0.79 |

Example 62

(Synthesis of Compound 70)

Trichloroacetonitrile (64 μl, 638 μmol) and DBU (19 μl, 127 μmol) was orderly added to compound 69 (100 mg, 63 μmol) in $ClCH_2CH_2Cl$ (2 ml) under cooling and to the mixture was further stirred for 2 h. The reaction mixture was purified by silica gel column chromatography ($CHCl_3$:methanol=30:1) to obtain 102 mg of compound 70 (92.7%).

[Compound 70]

R=0.40 ($CHCl_3$/MeOH=25:1)

$[\alpha]_D^{22}$ −0.8° (c=0.37, $CHCl_3$)

$\delta_6$ 8.649 (s, 1H, =NH), 6.506 (d, 1H, J=3.7 Hz, H-1a), 5.575 (t, 1H J=9.5 Hz, H-3a), 5.400 (d, 1H, J=8.0 Hz, NH), 5.375 (d, 1H, J=2.6 Hz, H-4d), 5.352 (d, 1H, J=3.3 Hz, H-4e), 5.318 (d, 1H, J=3.6 Hz, H-1e), 5.302 (d, 1H, J=4.0 Hz, H-4b), 5.183 (dd, 1H, J=3.6, 10.7 Hz, H-2e), 4.633 (d, 1H, J=7.3 Hz, H-1d), 4.409 (d, 1H, J=7.7 Hz, H-1b), 2.90~2.35 (m, 8H, 2×—$CH_2CH_2$—), 2.199, 2.176, 2.165, 2.142, 2.141, 2.123, 2.116, 2.115, 2.113, 2.075×2, 2.011, 1.968, 1939 (14s, 42H, 14×A c), 1.179 (d, 3H, J=6.6 Hz, H-6e), 1.129 (s, 9H, tBu).

Example 63

(Synthesis of Compound 71)

Compound 70 (94 mg, 54 μmol), R 18 (81 mg, 107 μmol), MS4A (1 g) and $CHCl_3$ (2 ml) were mixed by stirring for 15 minutes at room temperature and further stirred at −15° C. for 15 minutes. BF$_3$OEt$_2$ (15 μl, 164 μmol) was added to the mixture and stirred for 1 h. After the reaction mixture was neutralized with Et$_3$N, the mixture was filtered and the filtrate was extracted with $CHCl_3$. After the reaction mixture was washed with saturated NaHCO$_3$ solution followed by saturated NaCl solution, the organic phase was dried over MgSO$_4$ and the solvent was evaporated to dryness. The residue was purified by silica gel column chromatography ($CHCl_3$:methanol=60:1) to yield 78 mg of compound 71 (61%).

[Compound 71]

Rf=0.48 ($CHCl_3$/MeOH=26:1)

$[\alpha]_D^{22}$ −19.5° (c=1.1, $CHCl_3$)

$\delta_H$ 8.20~7.42 (m, 5H, aromatic H), 5.872 (dt, 1H, J=7.4, 15.0 Hz, H-5cer), 5.738 (d, 1H, J=9.2 Hz, NH), 5.539 (t, 1H, J=7.7 Hz, H-3cer), 5.454 (dd, 1H, J=7.7, 15.4 Hz, H-4cer), 5.375 (d, 1H, J=3.0 Hz, H-4d), 5.350 (d, 1H, J=3.3 Hz, H-4e), 4.626 (d, 1H, J=7.3 Hz, H-1d), 4.411 (d, 1H, J=7.7 Hz, H-1a), 4.314 (d, 1H, J=8.0 Hz, H-1b), 2.90~2.38 (m, 8H, 2×—$CH_2CH_2$—), 2.198, 2.174, 2.161, 2.142, 2.141, 2.132, 2.102, 2.101, 2.073, 2.034, 1.987, 1.966, 1928, 1.919 (14s, 42H, 12Ac+2Me), 1.178 (d, 3H, J=6.6 Hz, H-6e), 1.140 (s, 9H, tBu), 0.578 (t, 6H, J=7.0 Hz, 2 $CH_2CH_3$).

Example 64

(Synthesis of Compound 72, Compound 73 and Compound 74)

(1) The mixture of compound 71 (16 mg, 6.9 μmol), ethanol (1 ml), H$_2$NNH$_2$—AcOH (6.2 mg, 6.7 μmol) was stirred for 30 minutes at room temperature. The reaction mixture was diluted with CHCl$_3$ and was washed with saturated NaHCO$_3$ solution and saturated NaCl solution. After the organic phase was dried over MgSO$_4$, the solvent was evaporated to dryness and the resulting residue was purified LH-20 column chromatography (CHCl$_3$:methanol= 1:1) to yield 11 mg of compound 72 (75%).

(2) The mixture of compound 71 (35 mg, 15 μmol), ethanol (3 ml) and H$_2$NNH$_2$—AcOH (5 mg, 54 μmol) was stirred for 1.5 h at the temperature from −12° C. to −3° C. After the mixture was treated by the same manner of method (1), the reaction mixture was purified by silica gel column chromatography (toluene:acetone=8:5) followed by preparative TLC. This purification yielded 6.8 mg of compound 73 (21%), 3.4 mg of compound 74 (10%) and 6.2 mg of compound 72 (20%).

[Compound 72]

R=0.37 (CHCl$_3$/MeOH=25:1)

$[\alpha]_D^{22}$−21.5° (c=1.0, CHCl$_3$)

$\delta_H$ 8.02~7.42 (m, 5H, aromatic H), 5.872 (dt, 1H, J=7.7, 15.0 Hz, H-5cer), 5.742 (d, 1H, J=9.2 Hz, NH), 5.538 (t, 1H, J=7.7 Hz, H-3c), 5.453 (dd, 1H, J=7.7, 15.0 Hz, H-4cer), 4.432 (d, 1H, J=8.1 Hz, H-1d), 4.411 (d, 1H, J=7.7 Hz, H-1a), 4.305 (d, 1H, J=8.0 Hz, H-1b), 2.174, 2.144, 2.139, 2.124, 2.105, 2.104, 2.085, 2.031, 1.986, 1.976, 1.922, 1.916 (12s, 36H, 12×Ac), 1.142 (s, 9H, tBu), 1.101 (d, 3H, J=6.6 Hz, H-6e), 0.878 (t, 6H, J=7.0 Hz, 2 CH$_2$CH$_3$).

[Compound 73]

$\delta_H$ 8.02~7.41 (m, 5H, aromatic H), 5.872 (dt, 1H, J=7.7, 15.4 Hz, H-5cer), 5.724 (d, 1H, J=9.1 Hz, NH), 5.537 (t, 1H, J=7.7 Hz, H-3cer), 5.454 (dd, 1H, J=7.7, 15.4 Hz, H-4cer), 5.377 (d, 1H, J=3.7 Hz, H-4d), 4.533 (d, 1H, J=8.4 Hz, H-1d), 4.410 (d, 1H, J=7.7 Hz, H-1a), 4.303 (d, 1H, J=8.0 Hz, H-1b), 2.201, 2.195, 2.171, 2.157, 2.137, 2.124, 2.101, 2.094, 2.032, 1.985, 1970, 1.921, 1.920 (13s, 39H, 12Ac+ 1Me), 1.159 (d, 3H, J=6.6 Hz, H-6e), 1.140 (s, 9H, tBu), 0.880 (t, 6H, J=7.0 Hz, 2 CH$_2$CH$_3$)

Rf=0.45 (toluene/acetone=7:5)

$[\alpha]_D^{22}$−8.2° (c=0.17, CHCl$_3$)

[Compound 74]

R=0.42 (toluene/acetone=8:5)

$\delta_H$ 8.02~7.41 (m, 5H, aromatic H), 5.870 (dt, 1H, J=7.7, 15.4 Hz, H-5cer), 5.717 (d, 1H, J=9.2 Hz, NH), 5.521 (t, 1H, J=7.7 Hz, H-3cer), 4.410 (d, 1H, J=8.0 Hz, H-1a), 1.159 (d, 3H, J=7.0 Hz, H-6e), 1.139 (s, 9H, tBu), 0.878 (t, 6H, J=7.0 Hz, 2CH$_2$CH$_3$)

Example 65

(Synthesis of Compound 75)

The mixture of compound 72 (14 mg, 6.6 μmol), Me$_3$N.SO$_3$ (14 mg, 100 μmol) and DMF (0.8 ml) was stirred at 90° C. for 15 minutes. After the reaction mixture was purified by LH-20 column chromatography (CHCl$_3$:MeOH= 1:1), the solvent was evaporated and the residue was subjected to ion-exchange by Dowex 50 (Na+) (methanol:H$_2$O= 9:1). The mixture was finally purified by preparative TLC (CHCl$_3$:methanol=4:1) to yield 11.2 mg of compound 75 (73%).

[Compound 75]

R=0.30 (CHCl$_3$/MeOH=4:1)

$[\alpha]_D^{22}$−2° (c=0.25, CHCl$_3$)

$\delta_H$ (CD$_3$OD) 8.02~7.43 (m, 5H, aromatic H), 5.874 (dt, 1H, J=7.7, 15.1 Hz, H-5 cer), 5.692 (d, 1H, J=2.6 Hz, H-4e), 5.560 (t, 1H, J=7.7 Hz, H-3cer), 5.497 (dd, 1H, J=7.7, 15.1 Hz, H-4cer), 5.377 (d, 1H, J=3.3 Hz, H-4 d), 5.350 (d, 1H, J=3.3 Hz, H-4b), 5.323 (d, 1H, J=4.1 Hz, H-1e), 5.220 (dd, 1H, J=3.3, 10.6 Hz, H-3d), 5.174 (t, 1H, J=9.5 Hz, H-2a), 4.938 (dd, 1H, J=4.1, 11.0 Hz, H-2e), 4.629 (d, 1H, J=8.0 Hz, H-1d), 3.853 (dd, 1H, J=3.7, 10.3 Hz, H-3b), 2.150, 2.140, 2.125, 2.097, 2.094, 2.085, 2.081, 2.034, 1.988, 1.982, 1.922, 1865 (12s, 36H, 12×Ac), 1.190 (d, 3H, J=6.6 Hz, H-6e), 1.145 (s, 9H, tBu), 0.895 (t, 6H, 2 CH$_2$CH$_3$).

Example 66

(Synthesis of Compound 76)

The mixture of compound 73 (4 mg, 1.8 μmol), Me$_3$N.SO$_3$ (14 mg, 100 μmol) and DMF (0.4 ml) was stirred at 90 for 1.5 h. Then, treatment of the mixture by the same manner of synthesis of compound 75 yielded 3.2 mg of compound 76 (77%).

[Compound 76]

Rf=0.46 (CHCl$_3$:methanol=16:3)

$[\alpha]_D^{22}$−22° (c=0.1, CHCl$_3$)

$\delta_H$ (CD$_3$OD) 8.02~7.42 (m, 5H, aromatic H), 5.873 (dt, J=7.7, 15.0 Hz, H-5cer), 5.658 (d, 1H, J=3.7 Hz, H-4e), 5.559 (t, 1H, J=7.7 Hz, H-3cer), 5.495 (dd, J=7.7, 15.0 Hz, H-4cer), 5.394 (d, 1H, J=3.0 Hz, H-4d), 5.368 (d, 1H, J=3.6 Hz, H-4b), 5.304 (d, 1H, J=4.0 Hz, H-1e), 5.217 (dd, 1H, J=3.3, 11.0 Hz, H-3d), 5.174 (d, 1H, J=9.5 Hz, H-2a), 4.943 (dd, 1H, J=3.7, 11.0 Hz, H-2e), 4.722 (d, 1H, J=8.1 Hz, H-1c), 4.625 (d, 1H, J=8.0 Hz, H-1d), 4.565 (dd, 1H, J=3.7, 9.9 Hz, H-3e), 4.446 (d, 1H, J=8.1 Hz, H-1a), 3.850 (dd, 1H, J=3.7, 10.3 Hz, H-3b), 2.80~2.60 (m, 4H, —O CH$_2$CH$_2$COCH$_3$), 2.183, 2.162, 2.143, 2.124, 2.100, 2.094, 2.080, 2.076, 2.036, 1.981, 1.924, 1.896, 1.857 (13s, 39H, 13×Ac), 1.171 (d, 3H, J=6.2 Hz, H-6e), 1.145 (s, 9H, tBu), 0.895 (t, 6H, 2CH$_2$CH$_3$).

Example 67

(Synthesis of Compound 77)

A mixture of compound 75 (10.2 mg, 4.4 μmol), THF:MeOH (1:1) (0.7 ml), and 1N NaOHAq (0.3 ml) was stirred at room temperature for 2 h. The reaction mixture was purified by LH- 20 column chromatography (CHCl$_3$:MeOH:H$_2$O=60:30:5) to obtain compound 77 (6 mg, 82%).

[Compound 77]

Rf=0.48 (nBuOH:EtOH:H$_2$O=2:1:1)

$\delta_H$ (DMSOd$_6$:D$_2$O=49:1), 5.560 (dt, 1H, J=7.0, 15.4 Hz, H-5cer), 5.373 (dd, 1H, J=7.0, 15.4 Hz, H-4cer), 4.972 (d, 1H, J=7.6 Hz, H-1 c), 4.922 (d, 1H, J=2.9 Hz, H-1e), 4.432 (d, 1H, J=7.7 Hz, H-1d), 4.316 (d, 1H, J=3.0 Hz, H-4d), 4.285 (d, 1H, J=8.1 Hz, H-1b), 4.277 (t, 1H, J=8.0 Hz, H-2d), 4.232 (q, 1H, J=6.6 Hz, H-5e), 4.174 (d, 1H, J=7.7 Hz, H-1a), 4.032 (dd, 1H, J=3.0, 9.5 Hz, H-3d), 2.046 (t, 2H, J=7.2 Hz), 1.837 (s, 3H, NHAc), 1.092 (d, 3H, J=6.6 Hz, H-6e), 0.860 (t, 6H, J=7.0 Hz, 2 CH$_2$CH$_3$).

Example 68

(Synthesis of Compound 78)

Compound 76 (3.2 mg, 1.4 µmol) was deprotected in a similar manner for that of Example 67, and purified to obtain compound 78 (2.1 mg, 97%).

[Compound 78]

Rf=0.55 (nBuOH:EtOH:H$_2$O=2:1:1)

$\delta_H$ (DMSO:D$_2$O=49:1), 5.556 (dt, J=15.4, 7.0 Hz, H-5 cer), 5.376 (dd, J=15.4, 7.0 Hz, H-4 cer), 4.881 (d, 1H, J=3.7 Hz, H-1e), 4.725 (d, 1H, J=7.7 Hz, H-1c), 4.396 (d, 1H, J=7.7 Hz, H-1d), 4.280 (d, 1H, J=7.7 Hz, H-1b), 4.173 (d, 1H, J=7.7 Hz, H-1a), 3.968 (dd, 1H, J=3.0, 9.5 Hz, H-3d), 3.952 (d, 1H, J=3.0 Hz, H-4d), 1.833 (s, 3H, NHAc), 1.017 (d, 3H, J=6.6 Hz, H-6e), 0.858 (t, 6H, J=7.0 Hz, 2CH$_2$CH$_3$).

Example 69

(Synthesis of Compound 79)

Compound 65 (82.2 mg, 0.043 mmol) was dissolved in acetonitrile (1.0 ml), stirred with MS3A (400 mg) at room temperature for 10 min. To the reaction mixture cooled to −40° C. was added compound 42 (113 mg, 0.064 mmol) and the mixture was stirred further 10 min. Then BF$_3$.OEt$_2$ (8.5 µl, 0.064 mmol) was added to the reaction mixture and stirred for 1 h. The reaction mixture was diluted with ethyl acetate and quenched with triethylamine, washed with saturated NaHCO$_3$aq followed by saturated NaClaq, dried over MgSO$_4$. The organic layer was evaporated to dryness in vacuo. The residue was purified by silica gel column chromatography (WAKO-gel c-300, chloroform:acetone=5:1) followed by SX-1 (toluene) column chromatography to obtain compound 79 (77.7 mg, 51.6%).

[Compound 79]

Rf 0.48 (chloroform:acetone=3:1)

[α]$_D$−22.8° (c=1.0, CHCl$_3$)

Elementary Analysis C$_{199}$H$_{223}$O$_{55}$N$_3$

Calcd. Tor C 67.58, H 6.35, N 1.19

Found C 67.62, H 6.69, N 1.01

NMR (CDCl$_3$, TMS)

$\delta_H$, 5.508 (m, 1H, H-8g), 5.399 (dd, 1H, J=2.6, 11.7 Hz, H-7g), 5.346 (d, 1H, J=8.4, H-1e), 4.896 (d, 1H, J=3.7, H-1i or H-1h), 3.835 (s, 3H, OMe), 2.531 (dd, 1H, J=12.5, 4.8 Hz, H-3g eq), 2.246, 2.079, 2.066, 2.007, 2.007, 1.969, 1.855, 1.788 (8s, 24H, Ac), 1.114 (s, 9H, (CH$_3$)$_3$C), 0.796 (d, 3H, J=6.2 Hz, H-6i or H-6h).

Example 70

(Synthesis of Compound 80)

A mixture of compound 79 (77.7 mg, 0.022 mmol), acetic anhydride (1 ml), and pyridine (1 ml) was stirred at room temperature for 24 h. Then to the reaction mixture was added 4-DMAP and the mixture was stirred further for 3 days. After the addition of MeOH, the solvent was coevaporated with toluene. The residue was purified by silica gel column chromatography (WAKO-gel c-300, chloroform:acetone=4:1) to obtain compound 80 (74.5 mg, 93.7%).

[Compound 80]

Rf 0.7 (chloroform:acetone=3:1)

[α]$_D$−19.2° (c=0.8, CHCl$_3$)

NMR (CDCl$_3$, TMS)

$\delta_H$, 5.470 (d, 1H, J=4.0 Hz, H-4d), 5.390 (dd, 1H, J=2.6, 9.2 Hz, H-7g), 5.015 (d, 1H, J=3.7 Hz, H-1i or H-1h), 4.942 (d, 1H, J=2.9 Hz, H-4f), 3.844 (s, 3H, OMe), 3.599 (dd, 1H, J=10.6, 2.9 Hz, H-3d, or H-3f), 2.229, 2.132, 2.058, 2.007, 1.981, 1.967, 1.856, 1.777, 1.754, 1.607 (10s, 30H, 10Ac), 1.215 (d, 3H, J=6.6 Hz, H-6h), 1.121 (s, 9H, (CH$_3$)$_3$C), 0.882 (d, 3H, J=6.2 Hz, H-6i).

Example 71

(Synthesis of Compound 80a)

To a solution of compound 80 (24.2 mg, 6.76 µmol) in MeOH:H$_2$O (4:1, 4 ml) was added 10% Pd(OH)$_2$—C (24.2 mg) under Ar, and after Ar was replaced by H$_2$, the mixture was stirred for 26 h. After the reaction mixture was filtered through celite, the solvent was evaporated in vacuo to obtain 14.3 mg of compound 80a (97.1%).

[Compound 80a]

Rf 0.21 (BuOH:EtOH:H$_2$O=5:2:1)

0.29 (BuOH:EtOH:H$_2$O=5:2:1)

NMR (CD$_3$OD, TMS)

$\delta_H$ 5.642 (m, 1H, H-8g), 5.451 (d, 1H, H-4d), 3.862 (s, 3H, OMe), 2.304, 2.190, 2.134, 2.089, 2.080, 2.074, 1.974, 1.939, 1.815 (9s, 27H, 9Ac), 1.217 (s, 9H, (CH$_3$)$_3$C), 0.986 (d, 3H, J=6.2 Hz, H-6i).

Example 72

(Synthesis of Compound 81)

A mixture of compound 80a (14.3 mg, 6.56 µmol), pyridine (1 ml), acetic anhydride (1 ml), and DMAP stirred for 20.5 h at room temperature. To the reaction mixture was added MeOH, and the solvent was coevaporated with toluene. The residue was purified by silica gel column chromatography (WAKO-gel C-300, chloroform:MeOH=25:1) to obtain 18.5 mg of compound 81 (98.8%)

[Compound 81]

Rf 0.31, 0.36 (chloroform:MeOH=25:1)

NMR (CDCl$_3$, TMS)

$\delta_H$ 6.286 (d, 0.5H, J=3.6 Hz, H-1a(α)), 5.687 (d, 0.5H, J=8.4 Hz, H-1a(β)), 3.863 (s, 3H, OMe), 2.3~1.8 (26s, 78H, 26 Ac), 1.129, 1.116 (2s, 18H, (CH$_3$)$_3$C), 1.178 (d, 3H, J=7.0 Hz, H-6h), 0.826 (d, 3H, J=6.6 Hz, H-6i).

Example 73

(Synthesis of Compound 82)

To a solution of compound 81 (48.8 mg, 17 µmol) in DMF (1 ml) was added hydrazine acetate (3.15 mg, 34 µmol) and the mixture was stirred at room temperature for 1.5 h. The reaction mixture was diluted with ethyl acetate, washed with saturated Aq.NaHCO$_3$ followed by saturated Aq.NaCl. The organic layer was dried over MgSO$_4$, evaporated in vacuo, and purified by LH-20 column chromatography (chloroform:MeOH (1:1)) to obtain compound 82 (46.9 mg, 97.5%).

127

[Compound 82]

Rf 0.35 (chloroform:MeOH, 20:1)

Example 74

(Synthesis of Compound 83)

Compound 82 (46.9 mg, 17 µmol) was dissolved in dichloromethane (1 ml), and stirred at 0° C. To the mixture were added trichloroacetonitrile (26.0 µl, 0.26 mmol) and DBU (5.55 µl, 36 µmol), and the mixture was stirred for 1 h. The solution was purified directly by silica gel column chromatography (WAKO-gel c-300, chloroform:MeOH= 50:1) to obtain 45.3 mg of compound 83 (91.9%).

[Compound 83]

Rf 0.38 (chloroform:MeOH=25:1)

NMR (CDCl$_3$, TMS)

$\delta_H$ 8.648 (s, 1H, =NH), 6.498 (d, 1H, J=3.7 Hz, H-1a), 5.559 (t, 1H, J=9.5 Hz, H-3a), 5.498 (dd, 1H, J=2.6, 9.2 Hz, H-7g), 5.382 (d, 1H, J=3.7 Hz, H-1i or H-1h), 5.291 (d, 1H, J=3.3 Hz, H-4i), 3.865 (s, 3H, OMe), 1.177 (d, 3H, J=6.6 Hz, H-6h), 1.125 (s, 9H, (CH$_3$)$_3$C), 0.825 (d, 3H, J=6.6 Hz, H-6i).

Example 75

(Synthesis of Compound 84)

A solution of compound 83 (45.3 mg, 0.015 mmol) and (R18, 23.1 mg, 0.031 mmol) in chloroform (1 ml) was stirred with MS4A (500 mg) at room temperature for 15min, and then cooled to −15° C. To the reaction mixture was added BF$_3$.OEt$_2$ (5.6 µl, 0.062 mmol) and the reaction mixture was stirred for 5 h. After diluted with chloroform, triethylamine was added to the reaction mixture, which was washed with saturated Aq.NaHCO$_3$ followed by saturated Aq.NaCl. The organic layer was dried over MgSO$_4$, and the solvent was evaporated in vacuo. The residue was purified by silica gel column chromatography (WAKO-gel c-400 chloroform:MeOH (25:1), to obtain 24.5 mg of compound 84 (45.1%)

[Compound 84]

Rf 0.59 (chloroform:methanol 25:1)

$[\alpha]_D$−30.6° (c=1.0, CHCl$_3$)

NMR (CDCl$_3$, TMS)

$\delta_H$ 5.872 (dt, 1H, J=14.7, 7.3 Hz, 5cer), 5.728 (d, 1H, J=9.2 NH), 5.614 (m, 1H, H-8g), 5.534 (t, 1H, J=7.7 Hz, 3cer), 5.086 (d, 1H, J=3.7 Hz, H-1i), 4.904 (d, 1H, J=2.9 Hz, H-4f), 4.404 (d, 1H, J=7.7 Hz, H-1a), 4.242 (d, 1H, J=8.1 Hz, H-1b), 3.868 (s, 3H, OMe), 1.183 (d, 3H, J=6.6 Hz, H-6h), 1.138 (s, 9H, (CH$_3$)$_3$C), 0.880 (t, 6H, J=6.6 Hz, 2CH$_2$CH$_3$), 0.802 (d, 3H, J=6.2 Hz, CH$_3$-6i)

Example 76

(Synthesis of Compound 85)

Compound 84 (7.1 mg, 2.00 µmol) and dried LiI (5.5 mg, 0.04 mmol) was dissolved in pyridine (0.7 ml), and stirred for 10 h at 110° C. on oil bath. The reaction mixture was purified by LH-20 (MeOH) column chromatography without concentration followed by silica gel column chromatography (WAKO-gel c-300, chloroform:MeOH=10:1) to obtain compound 85 (4.5 mg, 63.6%).

128

[Compound 85]

Rf 0.13 (chloroform:MeOH 10:1)

0.76 (chloroform:MeOH 3:1)

$[\alpha]_D$−18.2° (c=0.5, CHCl$_3$)

NMR (CDCl$_3$, TMS)

$\delta_H$ 5.563 (t, 1H, J=6.6 Hz, 3-cer), 1.181 (d, 3H, J=6.6 Hz, H-6h), 0.897 (s, 9H, (CH$_3$)$_3$C), 0.787 (d, 3H, J=6.6 Hz, H-6i).

Example 77

(Synthesis of Compound 86)

To a solution of compound 85 (4.5 mg, 1.27 µmol) in EtOH (1 ml) was added MeNHNH$_2$ (0.5 ml), and the mixture was stirred for 6 h at 80° C. The solution was concentrated, and to the residue were added MeOH (0.6 ml) and acetic anhydride (0.3 ml), stirred for 1 h at room temperature. The solvent was coevaporated with toluene. To the residue dissolved in MeOH:THF=(1:1) (0.3 ml) was added 1N NaOH (0.1 ml) at room temperature, and the mixture was stirred for 1 h. The reaction mixture was purified by LH-20 (chloroform:MeOH:H$_2$O=60:30:5) column without concentration to obtain 2.2 mg of compound 86 (74.9%).

[Compound 86]

Rf 0.39 (BuOH:EtOH:H$_2$O=(2:1:1))

NMR DMSO:D$_2$O (50:1), TMS $\delta_H$ 5.572 (dt, 1H, J=15.4 Hz, 7.0 Hz, 5-cer), 5.362 (dd, 1H, J=7.0, 15.4 Hz, 4-cer), 4.914 (d, 2H, J=3.7 Hz, H-1c and H-1h), 4.780 (d, 1H, J=7.0 Hz, H-1c or H-1e), 4.747 (d, 1H, J=7.3 Hz, H-1e or H-1c), 4.650 (d, 1H, J=6.6 Hz, H-1d or H-1f), 4.600 (d, 1H, J=6.2 Hz, H-1f or H-1d), 4.356 (d, 1H, J=7.0 Hz, H-1b), 4.200 (d, 1H, J=7.7 Hz, H-1a).

Example 78

(Synthesis of Compounds 87α and 87β)

To activated-MS4A and 3A (1:1, 5 g) were added mercuric bromide-mercuric cyanide (1:1, 8.425 g, 13.54 mmol), compound 23 (2.500 g, 2.256 mmol) and acetonitrile (4 ml) under an Ar atmosphere, and the mixture was stirred at 20° C. for 1 h. To the reaction mixture was added compound R13 (3.451 g, 6.768 mmol) dissolved in acetonitrile (4 ml), and the mixture was stirred for 3 days at 20° C. The reaction mixture was diluted with chloroform, filtered through celite. The organic layer was washed with saturated Aq.NaHCO$_3$ followed by saturated Aq.NaCl, dried over MgSO$_4$, and evaporated in vacuo. The residue was purified by Bio-Rad S-X3 (toluene) silica gel column chromatography (c-300, toluene:methanol=10:1).

[Compound 87α]

1.370 g (38.4%)

Rf=0.24 (toluene:methanol=10:1)

$[\alpha]^{23}_D$−28.4° (c=0.3, CHCl$_3$)

500 MHz, $^1$H—NMR (CDCl$_3$, TMS) $\delta_H$; 1.120 (d, 3H, J=6.6 Hz, H-6d), 1.803 (t, 1H, J=13.2 Hz, H-3cax), 1.877, 1.988, 2.022, 2.044, 2.049 (5S, 15H, Ac×5), 2.425 (dd, 1H, J=4.8, 13.2 Hz, H-3ceq), 2.433 (bs, 1H, OH), 2.468 (bs, 1H, OH), 3.738 (s, 3H, OCH$_3$), 4.350 (dd, 1H, J=8.4, 11.0 Hz, H-3b), 4.459 (d, 1H, J=7.7 Hz, H-1b), 4.679 (d, 1H, J=4.0 Hz, H-1d), 4.870 (m, 1H, H-4c), 5.071 (d, 1H, J=8.4 Hz, H-1a), 5.230 (dd, 1H, J=1.8, 7.7 Hz, H-7c), 5.665 (m, 1H, CH$_2$CH=CH$_2$)

[Compound 87β]

0.529 g (16.6%)

Rf=0.28 (toluene:methanol=10:1)

500 MHz, $^1$H—NMR (CDCl$_3$, TMS) δ$_H$; 1.145 (d, 3H, J=6.6 Hz, H-6d), 1.904, 1.956, 1.969, 2.019, 2.099 (5S, 15H, Ac×5), 2.393 (dd, 1H, J=4.8, 13.6 Hz, H-3 ceq), 2.740 (d, 1H, J=2.6 Hz, OH), 3.149 (bs, 1H, OH), 3.520 (s, 3H, OCH$_3$), 4.323 (dd, 1H, J=8.4, 11.0 Hz, H-3b), 4.449 (d, 1H, J=7.3 Hz, H-1b), 4.682 (d, 1H, J=4.0 Hz, H-1d), 4.762 (dd, 1H, J=8.8, 11.0 Hz, H-2a), 5.047 (d, 1H, J=8.8 Hz, H-1a), 5.146 (m, 1H, H-8c), 5.324 (dd, 1H, J=2.2, 4.8 Hz, H-7c), 5.466 (d, 1H, J=9.9 Hz, NH), 5.646 (m, 1H, CH$_2$CH=CH$_2$).

Example 79

(Synthesis of Compound 88)

To dried LiI 9.2 mg (0.068 mmol) was added compound 87 (54 mg, 0.034 mmol) dissolved in pyridine (1 ml) and the mixture was stirred for 18 h at 110° C. The reaction mixture was purified by Sephadex LH-20 (methanol) followed by silica gel column chromatography (c-300, 20 g, chloroform:methanol=6:1).

[Compound 88]

31 mg (57.7%)

Rf=0.05 (chloroform:methanol=24:1)

500 MHz, $^1$H—NMR (CDCl$_3$, TMS) δ$_H$; 1.125 (d, 3H, J=6.6 Hz, CH$_3$), 1.852, 1.923, 2.003, 2.096, 2.156 (5S, 15H, Ac×5), 5.630 (m, 1H, CH$_2$CH=CH$_2$)

Example 80

(Synthesis of Compound 89)

To a solution of compound 88 (30 mg, 0.019 mmol) in ethanol (1 ml) was added methylhydrazine (3 ml), stirred for 18 h at 80° C. The reaction mixture was evaporated in vacuo, and then toluene was added and coevaporated in vacuo. The residue was purified by Sephadex LH-20 (methanol). To the product dissolved in methanol 2 ml, acetic anhydride (0.25 ml) was added, and stirred for 30 min at 20° C. To the reaction mixture was added sodium hydroxide to basify it, and then purified by Sephadex LH-20 (methanol) followed by TLC (ethyl acetate:ethanol:H$_2$O=5:2:1).

[Compound 89]

9.2 mg (35.9%)

500 MHz, $^1$H—NMR (CDCl$_3$:CD$_3$OD=1:1, TMS) δ$_H$; 1.215 (d, 3H, J=6.6 Hz, CH$_3$), 1.951, 2.023 (2s, 6H, Ac×2), 2.433 (dd, 1H, J=4.4, 12.8 Hz, H-3 ceq), 4.384 (d, 1H, J=7.7 Hz, H-1a or H-1b), 4.769 (d, 1H, J=11.0 Hz, CH$_2$Ph), 4.922 (d, 1H, J=11.4 Hz, CH$_2$Ph), 5.083 (d, 1H, J=3.7 Hz, H-1d), 5.863 (m, 1H, CH$_2$CH=CH$_2$).

Example 81

(Synthesis of Compound 90)

To compound 89 (9.2 mg, 6.6 μmol) dissolved in methanol (2 ml) and H$_2$O 0.5 ml was added 10% Pd—C 10 mg and the mixture was hydrogenated for 18 h at 20° C. The reaction mixture was filtered through chromatodisc and then purified by Sephadex LH-20 (methanol).

[Compound 90]

6.0 mg (99.2%)

Rf=0.20 (BuOH:EtOH:H$_2$O=2:1)

500 MHz, $^1$H—NMR (CD$_3$OD, TMS) δ$_H$; 0.907 (t, 3H, J=7.3 Hz, CH$_2$CH$_3$), 1.198 (d, 3H, J=6.6 Hz, CH$_3$), 1.641 (t, 1H, J=12.5 Hz, H-3cax), 1.976, 1.984 (2s, 6H, Ac×2), 2.399 (dd, 1H, J=4.8, 12.8 Hz, H-3ceq), 4.404 (d, 1H, J=7.7 Hz, H-1a or H-1b), 4.597 (d, 1H, J=8.4 Hz, H-1b or H-1a), 5.046 (d, 1H, J=4.0 Hz, H-1d).

Example 82

(Synthesis of Compound 91)

Ir (COD) (PMePh$_2$)$_2$]PF$_6$ (289.5 mg, 0.245 mmol) was dissolved in THF (5 ml) in H$_2$ atmosphere and then H$_2$ gas was replaced with Ar gas. To this solution was added compound 20 (1.0011 g, 1.227 mmol) in THF (7.3 ml) and stirred for 1.5 h at room temperature. To this reaction mixture was added I$_2$ (1.559 g, 6.14 mmol) and water (3 ml) and stirred at room temperature for 2 h. The reaction mixture was diluted with CHCl$_3$ (100 ml) and washed with saturated NaHCO$_3$ solution (100 ml). The washing was extracted with CHCl$_3$ (50 ml) and the CHCl$_3$ layer was washed with saturated Na$_2$S$_2$O$_3$ solution (100 ml). The washing was extracted with CHCl$_3$ (50 ml) and the CHCl$_3$ layer was washed with saturated NaCl solution (100 ml) dried over anhydrous MgSO$_4$ and evaporated in vacuo. The residue was purified by flash column chromatography (Merc Si60, 100 g, 40% AcOEt—PhCH$_3$) to obtain compound 91 (0.796 g, 84%).

[Compound 91]

[α]$_D$–3.1° (c=1.0 CHCl$_3$)

Rf 0.29 (PhMe—AcOEt=11:9)

$^1$H—NMR (CDCl$_3$): δ$_H$ 5.503, 5.496 (2s, 1H, Ph CH), 4.581 (d, 1H, J=7.7 Hz, H-1b), 1.991, 1.981 (2s, 3H, OAc), 1.839, 1.832 (2s, 3H, OAc), 1.573 (s, 3H, OAc).

Example 83

(Synthesis of Compound 92)

To compound 91 (789.4 mg, 1.02 mmol) dissolved in 1,2-dichloroethane (20 ml) was added DAST (265 μl, 2.01 mmol) at –10° C. and stirred for 2 h at the same temperature. The reaction mixture was diluted with CHCl$_3$ (100 ml) and washed with saturated NaHCO$_3$ solution (100 ml). The washing was extracted with CHCl$_3$ (100 ml) and the CHCl$_3$ layer was washed with saturated NaCl solution (200 ml), dried over anhydrous MgSO$_4$ and then evaporated in vacuo. The residue was purified by flash column chromatography (Merc Si60, 80 g, 25% AcOEt—PhMe) to obtain compound 92 (685.8 mg, 87%).

[Compound 92]

[α]$_D$–16.5° (c=1.0 CHCl$_3$)

Rf 0.45 (PhMe—AcOEt=3:2)

$^1$H—NMR (CDCl$_3$): δ$_H$ 5.835 (dd, 1H, J=8.1 and 53.5 Hz, H-1a), 5.501 (s, 1H, PhCH), 5.276 (dd, 1H, J=0.9 and 3.5 Hz, H-4b), 4.960 (dd, 1H, J=7.9 and 10.4 Hz, H-2b), 4.545 (d, 1H, J=8.1 Hz, H-1b), 2.000, 1.841, 1.551 (3s, 9H, 3 OAc).

Example 84

(Synthesis of Compound 93)

To compound 92 (453.7 mg, 0.583 mmol) dissolved in MeOH (12 ml) was added TEA (1.2 ml, 8.61 mmol) and stirred for 40 h at room temperature. The reaction mixture was evaporated to dryness in vacuo and the residue was recrystallized from PhMe—AcOEt—MeOH to obtain compound 93 (320.1 mg, 84%).

[Compound 93]

$[\alpha]_D$–13.1° (c=1.0, CHCl$_3$)

Rf 0.34 (PhMe—AcOEt—MeOH=23:23:4)

$^1$H—NMR (CDCl$_3$): $\delta_H$ 5.966 (dd, 1H, J=7.3 and 53.2 Hz, H-1a), 5.607 (s, 1H, PhC$\underline{H}$), 4.867 (t, 1H, J=9.2 Hz, H-3a), 4.241 (d, 1H, J=8.2 Hz, H-1b).

Example 85

[Synthesis of Compounds 94 (α-Anomer) and 95 (β-Anomer)]

Compound 93 (72.5 mg, 0.111 mmol) and compound R14 (87.4 mg, 0.168 mmol) were stirred with MS4A (0.17 g) in EtCN (2.4 ml) for 3 h at room temperature. To the reaction mixture cooled to –35° C. was added AgOTf (95.7 mg, 0.369 mmol) in EtCN (1.2 ml) followed by a solution of PhSeCl (72.2 mg, 0.369 mmol) in EtCN (1.2 ml) and then stirred for 4 h at the same temperature (–35° C.). The reaction mixture was diluted with CHCl$_3$ (50 ml) and filtered through celite. The filtrate was washed with saturated NaHCO$_3$ solution followed by saturated NaCl solution, dried over anhydrous MgSO$_4$ and evaporated in vacuo. The residue was purified by gel chromatography (LH-20, 280 ml, MeOH) and then purified by silica gel column chromatography (10 g, 6% MeOH—Et$_2$O) to obtain compounds 94 (57.9 mg, 46%) and 95 (5.9 mg, 5%).

[Compound 94]

$[\alpha]_D$–9.7° (c=1.0, CHCl$_3$)

Rf 0.26 (Et$_2$O—MeOH=93:7)

$^1$H—NMR (CDCl$_3$): $\delta_H$ 5.972 (dd, 1H, J=7.9 and 53.3 Hz, H-1a), 5.608 (s, 1H, PhC$\underline{H}$), 4.430 (d, 1H, J=8.1 Hz, H-1b), 3.725 (s, 3H, OMe), 2.453 (dd, 1H, J=4.6 and 13.0 Hz, H-3ceq), 2.054, 2.012, 1.985, 1.976 and 1.858 (5s, 15H, 5Ac), 1.900 (t, 1H, J=12.7 Hz, H-3cax).

[Compound 95]

$[\alpha]_D$–14.5° (c=0.18, CHCl$_3$)

Rf 0.33 (Et$_2$O—MeOH=93:7)

$^1$H—NMR (CDCl$_3$): $\delta_H$ 5.950 (dd, 1H, J=8.1 and 53.1 Hz, H-1a), 5.591 (s, 1H, PhC$\underline{H}$), 3.401 (s, 3H, OMe), 2.443 (dd, 1H, J=4.8 and 13.6 Hz, H-3ceq), 2.099, 2.012, 1.985, 1.959 and 1.849 (5s, 15H, 5Ac), 1.840 (dd, 1H, J=11.5 and 13.4 Hz, H-3 cax).

Example 86

(Synthesis of Compound 96)

To compound 94 (177.2 mg, 0.104 mmol) dissolved in pyridine (1.0 ml) was added 4-dimethylaminopyridine (1.5 mg, 0.0123 mmol) and Ac$_2$O (0.50 ml), and stirred at room temperature for 2.5 h. The reaction mixture was evaporated to dryness, the residue was purified by gel chromatography (Sephadex LH-20, 150 ml, MeOH) followed by silica gel column chromatography (12 g, 49:1 CHCl$_3$—MeOH) to obtain compound 96 (117.5 mg, 93%).

[Compound 96]

$[\alpha]_D$–18.1° (c=1.0, CHCl$_3$)

Rf 0.36 (CHCl$_3$—MeOH=97:3)

$^1$H—NMR (CDCl$_3$): $\delta_H$ 5.899 (dd, 1H, J=8.1 and 53.1 Hz, H-1a), 5.532 (s, 1H, PhC$\underline{H}$), 4.894 (d, 1H, J=3.3 Hz, H-4 b), 3.778 (s, 3H, OMe), 2.467 (dd, 1H, J=4.6 and 12.6 Hz, H-3ceq), 2.072, 2.006, 2.001, 2.000, 1.959, 1.817 and 1.704 (7s, 21H, 7Ac), 1.529 (t, 1H, J=12.5 Hz, H-3cax).

Example 87

(Synthesis of Compound 97)

AgOTf (36.1 mg, 0.139 mmol) and Cp$_2$HfCl$_2$ (27.6 mg, 0.0713 mmol) were stirred with MS3A (140 mg) in MeCN (1.0 ml) at 0° C. for 1.5 h. To this mixture was added a solution of compound 96 (27.4 mg, 0.0227 mmol) and compound R9 (19.6 mg, 0.0489 mmol) in MeCN (1.3 ml) and the mixture was stirred at room temperature for 50 h. The reaction mixture was diluted with CHCl$_3$ (25 ml), filtered through celite, and the filtrate was washed with saturated NaHCO$_3$ solution followed by saturated NaCl solution. The solvent was dried over anhydrous MgSO$_4$ and then evaporated in vacuo. The residue was purified by gel chromatography (Sephadex Lh-20, 150 ml, MeOH) followed by HPLC (GL Science, Inertsil PREP-SIL, 20.0×250 mm, 15 ml/min, 3% MeOH—CHCl$_3$) to obtain compound 97 (25.4 mg, 71%).

[Compound 97]

$[\alpha]_D$–1.8° (c=1:1, CHCl$_3$)

Rf 0.39 (AcOEt—EtOH=19:1)

$^1$H—NMR (CDCl$_3$): $\delta_H$ 5.744 (m, 1H, —C$\underline{H}$=CH$_2$), 5.521 (s, 1H, PhC$\underline{H}$), 3.772 (s, 3H, OMe), 2.456 (dd, 1H, J=4.6 and 12.6 Hz, H-3deq), 2.062, 2.019, 1.986, 1.985, 1.951, 1.811 and 1.691 (7s, 21H, 7Ac), 1.521 (t, 1H, J=12.3 Hz, H-3dax).

Example 88

(Synthesis of Compound 120)

To a solution of compound 35 (229.7 mg, 153 μmol) dissolved in pyridine (5 ml) and acetic anhydride (5 ml) was added a catalytic amount of 4-dimethylaminopyridine and stirred at 20° C. for 18 h. The reaction mixture was evaporated to dryness and the residue was purified by silica gel column chromatography (C-300, 30 g, toluene:MeOH= 10:1) followed by Sephadex LH-20 (MeOH) column chromatography to obtain compound 120 (226 mg, 93%).

[Compound 120]

Rf=0.18 (toluene:MeOH=10:1)

$[\alpha]^D$–47.9° (C=0.4, CHCl$_3$)

$^1$H—NMR (CDCl$_3$, TMS) δH; 1.006 (t, 3H, J=6.6 Hz, CH$_3$), 1.722 (t, 1H, J=12.5 Hz, H-3cax), 1.855, 1.923, 1.959, 1.981, 2.008, 2.069, 2.114, 2.204 (8s, 24H, 8Ac), 2.575 (d, 1H, J=4.8, 12.8 Hz, H-3ceq), 3.855 (s, 3H, OCH$_3$), 4.335, 4.359 (2d, 2H, J=12.1 Hz, CH$_2$Ph), 4.441 (d, 1H, J=11.7 Hz, CH$_2$Ph), 4.507 (d, 1H, J=12.1 Hz, CH$_2$Ph), 4.907 (m, 1H, H-4c), 4.956 (dd, 1H, J=8.1, 10.2 Hz, H-2b), 5.075 (d, 1H, J=8.1 Hz, H-1a), 5.151 (d, 1H, J=3.7 Hz, H-4b), 5.367 (dd, 1H, J=2.6, 9.2 Hz, H-7c), 5.591 (m, 1H, H-8c), 5.789 (m, 1H, CH$_2$C$\underline{H}$=CH$_2$).

Example 89

(Synthesis of Compound 121)

To a solution of compound 120 (150 mg, 94.3 mol) dissolved in MeOH (10 ml) was added sodium methoxide (100 μl, 51.8 μmol), and the mixture was stirred at 20° C. for 6 h. After the reaction mixture was evaporated, the residue was dissolved in methanol (10 ml) and water (1 ml) and stirred at 20° C. for 18 h. After the reaction mixture was evaporated in vacuo, the residue was purified with Sephadex LH-20 (methanol as the solvent) to obtain the deacetylated derivative (125.3 mg, 98.7%, $[\alpha]^{23}{}_D$ −41.5° (C=0.1, $CH_3OH$). A portion thereof (57 mg, 42 μmol) was dissolved in methanol (8 ml) was subjected to a catalytic hydrogenation in the presence of 10% palladium-carbon (50 mg) at 20° C. for 6 h. The reaction mixture was filtered through chromatodisc 25A, the residue was purified with Sephadex [LH-20 (methanol as the solvent) to obtain compound 121 (34.1 mg, 90%).

[Compound 121]

Rf=0.41 (butanol:ethanol:water=2:1:1)

$[\alpha]^{25}{}_D$ −43.5° (c=0.1, $CH_3OH$))

500 MHz, $^1H$—NMR ($CD_3OD$, TMS) δH; 0.903 (t, 3H, J=7.3 Hz, $CH_2CH_3$), 1.154 (d, 1H, J=6.6 Hz, $CH_3$) 1.713 (t, 1H, J=12.8 Hz, H-3cax), 1.943, 2.004 (2s, 6H, 2Ac), 2.872 (dd, 1H, J=3.7, 12.8 Hz, H-3ceq), 4.417 (d, 1H, J=8.1 Hz, H-1a or H-1b), 4.506 (d, 1H, J=8.1 Hz, H-1b or H-1a), 5.025 (d, 1H, J=3.7 Hz, H-1d).

Example 90

(Synthesis of Compound 122)

To a solution of compound 87, (200 mg, 0.126 mol) in pyridine (3 ml) and acetic anhydride (3 ml) was added 4-dimethylaminopyridine, and the mixture was stirred at 20° C. for 18 h. After the solvent was evaporated in vacuo, the residue was purified by Silica gel chromatography (C-300, 40 g, toluene:methanol=10:1) followed by gel chromatography (LH-20, MeOH). The residue which was dissolved in pyridine (4 ml) was added to lithium iodide (160 mg, 1.202 mmol) and the mixture was stirred at 100° C. for 6 h. After the reaction mixture was purified with Sephadex LH-20 (methanol), the residue was dissolved in ethanol (5 ml) and, after the addition of methyl hydrazine (10 ml), stirred at 80° C. for 18 h. The reaction mixture was evaporated in vacuo, the residue was purified with Sephadex LH-20 (methanol), and the residue was dissolved in methanol (2 ml) and, after the addition of acetic anhydride (200 μl), stirred at 20° C. for 1 h. After the reaction mixture was basified with NaOH solution, the residue was purified with Sephadex LH-20 (methanol) to obtain compound 122 (78.7 mg, 49%).

[Compound 122]

Rf=0.14 (chloroform:methanol=5:1)

500 MHz, $^1H$—NMR ($CD_3OD$, TMS) δH; 1.176 (d, 3H, J=6.2 Hz, $CH_3$), 1.747 (t, 1H, J=12.5 Hz, H-3cax), 1.971, 1.999 (2s, 6H, 2Ac), 2.868 (dd, 1H, J=4.0, 12.5 Hz, H-3ceq), 4.354 (d, 1H, J=12.1 Hz, $CH_2Ph$), 4.454 (d, 1H, J=11.7 Hz, $CH_2Ph$), 4.477 (d, 1H, J=12.1 Hz, $CH_2Ph$), 4.491 (d, 1H, J=7.7 Hz, H-1a or H-1b), 4.525 (d, 1H, J=11.7 Hz, $CH_2Ph$), 4.610 (d, 1H, J=11.h, $CH_2Ph$), 5.027 (d, 1H, J=3.7 Hz, H-1d), 5.860 (m, 1H, $CH_2\overline{CH}{=}CH_2$).

Example 91

(Synthesis of Compound 123)

Compound 122 (76.3 mg, 56.7 μmol) was dissolved in methanol (5 ml) and water (1 ml), added with 10% palladium-carbon (76 mg) and subjected to the catalytic hydrogenation at 20° C. for 18 h. After the reaction mixture was filtered through chromatodisc 25A, the residue was purified with Sephadex LH-20 (methanol) to obtain compound 123 (44.5 mg, 89%).

[Compound 123]

Rf=0.29 (butanol:ethanol:water=2:1:1)

500 MHz, $^1H$—NMR ($CD_3OD$, TMS) δH; 0.906 (t, 3H, J=7.3 Hz, $CH_2CH_3$), 1.159 (d, 3H, J=6.2 Hz, $CH_3$), 1.717 (t, 1H, J=12.1 Hz, H-3cax), 1.985, 1.997 (2s, 6H, 2NAc), 2.851 (dd, 1H, J=4.4, 12.1 Hz, H-3ceq), 4.441 (d, 1H, J=7.7 Hz, H-1a or H-1b), 4.530 (d, 1H, J=8.4 Hz, H-1b or H-1a), 5.027 (d, 1H, J=4.h, H-1d).

Reference Example 4

(Synthesis of Compound 132)

A mixture of compound 131 (5.0 g, 11.56 mmol), 1,2-dichloroethane (100 ml), triethylamine (8.9 ml, 63.8 mmol) and a catalytic amount of 4-DAMP was stirred at room temperature, and then, after the addition of pivaloyl chloride (7.9 ml, 64 mmol), further stirred at room temperature for 9.5 h. After the reaction mixture was cooled with methanol, it was diluted with chloroform, and washed with saturated $NaHCO_3$ solution followed by saturated NaCl solution. After the organic layer was dried over $MgSO_4$, the solvent was evaporated. After the addition of methanol to the residue, the precipitate was collected by filtration to recover compound 132 (2.41 g, 27%). Purification of the mother liquor with silica gel column chromatography (toluene:ethyl acetate=4:1) yielded further compound 132 (578 mg, 6.5%).

[Compound 132]

Rf=0.40 (toluene:ethyl acetate=4:1)

$\delta_H$ ($CDCl_3$): 6.923 (d, 2H, J=9.3 Hz, —O—$C_6H_4$—OMe), 6.759 (d, 2H, J=9.3 Hz, —O—$C_6H_4$—OMe), 5.091 (t, 1H, J=9.5 Hz, H-2b), 4.833 (d, 1H, J=8.1 Hz, H-1a), 4.454 (d, 1H, J=7.7 Hz, H-1b), 3.751 (s, 3H, —O—$C_6H_4$—O$\underline{Me}$), 1.534, 1.319 (2s, 6H, 2$CH_3$), 1.224, 1.219, 1.207, 1.202 (4s, 36H, 4tBu).

Example 92

(Synthesis of Compound 133)

After a mixture of compound 132 (825 mg, 1 mmol), R11 (2.6 g, 5.6 mmol), silver triflate (2.88 g, 11.2 mmol), MS4A (2 g) and diethylether was stirred at room temperature for 30 min, a solution of phenylselenyl chloride (2.15 g, 11.2 mmol) in diethylether (20 ml) was added to the above mixture at −20° C. over 20 min. After 30 min, the reaction mixture was neutralized with triethylamine, filtered through celite and then extracted with ethyl acetate. After the extract was washed successively with saturated $NaHCO_3$ solution and saturated NaCl solution, the organic layer was dried over $MgSO_4$, and the residue was purified with silica gel column chromatography to obtain compound 133 (1.17 g, 94.4%).

[Compound 133]

Rf=0.60 (toluene:ethyl acetate=4:1)

| $C_{69}H_{92}O_{20}$ | C (%) | H (%) |
| --- | --- | --- |
| Calcd. | 66.76 | 7.47 |
| Found | 66.77 | 7.46 |

$\delta_H$ (CDCl$_3$); 7.42~7.18 (m, 15H, 3×PhCH$_2$O—), 6.883 (d, 2H, J=9.2 Hz, —O—C$_6$H$_4$—OMe), 6.760 (d, 2H, J=9.2 Hz, —O—C$_6$H$_4$—OMe), 5.349 (d, 1H, J=3.7 Hz), 5.316 (dd, 1H, J=7.8, 8.8 Hz, H-2b), 4.887 (dd, 1H, J=7.7, 8.4 Hz, H-2a), 4.834 (d, 1H, J=7.7 Hz), 4.311 (d, 1H, J=7.8 Hz, H-1b), 3.745 (s, 3H, O Me), 1.403, 1.306 (2s, 6H, Me×2), 1.206, 1.197, 1.127, 1.106 (4s, 36H, 4×tBu).

Example 93

(Synthesis of Compound 134)

A mixture of compound 133 (812 mg, 0.65 mmol) and AcOH—H$_2$O (4:1) (50 ml) was stirred at 80° C. for 3 h. After the solvent was azeotropically evaporated with toluene, the residue was purified with silica gel column chromatography (toluene:ethyl acetate=8:3) to obtain compound 134 (500 mg, 64%).

[Compound 134]

Rf=0.32 (toluene:ethyl acetate=7:3)

$[\alpha]_D^{20}$-30.1° (C=0.87, CHCl$_3$)

| $C_{66}H_{80}O_{20}$ | C (%) | H (%) |
| --- | --- | --- |
| Calcd. | 65.98 | 7.38 |
| Found | 65.70 | 7.39 |

$\delta_H$ (CDCl$_3$): 7.38~7.13 (m, 15H, 3×PhCH$_2$O—), 6.822 (d, 2H, J=9.2 Hz, —O—C$_6$H$_4$—OMe), 6.690 (d, 2H, J=9.2 Hz, —O—C$_6$H$_4$—OMe), 5.297 (t, 1H, J=8.8 Hz, H-2a), 5.237 (d, 1H, J=3.6 Hz, H-1c), 4.768 (d, 1H, J=7.7 Hz, H-1a), 4.400 (d, 1H, J=8.1 Hz, H-1b), 4.089 (t,1H, J=9.5 Hz, H-3a or H-4a), 3.903 (t, 1H, J=9.5 Hz, H-4a or H-3a), 3.766 (br-s, 1H, H-4c), 3.677 (s, 3H, OMe), 1.145, 1.081, 1.079, 1.044 (4s, 36H, 4tBu), 1.107 (d, 3H, J=6.6 Hz, H-6c).

Example 94

(Synthesis of Compound 135)

A mixture of compound 134 (291 mg, 0.242 mmol), a solution of 1N levulinic anhydride/1,2-dichloroethane (4.6 ml), pyridine (2 ml) and a catalytic amount of 4-DAMP was stirred at room temperature for 2 days. The solvent was evaporated with toluene in vacuo, and the residue was purified with SX-8 (toluene), then further purified by silica gel column chromatography (toluene:ethyl acetate=2:1) to obtain compound 135 (254 mg, 81%). Furthermore, compound 134 mg (10%) was also recovered.

[Compound 135]

Rf=0.51 (toluene:ethyl acetate=7:3)

$[\alpha]_D^{20}$-33.2° (C=0.5, chloroform)

| $C_{71}H_{94}O_{22}$ | C (%) | H (%) |
| --- | --- | --- |
| Calcd. | 65.62 | 7.29 |
| Found | 65.18 | 7.28 |

$\delta_H$ (CDCl$_3$): 7.42~7.20 (m, 15H, 3×Ph—CH$_2$O—) 6.880 (d, 2H, J=9.2 Hz, —O—C$_6$H$_4$—OMe), 6.757 (d, 2H, J=9.2 Hz, —O—C$_6$H$_4$—OMe), 5.346 (t, 1H, J=9.2 Hz, H-2a), 5.317 (d, 1H, J=3.3 Hz, H-1c), 5.274 (dd, 1H, J=8.4 Hz, 10.3 Hz, H-2b), 4.819 (d, 1H, J=7.7 Hz, H-1a), 4.760 (dd, 1H, J=2.9, 10.3 Hz, H-3b), 4.509 (d, 1H, J=8.4 Hz, H-1b), 3.746 (s, 3H, —OMe), 2.82~2.42 (m, 4H, —CH$_2$CH$_2$—), 2.192 (s, 3H, Me), 1.269 (d, 3H, J=6.2 Hz, H-6c), 1.216, 1.159, 1.137, 1.104 (4s, 36H, 4×tBu)

Example 95

(Synthesis of Compounds 138 and 139)

A mixture of compound 134 (31 mg, 26 μmol), Me$_3$N.SO$_3$ (36 mg, 258 μmol) and DMF (1 ml) was stirred at 90 for 1 h. The reaction mixture was passed through a Sephadex LH-20 column (methanol) followed by an ion-exchange treatment with Dowex 50 (Na$^+$) to obtain a mixture of compounds 138 and 139 (32 mg). Then the purification using the preparative TLC (chloroform:methanol=5:1) yielded compound 138 (14.6 mg, 44%) and compound 139 (5 mg, 14%).

[Compound 138]

Rf=0.68 (chloroform:methanol=5:1)

$\delta_H$ (CDCl$_3$:CD$_3$OD=1:1): 6.908 (d, 2H, J=9.2 Hz, —O—C$_6$H$_4$—OMe), 6.789 (d, 2H, J=9.2 Hz, —O—C$_6$H$_4$—OMe), 5.280 (d, 1H, J=4.0 Hz, H-1c), 5.258 (dd, 1H, J=8.1, 9.2 Hz, H-2a), 5.179 (dd, 1H, J=8.1, 9.9 Hz, H-2b), 4.556 (d, 1H, J=8.1 Hz, H-1b), 3.738 (s, 3H, O Me), 1.460 (d, 3H, J=6.6 Hz, H-6c), 1.241, 1.225, 1.158, 1.116 (4s, 36H, 4×tBu)

[Compound 139]

Rf=0.40 (chloroform:methanol=5:1)

$\delta_H$ (CD$_3$OD): 7.42~7.18 (m, 15H, 3×PhCH$_2$O—), 6.909 (d, 2H, J=9.2 Hz, —O—C$_6$H$_4$—OMe), 6.793 (d, 2H, J=9.2 Hz, —O—C$_6$H$_4$—OMe), 5.275 (d, 1H, J=3.7 Hz, H-1c), 5.222 (t, 1H, J=9.2 Hz, H-2a), 5.082 (d, 1H, J=2.9 Hz, H-4b), 3.728 (s, 3H, OMe), 1.396 (d, 3H, J=6.2 Hz, H-6c), 1.250, 1.223, 1.102, 1.157 (4s, 36H, 4×tBu).

Example 96

(Synthesis of Compound 136)

After a mixture of compound 135 (207 mg, 0.159 mmol), pyridine (5 ml), Ac$_2$O (5 ml) and a catalytic amount of 4-DAMP was stirred at room temperature for 2 days, the solvent was evaporated in vacuo. The purification of the residue by gel filtration (SX-8, toluene) yielded compound 136 (154 mg, 72%).

[Compound 136]

Rf=0.50 (toluene:ethyl acetate=3:1)

[α]$_D^{20}$-25.2° (C=0.5, chloroform)

| C$_{70}$H$_{96}$O$_{23}$ | C (%) | H (%) |
|---|---|---|
| Calcd. | 65.36 | 7.21 |
| Found | 65.32 | 7.20 |

δ$_H$ (CDCl$_3$) 7.38~7.20 (m, 15H, 3×Ph—CH$_2$O—), 6.883 (d, 2H, J=9.2 Hz.—O—C$_6$H$_4$—OMe), 6.763 (d, 2H, J=9.2 Hz, —O—C$_6$H$_4$—OMe), 5.283 (d, 1H, J=3.3 Hz, H-4b), 5.137 (dd, 1H, J=8.1, 10.6 Hz, H-2b), 4.955 (d, 1H, J=3.3, 10.6 Hz, H-3b), 4.852 (d, 1H, J=7.7 Hz, H-1a), 4.543 (d, 1H, J=8.4 Hz, H-1b), 3.750 (s, 3H, OMe), 2.80~2.28 (m, 4H, —CH$_2$CH$_2$—), 2.152 (s, 3H, Me), 1.790 (s, 3H, Ac), 1.330 (d, 3H, J=6.6 Hz, H-6c), 1.211, 1.175, 1.140, 1.105 (4s, 36H, 4×tBu)

Example 97

(Synthesis of Compound 137)

A mixture of compound 136 (147 mg, 109 mmol), MeOH—H$_2$O (4:1, 10 ml) and 20% Pd(OH)$_2$—C (147 mg) was catalytically hydrogenated at room temperature for 3 h. After the catalyst was removed by filtration, the solvent was evaporated in vacuo. To the residue were added pyridine (5 ml), Ac$_2$O (5 ml) and a catalytic amount of 4-DAMP, and the mixture was stirred at room temperature for 14 h. The solvent was evaporated and the residue was purified by silica gel column chromatography (toluene:ethyl acetate=3:2) to yield 104 mg (81%) of compound 137.

[Compound 137]

Rf=0.46 (toluene:ethyl acetate=3:2)

δ$_H$ (CDCC$_3$): 6.861 (d, 2H, J=9.2 Hz, —O—C$_6$H$_4$—OMe), 6.763 (d, 2H, J=9.2 Hz, —O—C$_6$H$_4$—OMe), 5.486 (br-s, 1H, H-4c), 5.395 (d, 1H, J=3.3 Hz, H-4b), 5.156 (dd, 1H, J=8.1, 10.6 Hz, H-2b), 5.039 (m, 1H, H-5c), 5.009 (dd, 1H, J=3.3, 10.6 Hz, H-3b), 4.812 (d, 1H, J=7.7 Hz, H-1a), 4.537 (d, 1H, J=8.1 Hz, H-1b), 4.103 (t, 1H, J=9.5 Hz, H-3a or H-4a), 3.906 (t, 1H, J=9.5 Hz, H-4a or H-3a), 3.747 (s, 3H, OMe), 2.81~2.50 (m, 4H, —CH$_2$CH$_2$—), 2.201, 2.169, 2.156, 2.090, 1.944 (5s, 15H, 4Ac, CH$_3$), 1.244, 1.225, 1.180, 1.173 (4s, 36H, 4tBu)

Example 98

(Synthesis of Compound 140)

A mixture of compound 136 (48 mg, 36 μmol), hydrazine acetate (16 mg, 174 μmol) and EtOH (2 ml) was stirred at room temperature for 1 h. Purification of the reaction mixture by LH-20 (methanol) yielded compound 140 (43 mg, 97%).

[Compound 140]

Rf=0.46 (toluene:ethyl acetate=3:1)

| C$_{68}$H$_{90}$O$_{21}$ | C (%) | H (%) |
|---|---|---|
| Calcd. | 65.68 | 7.30 |
| Found | 65.33 | 7.12 |

δ$_H$ (CDCl$_3$): 7.40~7.20 (m, 15H, 3×Ph—CH$_2$O—), 6.895 (d, 2H, J=9.2 Hz,—O—C$_6$H$_4$—OMe), 6.768 (d, 2H, J=9.2 Hz, —O—C$_6$H$_4$—OMe), 5.237 (d, 1H, J=3.7 Hz, H-4b), 4.880 (d, 1H, J=7.3 Hz, H-1a), 4.482 (d, 1H, J=8.1 Hz, H-1b), 4.200 (t, 1H, J=9.5 Hz, H-3a or H-4a), 3.941(t, 1H, J=9.5 Hz, H-4a or H-3a), 3.751(s, 3H, OMe), 1.816 (s, 3H, Ac), 1.278 (d, 3H, J=6.6 Hz, H-6c), 1.213, 1.209, 1.136, 1.120 (4s, 36H, 4tBu)

EXAMPLE 99

(Synthesis of compound 141)

A mixture of compound 140 (37 mg, 30 μmol), Me$_3$N.SO$_3$ (52 mg, 0.374 mmol) and DMF (1 ml) was stirred at 90° C. for 30 min. The reaction mixture was passed through Sephadex LH-20 once, and then subjected to ion exchange treatment with Dowex 50 (Na$^+$) to yield compound 141 (30 mg, 75%).

[Compound 141]

Rf=0.64 (chloroform:methanol=8:1)

[α]$_D^{22}$-17.6° (c=0.9, chloroform)

δ$_H$ (CD$_3$OD): 7.42~7.30 (m, 15H, 3×Ph—CH$_2$O—), 6.910 (d, 2H, J=9.2 Hz, —O—C$_6$H$_4$—OMe), 6.796 (d, 2H, J=9.2 Hz, —O—C$_6$H$_4$—OMe), 5.693 (d, 1H,J=3.3 Hz, H-4b), 5.334 (d, 1H, J=2.6 Hz, H-1c), 5.231 (dd, 1H, J=7.7, 8.8 Hz, H-2a), 5.139(dd, 1H, J=8.0, 9.9 Hz,H-2b), 5.073 (d,1H, J=7.7Hz, H-1a), 4.703 (d, 1H, J=8.0 Hz, H-1b), 4.566 (dd, 1H, J=3.3, 10.7Hz, H-3b), 4.207 (t, 1H, J=9.2 Hz, H-3a or H-4a), 3.967 (t, 1H, J=9.2Hz, H-4a or H-3a), 3.729 (s, 3H, OMe), 1.973 (s, 3H, Ac), 1.320 (d, 3H, J=6.6 Hz, H-6c), 1.244, 1.207, 1.141, 1.138 (4s, 36H, 4tBu)

EXAMPLE 100

(Synthesis of compound 142)

A mixture of compound 141 (13.5 mg, 10 μmol), 20% Pd(OH)$_2$ —C (14 mg) and MeOH—H$_2$O (4:1, 1 ml) was catalytically hydrogenated at room temperature for 3 h. After the removal of the catalyst by filtration, 1 N NaOH (0.2 ml) was added to the filtrate and the mixture was stirred at room temperature for 16 h. The reaction mixture was purified by LH-20 (methanol) to yield compound 142 (8.5 mg, 98%).

[Compound 142]

Rf=0.78 (nBuOH:EtOH:H$_2$O=2:1:1)

δ$_H$ (CD$_3$OD): 6.909(d, 2H, J=9.2 Hz, —O—C$_6$H$_4$—OMe), 6.789 (d, 2H, J=9.2 Hz, —O—C$_6$H$_4$—OMe, 2H), 5.091 (d, 1H, J=4.0 Hz, H-1c), 5.021 (d, 1H, J=8.0 Hz, H-1a), 4.577 (d, 1H, J=8.0 Hz, H-1b), 4.347 (dd,1H, J=3.3, 10.3 Hz, H-3b), 4.307 (d, 1H, J=3.3 Hz, H-4b), 4.056(t, 1H, J=9.5Hz, H-3a or H-4a), 4.003(t,1H, J=9.5 Hz, H-4a or H-3a), 3.885 (dd, 1H, J=3.3, 10.3 Hz, H-3c), 3.781(d, 1H, J=3.3 Hz, H-4c), 3.728 (s, 3H, OMe), 3.641(dd, 1H, J=4.0, 10.3 Hz, H-2c), 1.282 (d, 3H, J=6.2 Hz, H-6c), 1.229, 1.216(2s, 18H, 2tBu).

EXAMPLE 101

(Synthesis of compound 143)

A mixture of compound 142 (5.5 mg, 6.36 μmol) and 1 N NaOH (0.2 ml) was stirred at 50° C. for 2 h. The reaction mixture was purified with G-10 (H$_2$O), lyophilized, and the resulting residue was purified again with LH-20 (methanol) to yield compound 143 (4.4 mg, 99%).

[Compound 143]

Rf=0.39 (nBUOH:EtOH:H$_2$O=2:1:1)

δ$_H$ (D$_2$O): 7.263(d, 2H, J=9.2 Hz, —O—C$_6$H$_4$—OMe), 7.133 (d, 2H, J=9.2 Hz, —O—C$_6$H$_4$—OMe), 5.619 (d, 1H, J=4.0 Hz, H-1c), 5.142 (d, 1H, J=8.1 Hz, H-1a), 4.909(m,

1H, H-5c), 4.698 (d, 1H, J=7.7 Hz, H-1b), 4.455 (dd, 1H, J=3.3, 9.9 Hz, H-3b), 4.409 (d, 1H, J=3.3 Hz, H-4b), 3.955 (s, 3H, OMe), 1.331(d, 3H, J=6.6 Hz, B-6c)

EXAMPLE 102

(Synthesis of compound 144)

A mixture of compound 138 (14.6 mg, 11.2 μmol), 20% Pd(OH)$_2$—C (12 mg) and MeOH—H$_2$O (4:1) (1 ml) was catalytically hydrogenated for 3 h. After the removal of the catalyst by filtration, the solvent was evaporated. To the residue were added THF—MeOH (1:1) (1 ml) and 1 N—NaOH 0.2 ml), and the mixture was stirred at room temperature for 11 h. Purification of the reaction mixture with LH-20 (methanol) yielded compound 144 (6.7 mg, 86%).

[Compound 144]
Rf=0.58 (nBUOH:EtOH:H$_2$O=2:1:1)
$\delta_H$ (D$_2$O, 60° C. ): 7.263(d, 2H, J=9.2 Hz, —O—C$_6$H$_4$—OMe), 7.134 (d, 2H, J=9.2 Hz, —O—C$_6$H$_4$—OMe), 5.598 (d, 1H, J=4.0 Hz, H-4b), 5.137(d,1H, J=7.7 Hz,H-1a), 4.936 (m, 1H, H-5c), 4.806 (d,1H, J=3.9 Hz,H-1c), 3.956 (s, 3H, OMe), 1.448(d, 3H, J=7.7 Hz, H-6c).

EXAMPLE 103

(Synthesis of compound 145)

A mixture of compound 139 (10.5 mg, 8.7 μmol), 20% Pd(OH)$_2$—C (10 mg) and MeOH—H$_2$O (4:1) (2 ml) was catalytically hydrogenated for 3.5 h. After the removal of the catalyst by filtration, the solvent was evaporated in vacuo, and residue was purified by preparative TLC (chloroform:methanol =2:1) to yield compound 145 (3.1 mg, 32%).

[Compound 145]
Rf=0.44 (chloroform:methanol=2:1)
$\delta_H$ (CD$_3$OD): 6.907 (d, 2H, J=9.2 Hz, —O—C$_6$H$_4$—OMe), 6.789 (d, 2H, J=9.2Hz, —O—C$_6$H$_4$—OMe), 5.164 (dd, 1H, J=8.0, 10.2Hz, H-2b), 5.119 (dd, 1H, J=8.1, 9.9Hz, H-2a), 5.071 (d, 1H, J=3.0 Hz, H-4b), 5.047(d, 1H, J=8.1Hz, H-1a), 5.043 (d, 1H, J=3.7 Hz, H-1c), 4.638(d, 1H,J=8.1 Hz, H-1b), 4.472(dd, 1H, J=3.0, 10.3 Hz, H-3b), 3.728(s, 3H, OMe), 1.324(d, 3H, J=6.6 Hz, H-6c), 1.295, 1.231, 1.221, 1.203 (4s, 36H, 4tBu) MASS (M—Na) 673

EXAMPLE 104

(Synthesis of compound 98)

To a solution of compound 97 (Example 87) (57.4 mg, 36.1 μmol) dissolved in pyridine (0.72 ml) were added DMAP (0.5 mg, 4.1 μmol) and acetic anhydride (0.24 ml) and the mixture was stirred at room temperature for 19 h. After the reaction mixture was evaporated to dryedness in vacuo, the residue was purified by silica gel column chromatography (Merc Si-60, 5 g, 2% EtOH—AcOEt) to yield compound 98 (43.4 mg, 74%).

[Compound 98]
[α]$_D$ −78° (C=1.49, CHCl$_3$)
$\delta_H$ (CDCl$_3$) :5.757(m, 1H, A11), 5.520(S, 1H, PhCH), 3.772(S, 3H, OMe), 2.455(dd, 1H, J=4.6, 12.6Hz, H-3deq), 2.167, 2.064, 2.017, 1.986, 1.978, 1.949, 1.808, 1.666(8S, 24H, 8Ac), 1.516(t, 1H, J=12.5Hz, H-3dax)

EXAMPLE 105

(Synthesis of compound 99)

To a solution of compound 98 (39.4 mg, 24.2 μmol) and BH$_3$.NMe$_3$(4.4 mg, 60.3 μmol) dissolved in THF (0.10 ml) was added TMSOTf (5.2 μl, 26.6 μmol) at 0° C. and the resulting mixture was stirred at the same temperature for 6 h. The reaction mixture was diluted with CHCl$_3$, washed with saturated NaHCO$_3$ solution and then with saturated NaCl solution, and then dried over MgSO$_4$. After the solvent was evaporated in vacuo, the residue was purified by silica gel column chromatography (Merc Si-60, 17 g, 5% MeOH—Et$_2$O) to yield compound 99 (17.4 mg, 44%).

[Compound 99]
[α]$_D$+10.40°(C=1.16, CHCl$_3$)
$\delta_H$(CDCl$_3$):5.742(m, 1H, —CH=CH$_2$), 3.790(S, 3H, OMe), 2.487(dd, 1H, J=4.8, 12.5Hz, H-3deq), 2.154, 2.109, 2.091, 2.019, 1.959, 1.856, 1.797, 1.483 (8S, 24H, 8Ac), 1.547(t, 1H, J=12.5Hz, H-3dax)

EXAMPLE 106

(Synthesis of compound 100)

Compound 99 (17.0 mg, 10.4 μmol) and compound R11 (25.7 mg, 55.3 μmol) were stirred in the presence of MS4A (57 mg) in Et$_2$O (0.50 ml) and CH$_2$Cl$_2$ (0.1 ml) at room temperature for 5 h. To this mixture was added MeOTf (7.5 μl, 66.3 μmol) and the resulting mixture was stirred at room temperature for 18 h. The reaction mixture was diluted with CHCl$_3$, washed with saturated NaHCO$_3$ solution and then saturated NaCl solution, and then dried over MgSO$_4$. After the solvent was evaporated in vacuo, the residue was purified by silica gel column chromatography (Merc Si-60, 3 g, 35% acetone/toluene) to obtain 12.1 mg of compound 100 (57%).

[Compound 100]
[α]$_D$ _12.9° (c=0.81, CHCl$_3$)
$\delta_H$ (CDCl$_3$):5.750(m, 1H, A11), 3.765(S, 3H, OMe), 2.441 (d, 1H, J=4.9, 12.6Hz, H-3deq), 2.136, 2.112, 2.049, 2.033, 1.976, 1.889, 1.814, 1.698 (8S, 24H, 8Ac), 1.331(d, 3H, J=6.6 Hz, CH$_3$-5e)

EXAMPLE 107

(Synthesis of compound 102)

To LiI (17.0 mg, 127 mol) which had been vacuum dried at 70° C. for 19 h on oil bath was added a solution of compound 100 (12.1 mg, 5.9 μmol) in pyridine (0.6 ml), and the mixture was stirred at 100° C. for 22 h. After the gel filtration (LH-20, 25 ml, MeOH), the reaction mixture was purified by silica gel column chromatography (Merc Si-60, 1.6 g, 10% MeOH—CHCl$_3$) to yield the lithium salt (5.8 mg).

To a solution of said lithium salt (5.8 mg) dissolved in in EtOH (0.2 ml) was added methyl hydrazine (0.3 ml), and the resulting mixture was stirred at 75° C. for 20 h. Then the reaction mixture was gel filtered (LH-60, 14, ml, MeOH) to yield the deacetylated derivative (4.6 mg).

To a solution of said deacetylated derivative (4.6 mg) dissolved in methanol (0.30 ml) was added acetic anhydride (15 μl), and the mixture was stirred at room tempwrature for 30 min. The reaction mixture was adjusted to pH 9 by the addition of 28% NaOMe, and further stirred at room temperature for 30 min. Gel filtration (LH-60, 10 ml, MeOH) of the reaction mixture yielded the N-acetyl derivative (4.8 mg).

To a solution of the N-acetyl derivative (4.8 mg) dissolved in MeOH (0.50 ml) and H$_2$O (0.10 ml) was added 10% Pd—C (8.0 mg) and the mixture was stirred in the H$_2$ atmosphere at room tempwrature for 22 h. The reaction mixture was filtered through celite, and then the solvent was evaporated in vacuo. The residue was gel-filtered (LH-20, 10 ml, MeOH) to obtain compound 102 (3.3 mg, 53%).

[Compound 102]
$[\alpha]_D$ −26.8° (c=0.20, MeOH)
$\delta_H$ (CD$_3$OD):5.021(d, 1H, J=4.0Hz, H-1e), 4.693(d, 1H, J=1.5Hz, H-1a), 2.856(dd, 1H, J=4.6, 12.3Hz, H-3deq), 1.999, 1.992 (2s, 6H, 2NAc), 1.711(t, 1H, J=11.9Hz, H-3dax), 1.163(d, 3H, J=6.6 Hz, CH$_3$-5e), 0.954(t, 3H, J=7.3Hz, CH$_2$CH$_3$)

EXAMPLE 108

(Synthesis of compound 146)

Compound 96 (106.5 mg) was converted into compound 146 in a similar manner for that of compound 99.

[Compound 146]
$[\alpha]_D$ +10.1° (c=0.65, CHCl$_3$)
$\delta_H$ (CDCl$_3$):5.774(dd, 1H, J=8.1, 53.1Hz, H-1a), 4.858 (br. d, 1H, J=2.9Hz, H-4b), 3.796(S, 3H, OMe), 2.494(dd, 1H, J=4.6, 12.6Hz, H-3ceq), 2.128, 2.109, 2.030, 1.966, 1.892, 1.807, 1.616 (7s, 21H, 7Ac), 1.553(t, 1H, J=12.5Hz, H-3cax)

EXAMPLE 109

(Synthesis of compound 147)

Compound 146 (126.1 mg, 0.104 mmol) and compound R11 (150.2 mg, 0.312 mmol) were stirred with MS4A (370 mg) in Et$_2$O (1.0 ml) and CH$_2$Cl$_2$ (1.0 ml) at room temperature for 4 h. After the addition of MeOTf (42 μl, 0.371 mmol), the reaction mixture was stirred at room temperature for 21 h, then diluted with chloroform and filtered through celite. After the filtrate was washed with saturated NaHCO$_3$ solution and then with saturated NaCl solution and dried over MgSO$_4$, the solvent was evaporated in vacuo. Purification of the residue by silica gel column chromatography (Merc Si-60, 30 g, 35% THF—CHCl$_3$) yielded compound 147 (149.5 mg, 88%).

[Compound 147]
$[\alpha]$ −17.2° (c=1.02, CHCl$_3$)
$\delta_H$ (CDCl$_3$) :5.597(dd, 1H, J=7.9, 54.4Hz, H-1a), 3.775 (s, 3H, OMe), 2.452(dd, 1H, J=4.8, 12.8Hz, H-3ceq), 2.133, 2.060, 2.050, 1.980, 1.915, 1.819, 1.696 (7s, 21H, 7Ac), 1.320(d, 3H, J=6.6Hz, CH$_3$)

REFERENCE EXAMPLE (Synthesis of compound R17)

To a solution of compound R5 (456 mg, 1.01 mmol) dissolved in pyridine (1.0 mg) was added a solution of DMAP(12.0 mg, 0.098 mmol) and levurinic anhydride (1.08 mol) in 1,2-dichloroethane (9.4 ml), and the mixture was stirred at room temperature for 22 h. The reaction mixture was evaporated to dryness in vacuo, and the residue was purified by silica gel column chromatography Merc Si-60, 18 g, 5% MeOH -toluene) to obtain Comound R17 (278 mg, 50%).

[Compound R17]
$[\alpha]_D$ −20.7° (c=0.98, CHCl$_3$)
$\delta_H$ (CDCl$_3$):4.452(d, 1H, J=7.3Hz, H-1), 4.317(dd, 1H, J=6.6, 11.0Hz, H-6), 4.151(dd, 1H, J=6.2, 11.0Hz, H-6'), 3.082(br. dd, J=1.1, 1.5Hz, H-4), 2.173(s, 3H, CH$_3$)

EXAMPLE 110

(Synthesis of compound 105)

AgOTf (28.3 mg, 109 μmol) and Cp$_2$HfCl$_2$ (18.9 mg, 48.8 μmol) were stirred with MS3A (90 mg) in MeCN (0.4 ml) at 0° C. for 3 h. To this mixture was added a solution of compound 147 (13.5 mg, 8.3 gmol) and Comound R17 (13.7 mg, 25.0 μmol) in MeCN (0.4 ml), and the mixture was stirred at room temperature for 24 h. The reaction mixture was diluted with CHCl$_3$ and filtered through celite. The filtrate was washed with saturated NaHCO$_3$ solution and then with saturated NaCl solution, dried over MgSO$_4$, and the solvent was evaporated in vacuo. Purification of the residue using silica gel column chromatography (Merc Si-60, 3.6 g, 3% MeOH—CHCl$_3$ yielded compound 105 (13.4 mg, 75%).

[Compound 105]
$[\alpha]_D$ −27.3° (c=0.68, CHb$_3$)
$\sigma_H$ (CDCl$_3$):3.763(s, 3H, OMe), 2.599(m, 2H, CH$_2$), 2.430 (dd, 1H, J=4.8, 12.5Hz, H-3deq), 2.342(m, 2H, CH$_2$), 2.115, 2.096, 2.028, 2.007, 1.968, 1.888, 1.803, 1.679(8s, 24H, 8Ac), 1.340(d, 3H, J=5.6Hz, CH$_3$-5e)

EXAMPLE 111

(Synthesis of compound 107)

To LiI (16.7 mg, 0.125 mmol), which had been vacuum-dried at 100° C. for 14 h on an oil bath, was added a solution of compound 105 (13.3 mg, 6.17 μmol) in pyridine (0.62 ml) and the mixture was stirred at 100° C. for 2 h. Gel-filtration of the reaction mixture (LH-20, 40 ml, MeOH) yielded the lithium salt of compound 105 (7.6 mg). To a solution of the lithium salt (7.6 g, 3.54 μmol) in EtOH (0.3 ml) was added MeHNNH$_2$ (0.3 ml) and the mixture was stirred at 90° C. for 10 h. Gel-filtration (LH-20, 13 ml, MeOH) of the reaction mixture yielded the deacylated derivative (4.7 mg). To a solution of the deacylated derivative (4.7 mg) in methanol (0.30 ml) was added acetic anhydride (0.10 ml), and the mixture was stirred at room temperature for 1 h. The reaction mixture was adjusted to pH 9 by the addition of 28% NaOMe, stirred for 30 min, and then evaporated to dryness in vacuo. Gel-filtration of the residue (LH-20, 13 ml, MeOH) gave 3.6 mg of the N-acetyl derivative. A solution of the N-acetyl derivative (3.6 mg) in methanol (0.50 ml) and water (0.10 ml) was stirred with 10% Pd—C in a H$_2$ atmosphere at room temperature for 24 h. The reaction mixture was filtered through celite and the filtrate was evaporated to dryness in vacuo. Gel-filtration of the residue (LH-20, 5 ml, MeOH) gave 1.8 mg of compound 107 (29%).

[Compound 107]
δH (CD$_3$OD):2.852(dd, 1H, J=4.2, 12.3Hz, H-3deq), 2.013 (1.-5H), 2.011(1.5H), 1.997(3s, 6H, 2NAc), 1.718(t, 1H, J=12.4Hz, H-3dax), 1.646(d, 3H, J=6.6Hz, CH$_3$-5e)

EXAMPLE 112

(Synthesis of compound 148)

A mixture of compound 22 (248 mg, 0.201 mmol) and Ir complex (23.8 mg, 0.1 eq)/THF (10.2 ml) was stirred at room temperature for 2 h. Then to this mixture were added H$_2$O (5.2 ml) and I$_2$ (302.4 mg), and it was further stirred for 1 h. The reaction mixture was diluted with chloroform, washed successively with saturated sodium thiosulfate solution, saturated NaHCO3 solution and saturated NaCl solution. After drying the organic layer over MgSO$_4$, the solvent was evaporated. Purification of the residue by silica gel column chromatography (toluene:ethyl acetate=5:1) gave 231.7 mg of compound 148 (96.6%).

[Compound 148]
Rf=0.20 (toluene:ethyl acetate=3:1)
Elementary Analysis C$_{67}$H$_{71}$O$_{19}$N Calcd. C% 67.38, H% 5.99, N% 1.17
Found. C 67.10, H 6.02, N 1.23
¹H—NMR (CDCl₃) δ1.271 (3H, d, J=6.5Hz, H-6c), 1.669 (3H, s, Ac), 1.833 (3H, s, Ac), 1.955 (3H, s, Ac), 3.281 (1H, m, H-6a or H-5a), 3.61 (3H, m, H-4c, H-6a', H-5a or H-6a), 3.901 (1H, dd, J=2.5, 10.5Hz, H-2c or H-3c), 3.963 (1H, t, J=9.5Hz, H-4a), 4.111 (1H, dd, J=3.5, 10.5Hz, H-3c or H-2c), 4.131 (1H, dd, J=9.0, 10.5Hz, H-3a), 4.198 (1H, d, J=8.0Hz, H-1b), 4.251 (1H, d, J=12.5Hz, OCH₂Ph), 4.340 (1H, d, J=12.5Hz, OCH₂Ph), 4.413 (1H, d, J=12.0Hz, OCH₂Ph), 4.429 (1H, dd, J=3.0, 9.5Hz, H-3b), 4.454 (1H, d, J=12.0Hz, OCH₂Ph), 4.583 (1H, d, J=11.0Hz, OCH₂Ph), 4.597 (1H, d, J=11.5Hz, OCH₂Ph), 4.684 (1H, d, J=11.0Hz, OCH₂Ph), 4.710 (1H, q, J=6.5Hz, H-5c), 4.733 (1H, d, J=12.5Hz, OCH₂Ph), 4.789 (1H, d, J=11.5Hz, OCH₂Ph), 4.819 (1H, dd, J=9.0, 10.5Hz, H-2a), 4.959 (1H, d, J=11.0Hz, OCH₂Ph), 4.967 (1H, dd, J=8.0, 10.0Hz, H-2b), 5.081 (1H, d, J=4.0Hz, H-1c), 5.138 (1H, d, J=8.0Hz, H-1a), 5.339 (1H, d, J=3.5Hz, H-4b), 7.12–7.38 (25H, m, Ph×5), 7.762 (2H, dd, J=3.0, 10.5Hz, Phth), 7.849 (2H, dd, J=3.0, 10.0Hz, Phth)

EXAMPLE 113

(Synthesis of compound 149)

A mixture of compound 148 (231.7 mg, 0.194 mmol), DAST (diethylaminosulfur trifluoride) (104 µl, 4 eq) and 1,2-di-chloroethane (2 ml) was stirred at −15° C. for 1 h. The reaction mixture was diluted with ethyl acetate, and then successively washed with saturated NaHCO₃ and saturated NaCl solution. After the organic layer was dried over MgSO₄, the solvent was evaporated. Purification of the residue by silica gel column chromatography (toluene:ethyl acetate=3:1) gave 231.9 mg of compound 149 (99.9%).

[Compound 149]
Rf=0.55 (toluene:ethyl acetate=2:1)
Elementary analysis C₆₇H₇₀O₁₈NF
Calcd. C% 67.27, H% 5.90, N% 1.17
Found. C 67.07, H 5.94, N 1.22
¹H—NMR (CDCl₃) δ1.275 (3H, d, J=6.5Hz, H-6c), 1.677 (3H, s, Ac), 1.840 (3H, s, Ac), 1.981 (3H, s, Ac), 3.894 (1H, dd, J=2.5, 10.0Hz, H-2c or H-3c), 4.171 (1H, d, J=8.5Hz, H-1b), 4.256 (1H, d, J=12.0Hz, OCH₂Ph), 5.132 (1H, d, J=3.5Hz, H-1c), 5.341 (1H, d, J=3.0Hz, H-4b), 5.678 (1H, dd, J=7.5, 54Hz, H-1a), 7.11–7.38 (25H, m, Ph×5), 7.805 (2H, dd, J=2.5, 5.0Hz, Phth), 7.888 (2H, dd, J=3.0, 5.0Hz, Phth)

EXAMPLE 114

(Synthesis of compound 150)

A mixture of compound 149 (97 mg, 0.081 mmol), NaOMe (0.1 N, 400 µl), MeOH (7 ml) and 1,2-dichloroethane (2 ml) was stirred at room temperature for 2 h. The reaction mixture was treated with Amberlyst 15E, filtered, and then the solvent was evaporated in vacuo. Purification of the residue by silica gel column chromatography (toluene:ethyl acetate=1:1) gave 66.5 mg of compound 150 (77.8%).

[Compound 150]
Rf=0.22 (toluene:ethyl acetate=1:2)
¹H—NMR (CDCl3, TMS) δH; 1.097 (d, 3H, J=6.6Hz, H-6c), 4.018 (d, 1H, J=7.7H H-1b), 4.833 (dd, 1H, J=9.2, 11.0Hz, H-2a), 5.112 (d, 1H, J=3.7Hz, H-1c), 5.776 (dd, 1H, J=7.7, 53.9Hz, H-1a), 7.759 (m, 4H, Phth)

EXAMPLE 115

(Synthesis of compound 151)

A mixture of compound 150 (49.1 mg, 0.046 mmol), compound R11 (64.2 mg, 3.0 eq), MS3A (300 Mg), acetonitrile (1.0 ml) and propionitrile (0.5 ml) was stirred at −40° C. (dry ice in acetonitrile). Then after the addition of silver triflate (AgOTf) (41.15 mg, 3.9 eq) and phenylselenyl chloride (PhSeCl) (30.64 Mg/CH₃CN (3.9 eq)), the reaction mixture was stirred under an Ar atmosphere for another 3 h. After the reaction mixture was diluted with ethyl acetate, triethylamine was added to the mixture, which was washed successively with saturated NaHCO₃ solution and saturated NaCl solution. After drying the organic layer over MgSO₄, the solvent was evaporated in vacuo. Purification of the residue by SX-4 column chromatography (toluene) followed by silica gel chromatography (toluene:ethyl acetate=1:2) gave 32.6 mg of compound 151 (46%) and 10.2 mg of β-anomer (4.4%).

[Compound 151]
Rf=0.18 (toluene:ethyl acetate=1:3)
0.26 (chloroform: acetone=3:1)
¹H—NMR (CDCl₃, TMS) δ_H; 1.120 (d, 3H, J=6.6Hz, H-6d), 1.878, 1.997, 2.017, 2.047, 2.052 (5s, 15H, 5Ac), 2.442 (d, 1H, J=4.8Hz, 12.8Hz, H-3ceq), 3.733 (s, 3H, OCH₃) 4.086 (d, 1H, J=9.2Hz, H-1b), 4.842 (t, 1H, J=9.9Hz, H-2a), 5.056 (m, 1H, H-8c), 5.099 (d, 1H, J=4.0Hz, H-1d), 5.236 (dd, 1H, J=1.8, 8.1Hz, H-7c), 5.786 (dd, 1H, J=7.7, 53.9Hz, H-1a), 7.812 (m, 4H, Phth)

EXAMPLE 116

(Synthesis of compound 152)

A mixture of compound 151 (172.7 mg, 0.112 mmol), acetic anhydride (5 ml) and pyridine (5 ml) was stirred for 5 days, and for 5 days more after the addition of DMAP. The solvent was coevaporated with toluene, and the residue was purified by silica gel column chromatography (toluene:MeOH=8:1) to yield 151.5 mg of compound 152 (83.2%).

[Compound 152]
Rf=0.50 (toluene:MeOH=5:1)
¹H—nmr(CDCl₃, TMS) δ_H: 1.321 (d, 3H, J=6.9Hz, H-6d), 1.699, 1.818, 1.915, 1.979, 2.049, 2.060, 2.133 (7S, 21H, 7Ac), 2.452 (dd, 1H, J=4.8, 12.5Hz, H-3c eq), 3.774 (s, 3H, OMe), 4.539 (t, 1H, J=8.1Hz, H-2b), 5.142 (d, 1H, J=3.7Hz, H-4b or H-1d), 5.278 (dd, 1H, J=2.6, 8.4Hz, H-7c), 5.590 (dd, 1H, J=7.7Hz, 54.6Hz, H-1a), 7.807 (m, 4H, Phth)

EXAMPLE 117

(Synthesis of compound 153)

A mixture of compound 152 (135 mg, 0.083 mmol), compound R11 (120.4 mg, 1.5 eq), MS3A (1.4 g), CH₃CN (1.5 ml) in an Ar atmosphere was stirred with silver triflate (AgOTf) (76.5 mg) and hafnocene dichloride (Cp₂HfCl₂) (56.6 mg, 1.75 eq) at −15° C. for 4.5 h. After the reaction mixture was diluted with ethyl acetate, triethylamine was added to the mixture, which was successively washed with saturated NaHCO₃ solution followed by saturated NaCl solution. The organic layer was dried over MgSO₄, and the solvent was evaporated in vacuo. Purification of the residue by SX-3 column chromatography (toluene) and silica gel column chromatography (chloroform:acetone=5:1) gave 137.7 mg of compound 153 (64.5%).

[Compound 153]
Rf=0.33 (toluene:ethyl acetate=1:3)
=0.43 (chloroform:acetone=3:1)
¹H—NMR(CDCl₃, TMS)δH; 1.086 (s, 9H, Piv), 1.677, 1.804, 1.874, 1.969, 2.006, 2.030, 2.084 (7s, 21H, 7Ac), 3.758 (s, 3H, OMe), 4.954 (d, 1H, J=4.0Hz, H-4d), 5.037 (d, 1H, J=3.7Hz, H-1f), 5.223 (dd, 1H, J=2.56, 8.8Hz, H-7e), 7.617 (m, 4H, Phth)

EXAMPLE 118

(Synthesis of compound 154)

Compound 153 (119 mg, 0.046 mmol), Pd(OH)$_2$—C (119 mg) and MeOH: H$_2$O (4:1) (8 ml) were stirred in a H$_2$ atmosphere for 19 h. The reaction mixture was filtered through celite and the solvent was evaporated in vacuo. The debenzylated derivative (75.5 mg, 100%) was obtained.
Rf=0.38 (BuOH:EtOH:H$_2$O=2:1:1)

The debenzylated derivative (75.5 mg, 0.046 mmol), acetic anhydride (3 ml), pyridine (3 ml) and DMAP were stirred at room temperature for 5 days. After the solvent was coevaporated with toluene, the residue was purified by LH-20 column chromatography (chloroform:MeOH=1:1) followed by silica gel column chromatography (chloroform:MeOH=20:1) to give 85.7 mg of compound 154 (87.1%).

[Compound 154]
Rf=0.27 (chloroform:MeOH=20:1)
$^1$H—nmr(CDCl$_3$, TMS) $\delta_H$; 1.091, 1.104 (2s, 9H, Piv), 1.274 (d, 3H, J=6.2Hz, H-6f), 2.463 (dd, 0.5H, J=4.7, 12.8Hz, H-3eeq), 3.784 (s, 3H, OMe), 4.881 (dd, 0.5H, 3.7, 10.3Hz, H-2a($\alpha$)), 5.198 (d, 0.5H, J=3.7Hz,H-1f), 5.613 (d, 0.5H, J=8.4Hz, H-1a($\beta$)), 6.237 (d, 0.5H, J=3.7Hz,H-1a($\alpha$)), 7.795 (m, 4H, Phth)

EXAMPLE 119

(Synthesis of compound 155)

Compound 154 (97.8 Mg, 0.048 mmol) and hydrazine acetate (8.9 mg, 20 eq) were stirred in DMF (1 ml) at room temperature for 1 h. After diluting with ethyl acetate, the reaction mixture was washed with saturated NaHCO$_3$ solution and then with saturated NaCl solution. After the organic layer was dried over MgSO$_4$, the solvent was evaporated in vacuo. Purification of the residue by LH-20 column chromatography (chloroform:MeOH=1:1) gave 90.3 mg of compound 155 (94.3%).

[Compound 155]
Rf=0.40 (chloroform:MeOH=10:1)
$^1$H—nmr(CDCl$_3$,TMS) $\delta_H$; 1.149 (s, 9H, Piv), 1.273 (d, 1H, J=6.6Hz, H-6f), 2.450 (dd, 0.5H, J=4.4, 12.8Hz, H-3eq), 3.783 (s, 3H, OMe), 4.208(d, 0.5H, 8.1Hz, H-1b), 5.012 (d, 0.5H, J=8.1Hz, H-1d), 5.220, 5.365(d, 1H, J=3.3Hz, J=3.9Hz, H-4b or H-4d), 5.276, 5.298 (d, 1H, J=3.7Hz, H-1f), 7.790 (m, 4H, Phth)

EXAMPLE 120

(Synthesis of compound 156)

Compound 155 (90.3 mg, 0.045 mmol), 1,8-diazabicyclo [5.4.0]-7-undecene (DBU)) (15 µl, 21 eq), trichloroacetonitril (70.3 µl) and 1,2-dichloroethane (1 ml) were stirred in an Ar atomosphere at 0° C. for 45 min. Purification of the reaction mixture directly by silica gel column chromatography (chloroform:MeOH=30:1) gave 89.1 mg of compound 156 (90.9%).

[Compound 156]
Rf=0.45 (chloroform:MeOH=15:1)
$^1$H—nmr(CDCl$_3$, TMS) $\delta$H; 1.099 (s, 9H, Piv), 1.274 (d, 1H, J=6.6Hz, H-6f), 1.810, 1.832, 1.942, 1.967, 2.001, 2.047, 2.074, 2.077, 2.079, 2.093, 2.103, 2.118, 2.160, 2.166 (14s, 51H, 17Ac), 2.462 (dd, 1H, J=4.8, 12.5Hz, H-3eeq), 3.782 (s, 3H, OMe) 4.229 (d, 1H, J=8.1Hz, H-1b), 4.470 (d, 1H, J=8.1Hz, H-1c), 4.658 (dd, J=8.1, 9.9Hz, H-2b), 4.754 (t, 1H, H-2d), 5.001 (d, 1H, J=7.3Hz, H-1d), 5.098 (d, 1H,J=10.3Hz, NH), 5.200 (d, 1H, J=3.7Hz, H-1f), 5.217 (d, 1H, J=3.3 Hz, H-4d), 5.245 (d, 1H, J=2.6Hz, H-4b), 6.452 (da, 1H, J=3.7Hz,H-1a), 7.793(m, 4H, Phth), 8.613 (s, 1H, NH)

EXAMPLE 121

(Synthesis of compound 157)

A mixture of compound 156 (49 mg, 0.023 mmol), compound R19 (P. Zimmerman et al., J. Carbohydr. Chem. 7, 435 (1988)) (26.1 mg, 20 eq), chloroform (1 ml) and MS4A (500 mg) was stirred in an Ar atmosphere at −15° C., and, after the addition of BF$_3$.OEt$_2$ (43 µl, 20 eq), the mixture was further stirred for 30 min. After the reaction mixture was diluted with ethyl acetate, triethylamine was added to the mixture, which was filtered through celite, and then washed successively with saturated NaHCO$_3$ solution and saturated NaCl solution. After the organic layer was dried over MgSO$_4$, the solvent was evaporated in vacuo. Purification of the residue by silica gel column chromatography (toluene:acetone=2:1) gave 50 mg of compound 157 (85.9%).

[Compound 157]
Rf=0.61 (toluene:acetone=1:1)
$[\alpha]^{27}_D$ −25.7° (c=0.78 CHCl$_3$)
$^1$H—nmr(CDCl$_3$,TMS) $\delta_H$; 1.067 (s, 9H, Piv), 1.810, 1.824, 1.916, 1.941, 1.957, 1.967, 1.999, 2.047, 2.060, 2.072, 2.079, 2.099, 2.105, 2.159, 2.161 (15s, 51H, 17Ac), 2.461 (dd, 1H, J=4.8, 12.8Hz, H-6e eq), 3.783 (s, 3H, OMe), 4.172 (d, 1H, 8.1Hz, H-1a), 4.282 (d, 1H, J=8.1Hz, H-1b), 4.467 (d, 1H, J=7.7Hz, H-1c), 4.630 (dd, 1H, J=8.1Hz,9.9Hz, H-2b), 4.809 (dd, 1H, J=7.7Hz, 9.5Hz, H-2d), 5.010 (d, 1H, J=8.4Hz, H-1d), 5.262 (d, 1H, J=2.6Hz, H-4b)

EXAMPLE 122

(Synthesis of compound 158)

To a solution of compound 157 (35 mg, 0.014 mmol) in toluene (2 ml) and H$_2$O (1 ml) was added triphenyl phosphine (7.2 Mg, 2 eq) and the mixture was stirred at 100° C. on an oil bath for 19 h. After the solvent was evaporated, the residue was purified by LH-20 column chromatography (chloroform:MeOH=1:1) to give 28.4 mg of the amino derivative (82%).

[Compound 158]

| Rf | = | 0.45 (chloroform:MeOH = 5:1) |
|---|---|---|
|  | = | 0.38 (toluene:acetone = 1:1) |

The amino derivative (28.4 mg, 0.011 mmol), 2-chloro-1-methylpyridinium iodide (65 mg, 23 eq) and lignoceric acid (CH$_3$(CH$_2$)$_{22}$COOH) (9.3 mg, 2.3 eq) were dissolved in 1,2-dichloroethane(1 ml) and stirred at room temperature. Tributylamine was added to this mixture and further stirred for 1 h. After the reaction mixture was washed with saturated NaHCO$_3$ solution and saturated NaCl solution. The organic layer was dried over MgSO$_4$, filtered through celite, and the solvent was evaporated. Purification of the residue by LH-20 column chromatography (chloroform:MeOH=1:1) and silica gel chromatography (toluene:acetone=3:1) gave 28.4 mg of compound 158 (87.8%).

[Compound 158]

Rf = 0.38 (chloroform:MeOH = 25:1)
= 0.56 (toluene:acetone = 3:1)

$[\alpha]^{25}_D$ −18.5 (c=1.0, chloroform)
$^1$H—nmr(CDCl$_3$, TMS) 1.092 (s, 9H, Piv), 1.811, 1.830, 1.929, 1.942, 1.967, 2.002, 2.050, 2.074, 2.080, 2.106, 2.115, 2.160, 2.164 (13s, 51H, 17Ac), 2.463 (dd, 1H, J=4.4, 12.8Hz, H-3eeq), 3.783 (s, 3H, OMe), 4.337 (d, 1H, J=7.7Hz, H-1b), 4.471 (d, 1H, J=8.1Hz, H-1c), 4.629 (dd, 1H, J=8.1, 9.5Hz, H-2b), 4.816 (dd, 1H, J=8.1, 9.9 Hz, H-2d), 5.013 (d, 1H, J=8.4Hz, H-1d), 5.408 (d, 1H, J=8.8, N H)

EXAMPLE 123

(Synthesis of compound 159)

To a solution of compound 158 (28.4 mg, 0.010 mmol) in pyridine (1.5 ml) was added LiI (30.2 Mg, 22 eq) and the mixture was stirred for 12.5 h at 110° C. Direct purification of the reaction mixture by LH-20 column chromatography (chloroform:MeOH=1:1) gave 22.4 Mg of compound 159 (79.1%).

[Compound 159]
Rf=0.65 (chloroform:MeOH=5:1)
$^1$H—nmr(CD$_3$OD, TMS) δH; 1.099 (s, 9H, Piv), 1.801, 1.823, 1.956, 1.961, 1.966, 2.028, 2.063, 2.072, 2.105, 2.110, 2.129, 2.134, 2.181, 2.185 (14s, 51H, 17Ac), 2.486 (dd, 1H, H-6eeq), 4.548 (d, 1H, J=8.1Hz, H-1c), 4.641 (dd, 1H, J=8.1, 9.9Hz, H-2b), 4.773 (t, 1H, J=9.2Hz, H-2a), 4.815 (dd, 1H, J=8.1Hz, 9.5Hz, H-2d), 5.075 (d, 1H, J=8.4Hz, H-1d)

EXAMPLE 124

(Synthesis of compound 160)

To compound 159 (22.4 mg, 7.82 μmol) were added ethanol (5 ml) and methylhydrazine (2.5 ml) and the mixture was stirred for 18 h at 80° C. After the solvent was evaporated, the residue was purified by LH-20 column chromatography (MeOH). To the residue were added acetic anhydride (70 μl) and MeOH (2 ml), and the mixture was stirred for 1 h, and directly purified by LH-20 column chromatography (MeOH).

Finally, the product was stirred with a solution of 1 N-NaOH (0.2 ml) and THF:MeOH (1:1, 0.6 ml) for 1 day, and purified again by LH-20 column chromatography (chloroform:MeOH:H$_2$O=60:30:5) to obtain 15.9 mg of the silylated derivative (quantitative).
Rf=0.33 (chloroform:MeOH:H$_2$O=60:30:5)

A mixture of the silylated derivative (4.6 mg, 23 μmol) and tetrabutylammonium fluoride (Bfor 14 h.u$_4$NF) (528 μl, 60 eq) was stirred for 14 h at 50°–60° C. Direct purification of the reaction mixture by LH-20 column chromatography (chloro-form:MeOH:H$_2$O=60:30:5) gave 4.0 mg of compound 160 (98.5%).

[Compound 160]
Rf=0.25 (chloroform:MeOH:H$_2$O =60:30:5)
$^1$H—nmr(DMSO: D$_2$O=50:1, TMS) δ$_H$, 1.023(d, 3H, J=6.6Hz, H-6f), 1.850, 1.899 (s, 6H, 2Ac), 2.773 (dd, 1H, J=4.8, 12.1Hz, B-3eeq), 4.185 (d, 1H, J=8.1Hz, H-1a), 4.289 (d, 1H, J=6.6Hz, H-1b), 4.366 (d, 1H, J=7.7Hz, H-1d), 4.771 (d, 1H, J=8.1Hz, H-1c), 4.813 (d, 1H, J=3.7Hz, H-1f), 5.366 (dd, 1H, J=7.0, 15.4Hz, H-4cer), 5.562 (dt, 1H, J=7.0, 15.0Hz, H-5cer)

EXAMPLE 125

(Synthesis of compound 161)

To compound 87α (67.5 mg, 0.043 mmol) were added acetic anhydride (3 ml) and pyridine (3 ml) and the mixture was stirred for 3 days. Then DMAP was added to the reaction mixture, which was stirred for 24 h. After quenched with MeOH, the solvent was evaporated and the residue was purified by silica gel column chromatography (toluene:acetone:=3:1) to yield 58.4 mg of compound 161 (82.2%).

[Compound 161]
Rf=0.49 (toluene:MeOR=5:1)
$^1$H—nmr(CDCl$_3$, TMS) δ$_H$H; 1.262, 1.336 (d, 3H, J=6.2, 6.6Hz, H-6d), 1.702, 1.814, 1.821, 1.916, 1.931, 1.977, 1.992, 2.048, 2.058, 2.074, 2.137, 2.147, 2.221 (13s, 13Ac), 3.773, 3.787 (2s, 3H, OMe), 5.521 (m, 1H, —OCH$_2$C H=CH$_2$), 7.833 (m, 4H, Phth)

EXAMPLE 126

(Synthesis of compound 162)

To compound 161 (187.3 mg, 0.112 mmol) was added a H$_2$— activated Ir complex ([Ir(COD) (PMePh$_2$)$_2$]PF$_6$) (13.4 mg)/THF (6 mg) and the mixture was stirred for 3 h. Then H$_2$O (3.2 ml), I$_2$ (172 Mg) and THF were added to the reaction mixture, which was stirred for 1 h. The reaction mixture was diluted with ethyl acetate, and washed with saturated sodium thiosulfate solution, saturated NaHCO$_3$ solution and saturated NaCl solution. The organic layer was dried over MgSO$_4$, filtered through celite, and then the solvent was evaporated in vacuo. Purification of the residue by silica gel column chromatography (chloroform:acetone= 3:1) gave 160.2 mg of compound 162 (87.6%).

[Compound 162]
Rf=0.10 (chloroform:acetone=3:1)
$^1$H—nmr(CDCl$_3$, TMS): 1.249, 1.324 (d, 3H, J=7.0, 6.6Hz, H-6d), 1.69, 1.798, 1.806, 1.913, 1.928, 1.964, 1.977, 2.036, 2.041, 2.067, 2.104, 2.115, 2.214 (13s, 39H, 13Ac), 3.760, 3.774 (2s, 3H, OMe), 7.765 (m, 4H, Phth)

EXAMPLE 127

(Synthesis of compound 163)

To a solution of compound 162 (160.2 mg, 0.099 mmol) dissolved in 1,2-dichloroethane (1 ml) were added at 0° C., after the air was replaced with Ar, trichloroacetonitrile (154.4 μl, 15.6 eq) and DBU (10.5 μl, 0.7 eq), the mixture was stirred for 1 h. Direct purification of the reaction mixture by silica gel column chromatography (chloroform:acetone=5:1) gave 144.3 mg of compound 163 (82.7%).

[Compound 163]
Rf=0.23 (chloroform:acetone=5:1)
$^1$H—nmr(CDCl$_3$, TMS) δ$_H$, 1.337 (d, J=6.6Hz, H-6d), 2.454 (dd, J=4.8, 12.8Hz, H-3ceq), 3.773, 3.788 (2s, 3H, OMe), 6.157, 6.170 (d, 1H, J=8.8Hz, 8.8Hz, H-1a), 7.762 (m, 4H, Phth), 8.407, 8.433 (2s, 1H, NH)

EXAMPLE 128

(Synthesis of compound 164)

To a solution of compound 163 (24.2 mg, 0.014 mmol) in 1,2-dichloroethane (1 ml) was added at −15° C., after the air was replaced with Ar, n—Bu$_3$SnSMe (14 μl, 3 eq) and BF$_3$.OEt$_2$ (48 μl, 2.6 eq) and the mixture was stirred for 2.5 h. The reaction mixture was diluted with ethyl acetate, washed with saturated KF solution, saturated NaHCO$_3$ solution and saturated NaCl solution. After the organic layer was dried over MgSO$_4$ and filtered through celite, the solvent was evaporated and the residue was purified by silica gel column chromatography (chloroform:acetone=4:1) to obtain 22.6 mg of compound 164 (100%).

[Compound 164]
Rf=0.41 (chloroform:acetone=3:1)
$^1$H—nmr(CDCl$_3$, TMS) δ$_H$, 1.274, 1.339 (d, 3H, J=6.2, 6.60Hz, H-6d), 2.447 (dd, J=4.6, 12.8Hz, H-3ceq), 3.774, 3.786 (2s, 3H, OMe), 7.796(m, 4H, Phth)

EXAMPLE 129

(Synthesis of compound 165)

(1) Compound R12 (157.7 mg, 13 eq), MS3A (600 mg) and a solution of CH$_3$CN:EtCN (1:1) (1.5 ml) was stirred after the air was replaced by Ar. To this mixture were added at −15° C. SnCl$_2$ (47.9 mg, 2 eq) and AgOTf (130.3 mg, 4 eq) and finally compound 149 (150 Mg, 0.13 mmol) and the mixture was stirred for 3 h. After diluted with ethyl acetate, Et$_3$N was added to the reaction mixture, which was washed with saturated NaHCO$_3$ solution and then with saturated NaCl solution. The organic layer was dried over MgSO$_4$, filtered through celite, and the solvent was evaporated. Purification of the residue by silica gel column chromatography (hexane:ethyl acetate=2:1) gave 221.1 Mg of compound 165 (82.3%) and recovered 46.7 mg of R12.

[Compound 165]
Rf=0.70 (hexane:ethyl acetate=1:1)
[α]$^{24}_D$ −35.4° (c=1.0, CHCl$_3$)
$^1$H—NMR(CDCl$_3$) δ1.085 (9H, s, Piv), 1.273 (3H, d, J=6.5Hz, CH$_3$-6c), 1.649 (3H, s, Ac), 1.812 (3H, s, Ac), 1.947 (3H, s, Ac), 2.957 (1H, br.d, J=10.0Hz,H-5a), 3.230 (1H, br.d, J=9.5Hz, H-6a), 3.35 (1H, m, H-6d), 3.358 (1H, dd, J=7.5, 9.5Hz, H-2b), 3.465 (1H, dd, J=4.0, 11.5Hz, H-6a'), 3.550 (1H, dd, J=5.0, 8.0Hz, H-5d), 3.64 (3H, m, H-5c, H-6'd, H-4e), 3.786 (1H, d, J=12.0 Hz, CH$_2$Ph), 3.897 (1H, t, J=9.0Hz, H-4a), 3.920 (1H, d, J=3.0Hz, H-4b), 3.947 (1H, m, H-3e), 3.984 (1H, t, J=9.0Hz, H-4c), 4.061 (1H, d, J=12.0, CH$_2$Ph), 4.119 (1H, d, J=8.0Hz, H-1d), 4.143 (1H, dd, J=3.5, 10.0Hz, H-2e), 4.182 (1H, d, J=8.0, H-1b), 4.202 (1H, d, J=12.0Hz, CH$_2$Ph), 4.241 (1H, d, J=12.0Hz, CH$_2$Ph), 4.258 (1H, d, J=12.5Hz, CH$_2$Ph), 4.282 (1H, d, J=8.0Hz,H-1a), 4.306 (1H, t, J=8.0Hz, H-2c), 4.341 (1H, dd, J=3.5, 10.0Hz, H-3d), 4.442 (1H, J=11.5Hz, CH$_2$Ph), 4.457 (1H, d, J=12.0Hz, CH$_2$Ph), 4.481 (1H, d, J=12.0Hz, CH$_2$Ph), 4.589 (1H, d, J=11.0Hz, CH$_2$Ph), 4.657 (1H, d, J=12.0Hz, CH$_2$Ph), 4.696 (1H, d, J=10.5Hz, CH$_2$Ph), 4.717 (1H, m, H-5e), 4.740 (1H, d, J=12.0Hz CH$_2$Ph), 4.769 (1H, d, J=12.5Hz, CH$_2$Ph), 4.841 (1H, d, J=11.0Hz, CH$_2$Ph), 4.871 (1H, d, J=9.5Hz, H-3c), 4.949 (1H, dd, J=8.0, 10.0Hz, H-2d), 4.960 (1H, d, J=11.5Hz, CH$_2$Ph), 5.102 (1H, dd, J=8.5, 10.0Hz, H-2a), 5.142 (1H, d, J=4.0Hz, H-1e), 5.193 (1H, d, J=8.0Hz, H-1c), 5.315 (1H, d, J=3.5Hz, H-4d), 7.2 (55H, m, Ph)

(2) compound R12 (13.8 mg, 0.014 mmol), MS3A (200 mg) and a solution of CH$_3$CN:EtCN (1:1) (1.0 ml) was stirred after the air was replaced by Ar. To this mixture were added at −15° C. Cp$_2$HfCl$_2$ (14.2 mg, 2.6 eq) and AgOTf (19.2 mg, 5.2 eq), and finally compound 142 (22.2 mg, 1.3 eq) and the mixture was stirred for 3 h. To this solution were further added Cp$_2$HfCl$_2$ (14.2 mg) and AgOTf (19.2 mg) and the mixture was stirred for 21 h. After diluted with ethyl acetate, Et$_3$N was added to the reaction mixture, which was washed with saturated NaHCO$_3$ solution, and saturated NaCl solution. The organic layer was dried over MgSO$_4$, filtered through celite, and the solvent was evaporated. Purification of the residue by SX-3 column chromatography (toluene) gave 15.8 mg of compound 165 (51.6%)

EXAMPLE 130

(Synthesis of compound 166)

To compound 165 (38.1 mg, 0.018 mmol) were added EtOH (890 μl) and hydrazine hydrate (100 eq), and the mixture was stirred for 3 h at 110° C. The solvent was evaporated and the residue was purified by LH-20 column chromatography (MeOH). To the reaction were added pyridine (1 ml) and acetic anhydride (1 ml) and the mixture was stirred for 2 h. After addition of MeOH, the solvent was coevaporated with toluene.

The residue was purified by LH-20 column chromatography (chloroform:MeOH=1:1).

Finally, to the mixture were added NaOMe (10 μl) and MeOH (1 ml) and the mixture was stirred for 1 h. The reaction mixture was neutralized with Amberlyst 15E, filtered, and the solvent was evaporated to give 29.5 mg of compound 166 (86.5%).

[Compound 166]
Rf=0.42 (toluene:ethyl acetate=1:6)
$^1$H—NMR(CDCl3) δ1.110 (3H, d, J=6.5Hz, CH$_3$-6e), 1.123 (9H, s, Piv), 1.537 (3H, s, NHAc), 3.340 (1H, dd, J=7.5, 8.5Hz, H-2d), 3.477 (1H, dd, J=3.0, 9.0Hz, H-3d), 3.562 (1H, br.t, J=9.0Hz, H-3a), 3.866 (1H, br.d, J=3.0Hz,H-4d), 3.923 (1H, dd, J=2.5, 10.5Hz, H-3e), 4.025 (1H, t, J=10.0Hz, H-4a), 4.038 (1H, dd, J=3.5, 10.0Hz, H-2e), 4.090 (1H, d, J=12.0Hz, CH$_2$Ph), 4.211 (1H, d, J=12.0Hz, CH$_2$Ph), 4.326 (1H, d, J=7.5Hz, H-1d), 4.351 (1H, d, J=7.0Hz, H-1c), 4.375 (1H, d, J=12.0Hz, CH$_2$Ph), 4.412 (1H, d, J=8.0Hz, H-1a), 4.449 (1H, d, J=11.5Hz, CH$_2$Ph), 4.482 (1H, d, J=12.0Hz, CH$_2$Ph), 4.495 (1H, d, J=11.5Hz, CH$_2$Ph), 4.541 (1H, d, J=11.5Hz, CH$_2$Ph), 4.569 (1H, d, J=11.5Hz, CH$_2$Ph), 4.606 (1H, d, J=11.5Hz, CH$_2$Ph), 4.695 (1H, d, J=12.0Hz, CH$_2$Ph), 4.725 (1H, d, J=11.5Hz, CH$_2$Ph), 4.795 (1H, d, J=11.5Hz, CH$_2$Ph), 4.833 (1H, d, J=12.5Hz, CH$_2$Ph), 4.921 (1H, d, J=12.0Hz, CH$_2$Ph), 5.006 (1H, d, J=11.0 Hz, CH$_2$Ph), 5.032 (1H, d, J=3.5Hz, H-1e), 5.097 (1H, dd, J=8.0, 9.5Hz,H-2a), 7.2 (55H, m, Ph)

EXAMPLE 131

(Synthesis of compound 167)

Compound 166 (39.5 mg, 0.020 mmol) (15 eq), MS3A (250 mg,) and CH$_3$CN (0.5 ml) were stirred, after the air was replaced by Ar, at room temperature for 15 min. To the reaction mixture, after the temperature was cooled to −20° C., were added compound 164 (22.6 mg, 0.014 mmol), CH$_3$CN:EtCN (1:1) (0.5 ml), AgOTf (12.7 mg, 3.9 eq) and PhSeCl (9.5 mg, 3.9 eq), and the mixture was stirred for 2 h. After the reaction mixture was diluted with ethyl acetate, Et$_3$N was added, and the mixture was washed with saturated NaHCO$_3$ solution and saturated NaCl solution. The organic layer was dried over MgSo$_4$, filtered through celite, and the solvent was evaporated. Purification of the residue by silica gel column chromatography (chloroform:acetone=5:1) gave 22.6 mg of compound 167 (46.8%).

[Compound 167]
Rf=0.60 (chloroform:acetone=3:1)
[α]$^{27}_D$ −12.3° (c=0.51 CHCl$_3$)
$^1$H—nmr(CDCl$_3$, TMS) (5H , 0.782 (d, 3H, J=6.6Hz, H-6i or H-6h), 1.323(d, 3H, J=6.6Hz, H-6h or H-6i), 1.819, 1.913, 1.959, 1.974, 2.022, 2.075, 2.172 (7s, 21H, 7Ac), 3.772 (s, 3H, OMe), 5.207, (dd, 1H, J=2.2, 7.3Hz, H-7g)

EXAMPLE 132

(Synthesis of compound 168)

To a suspension of compound 167 (58.8 mg, 0.017 mmol) in MeOH:H$_2$O (4:1) solution (19 ml) was added Pd(OH)$_2$—C (58.8 mg, and, after the air was replaced with H$_2$, the mixture was stirred at room temperature for 1 day. After filtration through celite, the solvent was evaporated to yield 34.8 mg of the debenzylated derivative (100%). To the debenzylated derivative (34.8 mg, 0.017 mmol) were added acetic anhydride (2 ml), pyridine (2 ml) and DMAP and the mixture was stirred for 3 days. After the addition of MeOH, the solvent was coevaporated with toluene. Purification of the residue by silica gel column chromatography (chloroform:MeOH=30:1) gave 41.7 mg of compound 168 (88.0%).

[Compound 168]
Rf=0.17 (chloroform:MeOH=20:1)
$^1$H—nmr(CDCl$_3$, TMS) δH: 1.134 (s, 9H, Piv), 3.786 (s, 3H, OMe), 5.692 (d, 0.5H, J=8.42Hz, H-1a(β)), 6.920 (d, 0.5H, J=4.03Hz, H-1a(α))

EXAMPLE 133

(Synthesis of compound 169)

To a solution of compound 168 (6.1 mg, 2.14 μmol) in DMF (0.5 ml) was added hydrazine acetate (H$_2$NNH$_2$·AcOH) (0.4 mg, 2 eq) and the mixture was stirred at room temperature for 1 h.

After diluted with ethyl acetate, the reaction mixture was washed with saturated NaHCO$_3$ solution and saturated NaCl solution. After the reaction mixture was filtered through celite, the solvent was evaporated. The residue was purified by silica gel column chromatography (chloroform:MeOH= 30:1) to obtain 4.3 mg of compound 169 (71.5%).

[Compound 169]
Rf=0.13 (chloroform:MeOH=20:1) $^1$H—nmr(CDCl$_3$, TMS) δ$_H$, 0.764 (d, 3H, J=6.2Hz H-6h or 6i), 0.804 (d, 3H, J=7.0Hz H-6h or 6i), 3.717 (s, 3H, OMe), 5.106 (d, 1H, J=3.7Hz H-1h or 1i), 5.230 (d, 1H, J=4.0Hz H-4h or 4d), 5.286 (d, 1H, J=3.7Hz H-1h or 1i)

EXAMPLE 134

(Synthesis of compound 170)

To a solution of compound 169 (27.2 mg, 9.68 μmol) in 1,2-dichloroethane (0.5 ml) were added at 0° C., after the air was replaced by Ar, DBU (3.3 μl, 2.1 eq) and CCl$_3$CN (15.2 μl, 15 eq) and the mixture was stirred for 1 h. Direct purification of the reaction mixture by silica gel column chromatography (chloroform:MeOH=40:1) gave 25.3 mg of compound 170 (88.5%).

[Compound 170]
Rf=0.18 (chloroform:MeOH=20:1)
[α]$^{21}_D$ −13.2° (c=0.5, CHCl$_3$)
$^1$H—nmr(CDCl$_3$, TMS) δ$_H$: 0.832 (d, 3H, J=6.6Hz, H-6h or H-6i), 3.785 (s, 3H, OMe), 3.824 (t, 1H, J=9.5Hz, H4a), 4.360 (d, 1H, J=7.7Hz, H-1b or H-1d), 4.376 (d, 1H, J=9.2Hz, H-1d or H-1b), 4.484 (d, 1H, J=8.4Hz, H-1e), 4.948 (d, 1H, J=2.9Hz, H-4f), 4.976 (d, 1H, J=8.1Hz, H-1e), 5.035 (dd, 1H, J=3.7, 10.3Hz, H-2a), 5.177 (b, s, 1H, H-1H or H-1i), 5.269 (d, 1H, J=4.4Hz, H-4b or H-4d), 5.306(d, 1H, J=4.0Hz, H-4d or H-4b), 5.357(bs, 1H, H-1i or H-1h), 5.568 (t, 1H, H-3a), 6.505 (d, 1H, J=3.7Hz, H-1a), 8.653(s, 1H, NH)

EXAMPLE 135

(Synthesis of compound 171)

A mixture of compound R19 (9.7 mg, 0.017 mmol) (2 eq), 1,2-dichloroethane (0.5 ml) and MS4A (500 mg) was stirred, after the air was replaced by Ar, at room temperature. After the temperature was lowered to −15° C., compound 170 (25.3 Mg, 8.56 μmol) and TMSOTf (0.33 μl, 0.3 eq) were added to the reaction mixture and stirred for 3.5 h. To the reaction mixture was further added BF$_3$·OEt$_2$ (40 μl, 2 eq), and stirred for 30 min. After the dilution with ethyl acetate followed by the addition of Et$_3$N, the reaction mixture was washed with saturated NaHCO$_3$ solution and saturated NaCl solution. The organic layer was dried over MgSO$_4$, filtered through celite, and then the solvent was evaporated. Purification of the residue by silica gel column chromatography (toluene:acetone=2:1) gave 16 mg of compound 171 (55.7%).

[Compound 171]
Rf=0.41 (toluene:acetone=1:1)

EXAMPLE 136

(Synthesis of compound 172)

To compound 171 (10.3 mg, 3.07 μmol) and triphenylphosphin (1.7 mg, 2.0 eq) were added toluene (2.1 ml) and H$_2$O (0.7 ml), and the mixture was stirred for 24 h at 110° C. After the solvent was evaporated, the residue was purified by LH-20 column chromatography (chloroform:MeOH=1:1) to obtain 8 mg of the amino derivative (78.3%).

Rf=0.26=0.26 (chloroform:MeOH=20:1)

To a solution of the amino derivative (8 mg, 2.40 μmol) in 1,2-dichloroethane (1.0 ml) were added, after the air was replaced by Ar, 2-chloro-1-methylpyridinium iodide (1.4 mg, 2.3 eq) and lignoceric acid (2.2 mg, 2.3 eq), and the mixture was stirred at room temperature. Then tri-n-butylamine (2.4 μl) was added, and the mixture was stirred for 1 h. After diluting with ethyl acetate, the reaction mixture was washed with H$_2$O and saturated NaCl solution. The organic layer was dried over MgSO$_4$, filtered through celite, and the solvent was evaporated. Purification of the residue by LH-20 column chromatography (chloroform:MeOH= 1:1) gave 8.3 mg of compound 172 (93.9%).

[Compound 172]
Rf=0.41 (chloroform:MeOH=20:1)
[α]$^{22}_D$ −21.2° (c=0.25, CHCl$_3$)

EXAMPLE 137

(Synthesis of compound 173)

To compound 172 (4.1 mg, 1.11 μmol) dissolved in pyridine (1.5 ml) was added LiI (3.4 mg, 2.2 eq), and the mixture was stirred in a 110 oil bath for 17 h. Direct purification of the reaction mixture by LH-20 column chromatography gave 4.1 mg of compound 173 (100%).

[Compound 173]
Rf=0.20 (chloroform:MeOH=5:1)

EXAMPLE 138

(Synthesis of compound 174)

To a suspension of compound 173 (4.1 mg, 1.11 μmol) in EtOH (3 ml) was added CH$_3$NHNH$_2$ (0.36 ml) and the mixture was stirred in a 80° C. oil bath for 1 day. The solvent was evaporated and the residue was purified by LH-20 column chromatography (chloroform:MeOH: H$_2$O= 60:30:5).

Then, to the above product were added acetic anhydride (0.1 ml) and MeOH (1.0 ml), and the mixture was stirred for 1 h. The solvent was evaporated again, and the residue was purified by LH-20 column chromatography (chloroform:MeOH:H$_2$O=60:30:5). The product was dissolved in MeOH:THF (1:1) (0.75 ml). To this solution was added 1 N NaOH (0.3 ml), and the mixture was stirred for 1 day. The reaction mixture was purified by LH-20 column chromatography (chloroform:MeOH:H$_2$O=60:30:5).

Then, the purified product was dissolved in Bu$_4$NF (528 µl), and the resulting solution was stirred at 50°–60° C. in an oil bath for 1 day. The reaction mixture was purified by LH-20 column chromatography (chloroform:MeOH:H$_2$O= 60:30:5) to yield 1.1 mg of compound 174 (43% calculated from compound 173).

[Compound 174]
Rf=0.14 (BuOH:EtOH:H$_2$O=2:1:1)

EXAMPLE 139

(Synthesis of compound 175)

To a solution of compound 25b (4.8 mg) in MeOH (0.4 ml) and H$_2$O (0.1 ml) was added 20% Pd(OH)$_2$—C (5 mg) and the mixture was stirred under an H$_2$ atmosphere at room temperature for 24 h. After 20% Pd(OH)$_2$—C was removed, the solvent was evaporated, and the residue was purified by LH-20 (MeOH) to obtain 2.9 mg of compound 175 (100%).

[Compound 175]
$[\alpha]_D$ −55.6° (c=0.19, MeOH)
$^1$H—NMR (CD$_3$OD) δ0.910 (3H, t, J=7.0Hz, CH$_2$CH$_3$), 1.220 (3H, d, J=7.0Hz, H-6c), 1.551 (2H, m, H-2Pr), 1.990 (3H, br.s, Ac), 3.643(1H, dd, J=3.5, 9.5Hz, H-3b), 3.858 (1H, d, J=3.5Hz, H-4b), 4.393 (1H, dd, J=8.0, 9.0Hz, H-2b), 4.445 (3H, br.d, J=8.0Hz, H-1b), 4.930 (1H, q,J=7.0Hz, H-5c), 5.032 (1H, d, J=4.0Hz, H-1c)

EXAMPLE 140

(Synthesis of compound 176)

To a solution of compound 25c (9 mg) in MeOH (0.8 ml) and H$_2$O (0.2 ml) was added 20% Pd(OH)$_2$—C (9 mg) and the mixture was stirred under a H$_2$ atmosphere at room temperature for 22 h. After the Pd(OH)$_2$—C was removed, the solvent was evaporated, and the residue was purified by LH-20 (MeOH) column chromatography to obtain 5.6 mg of compound 176 (94.0%).

[Compound 176]
Rf=0.37 (nBuOH:EtOH:H$_2$O=2:1:1), $[\alpha]_D$ −13.3° (c=0.37, MeOH)
FAB-MASS(Glycerin) 876(M—H), 854(M—Na)
$^1$H—NMR (CD$_3$OD) δ0.907 (3H, t, J=7.5Hz, CH$_2$CH$_3$), 1.285 (3H,d, J=6.5Hz, H-6c), 1.553(2H,qd, J=7.5, 14.0Hz, H-2Pr), 2.007 (3H, s, Ac), 3.431 (1H, td, J=7.5, 10.0Hz, H-1Pr), 3.713 (1H, dd, J=4.5, 6.5Hz, H-2c), 3.753 (1H, t, J=9.0Hz,, H-4a), 3.856 (1H, dd, J=3.5, 10.0Hz, H-3c), 3.944 (1H, d, J=3.0Hz, H-4c), 4.232 (1H, t, J=9.5Hz, H-3a), 4.342 (1H, dd, J=3.0, 10.0Hz, H-3b), 4.476 (1H, dd, J=7.5, 10.0Hz, H-2b), 4.519 (1H, d, J=7.5Hz, H-1b), 4.911 (1H, q, J=7.0Hz, H-5c), 4.977 (1H, br.d, J=8.0Hz, H-1a), 5.023 (1H, d, J=4.0Hz, H-1c), 5.066 (1H, d, J=3.0Hz, H-4b)

EXAMPLE 141

(Synthesis of compound 177)

To a solution of compound 149 (30.9 mg, 25.8 µmol) and nC$_8$H$_{17}$OH (40.8 µl, 258.7 µmol) in CH$_3$CN (2.2 ml) were added Cp$_2$HfCl$_2$ (49.0 mg, 129.1 µmol) and AgOTf (66.4 mg, 258.4 µmol), and the mixture was stirred in the presence of MS3A (300 mg) under ice-cooling for 6 h. After MS3A was removed by filtration, the solvent was evaporated, and the residue was extracted with AcOEt. The extract was washed with saturated NaHCO$_3$ solution and saturated NaCl solution, and then dried over MgSO$_4$. After the removal of MgSO$_4$, the solvent was evaporated, and the residue was purified by silica gel column chromatography (PhMe:AcOEt=5:1) to obtain 14.9 mg of compound 177 (44.2%).

[Compound 177]
Rf=0.36 (PhMe:AcOEt=5:1), $[\alpha]_D$ −37.2° (c=0.99, CHCl$_3$)
$^1$H—NMR (CHCl$_3$) δ0.818 (3H, t, J=7.5Hz, H-8Oct), 0.88–1.06 (10H, m, CH$_2$×5), 1.165 (2H, qd, J=7.5, 15.0Hz, H-2 Oct), 1.278 (3H, d, J=6.5Hz, H-6c), 1.677 (3H, s, Ac), 1.841 (3H, s, Ac), 1.984 (3H, s, Ac), 3.521 (1H, br.d, J=10.0Hz, H-5a), 3.737 (1H, td, J=6.0, 10.0 Hz, H-1Oct), 3.972 (1H, t, J=9.5 Hz, H-4a), 4.117 (1H, dd, J=3.5, 10.0Hz, H-2c), 4.205 (1H, d, J=8.5Hz, H-1b), 4.231 (1H, dd, J=8.0, 10.5Hz, H-2a), 4.258 (1H, d, J=12.5Hz, OCH$_2$Ph), 4.432 (1H, d, J=13.0Hz, OCH$_2$Ph), 4.444 (1H, dd, J=3.5, 10.5Hz, H-3b), 4.587 (1H, d, J=11.0Hz, OCH$_2$Ph), 4.627 (1H, d, J=11.5Hz, OCH$_2$Ph), 4.693 (1H, d, J=11.5Hz, OCH$_2$Ph), 4.718(1H, m, H-5c), 4.730 (1H, d, J=12.0Hz, OCH$_2$Ph), 4.778 (1H, dd, J=9.0, 10.5Hz, H-3a), 4.806 (1H, d, J=11.5Hz, OCH$_2$Ph), 4.885(1H, d, J=8.0Hz, H-1a), 4.959 (1H, d, J=12.0Hz, OCH$_2$Ph), 4.981 (1H, dd, J=8.5, 10.0Hz, H-2b), 5.157 (1H, d, J=3.5Hz, H-1c), 5.343 (1H, d, J=3.5Hz, H-4b), 7.11–7.39 (25H, m, Ph×5), 7.787 (2H, dd, J=3.0, 5.5Hz, Phth), 7.870 (2H, dd, J=3.0, 5.5Hz, Phth)

EXAMPLE 142

(Synthesis of compound 178)

Compound 177 (14.9 mg, 11.4 µmol) was dissolved in NH$_2$NH$_2$.H$_2$O (364 91) and EtOH (1 ml) and the solution was stirred at 75° C. for 2 h. The solvent was evaporated. To the residue were added Ac$_2$O (0.5 ml) and MeOH (1.0 ml), and the mixture was stirred at room temperature for 15 min. After the solvent was evaporated, the residue was purified by LH-20 (MeOH) to obtain 9.1 mg of compound 178 (73%).

[Compound 178]
Rf=0.63 (CHCl$_3$:MeOH=10:1), $[\alpha]_D$ −44.30° (c=0.61, CHCl$_3$)
$^1$H—NMR (CDCl$_3$) δ0.866 (3H, t, J=7.0Hz, H-8 Oct), 1.125 (3H, d, J=6.0Hz, H-6c), 1.254 (1OH, m, CH$_2$×5), 1.67 (2H, m, H-2 Oct), 4.047 (1H, dd, J=3.5, 10.0Hz, H-2c), 4.397 (1H, br.d, J=6.5Hz, H-1a), 4.558 (2H, S, OCH$_2$Ph), 4.599 (1H, d, J=11.5Hz, OCH$_2$Ph), 4.637 (1H, d, J=11.0 Hz, O CH$_2$Ph), 4.697 (1H, d, J=11.5Hz, OCH$_2$Ph), 4.737 (1H, d, J=10.5Hz, OCH$_2$Ph), 4.760 (1H, d, J=12.0Hz, OCH$_2$Ph), 4.950 (1H, d, J=11.5Hz, OCH$_2$Ph), 5.106 (1H, d, J=4.0Hz, H-1c), 7.008 (1H, d, J=7.5Hz, NH), 7.24–7.35 (25H, m, Ph×5)

EXAMPLE 143

(Synthesis of compound 179)

To a solution of compound 178 (9.1 mg) in MeOH (1.0 ml) and H$_2$O (0.25 ml) was added 20% Pd(OH)$_2$—C (9 mg), and the mixture was stirred under H$_2$ atmosphere at room temperature for 6.5 h. After removal of 20% Pd(OH)$_2$—C, the solvent was evaporated, and the residue was purified by LH-20 (MeOH) column chromatography to obtain 4.2 mg of compound 179 (78.6%).

[Compound 179]
Rf=0.54 (nBuOH:EtOH:H₂O=2:1:1), [α]$_D$-57.90° (c=0.28, MeOH)
¹H—NMR (CD₃OD) δ0.897 (3H, t, J=7.0Hz, H-8 Oct), 1.177 (3H, d, J=6.5Hz, H-6c), 1.294 (10H, m, CH₂×5), 1.538 (2H, m, H-2 Oct),1.961 (3H, s, Ac), 3.453(1H, td, J=6.5, 9.5Hz, H-1Oct), 3.499 (1H, dd, J=7.5, 9.5Hz, H-2b), 3.955 (1H, t, J=9.5Hz, H-3a), 4.378 (1H, d, J=8.0Hz, H-1b), 4.438 (1H, d, J=8.5Hz, H-1a), 5.036 (1H, d, J=3.5Hz, H-1c)

EXAMPLE 144

(Synthesis of compound 180)

To a solution of compound 22β(239.7 mg, 194 μmol) in ethanol (21 ml) was added MeNHNH₂ (6.3 ml) and the mixture was stirred at 75° C. for 18 h. After cooling the reaction mixture, the solvent was evaporated. To the residue were added Ac₂O (5 ml) and pyridine (10 ml), and the mixture was stirred at room temperature for 20 h. After the solvent was evaporated, the residue was purified by LH-20 column chromatography (MeOH) to obtain 200.4 mg of compound 180 (90.0%).

[Compound 180]
¹H—NMR (CDCl₃) δ1.063 (3H, d, J=6.5Hz, CH₃-6c), 1.621 (3H, s, Ac), 1.951 (3H, s, Ac), 1.976 (3H, s, Ac), 2.063 (3H, s, Ac), 3.183 (1H, q, J=6.5Hz, H-5c), 3.42 (2H, m, H-4c and H-6b), 3.453 (1H, dd, J=3.0, 9.5Hz, H-3b), 3.495 (1H, dd, J=6.5, 9.5Hz, H-6b'), 3.636 (1H, dd, J=7.5, 10.5Hz, H-6a), 3.77(2H, m, H-6a' and H-2c), 3.84 (1H, m, H-2a), 3.905 (1H, br.t, J=6.0Hz, H-5b), 3.954 (1H, m, H-5a), 4.029 (1H, dd, J=6.0, 9.5Hz, H-6a'), 4.040 (1H, br.t, J=4.5Hz, H-4a), 4.117 (1H, br.t, J=4.5Hz, H-3a), 4.285 (1H, tdd, J=1.5, 3.5, 16.5Hz, OCH₂CH=CH₂), 4.320 (1H, d, J=12.0Hz, CH₂Ph), 4.430 (1H, d, J=6CH.5Hz, H-1c), 4.436 (1H, d, J=12.0Hz, CH₂Ph), 4.516 (1H, d, J=12.0Hz, CH₂Ph), 4.598 (1H, d, J=12.0Hz, CH₂Ph), 4.649 (1H, 1H, d, J=11.5Hz, CH₂Ph), 4.692 (1H, d, J=11.5Hz, CH₂Ph), 4.709 (1H, d, J=6.0Hz, H-1a), 4.727 (1H, d, J=12.5Hz, CH₂Ph), 4.776 (1H, d, J=10.5Hz, CH₂Ph), 4.862 (1H, 1H, d, J=11.0Hz, CH₂Ph), 4.912 (1H, dd, J=4.0, 10.0Hz, H-3b), 4.931 (1H, d, J=11.5Hz, CH₂Ph), 5.056 (1H, d, J=7.5Hz, H-1b), 5.156 (1H, dd, J=8.0, 10.0Hz, H-2b), 5.159 (1H, dd, J=1.5, 10.5Hz, OCH₂CH=CH₂cis), 5.255 (1H, dd, J=1.5, 17.0Hz, OCH₂CH=CH₂trans), 5.394 (1H, d, J=3.0Hz, H-4b), 5.83–5.90 (1H, m, OCH₂CH=CH₂), 6.043 (1H, d, J=9.0Hz, NH), 7.20–7.39 (25H, m, Ph x5)

EXAMPLE 145

(Synthesis of compound 181)

To a solution of compound 180 (92.2 mg, 80.4 μmol) in MeOH (3.5 ml) was added 28% NaOMe-MeOH solution (4.9 μl, 24.1 μmol), and the mixture was stirred at room temperature for 16 h. After the solvent was evaporated, the residue was purified by LH-20 (MeOH) column chromatography to obtain 77.3 mg of compound 181 (94.2%).

[Compound 181]
Rf=0.28 (CHCl₃:MeOH=19:1), [α]$_D$ -17.30° (c=1.36, MeOH)
¹H—NMR (CD₃OD) δ1.045 (3H, d, J=6.5Hz, CH₃-6c), 1.935 (3H, s, Ac), 2.939 (1H, dd, J=3.5, 9.5Hz, H-3b), 3.267 (1H, d, J=3.5Hz, H-4b), 3.269 (1H, q, J=6.5Hz, H-5c), 3.434 (1H, dd, J=7.5, 9.5Hz, H-2b), 3.450 (1H, dd, J=7.5, 8.5Hz, H-2c), 3.568 (1H, d, J=3.5 Hz, H-4b), 3.611 (1H, dd, J=3.5, 8.5Hz, H-3c), 3.777 (1H, dd, J=8.5, 10.0Hz, H-2a), 3.811 (1H, t, J=8.5Hz, H-4a), 4.054 (1H, tdd, J=1.5, 5.5, 13.5Hz, OCH₂CH=CH₂), 4.186 (1H, dd, J=8.5, 10.0Hz, H-3a), 4.300 (1H, tdd, J=1.5, 5.0, 13.5Hz, OCH₂CH=CH₂), 4.327 (1H, d, J=11.0Hz, CH₂Ph), 4.358 (1H, d, J=11.0Hz, CH₂Ph), 4.498 (1H, d, J=12.0Hz, CH₂Ph), 4.510 (1H, d, J=8.5Hz, H-1a), 4.537 (1H, d, J=12.0Hz, CH₂Ph), 4.550 (1H, d, J=11.5Hz, CH₂Ph), 4.624 (1H, d, J=12.0Hz, CH₂Ph), 4.656 (1H, d, J=12.0Hz, CH₂Ph), 4.706 (1H, d, J=7.5Hz, H-1b), 4.792 (1H, d, J=11.0Hz, CH₂Ph), 4.906 (1H, d, J=7.5Hz, H-1c), 5.118 (1H, ddd, J=1.5, 3.0, 10.5Hz, OCH₂CH=CH₂cis), 5.259 (1H, ddd, J=1.5, 3.5, 17.5Hz, OCH₂CH=CH₂trans), 5.84-5.91 (1H, m, OCH₂CH=CH₂), 7.19–7.40 (25H, m, Ph×5)

EXAMPLE 146

(Synthesis of compound 182)

To a solution of compound 181 (40.0 mg, 39.2 μmol) in MeOH (1.2 ml) and H₂O (0.3 ml) was added 20% Pd(OH)₂—C (40 mg), and the mixture was stirred under a H₂ atmosphere and at room temperature for 6.5 h. After the removal of 20%Pd(OH)₂—C, the reaction mixture was purified by LH-20(MeOH) column chromatography to obtain 21.7 mg of compound 182 (96.8%).

[Compound 182]
Rf=0.42 (nBuOH:EtOH:H₂O=2:1:1), [α]$_d$-7.9° (c=1.45, MeOH)
¹H—NMR (CD₃OD) δ0.907 (3H, t, J=7.0Hz, H-3Pr), 1.274 (3H, d, J=6.5Hz, H-6c), 1.56 (2H, m, H-2Pr), 1.966 (3H, s, Ac), 3.37 (1H, m, H-5a), 3.436(1H, dd, J=3.5, 10.0Hz, H-3b), 3.484 (1H, br.t, J=7.0Hz, H-2c), 3.502 (1H, t, J=10.0Hz, H-2b), 3.509 (1H, dd, J=2.0, 9.5Hz, H-3c), 3.595 (1H, dd, J-1.0, 3.0Hz, H-4c), 3.67 (1H, m, H-5c), 3.671 (1H, d, J=9.0Hz, H-4a), 3.725 (1H, dd, J=4.5, 11.5Hz, H-6b), 3.938 (1H, dd, J=3.0, 12.5Hz, H-6a), 4.066 (1H, dd, J=8.5, 10.5 Hz, H-3a), 4.432 (1H, d, 8.5Hz, H-1a), 4.451 (1H, d, J=7.5Hz, H-1b), 4.562 (1H, d, J=7.5Hz, H-1c)

EXAMPLE 147

(Synthesis of compound 183~187)

A mixture of compound 181 (73.3 mg, 71.9 μmol) and Et₃N.SO₃ (26.0 mg, 143.4 μmol) dissolved in DMF (4.2 ml) was stirred at 90 ° C. for 1.25 h. After cooling, the reaction mixture was subjected to the purification by LH-20 column chromatography (CHCl₃:MeOH=1:1) and then the product was converted to Na salt by Dowex 50 (Na⁺ type) (CHCl₃:MeOH=1:1) column chromatography. Purification of the product by silica gel column chromatography (CHCl₃:MeOH=10:1) and HPLC (CH-Cl₃MeOH=10:1, 15:1) gave compound 183 (5.5 mg, 6.8%),compound 184 (9.7 mg, 12.0%), compound 185 (5.2 mg, 6.4%) and a mixture of compound 186 and compound 187 (mixing ratio=1:1, 33.2 mg, 37.7%).

[Compound 183]
Rf=0.27 (CHCl₃:MeOH=5:1), [α]$_D$-20.7° (c=0.37, MeOH)
¹H—NMR (CD₃OD) δ0.989 (3H, d, J=6.0Hz, H-6c), 2.055 (3H, s, Ac), 2.987 (1H, br.d, J=9.0Hz, H-3b), 3.19 (1H, m, H-5c), 3.780 (1H, t, J=8.5Hz, H-4a), 3.948 (1H, br.t, J=10.0Hz, H-2a), 4.155 (1H, dd, J=8.5, 10.5Hz, H-3a), 4.26 (1H, m, H-2b), 4.409 (1H, d, J=9.0Hz, H-1a), 5.017 (1H, d, J=7.5Hz, H-1b)

[Compound 184]
Rf=0.27 (CHCl₃: MeOH=5:1), [α]$_D$-17.4° (c=0.47, MeOH)
¹H—NMR (CD30D) δ1.014 (3H, d, J=6.5Hz, CH₃-6c), 1.9, 78 (3H, s, Ac), 3.179 (1H, d, J=2.5Hz, H-4c), 3.233 (1H, q, J=6.5Hz, H-5c), 3.43 (1H, m, H-5a), 3.521 (1H, dd, J=8.0, 10.0Hz, H-2c), 3.606 (1H, dd, J=2.5, 10.0Hz, H-3c), 3.670 (1H, dd, J=7.5, 10.0Hz, H-2b), 3.723 (1H, dd, J=8.5, 9.5Hz, H-4a), 3.752 (1H, dd, J=8.5, 10.5Hz, H-2a), 3.961 (1H, dd, J=2.5Hz, H-4b), 4.059 (1H, dd, J=2.5, 10.0 Hz, H-3b), 4.147 (1H, dd, J=8.0, 10.5Hz, H-3a), 4.315 (1H, d, J=11.0Hz, OCH$_2$Ph), 4.352 (1H, d, J=11.0Hz, OCH$_2$Ph), 4.444 (1H, d, J=8.5Hz, H-1a), 4.499 (1H, d, J=12.5Hz, OCH$_2$Ph), 4.538 (1H, d, J=12.0Hz, OCH$_2$Ph) 4.548 (1H, d, J=11.5Hz, O CH$_2$Ph), 4.603 (1H, d, J=12.0Hz, OCH$_2$Ph), 4.640 (1H, d, J=12.5Hz, OCH$_2$Ph), 4.715 (1H, d, J=11.0Hz, OCH$_2$Ph), 4.878 (1H, d, J=7.5Hz, H-1b), 4.886 (1H, d, J=7.5Hz, H-1c), 5.120 (1H, ddd, J=1.5, 2.0, 10.5Hz, OCH$_2$CH=CH$_2$cis), 5.260 (1H, ddd, J=1.5, 2.0, 17.5Hz, OCH$_2$CH=CH$_2$trans), 5.85–5.89 (1H, m, OCH$_2$CH=CH$_2$), 7.20–7.38 (25H, m, Ph×5)

[Compound 185]

Rf=0.25 (CHCl$_3$:MeOH=5:1), [α]$_D$ -20.7° (c=0.35, MeOH)
$^1$H—NMR (CD$_3$OD) δ1.028 (3H, d, J=6.0HZ, CH$_3$-6C), 1.965 (3H, s, Ac), 2.921 (1H, dd, J=3.0, 10.0Hz, H-3b), 3.399 (1H, dd, J=7. 5, 9.5Hz, H-2b), 3.488 (1H, dd, J=8.0, 10.0Hz, H-2c), 3.956 (1H, dd, J=2.0, 10.5Hz, H-6a), 4.063 (1H, tdd, J=1.5, 6.0, 13.0Hz, OCH$_2$CH=CH$_2$), 4.168 (1H, dd, J=8.0, 10.0Hz, H-3a), 4.355 (1H, d,J=11.0Hz, O CH$_2$Ph), 4.423 (1H, d, J=2.5Hz, H-4b), 4.479 (1H, d,J= 8.0Hz, H-1a), 4.671 (1H, d, J=12.0Hz, OCH$_2$Ph)$_1$ 4.708 (1H, dJ=11.5Hz, OCH$_2$Ph), 4.737 (1H, d, J=10.5Hz, O CH$_2$Ph), 4.748 (1H, d, J=7.5 Hz, H-1b), 4.990 (1H, d, J=7.5Hz, H-1c), 5.127 (1H, ddd, J=1.0, 2.0, 10.0Hz, OCH$_2$CH=CH$_2$Cis), 5.258 (1H, ddd, J=1.0, 2.0, 17.5Hz, OCH$_2$CH=CH$_2$ trans), 5.85–5.90 (1H, m, OCH$_2$CH=CH$_2$), 7.19–7.42 (25H, m, Ph×5)

[Compound 186 and 187] (mixing ratio=1:1)
$^1$H—NMR (CD$_3$OD) δ0.889 (3H, d, J=6.0Hz, H-6c), 1.000 (3H, d, J=6.5Hz, H-6c), 1.970 (3H, s, Ac), 2.054 (3H, s, Ac), 4.918 (1H, d, J=7.5Hz), 4.965 (1H, d, J=8.0Hz), 5.190 (1H, d, J=7.5Hz), 5.86 (2H, m, OCH$_2$CH=CH$_2$×2), 7.19–7.45 (50H, m, Ph×5×2)

EXAMPLE 148

(Synthesis of compound 188–192)

To a solution of compound 183 (5.5 mg) in MeOH (0.6 ml) and H$_2$O (0.15 ml) was added 20% Pd(OH)$_2$—C (6 mg), and the mixture was stirred under a H$_2$ atmosphere and at room temperature for 3.5 h. After removal of 20% Pd(OH)$_2$—C, the solvent was evaporated, and the residue was purified by LH-20 column chromatography (MeOH) to obtain 3.5 mg of compound 188 (100%).

Compound 184 (7.0 mg) was processed in a similar manner described above to obtain 4.3 mg of compound 189 (100%).

Compound 185 (5.2 mg) was processed in a similar manner described above to obtain 2.9 mg of compound 190 (92.9%).

A mixture of compounds 186 and 187 (mixing ratio=1:1) (17.6 mg) was processed in a similar manner described above to obtain 8.6 mg of a mixture of compounds 191 and 192 (mixing ratio=1:1) (71.1%).

[Compound 188]
Rf=0.49 (nBuOH:EtOH:H$_2$O=2:1:1), [α]$_D$+1.0° (c=0.23, MeOH)
FAB-MASS(Glycerin) 672(M—H), 650(M—Na)
$^1$H—NMR (CD$_3$OD) δ0.907 (3H, t, J=7.0Hz, H-3Pr), 1.264 (3H, d, J=6.5Hz, CH$_3$-6c), 1.551(2H, m, H-2Pr), 1.982 (3H, s, Ac), 3.447 (1H, dd, J=7.5, 9.0Hz, H-2c), 3.563 (1H, dd, J=3.5, 9.0Hz, H-3c), 3.593 (1H, d, J=3.5Hz, H-4c), 3.677 (1H, dd, J=3.5, 9.5Hz, H-3b), 3.864 (1H, br.d, J=3.0Hz, H-4b), 3.907 (1H, dd, J=2.5, 12.5 Hz, H-6a), 4.400 (1H, dd, J=7.5, 9.5Hz, H-2b), 4.599 (1H, d, J=7.5 Hz, H-1b), 4.718 (1H, d, J=8.0Hz, H-1c)

[Compound 189]
$^1$H—NMR (CD$_3$OD) δ0.904 (3H, t, J=7.0Hz, H-3Pr), 1.269 (3H, d, J=6.5Hz, H-6c), 1.553 (2H, q, J=7.0Hz, H-2Pr), 1.977 (3H, s, Ac), 3.452 (1H, dd, J=7.5, 9.5Hz, H-2c), 3.525 (1H, dd, J=3.5, 10.0Hz, H-3c), 3.595 (1H, d, J=2.0Hz, H-4c), 4.128 (1H, t, J=10.0Hz, H-3a), 4.192 (1H, dd, J=3.0, 9.5Hz, H-3b), 4.220 (1H, d, J=3.0Hz, H-4b), 4.465 (1H, br.d, J=8.5Hz, H-1a), 4.599 (1H, d, J=7.5Hz, H-1b), 4.614 (1H, d, J=7.5Hz, H-1c)

[Compound 190]
Rf=0.51 (nBuOH:EtOH:H$_2$O=2:1:1), [α]$_D$-5.4° (c=0.19, MeOH)
FAB-MASS(Glycerin) 672(M—H), 650(M—Na)
$^1$H—NMR (CD$_3$OD) δ0.905 (3H, t, J=7.5Hz, H-3Pr), 1.268 (3H, d, J=6.5Hz, H-6c), 1.555 (2H, m, H-2Pr), 1.965 (3H, s, Ac), 3.415 (H, td, J=6.5, 10.0Hz, H-1Pr), 3.500 (1H, dd, J=7.5, 10.0Hz, H-2b), 3.545 (1H, dd, J=3.5, 9.5Hz, H-3c), 3.584 (1H, dd, J=3.0, 10.5HZ, H-3b), 3.610 (1H, d, J=3.0Hz, H-4c), 3.926 (1H, dd, J=2.5, 12.5 Hz, H-6a), 4.053 (1H, dd, J=9.0, 10.0Hz, H-3a), 4.434 (1H, d, J=8.0Hz, H-1a), 4.478 (1H, J=7.5Hz, H-1b), 4.630 (1H, d, J=7.5Hz, H-1c), 4.643 (1H, d, J=3.5Hz, H-4b)

[Compounds 191 and 192] (mixing ratio=1:1)
$^1$H—NMR (CD$_3$OD) δ0.904 (3H, t, J=7.5Hz, H-3Pr), 0.906 (3H, t J=6.5Hz, H-6c), 1.55 (4H, m, H-2Pr×2), 1.983 (3H, s, Ac), 1.990 (3H, s, Ac), 4.100 (1H, t, J=9.5Hz, H-3a), 4.306 (1H, dd, J=3.5, 10.0Hz, H-3b), 4.367 (1H, dd, J=8.0, 10.0Hz, H-2b), 4.459 (1H, d, J=8.5Hz, H-1a), 4.582 (1H, d, J=7.5Hz, H-1c), 4.598 (1H, d, J=8.5Hz, H-1b), 4.610 (1H, d, J=8.0Hz, H-1b), 4.667 (1H, d, J=8.0Hz, H-1c), 4.679 (1H, d, J=4.0Hz, H-4b), 4.955 (1H, d, J=3.5Hz, H-4b)

EXAMPLE 149

(Synthesis of compounds 198 and 199)

To a solution of compound 166 (234.1 mg, 121.3 μmol) and a catalytic amount of DMAP in pyridine (8.8 ml) were added a solution of 1N-Lev$_2$O—ClCH$_2$CH$_2$Cl (2.4 ml, 2.4 mmol), and the mixture was stirred at room temperature for 12 h. After the second addition of a solution of 1N-Lev$_2$O—ClCH$_2$CH$_2$Cl (4.8 ml), the mixture was stirred for further 8 h. A solution of 1N-Lev$_2$O—ClCH$_2$CH$_2$Cl (4.8 ml) was further added to the mixture, which was stirred further for 65 h. After the solvent was evaporated, the residue was purified by silica gel column chromatography (n-hexane:AcOEt= 1:3) to obtain 112.5 mg of compound 198 (45.7%) and 19.0 mg of compound 199 (7.4%).

[Compound 198]
Rf=0.39 (n-hexane:AcOEt=1:3), [α]$_D$ -26.3° (c=1.40, CHCl$_3$)
$^1$H—NMR(CDCl$_3$) δ1.121 (9H, s, Piv), 1.137 (3H, d, J=6.5Hz, H-6c), 1.518 (3H, s, NHAC), 2.181(3H, S, OCOCH$_2$CH$_2$COCH$_3$), 2.512 (1H, ddd, J=5.0, 6.5, 16.5Hz, OCOCH$_2$CH$_2$COCH3), 2.635 (1H, ddd, J=5.0, 9.0, 16.5Hz, OCOCH$_2$CH$_2$COCH$_3$), 2.778 (1H, ddd, J=4.5, 6.5, 18.5Hz, OCOCH$_2$CH$_2$COCH$_3$), 2.884 (1H, ddd, J=5.0, 9.0, 19.0Hz, OCOCH$_2$CH$_2$COCH3), 3.29 (1H, m, H-5a), 3.698 (1H, dd, J=7.0, 10.0Hz, H-2d), 3.778 (1H, dd, J=7.0, 10.0Hz, H-3c), 3.930 (1H, d, J=2.5Hz, H-4e), 3.966 (1H, d, J=3.0, 10.0Hz, H-3e), 4.018 (1H, t, J=10.0, H-4a), 4.032 (1H, dd, J=4.0, 10.0Hz, H-2e), 4.076 (1H, br.s, H-4d), 4.088 (1H, d, J=12.0Hz, CH$_2$Ph), 4.214 (1H, d, J=11.5Hz, CH$_2$Ph), 4.309 (1H, d, J=7.0Hz, H-1d), 4.316 (2H, s, CH$_2$Ph), 4.340 (1H, d, J=7.0Hz, H-1c), 4.368 (1H, d, J=11.5Hz, CH₂Ph), 4.405 (1H, d, J=7.5Hz, H-1a), 4.559 (1H, d, J=12.0Hz, CH₂Ph), 4.565 (1H, d, J=12.0Hz, CH₂Ph), 4.575 (1H, d, J=11.5Hz, CH₂Ph), 4.612 (1H, d, J=11.5Hz, CH₂Ph), 4.645 (1H, dd, J=3.5, 10.0Hz, H-3d), 4.797 (1H, d, J=11.5Hz, CH₂Ph), 4.831 (1H, d, J=12.0Hz, CH₂Ph), 4.930 (1H, d, J=11.5Hz, CH₂Ph), 4.960 (1H, d, J=12.0Hz, CH₂Ph), 4.983 (1H, d, J=11.0 Hz, CH₂Ph), 5.028 (1H, d, J=3.5Hz, H-1e), 5.094 (1H, dd, J=8.0, 10.0Hz, H-2a), 7.10–7.34 (55H, m, Ph)

[Compound 199]

¹H—NMR(CDCl₃) δ1.119 (9H, s, Piv), 1.213 (3H, d, J=7.0Hz, H-6e), 1.576 (3H, s, NHAC), 2.051 (3H, s, OCOCH₂CH₂COCH₃), 2.168 (3H, S, OCO CH₂CH₂COCH3), 2.45-2.85 (8H, m, OCO CH₂CH₂COCH₃×2), 3.558 (1H, dd, J=4.0, 10., H-3b), 3.889 (1H, d, J=3.0Hz, H-4b), 4.068 (1H, d, J=12.0Hz, CH₂Ph), 4.166 (1H, br.s, H-4d), 4.194 (1H, d, J=12.0Hz, CH₂Ph), 4.334 (1H, d, J=6.5Hz, H-1b), 4.362 (1H, d, J=12.0Hz, CH₂Ph), 4.402 (1H, d, J=8.0Hz, H-1a), 4.431 (1H, d,J=8.0Hz, H-1d), 4.623 (1H, d, J=11.0 Hz, CH₂Ph), 4.708 (1H, dd, J=3.5, 10.0Hz, H-3d), 4.718 (1H, 2H, S, CH₂Ph), 4.933 (1H, d, J=11.5Hz, CH₂Ph), 4.950 (1H, d, J=12.0Hz, CH₂Ph), 4.973 (1H, d, J=11.5Hz, CH₂Ph), 5.076 (1H, d, J=3.0Hz, H-1e), 5.090 (1H, dd, J=8.0, 9.0Hz, H-2a), 5.155 (1H, dd, J=8.0, 10.0Hz, H-2d), 7.09–7.36 (55H, m, Ph)

EXAMPLE 150

(Synthesis of compound 200)

To a solution of compound 198 (115.8 mg) dissolved in Ac₂O (5 ml) and pyridine (5 ml) was added a catalytic amount of DMAP, and the mixture was stirred at room temperature for 4 h. After the solvent was evaporated, the residue was purified by silica gel column chromatography (n-hexane:AcOEt=1:3) and LH-20 column chromatography (CHCl₃3:MeOH=1:1) to give 121.2 mg of compound 200 (100%).

[Compound 200]

Rf=0.57 (n-hexane:AcOEt=1:2), 0.83 (CHCl₃:MeOH=20:1)
[α]_D −31.50° (c=1.06, CHCl₃)
¹H—NMR(CDCl₃) δ1.122 (9H, s, Piv), 1.212 (3H, d, J=6.5Hz, H-6e), 1.553 (3H, s, NHAc), 1.755 (3H, s, Ac), 2.025 (3H, s, Ac), 2.144 (3H, s, OCOCH₂CH₂COCH₃), 2.340 (1H, ddd, J=5.0, 6.5, 15.5Hz, OCO CH₂CH₂COCH₃), 2.494 (1H, ddd, J=5.0, 8.0, 17.0Hz, OCO CH₂CH₂COCH₃), 2.580 (1H, ddd, J=5.0, 10.5, 15.5Hz, OCOCH₂CH₂COCH₃), 2.727 (1H, ddd, J=6.0, 8.5, 17.0Hz, OCOCH₂CH₂COCH₃), 3.199 (1H, dd, J=5.5, 9.0Hz, H-6a), 3.297 (1H, dd, J=7.0, 9.5Hz, H-6a), 3.551 (1H, dd, J=4.0, 10.0Hz, H-3b), 3.590 (1H,t, J=9.0Hz, H-3a), 3.623 (1H, br.d, J=1.5Hz, H-4e), 3.651 (1H, dd, J=7.5, 10.0Hz, H-2b), 3.896 (1H, dd, J=2.5, 10.5Hz, H-3e), 4.026 (1H, t, J=9.0Hz, H-4a), 4.066 (1H, d, J=12.0Hz, CH₂Ph), 4.104 (1H, dd, J=4.0, 10.0Hz, H-2e), 4.179 (1H, d, J=12.0Hz, CH₂Ph), 4.369 (1H, d, J=7.5Hz, H-1b), 4.373 (1H, d, J=12.0Hz, CH₂Ph), 4.391 (1H, d, J=12.0Hz, CH₂Ph), 4.421 (1H, d, J=8.0Hz, H-1a), 4.441 (1H, d, J=12.0Hz, CH₂Ph), 4.487 (1H, d, J=12.5Hz, CH₂Ph), 4.513 (1H, d, J=11.5Hz, CH₂Ph), 4.546 (1H, d, J=7.0Hz, H-1d), 4.565 (1H, d, J=12.0Hz, CH₂Ph), 4.580 (1H, d, J=12.5Hz, CH₂Ph), 4.607 (1H, d, J=11.5Hz, CH₂Ph), 4.615 (1H, d, J=11.0Hz, CH₂Ph), 4.690 (1H, d, J=11.5Hz, CH₂Ph), 4.719 (1H, d, J=11.5Hz, CH₂Ph), 4.795 (1H, d, J=11.5Hz, CH₂Ph), 4.827 (1H, dd, J=3.5, 10.5Hz, H-3d), 5.022 (1H, dd, J=8.5, 10.5Hz, H-2d), 5.094 (1H, dd, J=4.0Hz, H-1e), 5.105 (1H, dd, J=8.0, 9.5Hz, H-2a), 5.415 (1H, d, J=4.0Hz, H-4d), 7.12–7.36 (55H, m, Ph)

EXAMPLE 151

(Synthesis of compound 201)

To a solution of compound 200 (102.0 mg) in MeOH (4 ml) and H₂O (1 ml) was added 20% Pd(OH)₂—C (100 mg), and the mixture was stirred under a H₂ atmosphere and at room temperature for 5 h. After the removal of the 20% Pd(OH)₂—C, the solvent was evaporated. To the residue dissolved in Ac₂O (5 ml) and pyridine (5 ml) was added a catalytic amount of DMAP, and the mixture was stirred at room temperature for 14 h. After the solvent was evaporated, the residue was purified by silica gel column chromatography (CHCl3:MeOH=20:1) to give 57.4 mg of compound 201 (75.1%).

[Compound 201]

Rf=0.47 (CHCl₃: MeOH=20:1)
¹H—NMR(CDCl₃) δ1.12 1(4.5H, s, Piv), 1.134 (4.5H, s, Piv), 1.242 (3H, br.d, J=6.5Hz, H-6e), 1.949, 1.951, 1.997, 2.002, 2.004, 2.013, 2.070, 2.084, 2.098, 2.111, 2.116, 2.117, 2.131, 2.133, 2.136, 2.142, 2.156, 2.173, 2.174 (each 1.5H, s, Ac), 2.052, 2.078, 2.160, 2.164 (each 3H, s, Ac), 2.108 (4.5H, br.s, Ac), 2.95 (1H, m, H-2c), 4.982 (1H, br.d, J=8.0Hz,H-1c), 5.478 (0.5H, t, J=10.0Hz, H-3a-α), 5.63 (0.5H, br.d, J=7.0Hz, NHAc), 5.96 (0.5H, br.d, J=7.0Hz, NHAc), 5.704 (0.5H, d, J=8.5Hz, H-1a-,β), 6.295 (0.5H, t, J=4.0Hz, H-1a-α)

EXAMPLE 152

(Synthesis of compound 202)

A solution of compound 201 (57.4 mg, 6.3 μmol) and piperidine-AcOH (36.9 mg, 254.1 μmol) dissolved in THF (2.5 ml) was stirred at room temperature for 16 h. After the reaction mixture was extracted with AcOEt, the extract was washed with saturated NaHCO₃ solution and saturated NaCl solution, and then dried over MgSO₄. After the removal of MgSO₄, the solvent was evaporated, and the residue was purified by silica gel column chromatography (CHCl₃:MeOH=−10:1) and LH-20 column chromatography (CHCl₃:MeOH=1:1) to obtain 33.4 mg of compound 202 (56.8%).

[Compound 202]

¹H—NMR(CDCl₃) δ1.176 (9H, s, Piv), 1.795, 1948, 2.004, 2.044, 2.052, 2.078, 2.085, 2.088, 2.101, 2.105, 2.110, 2.111, 2.135, 2.141, 2.144 2.153, 2.166, 2.173 (42H, 14s, Ac), 4.739 (1H, dd, J=4.0, 10.0Hz, H-3d), 5.087 (1H, dd, J=8.5, 10.0Hz, H-2d), 5.110 (1H, d, J=3.5Hz, H-1e), 5.181 (1H, dd, J=3.5, 10.5Hz, H-3e), 5.251 (1H, dd, J=3.5, 10.5Hz, H-2e), 5.311 (1H, d, J=3.5Hz, H-4b), 5.367 (2H, br.d, J=2.5Hz, H-4d, H-4e), 5.545 (0.7H, t, J=10.0Hz, H-3a), 5.20 (0.3H, br.d, J=6.5Hz, NHAc), 5.81 (0.7H, br.d, J=6.5Hz, NHAc)

EXAMPLE 153

(Synthesis of compound 203)

To a solution of compound 202 (33.4 mg, 21.7 μmol) in ClCH₂CH₂Cl (0.5 ml) were added Cl₃CCN (21.7 μl, 217 μmol) and DBU (6.5 μl, 43.4 μmol), and the mixture was stirred at 0° C. for 2 h. The reaction mixture was directly subjected to the purification by silica gel column chromatography (CHCl₃:MeOH=20:1) to obtain 32.7 mg of compound 203 (89.5%).

[Compound 203]

Rf=0.51 (CHCl₃:MeOH=20:1), [α]_D−3.4° (c=1.32, CHCl₃)
¹H—NMR(CDCl) δ1.131 (9H, s, Piv), 1.241 (3H, d, J=7.0Hz, H-6e), 1.949, 2.011, 2.014, 2.051, 2.076, 2.089, 2.109, 2.110, 2.113, 2.118, 2.132, 2.158, 2.162, 2.174 (each 3H, s, Ac), 2.95 (1H, m, H-2c), 3.490 (1H, td, J=2.5, 10.0Hz, H-5c), 3.69–3.80 (5H, m, H-3b, H-5b, H-4c, H-6c, H-5d), 3.841 (1H, t, J=10.0Hz, H-4a), 4.019 (1H, dd, J=6.5, 11.0Hz, H-6b or H-6d), 4.083 (1H, dd, J=6.5, 11.5Hz, H-6'b or H-6'd), 4.116 (1H, ddd, J=2.0, 5.0,10.0Hz, H-5a), 4.157 (1H, dd, J=5.0, 12.0Hz, H-6a), 4.255 (1H, dd, J=8.5, 11.5Hz, H-6d or H-6b), 4.392 (1H, br.t, J=9.0Hz, H-3c), 4.393(1H, d, J=8.0Hz, H-1b), 4.437 (1H, dd, J=2.0, 12.0Hz, H-6'a), 4.441 (1H, dd, J=6.0, 11.5Hz,H-6'd or H-6'b), 4.587 (1H, d, J=8.0Hz, H-1d), 4.848(1H, dd, J=2.0, 12.0Hz, H-6'c), 4.921 (1H, dd, J=3.5, 10.5Hz, H-3d), 4.966 (1H, dd, J=7.5, 10.0Hz, H-2b), 4.971 (1H, d, J=7.5, H-1c), 5.021 (1H, q, J=6.5Hz, H-5e), 5.042 (1H, dd, J=4.0, 9.5Hz, H-2a), 5.087 (1H, dd, J=8.0, 10.5Hz,H-2d), 5.118 (1H, d, J=3.5Hz), 5.181 (1H, dd, J=3.5, 11.0Hz,H-3e), 5.247 (1H, dd, J=3.5, 10.5Hz, H-2e), 5.315 (1H, d, J=4.0Hz, H-4b), 5.365 (1H, d,J=3.5Hz, H-4e), 5.373 (1H, d, J=4.5Hz, H-4d), 5.576 (1H, t, J=9.5Hz, H-3a), 5.602(1H, d, J=7.0Hz, NHAc), 6.510 (1H, d, J=4.0Hz, H-1a), 8.658 (1H, s, NHCCl3)

EXAMPLE 154

(Synthesis of compound 204)

To a solution of compound 203 (32.7 mg, 19.4 μmol) and compound R18 (53.5 mg, 38.8 μmol) in CHCl₃ (1.8 ml) was added BF₃.Et₂O (4.8 ml, 38.8 μmol) in the presence of MS4A (300 mg), and the mixture was stirred at −15° C. for 2 h. After the addition of a large amount of Et₃N, and the mixture was stirred for 5 min, filtered to remove MS4A, and extracted with CHCl₃. The extract was washed with saturated NaHCO₃ solution followed by saturated NaCl solution, and dried over MgSO₄. After the removal of MgSO₄, the solvent was evaporated, and the residue was purified by silica gel column chromatography (CHCl₃:MeOH=40:1, 60:1) to obtain 15.6 mg of compound 204 (35.3%).

[Compound 204]
Rf=0.75 (CHCl₃:MeOH=20:1), $[\alpha]_D$-20.0° (c=1.04, CHCl₃)
¹H—NMR(CDCl3) δ0.879 (6H, t, Me×2), 1.143 (9H, s, Piv), 1.929, 1.950, 1.988, 1.992 (each 3H, s, Ac), 2.050 (6H, s, Ac), 2.079, 2.094, 2.107, 2.118, 2.126, 2.156, 2.162, 2.172, (each 3H, s, Ac), 2.33–2.97 (4H, m, OCO CH₂CH₂COCH₃), 2.96 (1H, m, H-2c), 3.59 (1H, dd, J=4.0, 9.5Hz, H-1Cer), 3.806 (1H, dd, J=6.5, 8.0Hz, H-5d), 4.250 (1H, dd, J=8.0, 11.0Hz, H-6d), 4.298 (1H, d, J=7.5Hz, H-1b), 4.38 (1H, m, H-6'd), 4.415 (1H, d, J=7.5Hz, H-1a), 4.44 (1H, m, H-2Cer), 4.583 (1H, d, J=8.0Hz, H-1d), 4.894 (1H, dd, J=8.0, 9.0Hz, H-2a), 4.905 (1H, dd, J=7.0, 10.5Hz, H-2b), 4.915 (1H, dd, J=3.5, 10.5Hz, H-3d), 4.961 (1H, br.d, J=7.5Hz, H-1c), 5.021 (1H, q,J=6.5Hz, H-5e), 5.082 (1H, dd, J=8.0, 9.5Hz, H-2d), 5.100 (1H, d, J=3.5Hz, H-1e), 5.180 (1H, dd, J=3.5, 11.0Hz, H-3e), 5.186 (1H, t, J=9.5Hz, H-3a), 5.248 (1H, dd, J=4.0, 11.0Hz, H-2e), 5.298 (1H, d, J=3.5Hz, H-4b), 5.368 (2H, br.d, J=3.5Hz, H-4d, H-4e), 5.454 (1H, dd, J=7.5, 15.5Hz, H-4Cer), 5.538 (1H, t, J=7.5Hz, H-3Cer), 5.693 (1H, m, NHAc), 5.746 (1H, d, J=9.0Hz, NH—Cer), 5.874 (1H, td, J=7.0, 15.0Hz, H-5Cer), 7.438 (2H, t, J=7.5Hz,Bz), 7.562 (1H, t, J=7.5Hz, Bz), 8.002 (2H, d, J=7.5Hz, Bz)

EXAMPLE 155

(Synthesis of compound 205)

Compound 204 (15.6 mg, 6.85 μmol) and NH₂NH₂— AcOH (6.2 mg, 68.5 μmol) were dissolved in EtOH (1 ml), and the mixture was stirred at room temperature for 40 min. After the reaction mixture was extracted with CHCl₃, the extract was rinsed with saturated NaHCO₃ solution and saturated NaCl solution, and then dried over MgSO₄. After removal of MgSO₄, the solvent was evaporated, and the residue was purified by silica gel column chromatography (CHCl:MeOH=10:1) to give 7.6 mg of compound 205 (50.9%).

[Compound 205]
Rf=0.67 (CHCl₃:MeOH=20:1), $[\alpha]_D$-12.8° (c=0.51, CHCl₃)
¹H—NMR(CDCl₃) δ0.88 (6H, t, J=7.0Hz, Me×2), 1.143 (9H, s, Piv), 1.196 (3H, d, J=7.0Hz, H-6e), 1.929, 1.954, 1.989, 1.991, 2.046, 2.070, 2.076, 2.099, 2.108, 2.118, 2.159, 2.164, 2.195 (each 3H, S, Ac), 3.03 (1H, m, H-2c), 3.593 (1H, dd, J=4.0, 10.0Hz, H-1Cer), 3.75 (H-3d, overlapped with other peaks), 4.300 (1H, d, J=8.0Hz, H-1b), 4.333 (1H, br.t, J=8.5Hz, H-3c), 4.390 (1H, dd, J=5.5, 11.5Hz, H-6d), 4.413 (1H, d, J=8.0Hz, H-1a), 4.463 (1H, m, H-2Cer), 4.554 (1H, d, J=8.0Hz, H-1d), 4.872 (1H, dd, J=8.0, 9.5Hz, H-2d), 4.895 (1H, dd, J=7.5, 10.0Hz, H-2a), 4.918 (1H, dd, J=8.0,10.0Hz, H-2b), 4.964 (1H, d, J=7.5Hz, H-1c), 4.978 (1H, q, J=6.5Hz, H-5e), 5.106 (1H, d, J=3.5Hz, H-1e), 5.187 (1H, t, J=9.5Hz, H-3a), 5.194 (1H, dd,J=3.5, 11.0Hz, H-3e), 5.245 (1H, dd, J=4.0, 11.0Hz, H-2e), 5.314 (1H, d,J=4.0Hz, H-4e), 5.335 (2H, d, J=3.0Hz, H-4b, H-4d), 5.454 (1H, dd, J=7.5, 15.5Hz, H-4Cer), 5.538 (1H, t, J=8.0Hz, H-3Cer), 5.617 (1H, d, J=7.0Hz, NHAC), 5.740 (1H, d, NH—Cer), 5.847 (1H, td, J=7.0, 15.0Hz, H-5Cer), 7.42–8.01 (5H, m, Bz)

EXAMPLE 156

(Synthesis of compound 206)

Compound 205 (7.6 mg, 3.49 μmol) and Et₃N.SO₃ (6.3 mg, 34.9 μmol) were dissolved in DMF (0.5 ml), and the mixture was stirred at 90° C. for 2.75 h. After cooling, the reaction mixture was directly subjected to the purification by LH-20 gel column chromatography (CHCl₃:MeO H=1:1) and then the product was converted to the Na salt by Dowex50 (Na⁺ type) column chromatography (CHCl₃:MeOH=1:1). The product was further purified by silica gel column chromatography (CHCl₃:MeOH=5:1) to yield 6.4 mg of compound 206 (80.4%).

[Compound 206]
$[\alpha]_D$-14.9° (c=0.43, CHCl₃)
¹H—NMR(CD₃OD)δ0.895 (3H, t, J=7.0Hz, Me), 0.898 (3H, t, J=7.0Hz,Me), 1.146 (9H, s, Piv), 1.222 (3H, d, J=6.5Hz, H-6e), 1.926, 1.980, 1.984, 1.993, 2.050, 2.063, 2.068, 2.080, 2.086, 2.097, 2.101, 2.109, 2.141, 2.144 (each 3H, s, Ac), 3.685 (1H, t, J=9.5Hz, H-4a), 3.839 (1H, dd, J=3.5, 10.0Hz, H-3b), 4.432 (1H, dd, J=3.5, 10.5Hz, H-3d), 4.447 (1H, d, J=8.0Hz, H-1b), 4.642 (1H, d, J=8.0Hz, H-1a), 4.900 (1H, dd, J=8.0, 10.0Hz, H-2b), 5.047 (1H, J=6.5, 10.0Hz, H-2b), 5.060 (1H, d, J=4.0Hz, H-1e), 5.136 (1H,dd, J=3.5, 11.0Hz, H-2e), 5.181 (1H, t, J=9.5Hz, H-3a), 5.212 (1H, dd,J=3.0, 11.0Hz, H-3e), 5.357 (1H, d, J=3.5Hz, H-4b), 5.383 (1H, d, J=2.5Hz, H-4e), 5.499 (1H, dd, J=7.5, 15.0Hz, H-4Cer), 5.563 (1H, 1H, t, J=7.0Hz, H-3Cer), 5.663 (1H, d, J=4.0Hz, H-4d), 5.873 (1H, td, J=7.0, 15.0Hz, H-5Cer), 7.45–8.01 (5H, m, Bz)

EXAMPLE 157

(Synthesis of compound 207)

To a solution of compound 206 (6.4 mg) in THF (0.25 ml) and MeOH (0.25 ml) was added 1 N NaOH solution (0.2 ml), and the mixture was stirred at 40° C. for 4.5 h. The reaction mixture was purified by LH-20 column chromatography (C-HCl₃: MeOH:H₂O=60:30:5) to give 1.5 mg of compound 207 (33.7%).

163

[Compound 207]
FAB-MASS 1587.6 (M), 1564.1 (M—Na)
$^1$H—NMR (DMSO-d6:D$_2$O=49:1) δ3.860 (m, H-3d, overlapped with another peak), 3.992 (1H, br.s, H-4d), 4.164 (1H, d, J=8.0Hz, H-1a), 4.283 (1H, d, J=7.0Hz, H-1b), 4.418 (1H, d, J=7.0Hz, H-1d), 4.602 (1H, q, J=7.5Hz, H-5e), 4.740 (1H, d, J=8.0Hz, H-1c), 4.774 (1H, d, J=3.5Hz, H-1e), 5.345 (1H, dd, J=7.0, 15.5Hz, H-4Cer), 5.532 (1H, td, J=8.5, 15.5Hz, H-5Cer)

EXAMPLE 158

(Synthesis of compound 193)

To a solution of compound 180 (247 mg, 0.2 mmol) in THF (3 ml) was added a solution of H$_2$ gas-activated Ir complex (24 mg) in THF (3 ml) under stirring at room temperature, and the mixture was further stirred under a N$_2$ atmosphere for 2 h. To the reaction mixture were added iodine (305 mg, 1.2 mmol) and H$_2$O (2 ml), and the mixture was stirred at room temperature for 30 min. The reaction mixture was extracted with ethyl acetate, and the extract was successively rinsed with 10% sodium hypochlorite solution and saturated NaCl solution. After the organic layer was dried over MgSO$_4$, the solvent was evaporated, and the residue was purified by silica gel column chromatography (hexane:ethyl acetate=1:1) to give 195 mg of compound 193 (82%).

[Compound 193]
Rf=0.13 (hexane:ethyl acetate=4:3)
δH(CDCl$_3$) 7.90~7.13 (m, 29H, aromatic proton), 5.310 (t, 1H, J=8.4 Hz, H-2a), 5.184 (d, 1H, J=3.7 Hz, H-4b), 1.919, 1.887, 1.821 (3s, 9H,3×Ac), 1.116 (d, 3H, J=6.2 Hz, H-6c).

EXAMPLE 159

(Synthesis of compound 194)

To a solution of compound 193 (180 mg, 0.15 mmol) in 1,2-dichloroethane (2 ml) under ice cooling were added trichloroacetonitrile (151 μl, 1.5 mmol) and DBU (45 μl, 3 mmol), and the mixture was stirred for 2 h. The reaction mixture was purified directly by silica gel column chromatography (hexane:ethyl acetate=4:3) to give 159 mg of compound 194 (79%).

[Compound 194]
Rf=0.53 (hexane:ethyl acetate=5:3)
$[\alpha]_D^{22}$ +10.7° (c=0.84, chloroform) δ$_H$(CDCl$_3$) 8.537 (s, 1H,=NH), 7.90~7.10 (m, 29H, aromatic proton), 6.423 (d, 1H, J=8.8 Hz, H-1a), 5.191 (d, 1H, J=3.3 Hz, H-4b), 4.875 (t,1H, J=9.5 Hz, H-2b), 4.391 (dd, 1H, J=3.3, 9.5 Hz, H-3b), 4.078 (t, 1H, J=9.1Hz, H-4a), 1.936, 1.878, 1.826 (3s, 9H, 3×Ac), 1.016 (d, 3H, J=6.6Hz, H-6c)

EXAMPLE 160

(Synthesis of compound 195)

A mixture of compound 194 (96 mg, 71.7 μmol), n-octanol (23 μl, 146 mol), MS4A (850 mg) and 1,2-dichloroethane (1.5 ml) was stirred at room temperature for 10 min, and cooled to −15° C. To this cooled reaction mixture was added BF$_3$.OEt$_2$ (13 μl, 142 μmol), and the mixture was stirred for 30 min. After the reaction mixture was neutralized with triethylamine, diluted with chloroform, filtered through celite, and then successively washed with saturated NaHCO$_3$ solution and saturated NaCl solution. The organic layer was dried over MgSO$_4$, and the solvent was evaporated. The residue was purified by gel filtration (SX-4, toluene) to give 75 mg of compound 195 (80%).

164

[Compound 195]
Rf=0.33 (hexane:ethyl acetate=2:1)
$[\alpha]_D^{22}$ −12.4° (c=0.46, chloroform)
C$_{75}$H$_{87}$N$_1$O$_{19}$

|  | C (%) | H (%) | N (%) |
|---|---|---|---|
| Calcd. | 68.95 | 6.71 | 1.67 |
| Found | 68.55 | 6.19 | 1.25 |

δ$_H$(CDCl$_3$) 7.84~7.08 (m, 29H, aromatic proton), 5.177 (d, 1H, J=3.3 Hz, H-4b), 5.064 (d, 1H, J=8.4 Hz, H-1a), 4.777 (t,1H, J=8.4 Hz,H-2a), 4.198 (dd, 1H, J=8.4, 10.3 Hz, H-3a), 3.892 (t, 1H, J=8.4Hz, H-4a), 3.178 (m,1H, H-5c), 1.911, 1.877, 1.821 (3s, 9H, 3×Ac), 1.013 (d, 3H, J=6.6 Hz, H-6c), 0.817 (t, 3H, J=7.3 Hz, Me)

EXAMPLE 161

(Synthesis of compound 196)

After a mixture of compound 195 (68 mg, 52 μmol), EtOH (4 ml) and hydrazine hydrate (1 ml) was refluxed for 7 h, the solvent was coevaporated. The residue was purified by LH-20 column chromatography (methanol) to yield the aminotriol derivative. To this derivative were added MeOH (1 ml) and AC$_2$O (15 μl), and the mixture was stirred at room temperature for 10 min. The reaction mixture was purified again by LH-20 column chromatography (methanol) to give 41 mg of compound 196 (72%).

[Compound 196]
Rf=0.43 (chloroform:methanol=15:1)
$[\alpha]_D^{22}$ −13.6° (c=1.1, chloroform)
δ$_H$(CDCl$_3$) 7.42~7.19 (m, 25R, aromatic proton), 5.093 (d, 1H, J=6.6 Hz, NH), 1.774 (s, 3H, Ac), 1.084 (d,3H, J=6.2 Hz, H-6c), 0.859 (t, 3H, J=7.0 Hz, Me)

EXAMPLE 162

(Synthesis of compound 197)

A mixture of compound 196 (17 mg, 15.5 μmol), 20% Pd(OH)$_2$—C (17 mg) and MeOH-H$_2$O (4:1, 1 ml) was hydrogenated at room temperature (2.5 h). After the removal of the catalyst, the reaction mixture was purified by LH-20 column chromatography (methanol) to give 7.2 mg of compound 197 (72%).

[Compound 197]
Rf=0.45 (n-butanol:ethanol:water=2:1:1)
δ$_H$(CD$_3$OD) 4.561 (d, 1H, J=7.3Hz, H-1c), 4.443 (d, 1H, J=7.7 Hz, H-1b), 4.418 (d,1H, J=8.5 Hz, H-1a), 4.058 (t, 1H, J=9.5 Hz, H-2a), 3.804 (d, 1H,J=2.2 Hz, H-4b), 3.589 (d, 1H, J=2.2 Hz, H-4c), 1.963 (s, 3H, Ac), 1.271 (d, 3H, J=6.6 Hz, H-6c), 0.897 (t, 3H, J=7.0 Hz, Me)

EXAMPLE 163

(Synthesis of compound 208)

To a solution of H$_2$-activated [Ir(COD) (PMePh$_2$)$_2$]PF$_6$ in THF (25 ml) was added a solution of compound 1 (3.340 g, 4.109 mmol) in THF (10 ml), the mixture was stirred at 25° C. for 30 min. After solvent was evaporated, the residue was dissolved in 10% water-containing acetone (50 ml). To this solution were added mercury(II) chloride (6 g, 22.099 mmol) and mercury(II) oxide, yellow (120 mg, 0.554 mmol), and the mixture was stirred for 1 h. The reaction mixture was diluted with chloroform, and filtered through celite. The organic layer was washed successively with sodium thiosulfate solution, NaHCO₃ solution and saturated NaCl solution, dried over anhydrous MgSO₄, and then the solvent was evaporated in vacuo. Purification of the residue by silica gel column chromatography (C-300, 300 g, toluene:ethyl acetate=2:1) gave 3.104 g of compound 208 (97.8%).

[Compound 208]

Rf=0.25 (toluene:ethyl acetate=2:1)

500 MHz, $^1$H—NMR (CDCl₃, TMS) 6H: 1.961, 1.968, 2.038 (3s, 9H, 3Ac), 3.394 (dd, 1H, J=5.5, 9.2 Hz, H-6), 3.493 (dd, 1H, J=7.3, 9.5 Hz, H-6), 4.100 (dd, 1H, J=8.4, 11.0 Hz, H-2a), 4.477 (d, 1H, J=8.1 Hz, H-1a), 4.923 (dd, 1H, J=3.3, 10.6 Hz, H-3b), 5.162 (dd, 1H, J=8.1, 10.6 Hz, H-2b), 5.339 (d, 1H, J=8.8 Hz, H-1b), 5.364 (bd, 1H, J=2.6 Hz, H-4b)

EXAMPLE 164

(Synthesis of compound 208)

To a solution of compound 208 (3.05 g, 3.947 mmol) dissolved in pyridine (10 ml) and acetic anhydride (10 ml) was added a catalytic amount of 4-dimethylaminopyridine, and the mixture was stirred at 25° C. for 18 h. After the solvent was evaporated in vacuo, the residue was purified by silica gel column chromatography (C-300, 240 g, toluene:ethyl acetate=3:1) to yield 2.6 g of compound 209 (76.9%).

[Compound 209]

Rf=0.43 (toluene:ethyl acetate=2:1)

500 MHz, $^1$H—NMR (CDC13, TMS) &H: 1.805, 1..942, 1.948, 1.985, 1.998 (5s, 15H, 5Ac), 4.966 (dd, 1H, J=8.1, 10.3Hz, H-3b), 5.364 (dd, 1H, J=0.7, 3.3 Hz, H-4b), 5.756 (dd, 1H, J=8.8, 10.6Hz, H-2b), 6.469 (d, 1HJ=8.8Hz, H-1b), 7.730, 7.850 (2m, 4H, Phth)

EXAMPLE 165

(Synthesis of compound 210)

A solution of compound 209 (2.590 g, 3.023 mmol) in 1,2-dichloroethane (50 ml) were added n-Bu₃SnSCH₃ (1.771 g, 5.252 mmol) and SnCl₄ (1.095 g, 4.201 mmol) at 0° C. and the mixture was stirred at 25° C. for 1 h. To the reaction mixture were added NaHCO₃ solution and KF solution, and the mixture was filtered through celite. The celite was washed with ethyl acetate, and the organic layer was rinsed with saturated NaCl solution and then dried over anhydrous MgSO₄. After the solvent was evaporated, the residue was purified by silica gel column chromatography (C-300, 240 g, toluene:ethyl acetate=3:1) to give 2.197 g of compound 210 (86.0%).

[Compound 210]

Rf=0.44 (toluene:ethyl acetate=2:1)

500 MHz, $^1$H—NMR (CDCl₃, TMS) δH: 1.814, 1.953, 1.956, 2.005, 2.148 (5s, 15H, 5CH3), 4.847 (dd, 1H, J=3.7, 10.3Hz, H-3b), 5.001 (dd, 1H, J=7.7, 10.6Hz, H-3a), 5.383 (dd, 1H, J=1.1, 3.7Hz, H-4b), 5.756 (dd, 1H, J=9.2, 10.2Hz, H-2b).

EXAMPLE 166

(Synthesis of compound 211)

A mixture of MS-4A (600 mg), compound 210 (534 mg, 0.632 mmol) and compound R12 (306 mg, 0.316 mmol) in 1,2-dichloroethane (4 ml) was stirred at 25° C. for 1 h and then cooled to −10° C. After the addition of MeOTf (84 μl, 0.741 mmol), the mixture was stirred at 25° C. for 3 days. The reaction mixture was diluted with ethyl acetate, and filtered through celite into NaHCO₃ solution. The organic layer was successively washed with water and saturated NaCl solution, dried over anhydrous MgSO₄, and then the solvent was evaporated in vacuo. Purification of the residue by silica gel column chromatography (C-300, 200 g, toluene:ethyl acetate=4:1) followed by Bio-Beads S-X3 column chromatography (toluene) gave 482.8 mg of compound 211 (86.5%).

[Compound 211]

Rf=0.73 (toluene:ethyl acetate=2:1)

500 MHz, $^1$H—NMR (CDCl₃, TMS) δH: 1.089 (s, 9H, tBu), 1.778, 1.942, 1.955, 2.003 (4s, 12H, 4Ac), 5.385 (bd, 1H, J=2.9 Hz, H-4d), 5.594 (d, 1HJ=8.1Hz, H-1c), 5.764 (dd, 1H, J=8.8, 10.6Hz, H-2d)

EXAMPLE 167

(Synthesis of compound 212)

To a solution of compound 211 (351 mg, 0.199 mmol) in ethanol (15 ml) was added methylhydrazine (20 ml), and the mixture was stirred at 80° C. for 1 h. The reaction mixture was purified by Sephadex LH-20 column chromatography (methanol). To a solution of the product in methanol (5 ml) was added acetic anhydride (100 μl), and the mixture was stirred at 25° C. for 15 min. After the reaction mixture was basified with NaOH solution, it was purified by Sephadex LH-20 (methanol) to obtain 282.5 mg of compound 212 (94.2%).

[Compound 212]

Rf=0.33 (chloroform:methanol=12:1)

500 MHz, $^1$H—NMR (CDCl₃, TMS) 6H: 1.126 (s, 9H, tBu), 1.469 (s, 3H, NAc), 2.745 (s, 1H, OH), 2.794 (d, 1H, J=3.7Hz, OH), 3.246 (dd, 1H, J=5.5,9.2Hz, H-6), 5.102 (dd, 1H, J=8.4, 9.2Hz, H-2a)

EXAMPLE 168

(Synthesis of compound 213)

A mixture of MS-4A (600 mg), compound 42 (293 mg, 0.166) mmol) and compound 212 (282.5 mg, 0.187 mmol) in -1,2-dichloroethane (10 ml) was stirred at 25° C. for 30 min. To the reaction mixture cooled to −10° C. was added BF₃.OEt₂ (25 μl, 0.203 mmol), and the mixture was stirred at 25° C. for 18 h. The reaction mixture was diluted with ethyl acetate and filtered through celite. The organic layer was washed successively with NaHCO₃ solution and saturated NaCl solution, dried over anhydrous MgSO₄, and then evaporated in vacuo. The residue was purified by Bio-Beads S-X3 (toluene) and then by silica gel column chromatography (C-300, 200 g, chloroform:methanol=20:1) to obtain 160.9 mg of compound 213 (31.2%).

[Compound 213]

Rf=0.84 (chloroform:methanol=12:1)

500 MHz, $^1$H—NMR (CDCl₃, TMS) δH: 1.119 (s, 9H, tBu), 1.211 (d, 3H, J=6.2Hz, CH₃), 1.473, 1.789, 1.856, 1.982, 2.007, 2.062, 2.093, 2.211 (8s, 24H, 8Ac), 2.547 (dd, 1H, J=4.8, 12.8Hz, H-3geq), 5.089 (t, 1H, J=9.2Hz, H-2a), 5.302 (d, 1H, J=8.1Hz, NH), 5.404 (dd, 1H, J=2.2, 9.2Hz, H-7g), 5.566 (m, 1H, H-8g)

EXAMPLE 169

(Synthesis of compound 214)

To a solution of compound 213 (263.5 mg, 0.085 mmol) in pyridine (4 ml) and acetic anhydride (4 ml) was added a catalytic amount of 4-dimethylaminopyridine, and the mixture was stirred at 25° C. for 18 h. After the solvent was evaporated in vacuo, the residue was purified by silica gel column chromatography (C-300, 100 g, toluene:methanol= 10:1) followed by Sephadex LH-20 column chromatography (methanol) to obtain 204 mg of compound 214 (74.4%).

[Compound 214]

Rf=0.77 (chloroform:methanol=12:1)

500 MHz, $^1$H—NMR (CDCl$_3$, TMS) δH: 1.117 (s, 9H, tBu), 1.202 (d, 3H, J=6.6Hz, CH3), 1.419, 1.719, 1.774, 1.814, 1.855, 1.967, 2.006, 2.058,2.086, 2.137, 2.228 (11s, 33H, 33Ac), 5.391 (dd, 1H, J=2.6, 9.2Hz, H-7g), 5.445 (bd, 1H, J=3.3Hz, H-4d), 5.580 (m, 1H, H-8g)

EXAMPLE 170

(Synthesis of compound 215)

To a solution of compound 214 (200 mg, 0.062 mmol) in methanol (8 ml) and water (2 ml) was added 10% Pd—C (200 mg), and the mixture was hydrogenated at 25° C. for 18 h. The reaction mixture was filtered through chromatodisk 25A to obtain 123 mg of compound 215 (98.1%).

EXAMPLE 171

(synthesis of compound 216)

To a solution of compound 215 (123 mg, 0.061 mmol) in pyridine (4 ml) and acetic anhydride (4 ml) was added a catalytic amount of 4-dimethylaminopyridine, and the mixture was stirred at 25° C. for 18 h. After the reaction mixture was evaporated in vacuo, the residue was purified by silica gel column chromatography (C-300, 100 g, chloroform:methanol=15:1) followed by Sephadex LH-20 column chromatography (methanol) to obtain 148 mg of compound 216 (89.6%).

[Compound 216]

Rf=0.49 (chloroform:methanol=12:1)

500 MHz, $^1$H—NMR (CDCl$_3$, TMS) 6H: 1.114, 1.127 (2s, 9H, tBu) 1.172 (t, 3H, H-6h), 2.585 (dd, 1H, J=4.4, 12.5Hz, H-3geq), 3.864 (s, 3H,OCH$_3$), 5.687 (d, 0.5H, J=8.4Hz, H-1a β), 6.282 (d, 0.5H, J=4.0Hz, H-1aα), 7.770 (m, 4H, Phth)

EXAMPLE 172

(Synthesis of compound 217)

To a solution of compound 216 (140 mg, 0.051 mmol) in DMF (2 ml) was added H$_2$NNH$_2$.AcOH (9.49 mg, 0.103 mmol), and the mixture was stirred at 25° C. for 1 h. The reaction mixture was diluted with chloroform, rinsed successively with water and saturated NaCl solution, dried over anhydrous MgSO$_4$, and then evaporated in vacuo. The residue was purified by Sephadex LH-20 column chromatography (methanol) to obtain 132.1 mg of compound 217 (95.9%).

[Compound 217]

Rf=0.44 (ethyl acetate:acetone=8:1)

500 MHz, $^1$H—NMR (CDCl$_3$, TMS) δ$_H$: 1.173 (s, 9H, tBu), 1.261 (d, 3H,J=7.0Hz, H-6h), 2.586 (dd, 1H, J=4.4, 12.5Hz, H-3geq), 3.865 (s, 3H, OCH3), 7.780 (m, 4H, Phth)

EXAMPLE 173

(Synthesis of compound 218)

To a solution of compound 217 (130 mg, 0.048 mmol) in 1,2-dichloroethane (2 ml) were added trichloroacetonitrile (30μl, 0.300 mmol) and 1,8-diazabicyclo[5.4.0]-7-undecene (6 μl, 0.040 mmol), and the mixture was stirred at 10° C. for 1 h. The reaction mixture was purified by silica gel column chromatography (C-300, 40 g, ethyl acetate:acetone=10:1) to obtain 120.9 mg of compound 218 (86.4%).

[Compound 218]

Rf=0.44 (ethyl acetate:acetone=10:1)

EXAMPLE 174

(Synthesis of compound 219)

A mixture of MS-4A (600 mg), compound 218 (119 mg, 0.042 mmol) and compound R18 (72.8 mg, 0.097 mmol) in chloroform (3 ml) was stirred at 25° C. for 30 min, and then cooled to 0° C. After the addition of BF$_3$.OEt$_2$ (16 μl, 0.130 mmol), the mixture was further stirred for 18 h. The reaction mixture was diluted with chloroform and filtered through celite into sodium hydrogencarbonate solution. The organic layer was washed with saturated NaCl solution, dried over anhydrous MgSO$_4$ and then evaporated in vacuo. The residue was purified by silica gel column chromatography (C-300, 100 g, chloro-form:methanol=15:1) to obtain 76.6 mg of compound 219 (53.2%).

[Compound 219]

Rf=0.31 (chloroform:methanol=15:1)

500 MHz, $^1$H—NMR (CDCl$_3$, TMS)δH: 0.880 (t, 6H, J=6.6 Hz, CH$_3$), 1.137 (s, 9H, tBu), 1.172 (d, 3H, J=5.9Hz, H-6h), 2.585 (dd, 1H, J=4.4, 12.5Hz, H-3geq), 3.865 (s, 3H, OCH3), 5.449 (dd, 1H, J=7.7, 15.0Hz, H-4Cer), 5.530 (t, 1H, J=7.7 Hz, H-3Cer), 5.737 (d, 1H, J=9.2 Hz, N<u>H</u>), 5.867 (dt, 1H, J=7.0, 15.0Hz, H-5Cer)

EXAMPLE 175

(Synthesis of compound 220)

To LiI (60 mg, 0.448 mmol) which had been vacuum-dried at 120° C. for 12 h was added under an Ar atmosphere a solution of compound 219 (59.7 mg, 0.017 mmol) in pyridine (2 ml), and the mixture was stirred at 110° C. for 18 h. The reaction mixture was purified by Sephadex LH-20 (methanol) to obtain 59.6 mg of compound 220 (100%).

[Compound 220]

Rf=0.65 (chloroform:methanol=5:1)

500 MHz, $^1$H—NMR (CD$_3$OD, TMS) δH: 0.893 (t, 6H, J=6.6 Hz, 2CH$_3$) 1.154 (s, 9H, tBu), 1.160 (d, 3H, J=6.2Hz, H-6h), 5.565 (t, 1H, J=7.7Hz, H-3Cer)

EXAMPLE 176

(Synthesis of compound 221)

A solution of compound 220 (34.4 mg, 10.4 μmol) in ethanol (6 ml) and methylhydrazine (8 ml) was stirred at 80° C. for 18 h. After the solvent was evaporated in vacuo, the residue was purified by Sephadex E-20 (chloroform:methanol:water=10:10:1). The product from the column was dissolved in a mixture of methanol (1 ml), tetrahydrofuran (1 ml), water (0.5 ml) and chloroform (1 ml). To this solution was added acetic anhydride (100 μl), and the mixture was stirred at 25° C. for 30 min. The reaction mixture was basified with sodium hydroxide and then purified by Sephadex LH-20 (chloroform:methanol:water=5:4:1) to obtain 14.3 mg of compound 221 (63.3%).

[Compound 221]
Rf=0.54 (chloroform:methanol:water=5:4:1)
500 MHz, $^1$H—NMR (DMSO, TMS) δH: 0.856 (t, 6H, J=7.0Hz, 2CH$_3$), 1.010 (d, 3H, J=6.6Hz, H-6h), 1.822 (s, 6H, 2NAc), 1.888 (s, 3H, NAc), 4.174 (d, 1H, J=7.7Hz, H-1a), 4.280 (m, 3H, H-1b,d,f), 4.618 (d, IH, J=7.3Hz, H-5h), 4.686 (d, 1H, J=8.2Hz, H-1c or H-1e), 4.722 (d, 1H, J=7.7Hz, H-1e or H-1c), 4.878 (d, 1H, J=3.3Hz, H-1h)

EXAMPLE 177

(Synthesis of compound 222)

AgOTf (271.6 mg, 1.05 mmol) and Cp$_2$HfCl$_2$ (203.8 mg, 0.53 mmol) were stirred in the presence of MS3A (1.03 g) in MeCN (5.0 ml) at 0° C. for 5 h. To the above solution was added a solution of compound 92 (202.6 mg, 0.26 mmol) and compound R12 (373.6 mg, 0.39 mmol) in MeCN (5.0 ml), and the mixture was stirred at room temperature for 23 h. The reaction mixture was diluted with AcOEt, filtered through celite, and then the filtrate was washed with saturated NaHCO$_3$ solution and then saturated NaCl solution. After drying over MgSO$_4$, the solvent was evaporated in vacuo, and the residue obtained was purified by silica gel column chromatography (Merc Si-60, 90 g, 15% AcOEt-toluene) to obtain compound 222 (384.3 mg, 86%).

[Compound 222]
$[\alpha]_D$ -30.6° (c=0.87, CHCl$_3$)
Rf=0.29 (toluene:ethyl acetate=4:1)
$\delta_H$ (CDCl3): 5.515 (s, 1H, PhCH), 5.256 (d, 1H, J=2.9Hz, H-4d), 5.175 (dd,1H, J=8.1, 9.5Hz, H-2a), 4.721 (dd, 1H, J=3.5, 10.4Hz, H-3d), 4.523 (d, 1H, J=7.7Hz, H-1d), 1.975, 1.817, 1.444(3s, 9H, Ac), 1.092 (s, 9H,t-Bu)

EXAMPLE 178

(Synthesis of compound 223)

To a solution of compound 222 (302.3 mg, 0.175 mmol) in THF ((1.6 ml) and MeOH (1.6 ml) was added at 0° C. 2.8% NaOMe (0.34 ml) and the mixture was stirred at 0 for 2.5 h. The reaction mixture was adjusted to pH 7 with Ambelite IRC-50 and evaporated to dryness in vacuo. Purification of the residue by silica gel column chromatography (Merc Si-60, 30 g, 3% MeOH, CHCl$_3$) gave 260.1 mg of compound 223 (93%).

[Compound 223]
$[\alpha]_D$ -35.3° (c=1.02, CHCl$_3$)
Rf=0.55 (CHCl$_3$:MeOH=24:1)
$\delta_H$ (CDCl$_3$): 5.591 (s, 1H, PhCH), 5.498 (d, 1H, J=8.4Hz, H-1c) 5.011 (dd, 1H, J=8.1, 9.2Hz, H-2a), 1.091 (s, 9H, t-Bu)

EXAMPLE 179

(Synthesis of compound 224)

AgOTf (204.9 mg, 790 μmol) and Cp$_2$HfCl$_2$ (156.1 mg, 403 μmol) were stirred in MeCN (1.5 ml) in the presence of MS3A at 0° C. for 6 h. To this solution was added a solution of compound 147 (91.7 mg, 56 μmol) and compound 223 (218.8 mg, 137 μmol) in MeCN (1.3 ml), and the mixture was stirred at room temperature for 17 h. The reaction mixture was diluted with CHCl$_3$ and filtered through celite. The filtrate was washed with saturated NaHCO$_3$ solution and saturated NaCl solution. The solvent was dried over MgSO$_4$, evaporated in vacuo. The residue obtained was purified by silica gel column chromatography (Merc Si-60, 30 g, CHCl$_3$: acetone=4:1) to obtain 73.4 mg of compound 224 (41%).

[Compound 224]
$[\alpha]_D$ -30.1° (C=0.81, CHCl$_3$)
Rf=0.40(CHCl$_3$:acetone=3:1)
$\delta_H$ (CDCl$_3$): 5.470 (s, 1H, PhCH), 5.358 (d, 1H, J=8.4Hz, H-1c), 5.261 (dd, 1H, J=2.6, 8.4Hz, H-7g), 5.090 (d, 1H, J=3.3Hz, H-1h), 3.773 (s, 3H, OMe), 2.452 (dd, 1H, J=4.6, 12.6Hz, H-3geq), 2.112, 2.060, 2.040, 1.978, 1.899, 1.819, 1.698 (7s, 21H, 7Ac), 1.313 (d, 3H, J=6.6Hz, CH$_3$-5h), 1.095 (s, 9H, t-Bu)

EXAMPLE 180

(Synthesis of compound 225)

To a solution of compound 224 (21.2 mg, 6.6 μmol) in pyridine (0.66 ml) were added DMAP (1.7 mg, 13.8 μmol) and Ac$_2$O (0.66 ml) and the mixture was stirred at room temperature for 14 h. The reaction mixture was evaporated to dryness in vacuo, and the residue was purified by silica gel column chromatography (Merc Si-60, 4.2 g, 20% acetone-CHCl3) to give 20.8 mg of compound 225 (97%).

[Compound 225]
$[\alpha]_D$ -33.4° (C=0.96, CHCl$_3$)
Rf=0.27 (CHCl$_3$:acetone=4:1)
$\delta_H$ (CDCl$_3$) : 5.409 (s, 1H, PhCH), 5.301 (d, 1H, J=8.4Hz, H-1c) 5.235 (dd, 1H, J=2.2, 8.8Hz, H-7g), 5.135 (d, 1H, J=3.7Hz, H-1h), 3.747 (s, 3H, OMe), 2.406 (dd, 1H, J=4.9, 12.6Hz, H-3geq), 2.043, 2.027(6H), 1.986, 1.966, 1.893, 1.808, 1.663 (7s, 24H, 8Ac), 1.090 (s, 9H, t-Bu)

EXAMPLE 181

(Synthesis of compound 226)

A solution of compound 225 (31.8 mg, 9.8 μmol) in MeOH (2.0 ml), AcOEt (10 ml) and water (0.4 ml) was added 10%Pd—C (29.8 mg), and the mixture was stirred under a 12 atmosphere at room temperature for 21.5 h. After the reaction mixture was filtered through celite, and the filtrate was evaporated to dryness in vacuo. To the residue dissolved in pyridine (1.0 ml) were added DMAP (9.5 mg, 77 μmol) and Ac$_2$O (1.0 ml), and the mixture was stirred at room temperature for 17.5 h. The reaction mixture was evaporated to dryness in vacuo, the residue was purified by silica gel column chromatography (Merc Si-60, 5.0 g, 4% MeOH—CHCl$_3$) to obtain a mixture of compound 226 and it's benzylidene derivative (22.7 mg). To this mixture dissolved in CH$_2$Cl$_2$ (1.0 ml) was added a 90% CF$_3$COOH aqueous solution (0.10 ml), and the mixture was stirred at room temperature for 20 min. The reaction mixture was diluted with CHCl$_3$, washed with saturated NaHCO3 solution and saturated NaCl solution, dried over MgSO$_4$, dried over and then the solvent was evaporated in vacuo. A solution of the residue in pyridine (0.70 ml) was added DMAP (1.4 mg, 11.3 μmol) and Ac$_2$O (0.50 ml), and the mixture was stirred at room temperature for 26 h. The reaction mixture was evaporated o dryness in vacuo, the residue was purified by gel filtration (Sephadex LH-20, 50 ml, MeOH) to obtain 15.9 mg of compound 226 (60%).

[Compound 226]
Rf=0.38 (CHCl$_3$:MeOH=24:1)
$\delta_H$ (CDCl$_3$): 6.238 (d, 0.4H, J=4.0Hz, H-1aα), 6.174 (d, 0.6H, J=8.1Hz, H-1aβ), 3.776 (s, 3H, OMe), 2.453 (dd, 1H, J=4.8, 12.5Hz, H-3geq), 1.102 (s, 5.4H, t-Buα), 1.089 (s, 3.6H, t-Buβ)

EXAMPLE 182

(Synthesis of compound 227)

To a solution of compound 226 (15.9 mg, 5.9 μmol) in DMF (0.60 ml) was added hydrazine acetate (1.3 mg, 14.1

µmol), and the mixture was stirred for 20 min at 60° C. The reaction mixture was purified by gel filtration (Sephadex LH-20, 35 ml, MeOH) to obtain 15.5 mg of compound 227 (99%).

[Compound 227]
Rf=0.27 (CHCl$_3$:MeOH=19:1)
$\delta_H$ (CDCl$_3$): 7.836 (m, 4H, aromatic proton), 7.768 (br.s, 4H, aromatic proton), 3.774 (s, 3H, OMe), 2.452 (dd, 1H, J=4.9, 13.0Hz, H-3geq), 1.146 (s, 9H, t-Bu)

EXAMPLE 183

(Synthesis of compound 228)

To a solution of compound 227 (15.5 mg, 5.8 µmol) in 1,2-dichloroethane (0.17 ml) were added trichloroacetonitrile (12 µl, 117 µmol) and DBU (1.4 µl, 9.0 µmol) at 0° C., and the mixture was stirred at the same temperature for 4 h. The reaction mixture was purified by silica gel column chromatography (Merc Si-60, 3.2 g, 2:3 toluene-acetone) to obtain compound 228 (16.2 mg, 99%).

[Compound 228]
Rf=0.34(toluene:acetone=2:3)
$\delta_H$ (CDCl$_3$): 8.640 (s, 0.2H, C=NHβ), 8.613 (s, 0.8H, C=NHα), 6.452 (d, 0.8H, J=3.7Hz, H-1aα), 3.775 (s, 3H, OMe), 2.454 (dd, 1H, J=4.6, 12.6Hz,H-3geq), 1.560 (t, 1H, J=12.5Hz, H-3gax), 1.106 (s, 1.8H, t-Buβ), 1.099 (s, 7.2H, t-Bu α)

EXAMPLE 184

(Synthesis of compound 229)

To a mixture of compound 228 (16.2 mg, 5.76 µmol), compound R18 (13.4 mg, 17.77 µmol) and MS4A (28 mg) in chloroform (0.60 ml) was added BF$_3$.OEt$_2$ (3.6 µl, 29.3 µmol) at 0° C, and the mixture was stirred at 0° C. ~room temperature for 24 h. To the reaction mixture was added triethylamine (6 µl), filtered through celite, and the filtrate was evaporated to dryness in vacuo. The residue was purified by silica gel column chromatography (Merc Si-60, 4.8 g, 35% acetone-CHCl$_3$) to give 8.2 mg of compound 229 (40%).

[Compound 229]
Rf=0.29 (CHCl$_3$:acetone=13:7)
$\delta_H$ (CDCl$_3$): 5.849 (td, 1H, J=7.0, 15.0Hz, H-5Cer), 5.507 (t, 1H, J=7.5 Hz, H-3Cer), 5.431 (dd, 1H, J=7.7, 15.4Hz, H-4Cer), 3.776 (s, 3H, OMe), 2.452 (dd, 1H, J=4.6, 12.6Hz, H-3geq), 1.110 (s, 9H, t-Bu)

EXAMPLE 185

(Synthesis of compound 230)

To LiI (7.2 mg, 58.3 µmol), which had been vacuum-dried on a 80° C. oil bath for 8 h, was added a solution of compound 229 (7.2 mg, 2.04 µmol) in pyridine (0.80 ml), and the mixture was stirred at 100° C. for 20 h. The reaction mixture was subjected to gel filtration (Sephadex LH-20, 20 ml, 1:1 CH$_2$Cl$_2$—MeOH) to obtain the lithium salt (7.1 mg).

To a solution of the lithium salt (7.1 mg) in ethanol (0.30 ml) was added methylhydrazine (0.60 ml), and the mixture was stirred on a 90° C. oil bath for 16 h. The reaction mixture was evaporated to dryness in vacuo, and the residue was subjected to gel filtration (LH-20, 10 ml, 5:4:1 CHCl$_3$—MeOH—H$_2$O) to obtain the deacylated derivative (4.3 mg).

To a solution of the deacylated derivative (4.3 mg) in CH$_2$Cl$_2$—MeOH—H$_2$O (5:4:1) (0.30 ml) was added acetic anhydride (0.10 ml), and the mixture was stirred at room temperature for 15 min. The reaction mixture was adjusted to pH 8 with 28% NaOMe, and evaporated to dryness. The residue was purified by gel filtration (Sephadex LH-20, 20 ml, 5:4:1 CHCl$_3$—MeOH—H$_2$O) to obtain 3.3 mg of compound 230 (72%).

[Compound 230]

Rf=0.43 (CHCl$_3$—MeOH—H$_2$O=5:4:1)

$\delta_H$ (DMSO-d6, 60° C.): 5.566 (td, 1H, J=6.5, 14.7Hz, H-5Cer), 5.383 (dd, 1H, J=7.1, 15.6Hz, H-4Cer), 4.832–4.773 (m, 3H, H-1c, H-1e, H-1h), 4.624 (q, 1H, J=6.6Hz, H-5h), 4.380 (d, 1H, J=7.3Hz, H-1b or H-1d or H-1f), 4.290 (d, 1H, J=7.0Hz, H-1b or H-1d or H-1f), 4.227 (br.s, 1H, H-1b or H-1d or H-1f), 4.182 (d, 1H, J=7.7Hz, H-1a), 2.777 (dd, 1H, J=5.3, 12.3Hz, H-3geq), 1.893 (s, 3H, NAc), 1.839 (s, 6H, 2NAc), 1.023 (d, 3H, J=6.2Hz, C283H$_3$-5h), 0.859 (t, 6H, J=6.8Hz, 2CH$_3$Cer)

What is claimed is:

1. A Lewis-associated compound, represented by the formula (I), (II), (III), (IV), (V) or (VI):

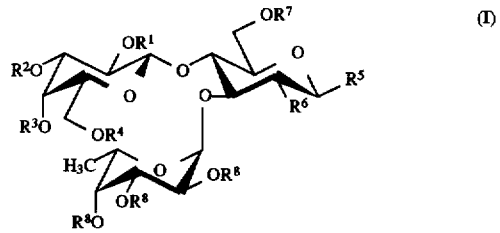

(I)

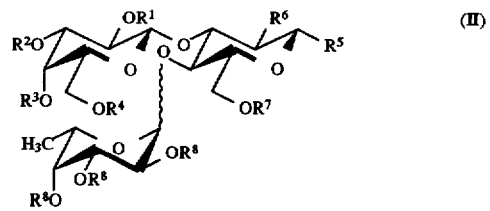

(II)

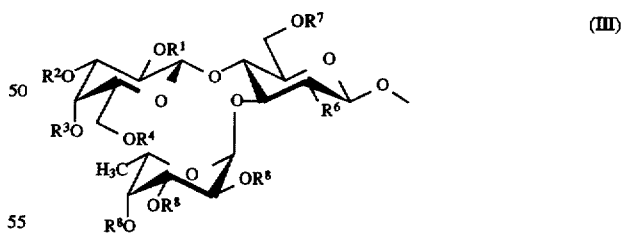

(III)

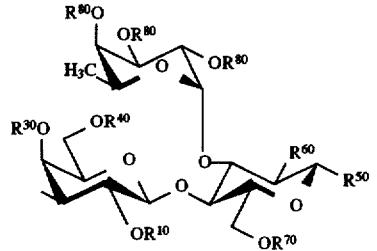

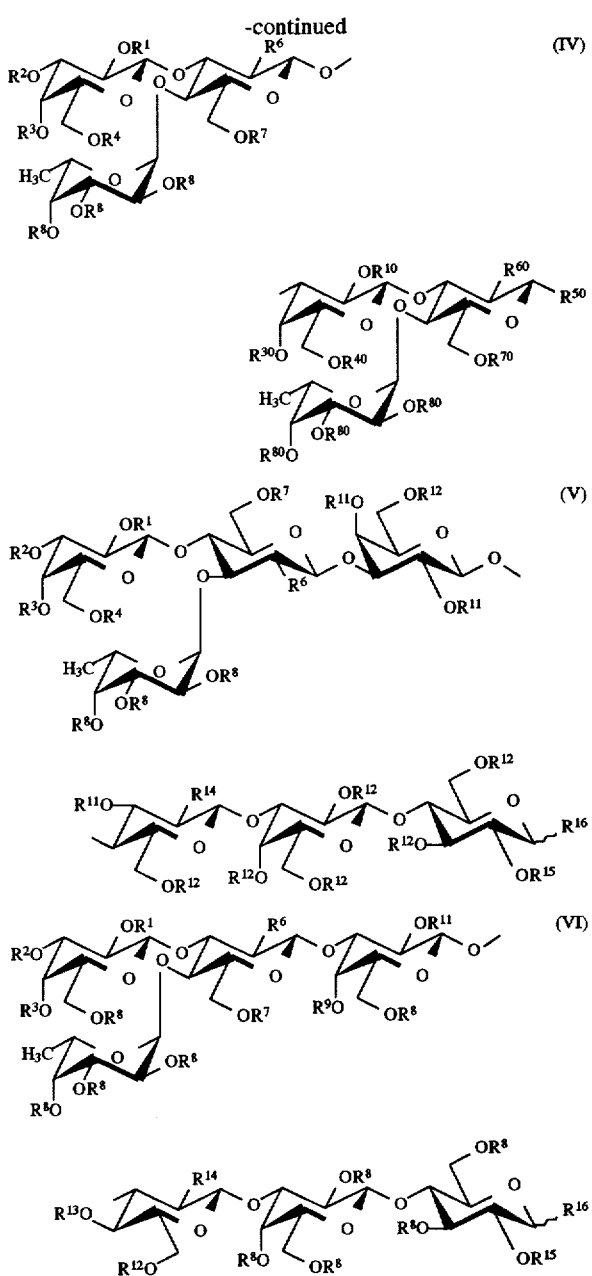

wherein $R^1$ represents hydrogen atom, acetyl group, pivaloyl group, levulinoyl group, or $SO_3M$ or $CH_2COOM$ where M represents hydrogen atom, alkali metal or lower alkyl group;

$R^2$ represents hydrogen atom, $SO_3M$, $CH_2COOM$, acetyl group, levulinoyl group or α-N-acetylneuraminic acid residue;

$R^3$ represents hydrogen atom, $SO_3M$, $CH_2COOM$, acetyl group or levulinoyl group;

$R^2$ and $R^3$ may cooperate to form benzylidene group;

$R^4$ represents hydrogen atom, acetyl group, benzyl group or pivaloyl group;

$R^5$ represents O-1-imino-2,2,2-trichloro-ethyl group or fluorine atom;

$R^6$ represents acetylamino group, phthaloylamino group, hydroxyl group or O-pivaloyl group;

R7 represents hydrogen atom, acetyl group, benzyl group or pivaloyl group;

$R^8$ represents hydrogen atom, acetyl group or benzyl group;

$R^{10}$ represents hydrogen atom, acetyl group or benzyl group;

$R^{30}$ represents hydrogen atom, acetyl group or benzyl group;

$R^{40}$ represents hydrogen atom, acetyl group or benzyl group;

$R^{50}$ represents O-lactose residue or O-lactosylceramide residue;

$R^{60}$ represents acetylamino group or phthaloylamino group;

$R^{70}$ represents hydrogen atom, acetyl group or benzyl group;

$R^{80}$ represents hydrogen atom, acetyl group or benzyl group;

$R^{11}$ represents hydrogen atom, acetyl group or benzyl group;

$R^{12}$ represents hydrogen atom, acetyl group or benzyl group;

$R^{13}$ represents hydrogen atom, acetyl group or benzyl group;

$R^{12}$ and $R^{13}$ may cooperate to form benzylidene group;

$R^{14}$ represents acetylamino group or phthaloylamino group;

$R^{15}$ represents hydrogen atom or pivaloyl group; and $R^{16}$ represents hydroxyl group, acetyloxy group, benzyloxy group or O-ceramide residue;

except that (a) when the compounds in which $R^1$, $R^3$, R4, $R^7$ and $R^{14}$ are all hydrogen atom, $R^2$ is a-N-acetylneuraminic acid residue; (b) in formula (I), when $R^2$ is not α-N-acetylneuraminic acid residue, at least one of $R^1$, $R^2$ and $R^3$ is $SO_3M$ or $CH_2COOM$; (c) in formula (II), when fucose residue is α-fucose, $R^2$ is not α-N- acetylneuraminic acid residue; and (d) in formula (III), $R^2$ is α-N-acetylneuraminic acid residue.

2. A Lewis-associated compound, represented by formula (VII), (IX) or (X):

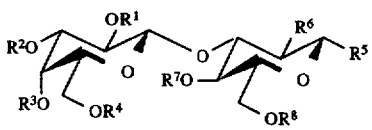

(VII)

-continued

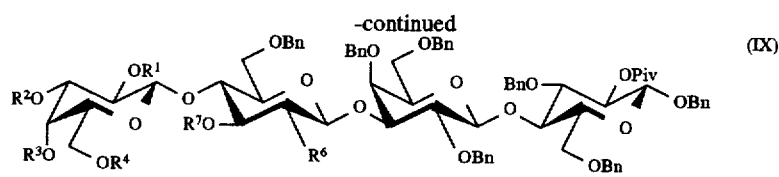
(IX)

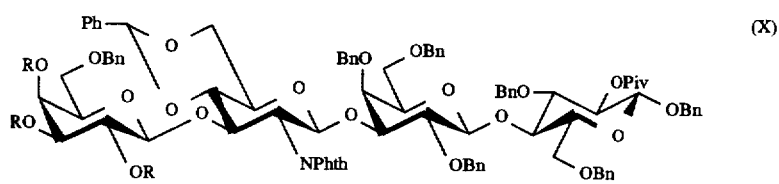
(X)

wherein R¹ represents hydrogen atom, acetyl group or benzyl group; and

R² represents acetyl group or N-acetylneuraminic acid residue;

R³ represents hydrogen atom, acetyl group or benzyl group;

R⁴ represents benzyl group;

R⁵ represents acetyloxy group, alkylthio group, or fluorine atom;

R⁶ represents acetylamino group or phthaloylamino group;

R⁷ represents hydrogen atom, acetyl group or benzyl group;

R⁸ represents hydrogen atom, acetyl group or benzyl group;

R⁷ and R⁸ may cooperate to form benzylidene group.

3. An anti-inflammatory agent comprising a Lewis-associated compound represented by general formula (III), (IV), (V) or (VI), or a pharmacologically acceptable salt thereof as an effective component:

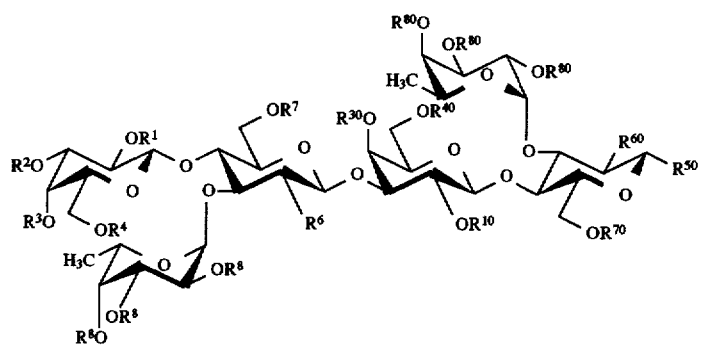
(III)

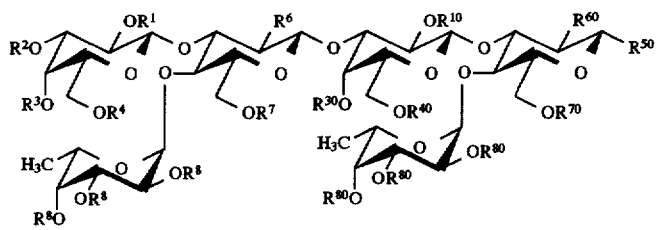
(IV)

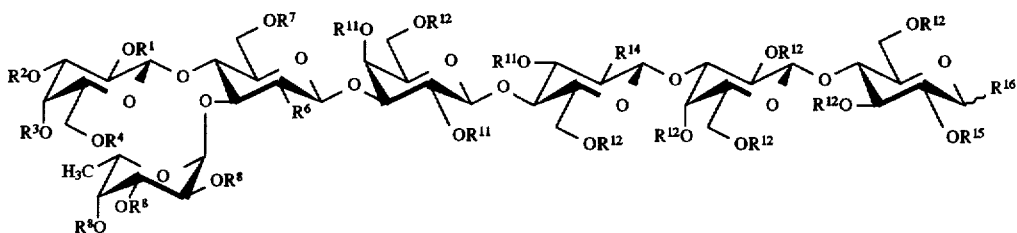
(V)

-continued

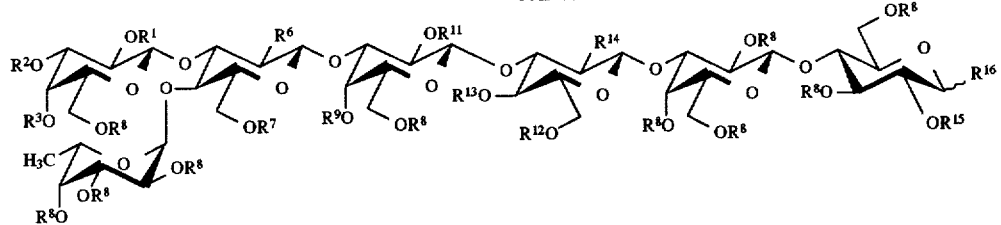
(VI)

wherein $R^1$ represents hydrogen atom, $SO_3H$ OR $CH_2COOH$;

$R^2$ represents hydrogen atom, $SO_3H$, $CH_2COOH$ or N-acetylneuraminic acid residue;

$R^3$ represents hydrogen atom, $SO_3H$ or $CH_2COOH$;

$R^4$ represents hydrogen atom;

$R^6$ represents acetylamino group;

$R^7$ represents hydrogen atom;

$R^8$ represents hydrogen atom;

$R^{10}$ represents hydrogen atom;

$R^{30}$ represents hydrogen atom;

$R^{40}$ represents hydrogen atom;

$R^{50}$ represents O-lactose residue or O-lactosylceramide residue;

$R^{60}$ represents acetylamino group;

$R^{70}$ represents hydrogen atom;

$R^{80}$ represents hydrogen atom;

$R^{11}$ represents hydrogen atom;

$R^{12}$ represents hydrogen atom;

$R^{13}$ represents hydrogen atom;

$R^{14}$ represents acetylamino group;

$R^{15}$ represents hydrogen atom; and $R^{16}$ represents hydroxyl group or O-ceramide residue.

4. A process for producing compound 86, comprising the steps of:

(a) reacting compound 42 and compound 65 with glycosylation catalyst to yield compound 79;

(b) acetylating compound 79 to yield compound 80;

(c) debenzylating and then acetylating compound 80 to yield compound 81;

(d) deacetylating anomeric acetate of compound 81 to yield compound 82;

(e) reacting compound 82 and trichloroacetonitrile to yield compound 83;

(f) reacting compound 83 and benzoyl ceramide to yield compound 84;

(g) converting compound 84 into its lithium salt 85; and (h) then depriving the lithium salt 85 of protecting groups, wherein compounds 42, 65 and 79–86 have the following structures:

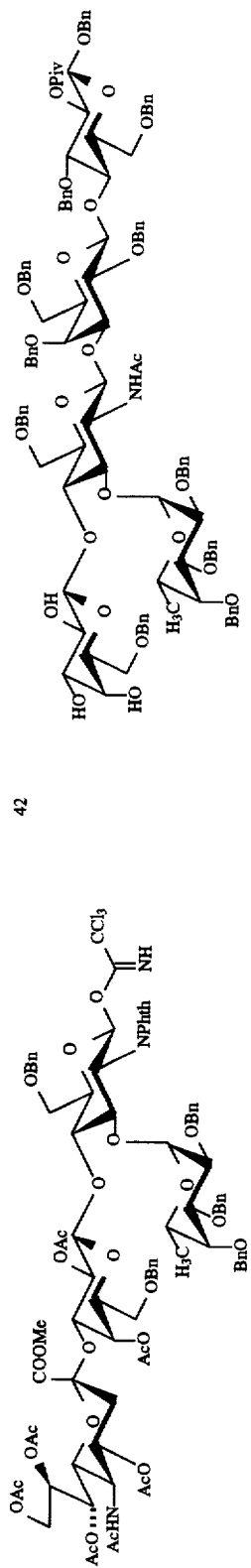
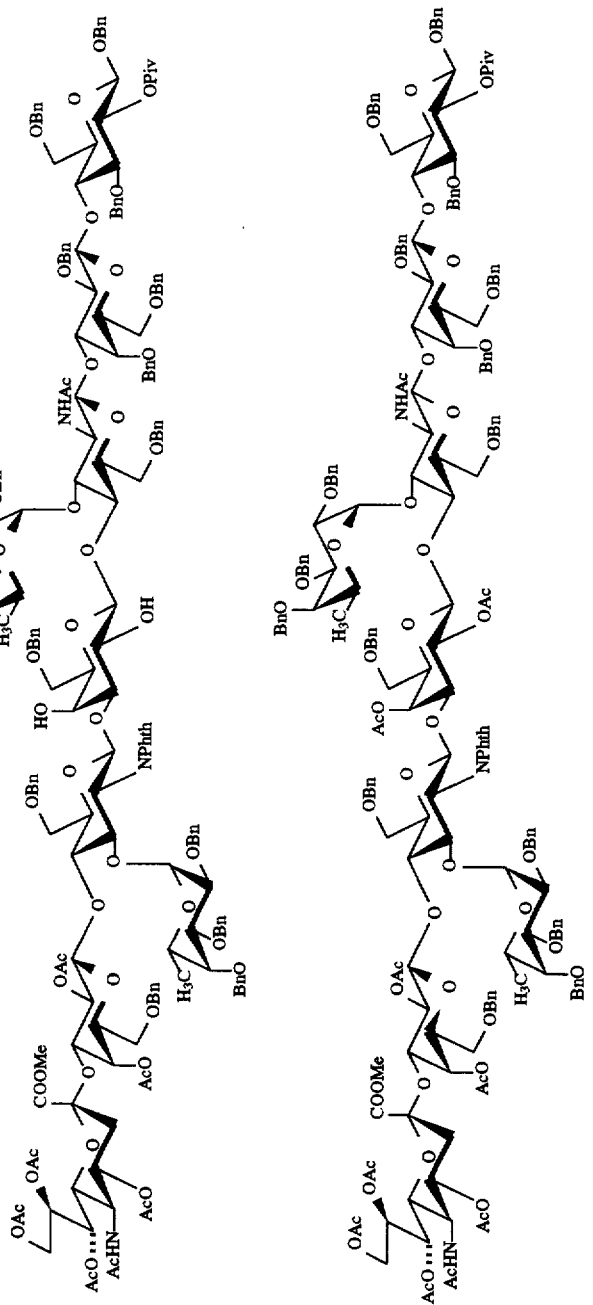

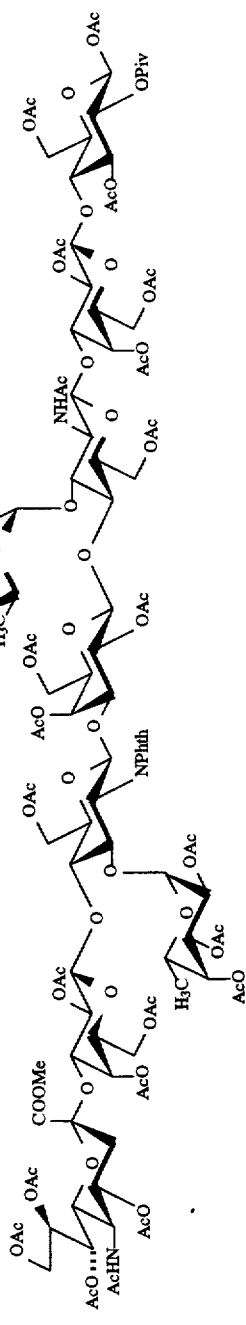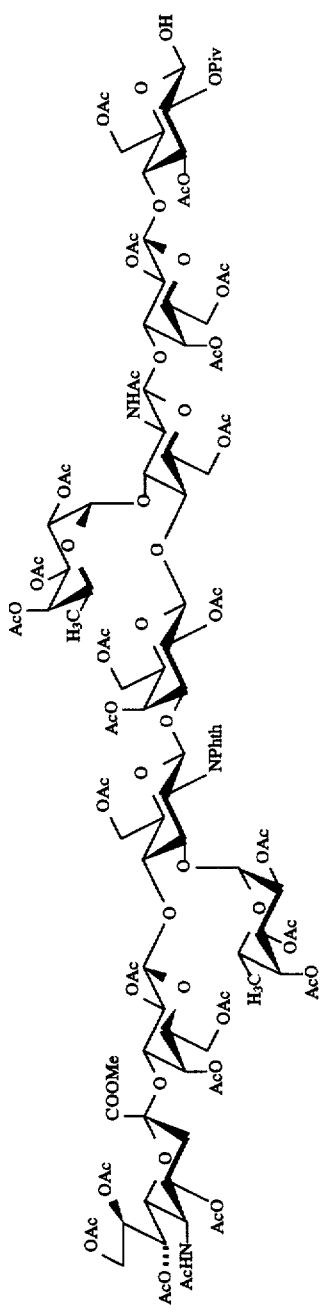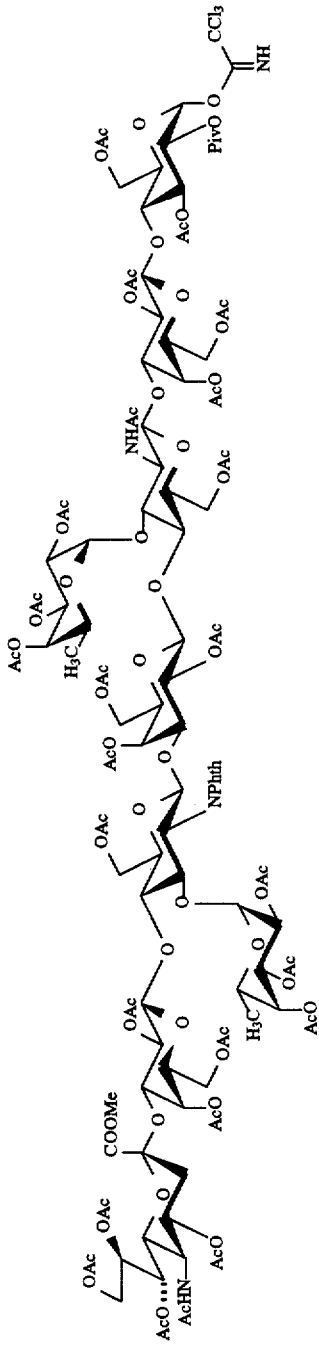

-continued
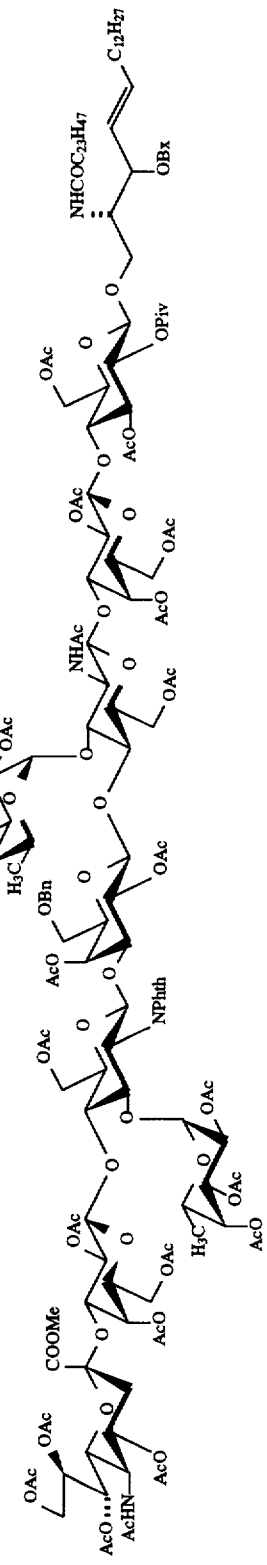
84
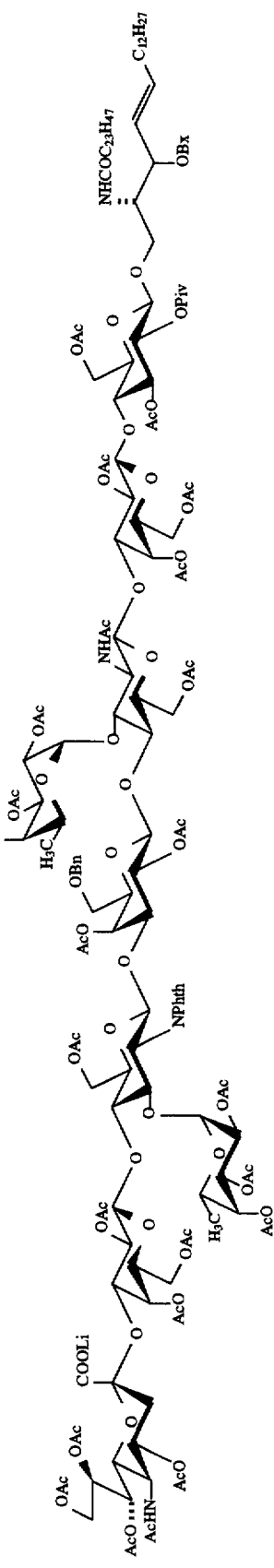
85
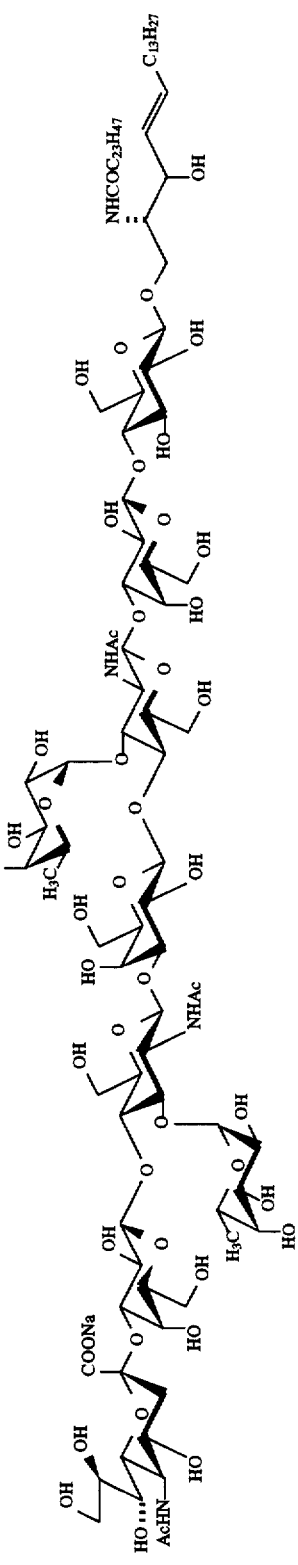
86

5. The anti-inflammatory agent according to claim 3, wherein if $R^1$ and $R^3$ of the Lewis-associated compound are each hydrogen atom, $R^2$ is α-N-acetylneuraminic acid residue.

6. The anti-inflammatory agent according to claim 3, wherein the agent further comprises a carrier.

* * * * *